United States Patent
Torisu et al.

(10) Patent No.: US 7,135,495 B2
(45) Date of Patent: Nov. 14, 2006

(54) INDOLE DERIVATIVES

(75) Inventors: Kazuhiko Torisu, Mishima-gun (JP); Maki Iwahashi, Mishima-gun (JP); Kaoru Kobayashi, Mishima-gun (JP); Fumio Nambu, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/488,835

(22) PCT Filed: Sep. 6, 2002

(86) PCT No.: PCT/JP02/09078

§ 371 (c)(1), (2), (4) Date: Mar. 8, 2004

(87) PCT Pub. No.: WO03/022814

PCT Pub. Date: Mar. 20, 2003

(65) Prior Publication Data

US 2005/0004097 A1    Jan. 6, 2005

(30) Foreign Application Priority Data

Sep. 7, 2001    (JP) .............................. 2001-271282

(51) Int. Cl.
- A61K 31/335 (2006.01)
- C07D 265/36 (2006.01)
- C07D 405/00 (2006.01)
- C07D 209/02 (2006.01)
- C07D 209/04 (2006.01)

(52) U.S. Cl. .............. 514/452; 544/105; 548/454; 548/465; 548/491

(58) Field of Classification Search .............. 548/454, 548/465, 491; 544/105; 514/419, 452
See application file for complete search history.

(56) References Cited

U.S. PATENT DOCUMENTS

| | | | |
|---|---|---|---|
| 3,285,908 A | 11/1966 | Shen | |
| 3,336,194 A | 8/1967 | Shen | |
| 5,436,265 A * | 7/1995 | Black et al. | 514/420 |
| 6,743,793 B1 * | 6/2004 | Torisu et al. | 514/249 |

FOREIGN PATENT DOCUMENTS

EP    458642 A1    11/1991
GB    997638 A    7/1965

OTHER PUBLICATIONS

Moreland et al, Treatment of Rheumatoid Arthritis with a Recombinant Human Tumor Necrosis Factor Receptor (p75)-Fc Fusion Protein, The New England Journal of Medicine, vol. 337, No. 3, pp. 141-147, 1997.*

Lo et al, Interleukin-1β Induction of c-fos and Collagenase Expression in Articular Chondrocytes: Involvement of Reactive Oxygen Species, Journal of Cellular Biochemistry, vol. 69, pp. 19-29, 1998.*

Neff et al, NF-kB and the MAP kinases/AP-1 pathways are both involved in interleukin-6 and interleukin-8 expression in fibroblast-like synoviocytes stimulated by protein I/II, Cellular Microbiology, vol. 3, No. 10, pp. 703-712, 2001.*

San-Bao Hwang, et al., "Effects of Nonsteroid Antiinflammatory Drugs on the Specific Binding of Platelet Activating Factor to Membrane Preparations of Rabbit Platelets," *Thrombosis Research*, vol. 34, pp. 519-531, 1984.

* cited by examiner

*Primary Examiner*—Kamal A. Saeed
*Assistant Examiner*—Susannah L. Chung
(74) *Attorney, Agent, or Firm*—Sughrue Mion, PLLC

(57) ABSTRACT

Compounds represented by formula (I)

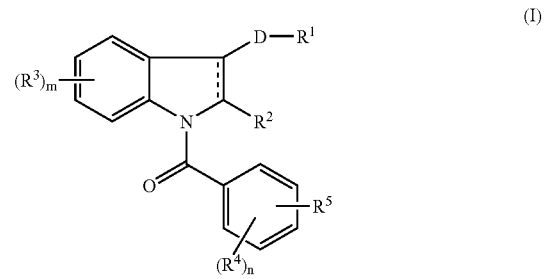

wherein all symbols represent the same meanings as described in specification. and salts thereof.

Since the compound represented by the formula (I) binds and antagonizes to DP receptor, it is useful for the prevention or treatment against the disease such as allergic disorder, diseases accompanied with itching, secondary diseases generated by behaviors caused by itching, inflammation, chronic obstructive pulmonary disease, ischemic reperfusion disorder, pleuritis complicated by rheumatoid arthritis, cerebrovascular disease, and ulcerative colitis.

4 Claims, No Drawings

INDOLE DERIVATIVES

TECHNICAL FIELD

The present invention relates to indole derivatives.

More specifically, the present invention relates to indole derivatives represented by formula (I):

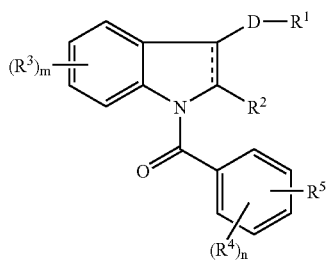

wherein all symbols have the same meanings as described below, the non-toxic salts,
(2) a process for the preparation of the same, and
(3) a medicine comprising them as an active ingredient.

BACKGROUND ART

Prostaglandin $D_2$ (hereinafter referred to as "$PGD_2$") are known as a metabolite in the arachidonic acid cascade, and are thought to be one of chemical transmitters that take part in allergic disease, for example, allergic rhinitis, bronchial asthma, and conjunctivitis allergic. It has been known that $PGD_2$ is produced from mast cells and free $PGD_2$ shows bronchoconstriction, permeability accentuation, vasodilation or shrinkage, mucus secretion promotion, and platelet aggregation inhibitory effect. It has been reported that $PGD_2$ induces airway contraction and rhinostenosis symptom in vivo and the increase in $PGD_2$ concentration has been recognized in the pathologic topical of systemic mast cytosis (mastocytosis) patients, nasal allergy patients, bronchial asthma patients, atopic dermatitis patients, and urticaria patients, etc (New Eng. J. Med., 303, 1400–1404 (1980), Am. Rev. Respir. Dis., 128, 597–602 (1983), J. Allergy Clin. Immunol., 88, 33–42 (1991), Arch Otolaryngol Head Neck Surg, 113, 179–83 (1987), J. Allergy Clin. Immunol., 82, 869–77 (1988), J. Immunol., 146, 671–6 (1991), J. Allergy Clin. Immunol., 83, 905–12 (1989), N. Engl. J. Med., 315, 800–4 (1986), Am. Rev. Respir. Dis., 142, 126–32 (1990), J. Allergy Clin. Immunol., 87, 540–8 (1991), J. Allergy Clin. Immunol., 78, 458–61 (1986)). Also, PGD is considered to relate to neuro activities, especially, sleep, hormone secretion, and pain. Furthermore, there are reports suggesting participations in platelet aggregation, glycogen metabolism, ocular tension adjustment and the like.

$PGD_2$ shows its effects by binding to DP receptor which is one of receptor thereof. A DP receptor antagonist binds and is antagonistic to its receptor so that it can inhibit the function. Accordingly, it is considered to be useful for the prevention and/or treatment of diseases, for example, allergic diseases (allergic rhinitis, allergic conjunctivitis, atopic dermatitis, bronchial asthma, food allergy, etc.), systemic mastocytosis, disorders due to systemic mastocyte activation, anaphylactic shock, bronchoconstriction, urticaria, eczema, allergic bronchopulmonary aspergillosis, paranasal sinusitis, migraine, nasal polyp, hypersensitive angitis, eosinophilia, contact dermatitis, diseases accompanied with itching (such as atopic dermatitis, urticaria, allergic conjunctivitis, allergic rhinitis, contact dermatitis, etc.), secondary diseases (such as cataracta, retinodialysis, inflammation, infection, dysgryphia, etc.) generated by behaviors caused by itching (scratching behaviors, beating, etc.), inflammation, chronic obstructive pulmonary disease, ischemic reperfusion disorder, cerebrovascular disorder, pleuritis complicated by rheumatoid arthritis, ulcerative colitis and the like. Moreover, it is considered to relate to sleeping and platelet aggregation and to be useful for these diseases.

It is known that $PGD_2$ binds with chemoattractant receptor-homologous molecule expressed on Th2 cells (CRTH2 besides DP receptor, and has the migration action on Th 2 cell, eosinophil, and basophil (J. Exp. Med., 193, 255–261 (2001), Blood, 98, 1942–1948 (2001)). Since $PGD_2$ is a ligand to both of DP and CRTH2 receptors in vivo, DP receptor antagonists are expected to bind with CRTH2 receptor, and to antagonize the biological activity.

So, it is considered to be useful for the prevention and/or treatment of diseases, allergic diseases, for example, allergic rhinitis, allergic conjunctivitis, atopic dermatitis, bronchial asthma, food allergy, etc., systemic mastocytosis, disorders due to systemic mastocyte activation, anaphylactic shock, bronchoconstriction, urticaria, eczema, allergic bronchopulmonary aspergillosis, paranasal sinusitis, migraine, nasal polyp, hypersensitive angitis, eosinophilia, contact dermatitis, diseases accompanied with itching such as atopic dermatitis, urticaria, allergic conjunctivitis, allergic rhinitis, contact dermatitis, etc.; secondary diseases such as cataracta, retinodialysis, inflammation, infection, dysgryphia, etc. generated by behaviors caused by itching (scratching behaviors, beating, etc.), inflammation, chronic obstructive pulmonary disease, ischemic reperfusion disorder, cerebrovascular disorder, pleuritis complicated by rheumatoid arthritis, ulcerative colitis and the like.

Some $PGD_2$ receptor antagonists are known conventionally, and BW-A868C represented by the following formula (A) is considered to be the most selective:

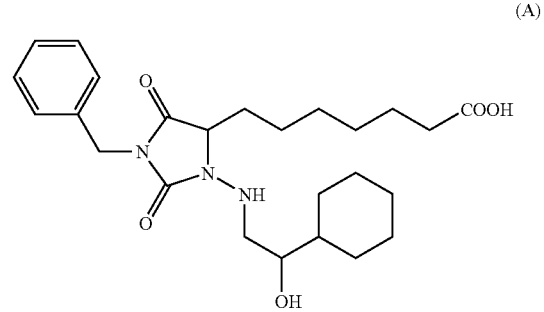

Recently, $PGD_2$ receptor antagonists comprising thromboxane derivatives have been published in WO 98/25915, WO 98/25919, WO 97/00853, WO 98/15502 and the like.

As prostaglandin receptors, a lot of receptor including the subtype exist and the pharmacological action is respectively different. Then, if new compounds that weakly bind to other prostaglandin receptors and specifically bind to $PGD_2$ receptor, especially DP receptor can be found, there is a possibility to become a medicine having a little side effect because of disappear of other actions, and discovery of such a medicine is necessary.

DISCLOSURE OF THE INVENTION

The present inventors intensively studied to find a compound which specifically binds to PGD$_2$ receptor, especially DP receptor and show an antagonistic activity and found that the object could be attained by indole derivatives represented by formula (I), and thus the present invention has been completed.

That is, the present invention relates to indole derivatives represented by formula (I):

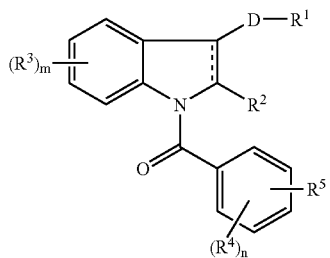

wherein R$^1$ represents (1) —COR$^6$ or (2) —CH$_2$OR$^7$,

R$^6$ represents (1) hydroxyl group, (2) C1–6 alkoxy group, (3) —NR$^8$R$^9$, (4) C1–6 alkoxy group substituted by phenyl group, or (5) C2–6 alkenyloxy group, R$^7$ represents (1) hydrogen atom or (2) C2–6 acyl group, R$^8$ and R$^9$ represent (1) hydrogen atom, (2) C1–6 alkyl group or (3) —SO$_2$R$^{10}$, respectively, R$^{10}$ represents (1) C1–6 alkyl group, (2) carbocyclic ring 1 (3) or heterocycle 1, D represents (1) a single bond, (2) C1–6 alkylene group, (3) C2–6 alkenylene group, (4) —O—(C1–6 alkylene)- group, R$^2$ represents (1) C1–6 alkyl group, (2) C1–6 alkoxy group, (3) halogen atom(s), (4) trihalomethyl group, (5) cyano group, or (6) hydroxyl group, R$^3$ and R$^4$ represent (1) hydrogen atom, (2) C1–6 alkyl group, and (3) C1–6 alkoxy group, (4) C1–6 alkyl group substituted in C1–6 alkoxy group, (5) halogen atom, (6) nitro group, (7) —NR$^{11}$R$^{12}$, (8) trihalomethyl group, (9) cyano group, (10) hydroxyl group, or (11) methoxy groups, respectively, R$^{11}$ and R$^{12}$ represent a hydrogen atom or C1–6 alkyl group, respectively, m represents 1 to 4, n represents 1 to 4, R$^5$ represents (1)

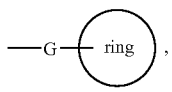

(2) C1–6 alkyl group substituted in C1–6 alkoxy group, or (3) C1–6 alkoxy group substituted by C1–6 alkoxy group, G represents (1) a single bond, (2) C1–6 alkylene group (alkylene group may be substituted by hydroxyl group or C1–4 alkoxy group) that may be replaced by 1 or 2 of oxygen atom(s) and/or sulfur atom(s), (3) C2–6 alkenylene group (alkenylene group may be substituted by hydroxyl or C1–4 alkoxy group) that may be replaced by 1–2 of oxygen atom(s) and sulfur atom(s), (4) —CONR$^{13}$—, (5) —NR$^{14}$CO—, (6) —SO$_2$NR$^{15}$—, (7) —NR$^{16}$SO$_2$—, or (8) —N=N—, R$^{13}$, R$^{14}$, R$^{15}$, and R$^{16}$ represent hydrogen atom or C1–6 alkyl group, respectively,

represents (1) carbocyclic ring 2 (2) or heterocycle 2, carbocyclic ring 1 and carbocyclic ring 2 represent C3–15 monocycle, dicyclic or tricycle carbocyclic ring aryls that may be saturated all or partially, respectively, heterocycle 1 and heterocycle 2 represent C3–15 monocycle, dicyclic, or tricycle heterocyclic ring aryls that may be saturated all or partially, which contained 1–5 hetero atom(s) selected from oxygen atom(s), nitrogen atom(s) or sulfur atom(s), respectively, carbocyclic ring 1, carbocyclic ring 2, heterocycle 1, and heterocycle 2 may be substituted by 1–5 group(s) selected from (1) C1–6 alkyl group, (2) C1–10 alkoxy group, (3) C1–6 alkyl group substituted by C1–6 alkoxy group, (4) halogen atom, (5) hydroxyl group, (6) trihalomethyl group, (7) nitro group, (8) —NR$^{17}$R$^{18}$, (9) phenyl group, (10) phenoxy group, (11) oxo group, (12) C2–6 acyl group, (13) cyano group, and (14) —SO$_2$R$^{19}$, respectively, R$^{17}$ and R$^{18}$ represent hydrogen atom or C1–6 alkyl group, respectively, R$^{19}$ represents C1–6 alkyl group, and ----- represents (1) a single bond or (2) a double bond, except for 2-(1-(4-benzyloxybenzoyl)-2-methyl-5-methoxyindol-3-yl) acetic acid methyl) or non-toxic salts thereof, (2) the manufacturing methods, and (3) the medicines that contains them as active ingredients.

The C1–6 alkyl group in this specification includes methyl, ethyl, propyl, butyl, pentyl, hexyl group, and isomers thereof.

The C1–4 alkoxy group in this specification includes methoxy, ethoxy, propoxy, butoxy group, and isomers thereof.

The C1–6 alkoxy group in this specification includes methoxy, ethoxy, propoxy, butoxy, pentyloxy, hexyloxy group, and isomers thereof.

The C1–10 alkoxy group in this specification includes methoxy, ethoxy, propoxy, butoxy, pentyloxy, hexyloxy, heptyloxy, octyloxy, nonyloxy, decyloxy group, and isomers thereof.

The C2–6 alkenyloxy group in this specification includes ethenyloxy, propenyloxy, butenyloxy, pentenyloxy, hexenyloxy group and isomers thereof.

The C1–6 alkylene group in this specification includes methylene, ethylene, trimethylene, tetramethylene, pentamethylene, hexamethylene group, and isomers thereof.

The C2–6 alkenylene group in this specification includes ethenylene, propenylene, butenylene, pentenylene, hexenylene group and isomers thereof.

The halogen atom in this specification includes fluorine, chlorine, the bromide, and iodine atom.

The trihalomethyl group in this specification means methyl group substituted by three halogen atoms.

The trihalomethoxy group in this specification means methoxy group substituted by three halogen atoms.

The C1–6 alkylene group that may be replaced by 1 to 2 oxygen atom(s) and/or sulfur atom(s) in this specification includes methylene, ethylene, trimethylene, tetramethylene, pentamethylene, hexamethylene group, and group replaced 1 to 2 arbitrary carbon atoms of the above alkylene by 1 to 2 oxygen atom(s) and/or sulfur atom(s).

The C2–6 alkenylene group that may be replaced by 1 to 2 oxygen atom and/or sulfur atoms in this specification includes ethenylene, propenylene, butenylene, pentenylene, hexenylene group, and group replaced 1 to 2 arbitrary carbon atom(s) of the above alkenylene by 1 to 2 oxygen atom(s) and/or sulfur atom(s).

The C2–4 acyl group in this specification includes acetyl, propanoyl, butanoyl, pentanoyl, hexanoyl group, and isomers thereof.

In this specification, as 3 to 15-membered monocycle, dicycle or tricycle carbocyclic ring aryl that may be saturated all or partially, which are represented by carbocyclic ring 1 and carbocyclic rings, for example, cyclopropane, cyclobutane, cyclopentane, cyelohexane, cycloheptane, cyclooctane, cyclononane, cyclodecane, cycloundecane, cyclododecane, cyclotridecane, cyclotetradecane, cyclopentadecane, cyclopropene, cyclobutene, cyclopentene, cyclohexene, cycloheptene, cyclooctene, cyclopentadiene, cyclohexadiene, cycloheptadiene, cyclooctadiene, benzene, pentalene, azulene, perhydroazulene, perhydropentalene, indene, perhydroindene, indane, naphthalene, tetrahydronaphthalene, perhydronaphthalene, heptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[3.1.1]heptane, bicyclo[3.3.1]-2-heptene, bicyclo[2.2.2]octane, adamantane, and noradamantane ring, etc. are included.

In this specification, as 3 to 15-membered monocycle, dicycle or tricycle heterocyclic ring aryls that includes 1 to 5 hetero atoms selected from oxygen atom, nitrogen atom or sulfur atom, among 3 to 15-membered monocycle, dicyclic ring or tricycle heterocycle aryls that may be saturated all or partally and includes 1 to 5 hetero atom(s) selected from oxygen atom, nitrogen atom or sulfur atom, which are represented by heterocycle 1 and heterocycle 2, pyrrole, imidazole, triazole, tetrazole, pyrazol, pyridine, pyrazine, pyrimidine, pyridazine, azepine, diazepine, furan, pyran, oxepin, thiophene, thiin, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepin, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepin, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiine, thianthrene, phenanthridine, phenanthroline, perimidine ring, etc. are included.

As 3 to 15-membered monocycle, dicycle or tricycle heterocyclic ring aryls that may be saturated all or partially and includes 1 to 5 hetero atom(s) selected from oxygen atom, nitrogen atom or sulfur atom, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazin, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiin (dihydrothiopyran), tetrahydrothiin (tetrahydrothiopyran), dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydroxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, indoline, isoindolin, dihydrobenzofuran, perhydrobenzofuran, dihydroisobenzofuran, perhydroisobenzofuran, dihydrobenzothiophene, perhydrodibenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzooxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzooxazepine, tetrahydrobenzooxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxan, chroman, benzodithiolane, and benzodithiane ring, etc. are included.

Unless otherwise specified, all isomers are included in the present invention. For example, alkyl, alkoxy and alkylene group includes straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, I-isomer), polar compounds generated by chromatographic separation (more polar compound, less polar compound), equilibrium compounds, rotamer, mixtures thereof at voluntary ratios and racemic mixtures are also included in the present invention.

According to the present invention, unless otherwise indicated and as is apparent for those skilled in the art, symbol 

indicates that it is bound to the opposite side of the sheet (namely α-configuration), symbol ![arrow], indicates that it is bound to the front side of the sheet (namely β-configuration), symbol ![wavy], indicates that it is α-, β- or a mixture thereof, and symbol ![slash] indicates that it is a mixture of α-configuration and β-configuration.

PGD$_2$ receptor in this specification represents a receptor that PGD$_2$ binds, not only the one found by present, but also the one that will be found in the future is included in the receptor. The desirable one is DP receptor or CRTH2 receptor, and more desirably DP receptor.

The compounds in the present invention may be converted into the non-toxic salt by a well-known method. The non-toxic salts are suitable to be allowed in pharmacology, and water-soluble.

Non-toxic salts include, for example, alkali metal salts (potassium, sodium, lithium, etc.), alkaline earth metal salts (calcium, magnesium, etc.), ammonium salts (tetramethylammonium, tetrabutylammmonium, etc.), organic amine salts (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid-addition salts (inorganic acid salts (hydrochloride, hydrobromate, hydroiodate, sulfate, phosphate, and nitrate, etc.), organic acid salts(acetate, trifluoroacetate, lactate, tartrate, oxalate, fumarate, maleate, benzoate, citrate, methane sulfonate, ethane sulfonate, benzene sulfonate, toluene sulfonate, isethionate, glucuronate, gluconate, etc.), etc.

In non-toxic salts of compound in the present invention, solvates thereof, or solvates of alkali (earth) metal salts, ammonium salts, organic amine salts, and acid-addition salts of the above compound in the present invention, are included.

The solvates are preferably non-toxic and water-soluble. Appropriate solvates, for example, solvates such as water, alcohol solvents (ethanol, etc.), etc. are included.

As $R^1$ in formula (I), —$COR^6$ or —$CH_2OR^7$ is suitable and $COR^6$ is more suitable.

As $R^6$ in formula (I), a hydroxyl or C1–6 alkyl group is suitable.

As $R^7$ in formula (I), a hydrogen atom or C2–6 acyl group is suitable and a hydrogen atom is more suitable.

As D in formula (I), a single bond or C1–6 alkyl group is suitable and C1–6 alkyl group is more suitable.

As $R^2$ in formula (I), C1–6 alkyl group is suitable and methyl group is more suitable.

As $R^5$ in formula (I),

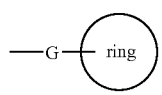

is suitable.

As G in formula (I), C1–6 alkylene group that may be replaced by 1 to 2 oxygen atom(s) and/or sulfur atom(s) is suitable and C1–6 alkylene group that may be replaced by an oxygen atom is more suitable.

As

in formula (I), heterocycle 2 is suitable and 3 to 10-membered monocycle or bicyclic heterocycle aryl that may be saturated all or partially and includes 1 to 3 hetero atom(s) selected from oxygen atom, nitrogen atom or sulfur atom, is more suitable.

As

---- in formula (I), double bond is suitable.

In the compounds represented by formula (I), as suitable compounds, a compound represented by formula(I-A-1);

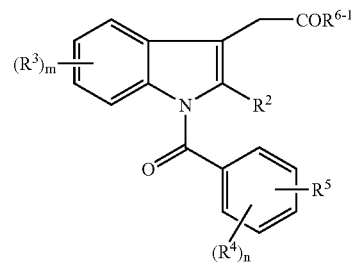

(I-A-1)

wherein $R^{6-1}$ in the formula represents hydroxyl or C1–6 alkoxy group, and other symbols represent the same meanings as described above, a compound represented by formula(I-A-2);

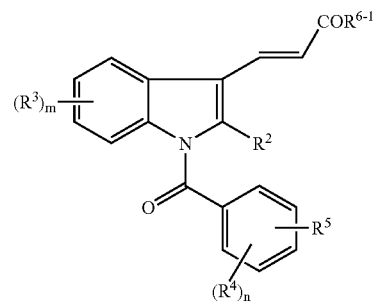

(I-A-2)

wherein all symbols represent the same meanings as described above, a compound represented by formula(I-A-3);

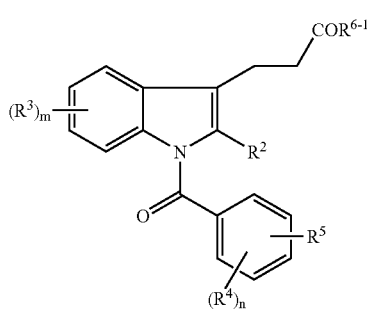

(I-A-3)

wherein all symbols represent the same meanings as described above, a compound represented by formula(I-A4);

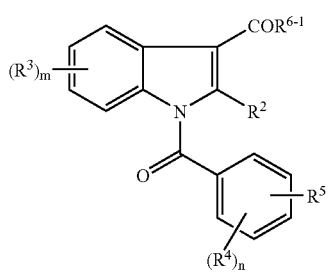

(I-A-4)

wherein all symbols represent the same meanings as described above, a compound represented by formula(I-A-5);

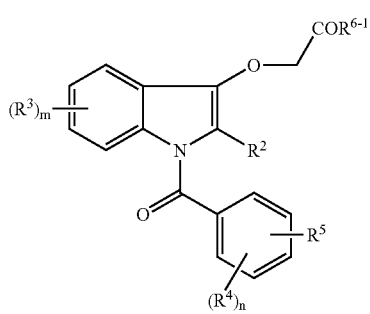

(I-A-5)

wherein all symbols represent the same meanings as described above, a compound represented by formula(I-A6);

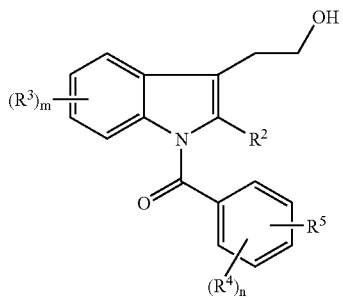

(I-A-6)

wherein all symbols represent the same meanings as described above, a compound represented by formula(I-A-7);

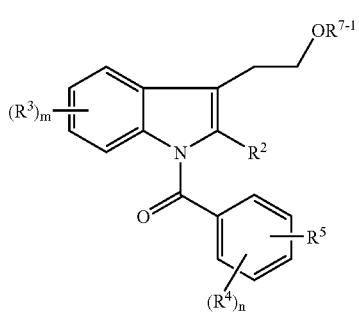

(I-A-7)

wherein $R^{7-1}$ in the formula represents C2–6 acyl group, and other symbols represent the same meanings as described above, a compound represented by formula(I-A-8);

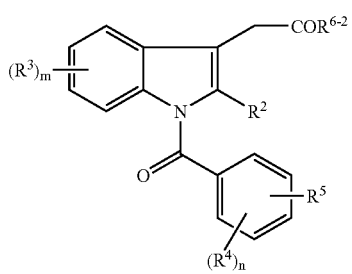

(I-A-8)

wherein $R^{6-2}$ in the formula represents —$NR^8R^9$, and other symbols represent the same meanings as described above are included.

In concrete compounds of the present invention, the compounds represented in the following table 1 to 54, the compounds of examples, and non-toxic salts thereof are included.

In the tables, Me represents methyl group, and Et represents ethyl group, and other symbols represent the same meanings as described above.

TABLE 1

(I-A-1-1)

| No. | R⁵ |
|---|---|
| 1 | 4-methyl-2-(methoxymethyl)-3,4-dihydro-2H-1,4-benzoxazin-7-yl |
| 2 | 7-fluoro-4-methyl-2-(methoxymethyl)-3,4-dihydro-2H-1,4-benzoxazin-yl |
| 3 | 7-methyl-4-methyl-2-(methoxymethyl)-3,4-dihydro-2H-1,4-benzoxazin-yl |
| 4 | 6-methyl-4-methyl-2-(methoxymethyl)-3,4-dihydro-2H-1,4-benzoxazin-yl |
| 5 | 7-methoxy-4-methyl-2-(methoxymethyl)-3,4-dihydro-2H-1,4-benzoxazin-yl |
| 6 | 2-(methoxymethyl)-3,4-dihydro-2H-1,4-benzothiazin-yl |
| 7 | 7-fluoro-2-(methoxymethyl)-3,4-dihydro-2H-1,4-benzothiazin-yl |
| 8 | 3-(methoxymethyl)-2,3-dihydrobenzofuran-yl |

TABLE 1-continued (I-A-1-1)

| No. | R⁵ |
|---|---|
| 9 | 5-fluoro-3-(methoxymethyl)-2,3-dihydrobenzofuran-yl |
| 10 | 2-(methoxymethyl)-2,3-dihydrobenzofuran-yl |
| 11 | 2-(methoxymethyl)-1,3-benzodioxol-yl |
| 12 | 5-fluoro-2-(methoxymethyl)-1,3-benzodioxol-yl |
| 13 | 2-(methoxymethyl)-2,3-dihydro-1,4-benzodioxin-yl |
| 14 | 5-fluoro-2-(methoxymethyl)-2,3-dihydro-1,4-benzodioxin-yl |
| 15 | 6-methyl-2-(2-methoxyethyl)pyridin-yl |
| 16 | 3-methyl-2-(2-methoxyethyl)pyridin-yl |
| 17 | 1-ethyl-2-(methoxymethyl)-2,3-dihydro-1H-indol-yl |

TABLE 1-continued (I-A-1-1)

| No. | R⁵ |
|---|---|
| 18 | methoxyethyl-phenyl group |
| 19 | MeO-CH₂CH₂-O-CH₂CH₂-OMe type |
| 20 | propyl ether chain |
| 21 | propyl ether chain |

TABLE 2

(I-A-1-2)

| No. | R⁵ |
|---|---|
| 1 | (2S)-2-(methoxymethyl)-4-methyl-3,4-dihydro-2H-1,4-benzoxazine |
| 2 | (2S)-2-(methoxymethyl)-7-fluoro-4-methyl-3,4-dihydro-2H-1,4-benzoxazine |
| 3 | (2S)-2-(methoxymethyl)-7-methyl-4-methyl-3,4-dihydro-2H-1,4-benzoxazine |

TABLE 2-continued (I-A-1-2)

| No. | R⁵ |
|---|---|
| 4 | (2S)-2-(methoxymethyl)-6-methyl-4-methyl-3,4-dihydro-2H-1,4-benzoxazine |
| 5 | (2S)-2-(methoxymethyl)-7-methoxy-4-methyl-3,4-dihydro-2H-1,4-benzoxazine |
| 6 | (2S)-2-(methoxymethyl)-2,3-dihydro-1,4-benzoxathiine |
| 7 | (2S)-2-(methoxymethyl)-7-fluoro-2,3-dihydro-1,4-benzoxathiine |
| 8 | (3S)-3-(methoxymethyl)-2,3-dihydrobenzofuran |
| 9 | (3S)-3-(methoxymethyl)-5-fluoro-2,3-dihydrobenzofuran |
| 10 | (2S)-2-(methoxymethyl)-2,3-dihydrobenzofuran |
| 11 | (2S)-2-(methoxymethyl)-2,3-dihydro-1,4-benzodioxine |

TABLE 2-continued (I-A-1-2)

| No. | R⁵ |
|---|---|
| 12 | 5-fluoro-2,3-dihydro-1,4-benzodioxin-2-yl methoxymethyl |
| 13 | 1-ethyl-2,3-dihydro-1H-indol-2-yl methoxymethyl |
| 14 | 6-fluoro-4-methyl-3,4-dihydro-2H-1,4-benzoxazin-2-yl methoxymethyl |
| 15 | 5-methyl-2,3-dihydro-1-benzofuran-2-yl methoxymethyl |
| 16 | 7-methyl-2,3-dihydro-1-benzofuran-2-yl methoxymethyl |
| 17 | 4-methyl-1,3-benzodioxol-2-yl methoxymethyl |
| 18 | 5-methyl-1,3-benzodioxol-2-yl methoxymethyl |
| 19 | 1-methyl-1H-indol-2-yl methoxymethyl |

TABLE 2-continued (I-A-1-2)

| No. | R⁵ |
|---|---|
| 20 | 5-methylpyridin-2-yl methoxyethyl |
| 21 | 2-phenyl-1,3-oxazol-5-yl methoxymethyl |
| 22 | quinolin-3-yl methoxymethyl |

TABLE 3

(I-A-2-1)

| No. | R⁵ |
|---|---|
| 1 | 4-methyl-3,4-dihydro-2H-1,4-benzoxazin-2-yl methoxymethyl |
| 2 | 7-fluoro-4-methyl-3,4-dihydro-2H-1,4-benzoxazin-2-yl methoxymethyl |
| 3 | 4,7-dimethyl-3,4-dihydro-2H-1,4-benzoxazin-2-yl methoxymethyl |

TABLE 3-continued (I-A-2-1)

| No. | R⁵ |
|-----|-----|
| 4 | 2-(methoxymethyl)-4,6-dimethyl-3,4-dihydro-2H-benzo[b][1,4]oxazine |
| 5 | 2-(methoxymethyl)-7-methoxy-4-methyl-3,4-dihydro-2H-benzo[b][1,4]oxazine |
| 6 | 2-(methoxymethyl)-2,3-dihydro-benzo[1,4]oxathiine |
| 7 | 2-(methoxymethyl)-7-fluoro-2,3-dihydro-benzo[1,4]oxathiine |
| 8 | 3-(methoxymethyl)-2,3-dihydrobenzofuran |
| 9 | 3-(methoxymethyl)-5-fluoro-2,3-dihydrobenzofuran |
| 10 | 2-(methoxymethyl)-2,3-dihydrobenzofuran |
| 11 | 2-(methoxymethyl)-benzo[1,3]dioxole |
| 12 | 2-(methoxymethyl)-5-fluoro-benzo[1,3]dioxole |
| 13 | 2-(methoxymethyl)-2,3-dihydro-benzo[1,4]dioxine |
| 14 | 2-(methoxymethyl)-5-fluoro-2,3-dihydro-benzo[1,4]dioxine |
| 15 | 2-(2-methoxyethyl)-6-methylpyridine |
| 16 | 2-(2-methoxyethyl)-3-methylpyridine |
| 17 | 2-(methoxymethyl)-1-ethyl-2,3-dihydro-1H-indole |
| 18 | 2-methoxyethyl-phenyl |
| 19 | CH₃OCH₂CH₂OC₂H₅ |
| 20 | C₂H₅OCH₂CH₂OCH₃ (approx) |
| 21 | C₃H₇OC₂H₅ (approx) |

TABLE 4

(I-A-2-2)

[Structure: indole with 2-methyl group, N-substituted with C(=O)-phenyl-R⁵ (para), 3-substituted with CH=CH-COOH (trans)]

| No. | R⁵ |
|---|---|
| 1 | 2-(methoxymethyl)-4-methyl-3,4-dihydro-2H-1,4-benzoxazin-2-yl |
| 2 | 7-fluoro-2-(methoxymethyl)-4-methyl-3,4-dihydro-2H-1,4-benzoxazin-2-yl |
| 3 | 2-(methoxymethyl)-4,7-dimethyl-3,4-dihydro-2H-1,4-benzoxazin-2-yl |
| 4 | 2-(methoxymethyl)-4,6-dimethyl-3,4-dihydro-2H-1,4-benzoxazin-2-yl |
| 5 | 2-(methoxymethyl)-7-methoxy-4-methyl-3,4-dihydro-2H-1,4-benzoxazin-2-yl |
| 6 | 2-(methoxymethyl)-3,4-dihydro-2H-1,4-benzothiazin-2-yl |
| 7 | 7-fluoro-2-(methoxymethyl)-3,4-dihydro-2H-1,4-benzothiazin-2-yl |
| 8 | 3-(methoxymethyl)-2,3-dihydrobenzofuran-3-yl |
| 9 | 5-fluoro-3-(methoxymethyl)-2,3-dihydrobenzofuran-3-yl |
| 10 | 2-(methoxymethyl)-2,3-dihydrobenzofuran-2-yl |
| 11 | 2-(methoxymethyl)-2,3-dihydro-1,4-benzodioxin-2-yl |
| 12 | 5-fluoro-2-(methoxymethyl)-2,3-dihydro-1,4-benzodioxin-2-yl |
| 13 | 1-ethyl-2-(methoxymethyl)-2,3-dihydro-1H-indol-2-yl |
| 14 | 6-fluoro-2-(methoxymethyl)-4-methyl-3,4-dihydro-2H-1,4-benzoxazin-2-yl |
| 15 | 2-(methoxymethyl)-5-methyl-2,3-dihydrobenzofuran-2-yl |
| 16 | 2-(methoxymethyl)-7-methyl-2,3-dihydrobenzofuran-2-yl |

TABLE 4-continued (I-A-2-2)

| No. | R⁵ |
|---|---|
| 17 | 4-methyl-benzo[1,3]dioxol-2-yl-methoxymethyl |
| 18 | 5-methyl-benzo[1,3]dioxol-2-yl-methoxymethyl |
| 19 | (1-methyl-1H-indol-2-yl)-methoxymethyl |
| 20 | 2-(5-methyl-pyridin-2-yl)-ethoxymethyl |
| 21 | (2-phenyl-oxazol-5-yl)-methoxymethyl |
| 22 | quinolin-3-yl-methoxymethyl |

TABLE 5

(I-A-3-1)

| No. | R⁵ |
|---|---|
| 1 | (4-methyl-3,4-dihydro-2H-benzo[1,4]oxazin-2-yl)-methoxymethyl |
| 2 | (7-fluoro-4-methyl-3,4-dihydro-2H-benzo[1,4]oxazin-2-yl)-methoxymethyl |
| 3 | (4,7-dimethyl-3,4-dihydro-2H-benzo[1,4]oxazin-2-yl)-methoxymethyl |
| 4 | (4,6-dimethyl-3,4-dihydro-2H-benzo[1,4]oxazin-2-yl)-methoxymethyl |
| 5 | (7-methoxy-4-methyl-3,4-dihydro-2H-benzo[1,4]oxazin-2-yl)-methoxymethyl |
| 6 | (2,3-dihydro-benzo[1,4]oxathiin-2-yl)-methoxymethyl |
| 7 | (7-fluoro-2,3-dihydro-benzo[1,4]oxathiin-2-yl)-methoxymethyl |
| 8 | (2,3-dihydro-benzofuran-3-yl)-methoxymethyl |

TABLE 5-continued (I-A-3-1)

| No. | R⁵ |
|---|---|
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-1,3-benzodioxole |
| 12 | 5-fluoro-2-(methoxymethyl)-1,3-benzodioxole |
| 13 | 2-(methoxymethyl)-2,3-dihydro-1,4-benzodioxine |
| 14 | 5-fluoro-2-(methoxymethyl)-2,3-dihydro-1,4-benzodioxine |
| 15 | 2-(2-methoxyethyl)-6-methylpyridine |
| 16 | 2-(2-methoxyethyl)-3-methylpyridine |
| 17 | 1-ethyl-2-(methoxymethyl)-2,3-dihydro-1H-indole |
| 18 | (2-methoxyethyl)benzene |
| 19 | 1-methoxy-2-ethoxyethane |
| 20 | 1-ethoxy-2-methoxyethane variant |
| 21 | 1-propoxy-ethane variant |

TABLE 6

(I-A-3-2)

| No. | R⁵ |
|---|---|
| 1 | 2-(methoxymethyl)-4-methyl-3,4-dihydro-2H-1,4-benzoxazine |
| 2 | 7-fluoro-2-(methoxymethyl)-4-methyl-3,4-dihydro-2H-1,4-benzoxazine |

TABLE 6-continued
(I-A-3-2)
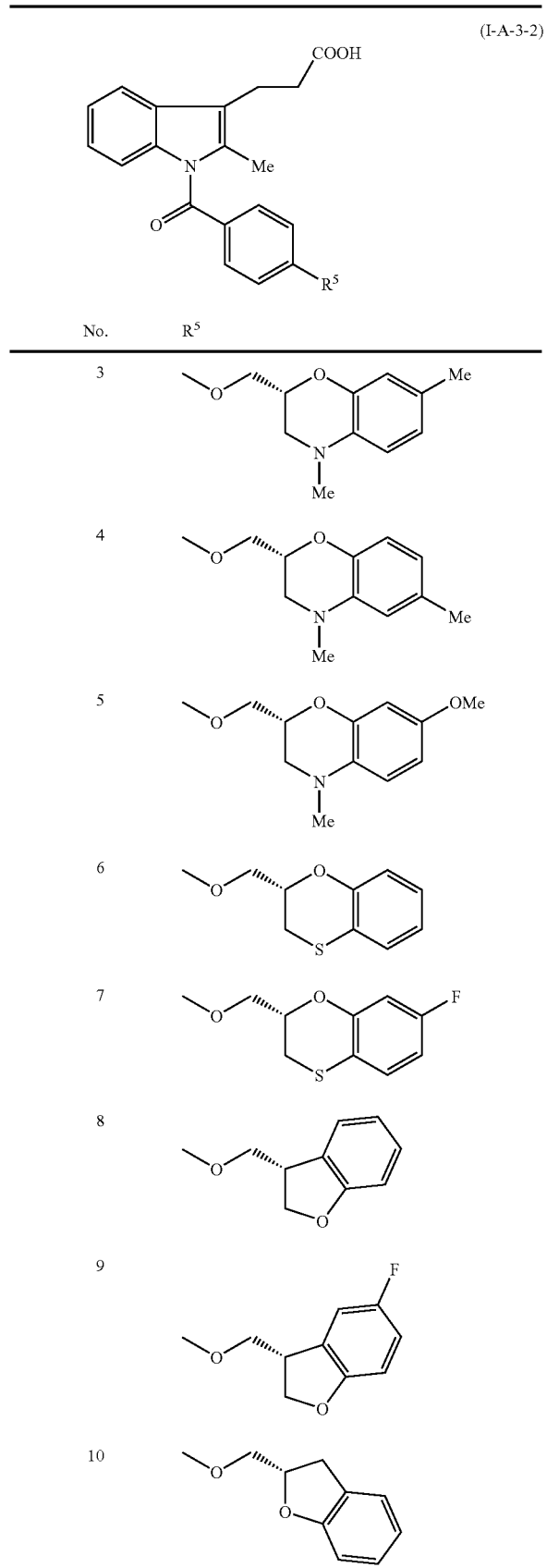
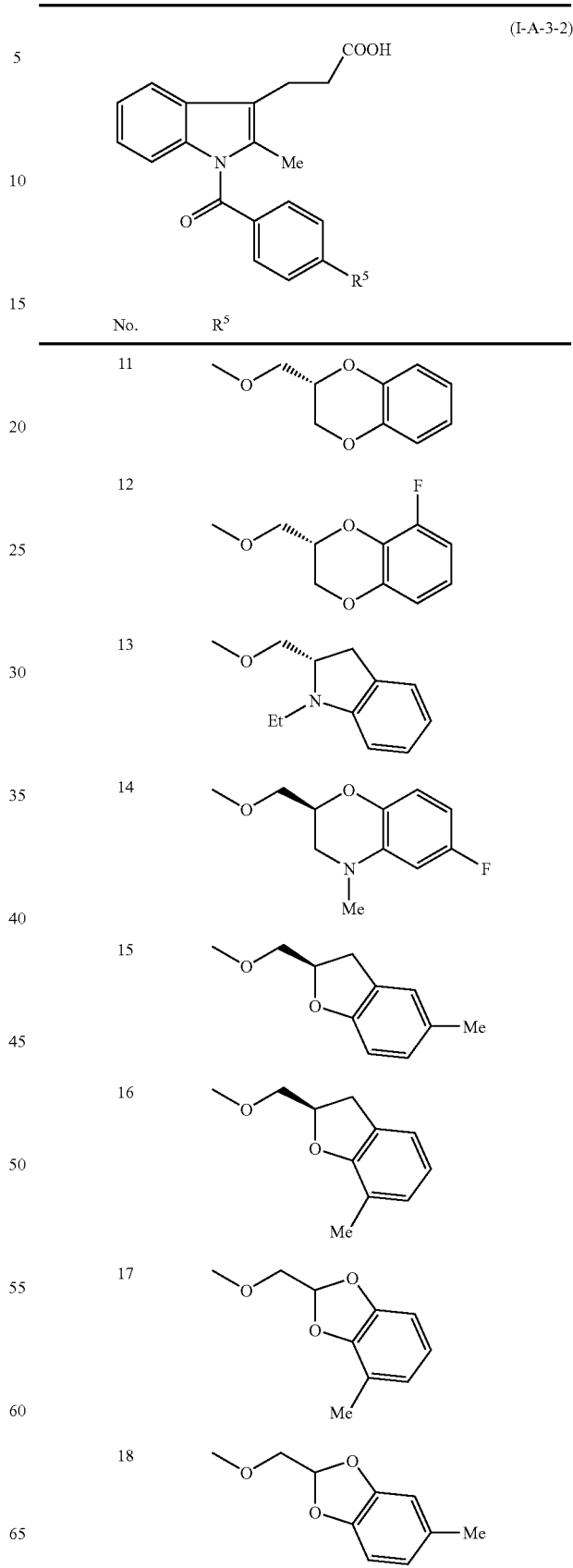

TABLE 6-continued (I-A-3-2)

| No. | R⁵ |
|---|---|
| 19 | 2-(methoxymethyl)-1-methyl-1H-indole |
| 20 | 2-(2-methoxyethyl)-5-methylpyridine |
| 21 | 5-(methoxymethyl)-2-phenyloxazole |
| 22 | 3-(methoxymethyl)quinoline |

TABLE 7

(I-A-4-1)

| No. | R⁵ |
|---|---|
| 1 | 2-(methoxymethyl)-4-methyl-3,4-dihydro-2H-benzo[b][1,4]oxazine |
| 2 | 7-fluoro-2-(methoxymethyl)-4-methyl-3,4-dihydro-2H-benzo[b][1,4]oxazine |

TABLE 7-continued (I-A-4-1)

| No. | R⁵ |
|---|---|
| 3 | 2-(methoxymethyl)-4,7-dimethyl-3,4-dihydro-2H-benzo[b][1,4]oxazine |
| 4 | 2-(methoxymethyl)-4,6-dimethyl-3,4-dihydro-2H-benzo[b][1,4]oxazine |
| 5 | 7-methoxy-2-(methoxymethyl)-4-methyl-3,4-dihydro-2H-benzo[b][1,4]oxazine |
| 6 | 2-(methoxymethyl)-2,3-dihydrobenzo[b][1,4]oxathiine |
| 7 | 7-fluoro-2-(methoxymethyl)-2,3-dihydrobenzo[b][1,4]oxathiine |
| 8 | 3-(methoxymethyl)-2,3-dihydrobenzofuran |
| 9 | 5-fluoro-3-(methoxymethyl)-2,3-dihydrobenzofuran |
| 10 | 2-(methoxymethyl)-2,3-dihydrobenzofuran |

TABLE 7-continued
(I-A-4-1)
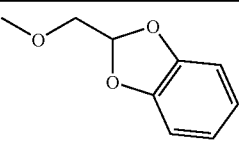
| No. | R⁵ |
|---|---|
| 11 | 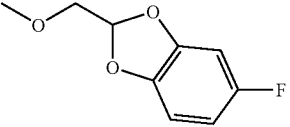 |
| 12 | 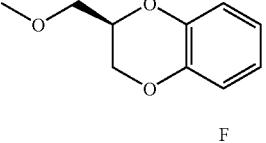 |
| 13 | 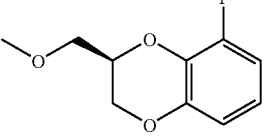 |
| 14 | 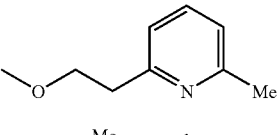 |
| 15 | 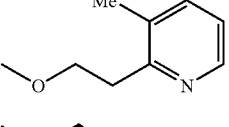 |
| 16 | 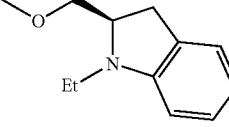 |
| 17 | 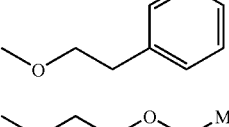 |
| 18 | 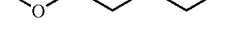 |
| 19 | 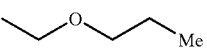 |
| 20 |  |
| 21 | 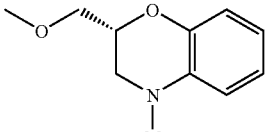 |
TABLE 8
(I-A-4-2)
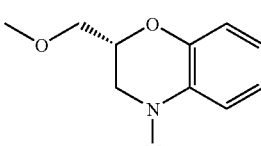
| No. | R⁵ |
|---|---|
| 1 | 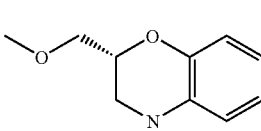 |
| 2 | 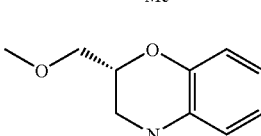 |
| 3 | 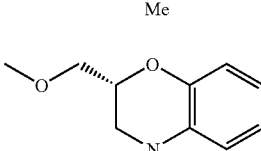 |
| 4 | 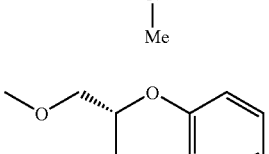 |
| 5 | 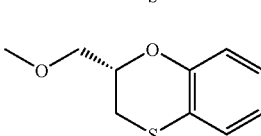 |
| 6 | 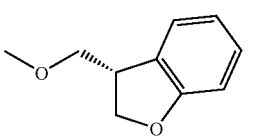 |
| 7 |  |
| 8 |  |

TABLE 8-continued (I-A-4-2)

| No. | R⁵ |
|---|---|
| 9 | 5-fluoro-2,3-dihydrobenzofuran-3-yl methoxymethyl |
| 10 | 2,3-dihydrobenzofuran-2-yl methoxymethyl |
| 11 | 2,3-dihydro-1,4-benzodioxin-2-yl methoxymethyl |
| 12 | 5-fluoro-2,3-dihydro-1,4-benzodioxin-2-yl methoxymethyl |
| 13 | 1-ethyl-2,3-dihydroindol-2-yl methoxymethyl |

TABLE 9

(I-A-5-1)

| No. | R⁵ |
|---|---|
| 1 | 4-methyl-3,4-dihydro-2H-1,4-benzoxazin-2-yl methoxymethyl |
| 2 | 7-fluoro-4-methyl-3,4-dihydro-2H-1,4-benzoxazin-2-yl methoxymethyl |
| 3 | 4,7-dimethyl-3,4-dihydro-2H-1,4-benzoxazin-2-yl methoxymethyl |
| 4 | 4,6-dimethyl-3,4-dihydro-2H-1,4-benzoxazin-2-yl methoxymethyl |
| 5 | 7-methoxy-4-methyl-3,4-dihydro-2H-1,4-benzoxazin-2-yl methoxymethyl |
| 6 | 3,4-dihydro-2H-1,4-benzothiazin-2-yl methoxymethyl |
| 7 | 7-fluoro-3,4-dihydro-2H-1,4-benzothiazin-2-yl methoxymethyl |
| 8 | 2,3-dihydrobenzofuran-3-yl methoxymethyl |

TABLE 9-continued (I-A-5-1)

| No. | R⁵ |
|---|---|
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-1,3-benzodioxole |
| 12 | 5-fluoro-2-(methoxymethyl)-1,3-benzodioxole |
| 13 | 2-(methoxymethyl)-2,3-dihydro-1,4-benzodioxine |
| 14 | 5-fluoro-2-(methoxymethyl)-2,3-dihydro-1,4-benzodioxine |
| 15 | 2-(2-methoxyethyl)-6-methylpyridine |
| 16 | 2-(2-methoxyethyl)-3-methylpyridine |

TABLE 9-continued (I-A-5-1)

| No. | R⁵ |
|---|---|
| 17 | 1-ethyl-2-(methoxymethyl)-2,3-dihydro-1H-indole |
| 18 | (2-methoxyethyl)benzene |
| 19 | 1-methoxy-2-ethoxyethane (MeOCH₂CH₂OEt) |
| 20 | 1-ethoxypropane branch (EtOCH₂CH(Me)–) |
| 21 | 1-ethoxy-propyl (PrOEt) |

TABLE 10

(I-A-5-2)

| No. | R⁵ |
|---|---|
| 1 | 2-(methoxymethyl)-4-methyl-3,4-dihydro-2H-1,4-benzoxazine |
| 2 | 7-fluoro-2-(methoxymethyl)-4-methyl-3,4-dihydro-2H-1,4-benzoxazine |

TABLE 10-continued (I-A-5-2)

| No. | R⁵ |
|---|---|
| 3 | 2-(methoxymethyl)-4-methyl-7-methyl-3,4-dihydro-2H-benzo[b][1,4]oxazine |
| 4 | 2-(methoxymethyl)-4-methyl-6-methyl-3,4-dihydro-2H-benzo[b][1,4]oxazine |
| 5 | 2-(methoxymethyl)-4-methyl-7-methoxy-3,4-dihydro-2H-benzo[b][1,4]oxazine |
| 6 | 2-(methoxymethyl)-2,3-dihydro-1,4-benzoxathiine |
| 7 | 2-(methoxymethyl)-7-fluoro-2,3-dihydro-1,4-benzoxathiine |
| 8 | 3-(methoxymethyl)-2,3-dihydrobenzofuran |
| 9 | 3-(methoxymethyl)-5-fluoro-2,3-dihydrobenzofuran |
| 10 | 2-(methoxymethyl)-2,3-dihydrobenzofuran |
| 11 | 2-(methoxymethyl)-2,3-dihydro-1,4-benzodioxine |
| 12 | 2-(methoxymethyl)-5-fluoro-2,3-dihydro-1,4-benzodioxine |
| 13 | 2-(methoxymethyl)-1-ethyl-indoline |
| 14 | 2-(methoxymethyl)-4-methyl-6-fluoro-3,4-dihydro-2H-benzo[b][1,4]oxazine |
| 15 | 2-(methoxymethyl)-5-methyl-2,3-dihydrobenzofuran |
| 16 | 2-(methoxymethyl)-7-methyl-2,3-dihydrobenzofuran |
| 17 | 2-(methoxymethyl)-4-methyl-1,3-benzodioxole |
| 18 | 2-(methoxymethyl)-5-methyl-1,3-benzodioxole |

TABLE 10-continued (I-A-5-2)

| No. | R⁵ |
|---|---|
| 19 | 1-methyl-2-(methoxymethyl)indole |
| 20 | 5-methyl-2-(methoxyethyl)pyridine |
| 21 | 2-phenyl-5-(methoxymethyl)oxazole |
| 22 | 3-(methoxymethyl)quinoline |

TABLE 11

(I-A-6-1)

| No. | R⁵ |
|---|---|
| 1 | 4-methyl-2-(methoxymethyl)-3,4-dihydro-2H-benzo[1,4]oxazine |
| 2 | 7-fluoro-4-methyl-2-(methoxymethyl)-3,4-dihydro-2H-benzo[1,4]oxazine |

TABLE 11-continued (I-A-6-1)

| No. | R⁵ |
|---|---|
| 3 | 7-methyl-4-methyl-2-(methoxymethyl)-3,4-dihydro-2H-benzo[1,4]oxazine |
| 4 | 6-methyl-4-methyl-2-(methoxymethyl)-3,4-dihydro-2H-benzo[1,4]oxazine |
| 5 | 7-methoxy-4-methyl-2-(methoxymethyl)-3,4-dihydro-2H-benzo[1,4]oxazine |
| 6 | 2-(methoxymethyl)-2,3-dihydro-benzo[1,4]oxathiine |
| 7 | 7-fluoro-2-(methoxymethyl)-2,3-dihydro-benzo[1,4]oxathiine |
| 8 | 3-(methoxymethyl)-2,3-dihydrobenzofuran |
| 9 | 5-fluoro-3-(methoxymethyl)-2,3-dihydrobenzofuran |
| 10 | 2-(methoxymethyl)-2,3-dihydrobenzofuran |

TABLE 11-continued
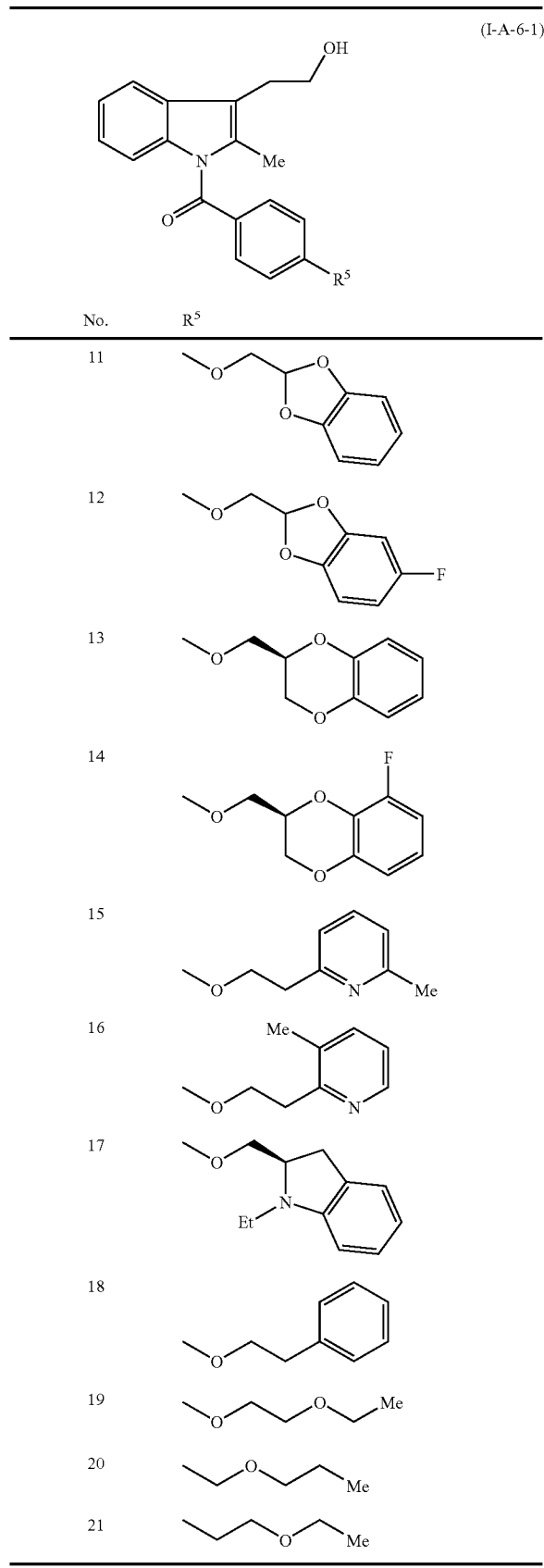
TABLE 12
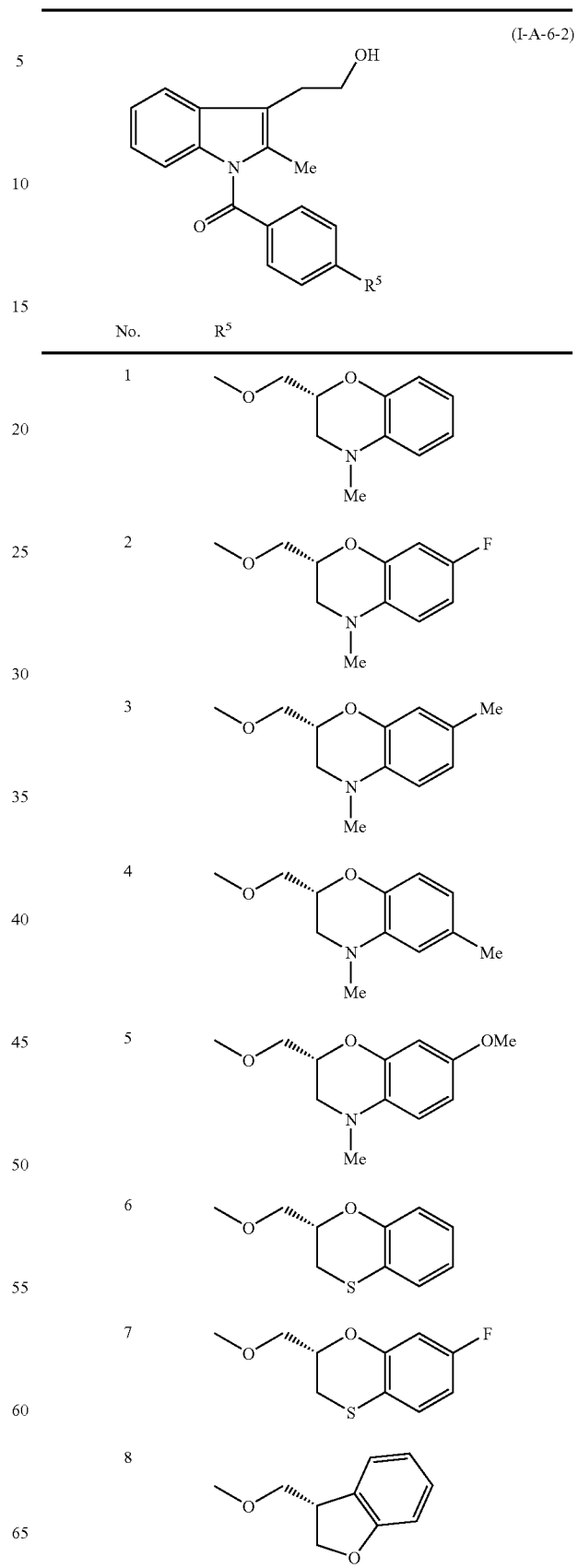

TABLE 12-continued (I-A-6-2)

| No. | R⁵ |
|---|---|
| 9 | 5-fluoro-2,3-dihydrobenzofuran-3-yl methoxymethyl |
| 10 | 2,3-dihydrobenzofuran-2-yl methoxymethyl |
| 11 | 2,3-dihydro-1,4-benzodioxin-2-yl methoxymethyl |
| 12 | 5-fluoro-2,3-dihydro-1,4-benzodioxin-2-yl methoxymethyl |
| 13 | 1-ethylindolin-2-yl methoxymethyl |
| 14 | 6-fluoro-4-methyl-3,4-dihydro-2H-1,4-benzoxazin-2-yl methoxymethyl |
| 15 | 6-methyl-2,3-dihydrobenzofuran-2-yl methoxymethyl |
| 16 | 7-methyl-2,3-dihydrobenzofuran-2-yl methoxymethyl |
| 17 | 7-methyl-1,3-benzodioxol-2-yl methoxymethyl |
| 18 | 5-methyl-1,3-benzodioxol-2-yl methoxymethyl |
| 19 | 1-methylindol-2-yl methoxymethyl |
| 20 | 5-methylpyridin-2-yl methoxyethyl |
| 21 | 2-phenyloxazol-5-yl methoxymethyl |
| 22 | quinolin-3-yl methoxymethyl |

TABLE 13

(I-A-7-1)

| No. | R⁵ |
|---|---|
| 1 | N-methyl-2-(methoxymethyl)-3,4-dihydro-2H-benzo[1,4]oxazine |
| 2 | N-methyl-2-(methoxymethyl)-7-fluoro-3,4-dihydro-2H-benzo[1,4]oxazine |
| 3 | N-methyl-2-(methoxymethyl)-7-methyl-3,4-dihydro-2H-benzo[1,4]oxazine |
| 4 | N-methyl-2-(methoxymethyl)-6-methyl-3,4-dihydro-2H-benzo[1,4]oxazine |
| 5 | N-methyl-2-(methoxymethyl)-7-methoxy-3,4-dihydro-2H-benzo[1,4]oxazine |
| 6 | 2-(methoxymethyl)-3,4-dihydro-2H-benzo[1,4]oxathiine |
| 7 | 2-(methoxymethyl)-7-fluoro-3,4-dihydro-2H-benzo[1,4]oxathiine |
| 8 | 3-(methoxymethyl)-2,3-dihydrobenzofuran |

TABLE 13-continued (I-A-7-1)

| No. | R⁵ |
|---|---|
| 9 | 3-(methoxymethyl)-5-fluoro-2,3-dihydrobenzofuran |
| 10 | 2-(methoxymethyl)-2,3-dihydrobenzofuran |
| 11 | 2-(methoxymethyl)-1,3-benzodioxole |
| 12 | 2-(methoxymethyl)-5-fluoro-1,3-benzodioxole |
| 13 | 2-(methoxymethyl)-2,3-dihydro-1,4-benzodioxine |
| 14 | 2-(methoxymethyl)-5-fluoro-2,3-dihydro-1,4-benzodioxine |
| 15 | 2-(2-methoxyethyl)-6-methylpyridine |
| 16 | 2-(2-methoxyethyl)-3-methylpyridine |

TABLE 13-continued
(I-A-7-1)
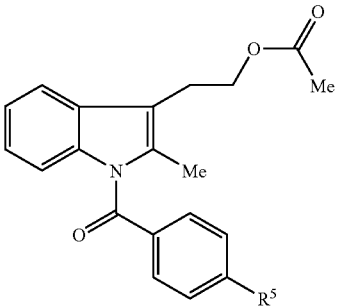
| No. | R⁵ |
|---|---|
| 17 | 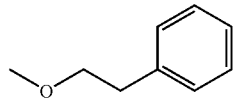 |
| 18 | 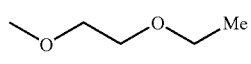 |
| 19 | 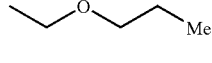 |
| 20 | 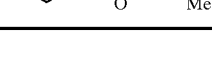 |
| 21 | 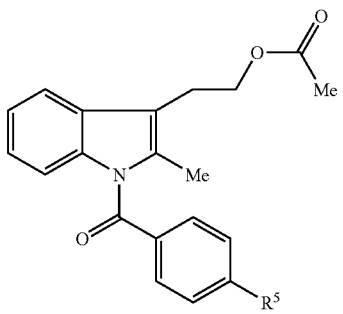 |
TABLE 14
(I-A-7-2)
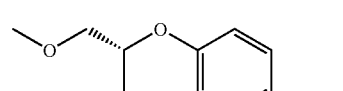
| No. | R⁵ |
|---|---|
| 1 | 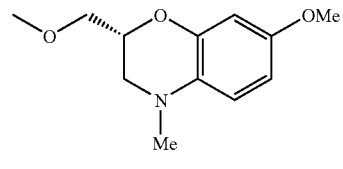 |
| 2 | 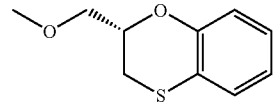 |
TABLE 14-continued
(I-A-7-2)
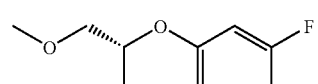
| No. | R⁵ |
|---|---|
| 3 | 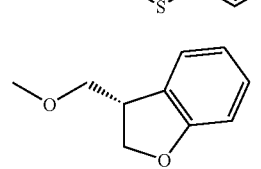 |
| 4 | 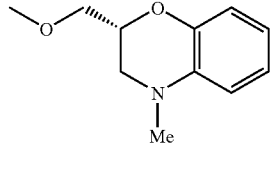 |
| 5 | 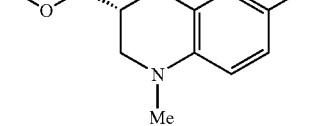 |
| 6 | |
| 7 | |
| 8 | |
| 9 | |
| 10 | 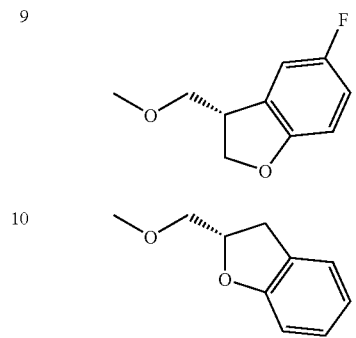 |

TABLE 14-continued (I-A-7-2)

| No. | R⁵ |
|---|---|
| 11 | 2,3-dihydro-1,4-benzodioxin-2-ylmethoxy |
| 12 | 5-fluoro-2,3-dihydro-1,4-benzodioxin-2-ylmethoxy |
| 13 | 1-ethyl-2,3-dihydro-1H-indol-2-ylmethoxy |
| 14 | 6-fluoro-4-methyl-3,4-dihydro-2H-1,4-benzoxazin-2-ylmethoxy |
| 15 | 5-methyl-2,3-dihydro-1-benzofuran-2-ylmethoxy |
| 16 | 7-methyl-2,3-dihydro-1-benzofuran-2-ylmethoxy |
| 17 | 4-methyl-1,3-benzodioxol-2-ylmethoxy |
| 18 | 6-methyl-1,3-benzodioxol-2-ylmethoxy |
| 19 | 1-methyl-1H-indol-2-ylmethoxy |
| 20 | 2-(5-methylpyridin-2-yl)ethoxy (methoxymethyl on pyridine) |
| 21 | 2-phenyl-1,3-oxazol-5-ylmethoxy |
| 22 | quinolin-3-ylmethoxy |

TABLE 15

(I-A-8-1)

| No. | R⁵ |
|---|---|
| 1 | 4-methyl-3,4-dihydro-2H-1,4-benzoxazin-2-ylmethoxy |

TABLE 15-continued (I-A-8-1)

| No. | R⁵ |
|-----|-----|
| 2 | 2-methoxymethyl-7-fluoro-4-methyl-3,4-dihydro-2H-1,4-benzoxazin-6-yl |
| 3 | 2-methoxymethyl-7-methyl-4-methyl-3,4-dihydro-2H-1,4-benzoxazin-6-yl |
| 4 | 2-methoxymethyl-6-methyl-4-methyl-3,4-dihydro-2H-1,4-benzoxazin-7-yl |
| 5 | 2-methoxymethyl-7-methoxy-4-methyl-3,4-dihydro-2H-1,4-benzoxazin-6-yl |
| 6 | 2-methoxymethyl-3,4-dihydro-2H-1,4-benzothiazin-6-yl |
| 7 | 2-methoxymethyl-7-fluoro-3,4-dihydro-2H-1,4-benzothiazin-6-yl |
| 8 | 3-methoxymethyl-2,3-dihydrobenzofuran-? |
| 9 | 3-methoxymethyl-5-fluoro-2,3-dihydrobenzofuran-? |
| 10 | 2-methoxymethyl-2,3-dihydrobenzofuran-? |
| 11 | 2-methoxymethyl-1,3-benzodioxol-? |
| 12 | 2-methoxymethyl-5-fluoro-1,3-benzodioxol-? |
| 13 | 2-methoxymethyl-2,3-dihydro-1,4-benzodioxin-? |
| 14 | 2-methoxymethyl-5-fluoro-2,3-dihydro-1,4-benzodioxin-? |
| 15 | 2-(2-methoxyethyl)-6-methylpyridin-? |
| 16 | 2-(2-methoxyethyl)-3-methylpyridin-? |
| 17 | 2-methoxymethyl-1-ethyl-2,3-dihydro-1H-indol-? |
| 18 | 2-methoxyethyl-phenyl |

Note: structures shown as chemical drawings in the original.

TABLE 15-continued (I-A-8-1)

| No. | R⁵ |
|---|---|
| 19 | MeO-CH₂CH₂-O-CH₂CH₂-Me (methoxyethoxyethyl) |
| 20 | EtO-CH₂CH₂-Me |
| 21 | PrO-Et |

TABLE 16

(I-A-8-2)

| No. | R⁵ |
|---|---|
| 1 | (2S)-2-(methoxymethyl)-4-methyl-3,4-dihydro-2H-1,4-benzoxazine |
| 2 | (2S)-2-(methoxymethyl)-7-fluoro-4-methyl-3,4-dihydro-2H-1,4-benzoxazine |
| 3 | (2S)-2-(methoxymethyl)-7-methyl-4-methyl-3,4-dihydro-2H-1,4-benzoxazine |

TABLE 16-continued (I-A-8-2)

| No. | R⁵ |
|---|---|
| 4 | (2S)-2-(methoxymethyl)-6-methyl-4-methyl-3,4-dihydro-2H-1,4-benzoxazine |
| 5 | (2S)-2-(methoxymethyl)-7-methoxy-4-methyl-3,4-dihydro-2H-1,4-benzoxazine |
| 6 | (2S)-2-(methoxymethyl)-2,3-dihydro-1,4-benzoxathiine |
| 7 | (2S)-2-(methoxymethyl)-7-fluoro-2,3-dihydro-1,4-benzoxathiine |
| 8 | (3S)-3-(methoxymethyl)-2,3-dihydrobenzofuran |
| 9 | (3S)-3-(methoxymethyl)-5-fluoro-2,3-dihydrobenzofuran |
| 10 | (2S)-2-(methoxymethyl)-2,3-dihydrobenzofuran |
| 11 | (2S)-2-(methoxymethyl)-2,3-dihydro-1,4-benzodioxine |

TABLE 16-continued (I-A-8-2)

| No. | R⁵ |
|---|---|
| 12 | 8-fluoro-2,3-dihydro-1,4-benzodioxin-2-ylmethoxymethyl |
| 13 | 1-ethyl-2,3-dihydro-1H-indol-2-ylmethoxymethyl |
| 14 | 6-fluoro-4-methyl-3,4-dihydro-2H-1,4-benzoxazin-2-ylmethoxymethyl |
| 15 | 5-methyl-2,3-dihydro-1-benzofuran-2-ylmethoxymethyl |
| 16 | 7-methyl-2,3-dihydro-1-benzofuran-2-ylmethoxymethyl |
| 17 | 4-methyl-1,3-benzodioxol-2-ylmethoxymethyl |
| 18 | 5-methyl-1,3-benzodioxol-2-ylmethoxymethyl |
| 19 | 1-methyl-1H-indol-2-ylmethoxymethyl |
| 20 | 2-(5-methylpyridin-2-yl)ethoxymethyl |
| 21 | (2-phenyl-1,3-oxazol-5-yl)methoxymethyl |
| 22 | quinolin-3-ylmethoxymethyl |

TABLE 17

(I-A-1-3)

| No. | R⁵ |
|---|---|
| 1 | 4-methyl-3,4-dihydro-2H-1,4-benzoxazin-2-ylmethoxymethyl |
| 2 | 7-fluoro-4-methyl-3,4-dihydro-2H-1,4-benzoxazin-2-ylmethoxymethyl |

TABLE 17-continued (I-A-1-3) structure: indole with 5-Me, 2-Me, N-C(=O)-C6H4-R5(para), 3-CH2COOH

| No. | R5 |
|---|---|
| 3 | 2-(methoxymethyl)-4-methyl-7-methyl-3,4-dihydro-2H-1,4-benzoxazine |
| 4 | 2-(methoxymethyl)-4-methyl-6-methyl-3,4-dihydro-2H-1,4-benzoxazine |
| 5 | 2-(methoxymethyl)-4-methyl-7-methoxy-3,4-dihydro-2H-1,4-benzoxazine |
| 6 | 2-(methoxymethyl)-2,3-dihydro-1,4-benzoxathiine |
| 7 | 2-(methoxymethyl)-7-fluoro-2,3-dihydro-1,4-benzoxathiine |
| 8 | 3-(methoxymethyl)-2,3-dihydrobenzofuran |
| 9 | 3-(methoxymethyl)-5-fluoro-2,3-dihydrobenzofuran |
| 10 | 2-(methoxymethyl)-2,3-dihydrobenzofuran |
| 11 | 2-(methoxymethyl)-1,3-benzodioxole |
| 12 | 2-(methoxymethyl)-5-fluoro-1,3-benzodioxole |
| 13 | 2-(methoxymethyl)-2,3-dihydro-1,4-benzodioxine |
| 14 | 2-(methoxymethyl)-5-fluoro-2,3-dihydro-1,4-benzodioxine |
| 15 | 2-(2-methoxyethyl)-6-methylpyridine |
| 16 | 2-(2-methoxyethyl)-3-methylpyridine |
| 17 | 2-(methoxymethyl)-1-ethyl-2,3-dihydro-1H-indole |
| 18 | 2-methoxyethylbenzene |
| 19 | MeOCH2CH2OCH2CH2- (methoxyethoxyethyl) |
| 20 | EtOCH2CH2- |
| 21 | EtOCH2CH2CH2- |

TABLE 18

(I-A-1-4)

| No. | R⁵ |
|---|---|
| 1 | 2,3-dihydro-4-methyl-2-(methoxymethyl)-1,4-benzoxazin-yl |
| 2 | 7-fluoro-2,3-dihydro-4-methyl-2-(methoxymethyl)-1,4-benzoxazin-yl |
| 3 | 7-methyl-2,3-dihydro-4-methyl-2-(methoxymethyl)-1,4-benzoxazin-yl |
| 4 | 6-methyl-2,3-dihydro-4-methyl-2-(methoxymethyl)-1,4-benzoxazin-yl |
| 5 | 7-methoxy-2,3-dihydro-4-methyl-2-(methoxymethyl)-1,4-benzoxazin-yl |
| 6 | 2,3-dihydro-2-(methoxymethyl)-1,4-benzoxathiin-yl |
| 7 | 7-fluoro-2,3-dihydro-2-(methoxymethyl)-1,4-benzoxathiin-yl |
| 8 | 2,3-dihydro-3-(methoxymethyl)benzofuran-yl |
| 9 | 5-fluoro-2,3-dihydro-3-(methoxymethyl)benzofuran-yl |
| 10 | 2,3-dihydro-2-(methoxymethyl)benzofuran-yl |
| 11 | 2,3-dihydro-2-(methoxymethyl)-1,4-benzodioxin-yl |
| 12 | 5-fluoro-2,3-dihydro-2-(methoxymethyl)-1,4-benzodioxin-yl |
| 13 | 1-ethyl-2,3-dihydro-2-(methoxymethyl)-1H-indol-yl |
| 14 | 6-fluoro-2,3-dihydro-4-methyl-2-(methoxymethyl)-1,4-benzoxazin-yl |
| 15 | 5-methyl-2,3-dihydro-2-(methoxymethyl)benzofuran-yl |
| 16 | 7-methyl-2,3-dihydro-2-(methoxymethyl)benzofuran-yl |

TABLE 18-continued (I-A-1-4)

| No. | R⁵ |
|---|---|
| 17 | 4-methyl-2-(methoxymethyl)-1,3-benzodioxole |
| 18 | 5-methyl-2-(methoxymethyl)-1,3-benzodioxole |
| 19 | 1-methyl-2-(methoxymethyl)-1H-indole |
| 20 | 5-methyl-2-(2-methoxyethyl)pyridine |
| 21 | 2-phenyl-5-(methoxymethyl)oxazole |
| 22 | 3-(methoxymethyl)quinoline |

TABLE 19

(I-A-1-5)

| No. | R⁵ |
|---|---|
| 1 | 4-methyl-2-(methoxymethyl)-3,4-dihydro-2H-1,4-benzoxazine |
| 2 | 7-fluoro-4-methyl-2-(methoxymethyl)-3,4-dihydro-2H-1,4-benzoxazine |
| 3 | 4,7-dimethyl-2-(methoxymethyl)-3,4-dihydro-2H-1,4-benzoxazine |
| 4 | 4,6-dimethyl-2-(methoxymethyl)-3,4-dihydro-2H-1,4-benzoxazine |
| 5 | 7-methoxy-4-methyl-2-(methoxymethyl)-3,4-dihydro-2H-1,4-benzoxazine |
| 6 | 2-(methoxymethyl)-2,3-dihydro-1,4-benzoxathiine |
| 7 | 7-fluoro-2-(methoxymethyl)-2,3-dihydro-1,4-benzoxathiine |
| 8 | 3-(methoxymethyl)-2,3-dihydrobenzofuran |

TABLE 19-continued (I-A-1-5)

| No. | R⁵ |
|---|---|
| 9 | 5-fluoro-3-(methoxymethyl)-2,3-dihydrobenzofuran-3-yl |
| 10 | 2-(methoxymethyl)-2,3-dihydrobenzofuran-2-yl |
| 11 | 2-(methoxymethyl)-1,3-benzodioxol-2-yl |
| 12 | 5-fluoro-2-(methoxymethyl)-1,3-benzodioxol-2-yl |
| 13 | 2-(methoxymethyl)-2,3-dihydro-1,4-benzodioxin-2-yl |
| 14 | 5-fluoro-2-(methoxymethyl)-2,3-dihydro-1,4-benzodioxin-2-yl |
| 15 | 2-(2-methoxyethyl)-6-methylpyridin-... |
| 16 | 3-methyl-2-(2-methoxyethyl)pyridin-... |
| 17 | 1-ethyl-2-(methoxymethyl)indolin-2-yl |

TABLE 19-continued (I-A-1-5)

| No. | R⁵ |
|---|---|
| 18 | 2-methoxyethylphenyl |
| 19 | methoxyethoxyethyl (Me) |
| 20 | ethoxypropyl (Me) |
| 21 | propoxyethyl (Me) |

TABLE 20

(I-A-1-6)

| No. | R⁵ |
|---|---|
| 1 | 2-(methoxymethyl)-4-methyl-3,4-dihydro-2H-1,4-benzoxazin-2-yl |
| 2 | 7-fluoro-2-(methoxymethyl)-4-methyl-3,4-dihydro-2H-1,4-benzoxazin-2-yl |
| 3 | 2-(methoxymethyl)-4,7-dimethyl-3,4-dihydro-2H-1,4-benzoxazin-2-yl |

TABLE 20-continued (I-A-1-6)

| No. | R⁵ |
|---|---|
| 4 | 2-(methoxymethyl)-4-methyl-6-methyl-3,4-dihydro-2H-benzo[b][1,4]oxazine |
| 5 | 2-(methoxymethyl)-7-methoxy-4-methyl-3,4-dihydro-2H-benzo[b][1,4]oxazine |
| 6 | 2-(methoxymethyl)-2,3-dihydro-1,4-benzoxathiine |
| 7 | 2-(methoxymethyl)-7-fluoro-2,3-dihydro-1,4-benzoxathiine |
| 8 | 3-(methoxymethyl)-2,3-dihydrobenzofuran |
| 9 | 3-(methoxymethyl)-5-fluoro-2,3-dihydrobenzofuran |
| 10 | 2-(methoxymethyl)-2,3-dihydrobenzofuran |
| 11 | 2-(methoxymethyl)-2,3-dihydro-1,4-benzodioxine |
| 12 | 2-(methoxymethyl)-8-fluoro-2,3-dihydro-1,4-benzodioxine |
| 13 | 2-(methoxymethyl)-1-ethyl-2,3-dihydro-1H-indole |
| 14 | 2-(methoxymethyl)-4-methyl-6-fluoro-3,4-dihydro-2H-benzo[b][1,4]oxazine |
| 15 | 2-(methoxymethyl)-5-methyl-2,3-dihydrobenzofuran |
| 16 | 2-(methoxymethyl)-7-methyl-2,3-dihydrobenzofuran |
| 17 | 2-(methoxymethyl)-4-methyl-1,3-benzodioxole |
| 18 | 2-(methoxymethyl)-5-methyl-1,3-benzodioxole |
| 19 | 2-(methoxymethyl)-1-methyl-1H-indole |

TABLE 20-continued (I-A-1-6)

| No. | R⁵ |
|---|---|
| 20 | 5-methyl-2-(methoxymethyl)pyridine |
| 21 | 5-(methoxymethyl)-2-phenyloxazole |
| 22 | 3-(methoxymethyl)quinoline |

TABLE 21

(I-A-1-7)

| No. | R⁵ |
|---|---|
| 1 | 2-(methoxymethyl)-4-methyl-3,4-dihydro-2H-benzo[1,4]oxazine |
| 2 | 7-fluoro-2-(methoxymethyl)-4-methyl-3,4-dihydro-2H-benzo[1,4]oxazine |
| 3 | 2-(methoxymethyl)-4,7-dimethyl-3,4-dihydro-2H-benzo[1,4]oxazine |

TABLE 21-continued (I-A-1-7)

| No. | R⁵ |
|---|---|
| 4 | 2-(methoxymethyl)-4,6-dimethyl-3,4-dihydro-2H-benzo[1,4]oxazine |
| 5 | 7-methoxy-2-(methoxymethyl)-4-methyl-3,4-dihydro-2H-benzo[1,4]oxazine |
| 6 | 2-(methoxymethyl)-2,3-dihydrobenzo[1,4]oxathiine |
| 7 | 7-fluoro-2-(methoxymethyl)-2,3-dihydrobenzo[1,4]oxathiine |
| 8 | 3-(methoxymethyl)-2,3-dihydrobenzofuran |
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)benzo[1,3]dioxole |

TABLE 21-continued
(I-A-1-7)
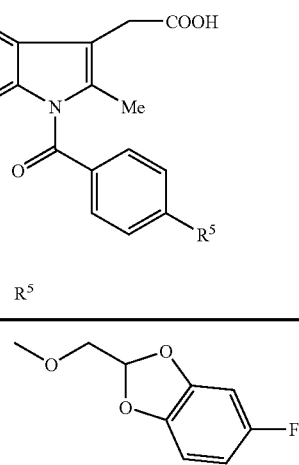
| No. | R⁵ |
|---|---|
| 12 | 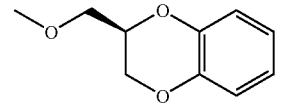 |
| 13 | 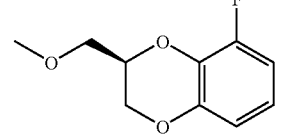 |
| 14 | 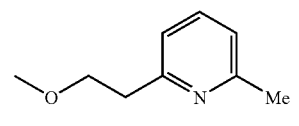 |
| 15 | 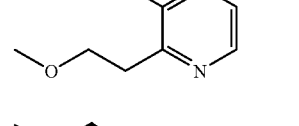 |
| 16 | 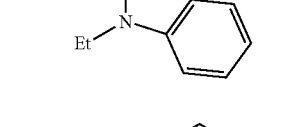 |
| 17 | 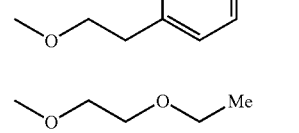 |
| 18 | 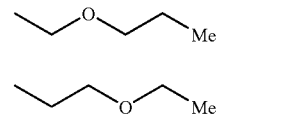 |
| 19 |  |
| 20 |  |
| 21 | 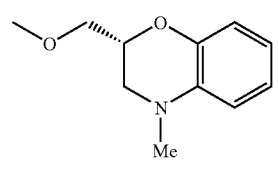 |
TABLE 22
(I-A-1-8)
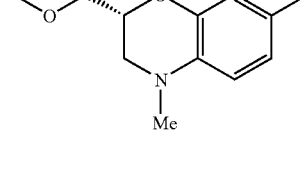
| No. | R⁵ |
|---|---|
| 1 | 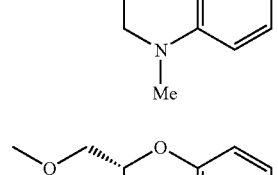 |
| 2 | 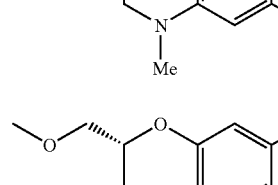 |
| 3 | 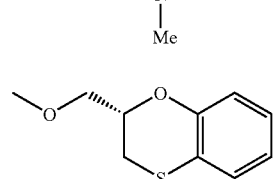 |
| 4 | 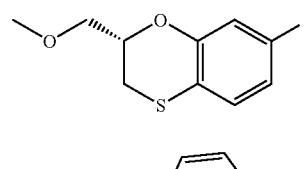 |
| 5 | 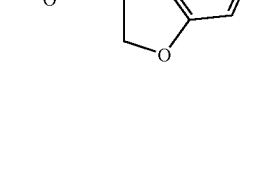 |
| 6 |  |
| 7 |  |
| 8 |  |

TABLE 22-continued (I-A-1-8)

[Structure: 5-fluoro-2-methyl-1-(4-R5-benzoyl)-indol-3-yl acetic acid]

| No. | R5 |
|-----|-----|
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-2,3-dihydro-1,4-benzodioxine |
| 12 | 5-fluoro-2-(methoxymethyl)-2,3-dihydro-1,4-benzodioxine |
| 13 | 1-ethyl-2-(methoxymethyl)indoline |
| 14 | 6-fluoro-4-methyl-2-(methoxymethyl)-3,4-dihydro-2H-1,4-benzoxazine |
| 15 | 6-methyl-2-(methoxymethyl)-2,3-dihydrobenzofuran |
| 16 | 7-methyl-2-(methoxymethyl)-2,3-dihydrobenzofuran |
| 17 | 7-methyl-2-(methoxymethyl)-1,3-benzodioxole |
| 18 | 5-methyl-2-(methoxymethyl)-1,3-benzodioxole |
| 19 | 1-methyl-2-(methoxymethyl)indole |
| 20 | 5-methyl-2-(2-methoxyethyl)pyridine |
| 21 | 5-(methoxymethyl)-2-phenyloxazole |
| 22 | 3-(methoxymethyl)quinoline |

TABLE 23
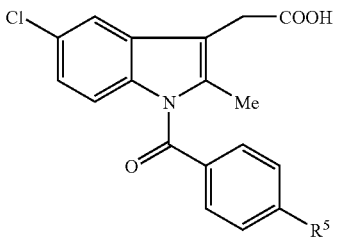
(I-A-1-9)
| No. | R⁵ |
|---|---|
| 1 | 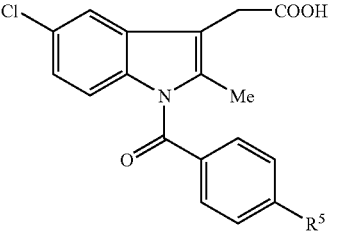 |
| 2 | 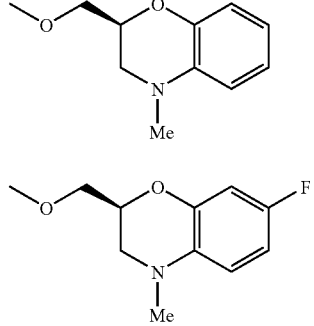 |
| 3 | 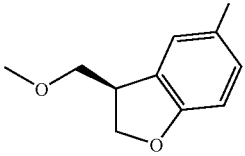 |
| 4 | 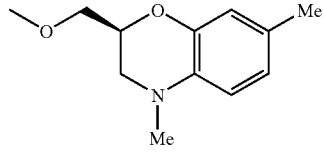 |
| 5 | 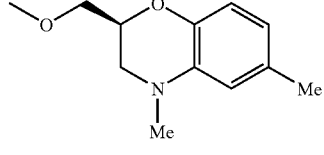 |
| 6 | 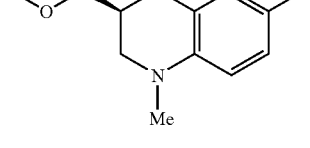 |
| 7 | 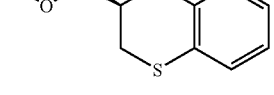 |
| 8 | 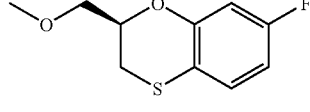 |
TABLE 23-continued
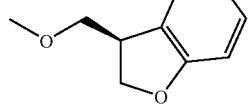
(I-A-1-9)
| No. | R⁵ |
|---|---|
| 9 | 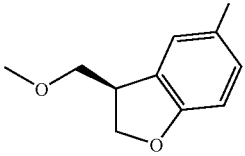 |
| 10 | 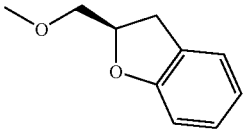 |
| 11 | 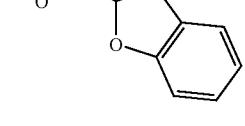 |
| 12 | 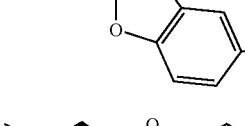 |
| 13 | 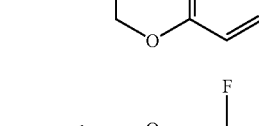 |
| 14 | 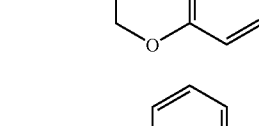 |
| 15 | 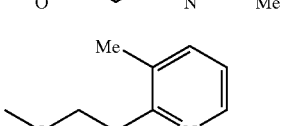 |
| 16 | 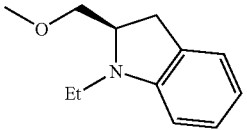 |
| 17 | 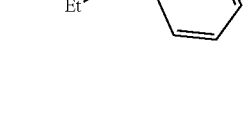 |

TABLE 23-continued

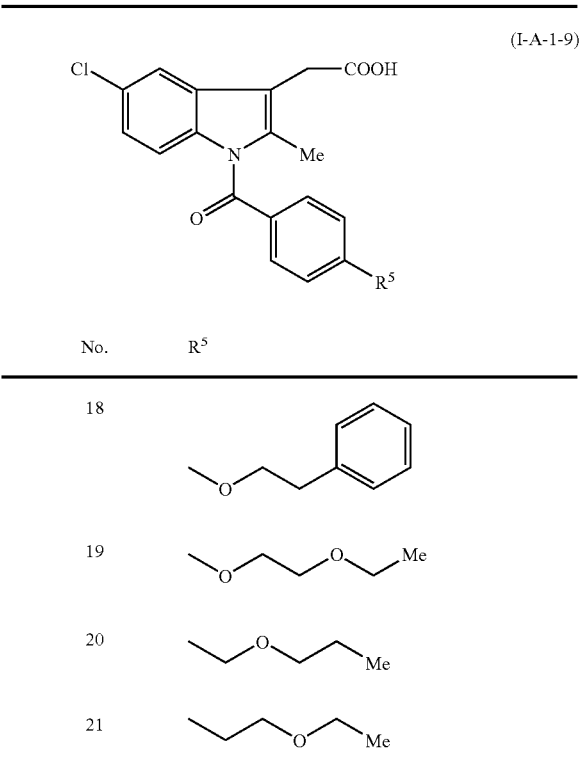

| No. | R⁵ |
|---|---|
| 18 | (2-phenylethoxymethyl) |
| 19 | MeOCH₂CH₂OCH₂- (methoxyethoxymethyl) |
| 20 | EtOCH₂CH₂- (ethoxyethyl) |
| 21 | EtOCH₂CH₂CH₂- (ethoxypropyl) |

TABLE 24

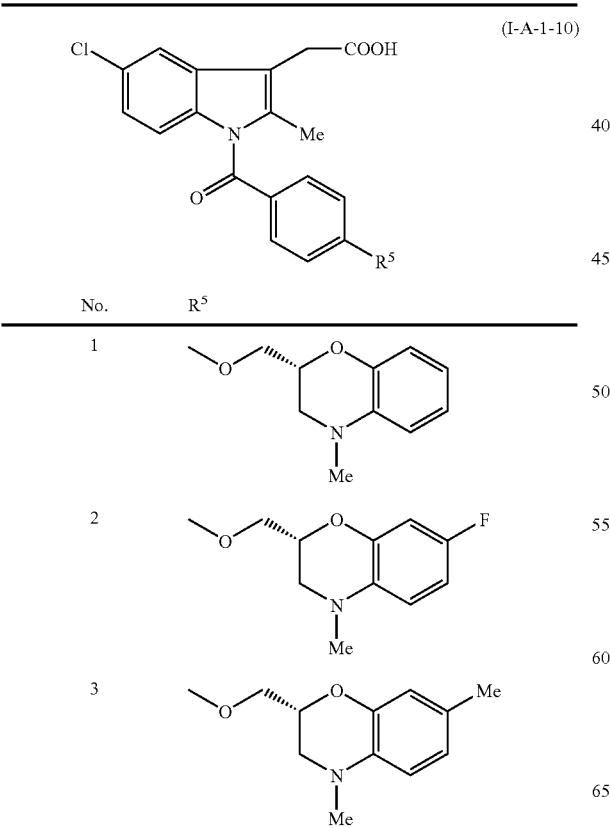

| No. | R⁵ |
|---|---|
| 1 | 4-methyl-2-(methoxymethyl)-3,4-dihydro-2H-1,4-benzoxazin-6-yl |
| 2 | 7-fluoro-4-methyl-2-(methoxymethyl)-3,4-dihydro-2H-1,4-benzoxazin-6-yl |
| 3 | 7-methyl-4-methyl-2-(methoxymethyl)-3,4-dihydro-2H-1,4-benzoxazin-6-yl |

TABLE 24-continued

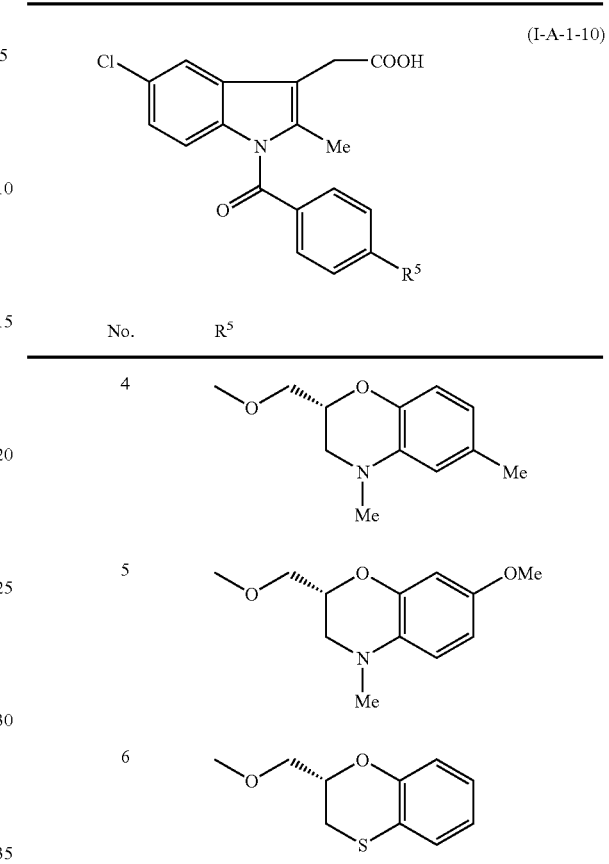

| No. | R⁵ |
|---|---|
| 4 | 6-methyl-4-methyl-2-(methoxymethyl)-3,4-dihydro-2H-1,4-benzoxazin-7-yl |
| 5 | 7-methoxy-4-methyl-2-(methoxymethyl)-3,4-dihydro-2H-1,4-benzoxazin-6-yl |
| 6 | 2-(methoxymethyl)-2,3-dihydro-1,4-benzoxathiin-6-yl |
| 7 | 7-fluoro-2-(methoxymethyl)-2,3-dihydro-1,4-benzoxathiin-6-yl |
| 8 | 3-(methoxymethyl)-2,3-dihydrobenzofuran-5-yl |
| 9 | 5-fluoro-3-(methoxymethyl)-2,3-dihydrobenzofuran-6-yl |
| 10 | 2-(methoxymethyl)-2,3-dihydrobenzofuran-5-yl |
| 11 | 2-(methoxymethyl)-2,3-dihydro-1,4-benzodioxin-6-yl |

TABLE 24-continued (I-A-1-10)

| No. | R⁵ |
|---|---|
| 12 | 5-fluoro-2,3-dihydro-1,4-benzodioxin-2-yl methoxymethyl |
| 13 | 1-ethyl-2,3-dihydro-1H-indol-2-yl methoxymethyl |
| 14 | 6-fluoro-4-methyl-3,4-dihydro-2H-1,4-benzoxazin-2-yl methoxymethyl |
| 15 | 5-methyl-2,3-dihydrobenzofuran-2-yl methoxymethyl |
| 16 | 7-methyl-2,3-dihydrobenzofuran-2-yl methoxymethyl |
| 17 | 4-methyl-1,3-benzodioxol-2-yl methoxymethyl |
| 18 | 5-methyl-1,3-benzodioxol-2-yl methoxymethyl |
| 19 | 1-methyl-1H-indol-2-yl methoxymethyl |

TABLE 24-continued (I-A-1-10)

| No. | R⁵ |
|---|---|
| 20 | 5-methylpyridin-2-yl methoxymethyl |
| 21 | 2-phenyloxazol-5-yl methoxymethyl |
| 22 | quinolin-3-yl methoxymethyl |

TABLE 25

(I-A-1-11)

| No. | R⁵ |
|---|---|
| 1 | 4-methyl-3,4-dihydro-2H-1,4-benzoxazin-2-yl methoxymethyl |
| 2 | 7-fluoro-4-methyl-3,4-dihydro-2H-1,4-benzoxazin-2-yl methoxymethyl |
| 3 | 4,7-dimethyl-3,4-dihydro-2H-1,4-benzoxazin-2-yl methoxymethyl |

TABLE 25-continued
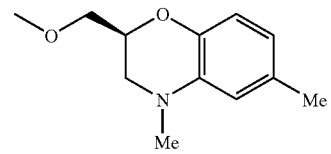
(I-A-1-11)
| No. | R⁵ |
|---|---|
| 4 | 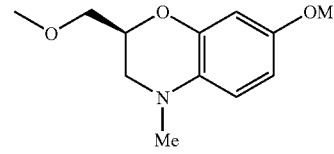 |
| 5 | 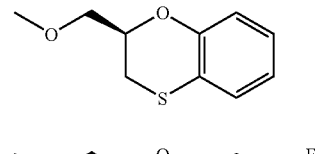 |
| 6 | 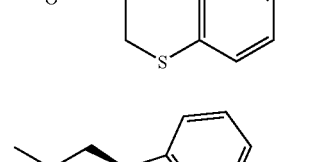 |
| 7 | 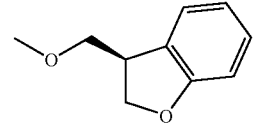 |
| 8 | 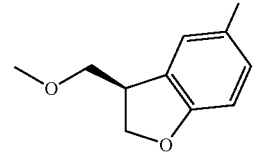 |
| 9 | 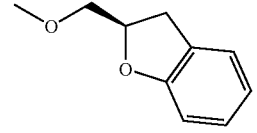 |
| 10 | 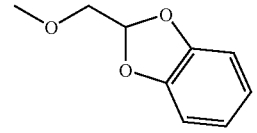 |
| 11 | 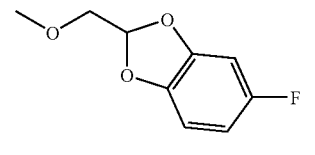 |
TABLE 25-continued
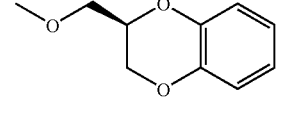
(I-A-1-11)
| No. | R⁵ |
|---|---|
| 12 | 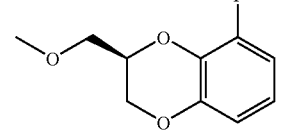 |
| 13 | 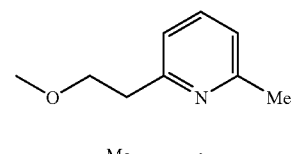 |
| 14 | 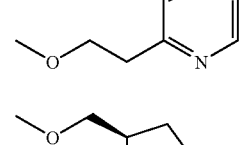 |
| 15 | 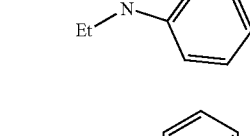 |
| 16 | 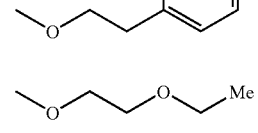 |
| 17 | 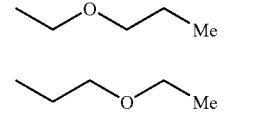 |
| 18 | 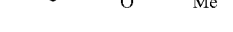 |
| 19 | 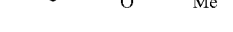 |
| 20 | ⟍⟋O⟍⟋Me |
| 21 | ⟍⟋⟍O⟍Me |

TABLE 26

(I-A-1-12)

| No. | R⁵ |
|---|---|
| 1 | 4-methyl-3,4-dihydro-2H-benzo[1,4]oxazin-2-yl-methoxymethyl |
| 2 | 7-fluoro-4-methyl-3,4-dihydro-2H-benzo[1,4]oxazin-2-yl-methoxymethyl |
| 3 | 7-methyl-4-methyl-3,4-dihydro-2H-benzo[1,4]oxazin-2-yl-methoxymethyl |
| 4 | 6-methyl-4-methyl-3,4-dihydro-2H-benzo[1,4]oxazin-2-yl-methoxymethyl |
| 5 | 7-methoxy-4-methyl-3,4-dihydro-2H-benzo[1,4]oxazin-2-yl-methoxymethyl |
| 6 | 3,4-dihydro-2H-benzo[1,4]thiazin-2-yl-methoxymethyl |
| 7 | 7-fluoro-3,4-dihydro-2H-benzo[1,4]thiazin-2-yl-methoxymethyl |
| 8 | 2,3-dihydrobenzofuran-3-yl-methoxymethyl |

TABLE 26-continued (I-A-1-12)

| No. | R⁵ |
|---|---|
| 9 | 5-fluoro-2,3-dihydrobenzofuran-3-yl-methoxymethyl |
| 10 | 2,3-dihydrobenzofuran-2-yl-methoxymethyl |
| 11 | 2,3-dihydrobenzo[1,4]dioxin-2-yl-methoxymethyl |
| 12 | 5-fluoro-2,3-dihydrobenzo[1,4]dioxin-2-yl-methoxymethyl |
| 13 | 1-ethyl-2,3-dihydro-1H-indol-2-yl-methoxymethyl |
| 14 | 6-fluoro-4-methyl-3,4-dihydro-2H-benzo[1,4]oxazin-2-yl-methoxymethyl |
| 15 | 5-methyl-2,3-dihydrobenzofuran-2-yl-methoxymethyl |
| 16 | 7-methyl-2,3-dihydrobenzofuran-2-yl-methoxymethyl |

TABLE 26-continued (I-A-1-12)

[Structure: indole-3-acetic acid with N-acyl group bearing 2-methyl and 4-R⁵ substituted benzoyl, and 2-methyl on indole]

| No. | R⁵ |
|---|---|
| 17 | 4-methyl-1,3-benzodioxol-2-yl-methoxymethyl |
| 18 | 5-methyl-1,3-benzodioxol-2-yl-methoxymethyl |
| 19 | (1-methyl-1H-indol-2-yl)methoxymethyl |
| 20 | 2-(5-methylpyridin-2-yl)ethoxymethyl |
| 21 | (2-phenyl-1,3-oxazol-5-yl)methoxymethyl |
| 22 | (quinolin-3-yl)methoxymethyl |

TABLE 27

(I-A-1-13)

[Structure: indole-3-acetic acid with N-acyl group bearing 2-fluoro and 4-R⁵ substituted benzoyl, and 2-methyl on indole]

| No. | R⁵ |
|---|---|
| 1 | (4-methyl-3,4-dihydro-2H-1,4-benzoxazin-2-yl)methoxymethyl |
| 2 | (7-fluoro-4-methyl-3,4-dihydro-2H-1,4-benzoxazin-2-yl)methoxymethyl |
| 3 | (4,7-dimethyl-3,4-dihydro-2H-1,4-benzoxazin-2-yl)methoxymethyl |
| 4 | (4,6-dimethyl-3,4-dihydro-2H-1,4-benzoxazin-2-yl)methoxymethyl |
| 5 | (7-methoxy-4-methyl-3,4-dihydro-2H-1,4-benzoxazin-2-yl)methoxymethyl |
| 6 | (2,3-dihydro-1,4-benzoxathiin-2-yl)methoxymethyl |
| 7 | (7-fluoro-2,3-dihydro-1,4-benzoxathiin-2-yl)methoxymethyl |
| 8 | (2,3-dihydro-1-benzofuran-3-yl)methoxymethyl |

TABLE 27-continued (I-A-1-13)

| No. | R⁵ |
|---|---|
| 9 | 5-fluoro-3-(methoxymethyl)-2,3-dihydrobenzofuran-3-yl |
| 10 | 2-(methoxymethyl)-2,3-dihydrobenzofuran-2-yl |
| 11 | 2-(methoxymethyl)-1,3-benzodioxol-2-yl |
| 12 | 5-fluoro-2-(methoxymethyl)-1,3-benzodioxol-2-yl |
| 13 | 3-(methoxymethyl)-2,3-dihydro-1,4-benzodioxin-3-yl |
| 14 | 5-fluoro-3-(methoxymethyl)-2,3-dihydro-1,4-benzodioxin-3-yl |
| 15 | (6-methylpyridin-2-yl)methoxyethyl |
| 16 | (3-methylpyridin-2-yl)methoxyethyl |
| 17 | 1-ethyl-2-(methoxymethyl)indolin-2-yl |
| 18 | 2-(methoxyethyl)phenyl |
| 19 | methoxyethoxyethyl-Me |
| 20 | ethoxyethyl-Me |
| 21 | propoxyethyl-Me |

TABLE 28

(I-A-1-14)

| No. | R⁵ |
|---|---|
| 1 | 2-(methoxymethyl)-4-methyl-3,4-dihydro-2H-1,4-benzoxazin-2-yl |
| 2 | 7-fluoro-2-(methoxymethyl)-4-methyl-3,4-dihydro-2H-1,4-benzoxazin-2-yl |
| 3 | 2-(methoxymethyl)-4,7-dimethyl-3,4-dihydro-2H-1,4-benzoxazin-2-yl |

TABLE 28-continued (I-A-1-14)

| No. | R⁵ |
|---|---|
| 4 | 6-methyl-4-methyl-3,4-dihydro-2H-benzo[1,4]oxazin-2-yl methoxymethyl |
| 5 | 7-methoxy-4-methyl-3,4-dihydro-2H-benzo[1,4]oxazin-2-yl methoxymethyl |
| 6 | 2,3-dihydro-benzo[1,4]oxathiin-2-yl methoxymethyl |
| 7 | 7-fluoro-2,3-dihydro-benzo[1,4]oxathiin-2-yl methoxymethyl |
| 8 | 2,3-dihydro-benzofuran-3-yl methoxymethyl |
| 9 | 5-fluoro-2,3-dihydro-benzofuran-3-yl methoxymethyl |
| 10 | 2,3-dihydro-benzofuran-2-yl methoxymethyl |
| 11 | 2,3-dihydro-benzo[1,4]dioxin-2-yl methoxymethyl |
| 12 | 8-fluoro-2,3-dihydro-benzo[1,4]dioxin-2-yl methoxymethyl |
| 13 | 1-ethyl-2,3-dihydro-1H-indol-2-yl methoxymethyl |
| 14 | 6-fluoro-4-methyl-3,4-dihydro-2H-benzo[1,4]oxazin-2-yl methoxymethyl |
| 15 | 5-methyl-2,3-dihydro-benzofuran-2-yl methoxymethyl |
| 16 | 7-methyl-2,3-dihydro-benzofuran-2-yl methoxymethyl |
| 17 | 4-methyl-benzo[1,3]dioxol-2-yl methoxymethyl |
| 18 | 5-methyl-benzo[1,3]dioxol-2-yl methoxymethyl |
| 19 | 1-methyl-1H-indol-2-yl methoxymethyl |

TABLE 28-continued
(I-A-1-14)
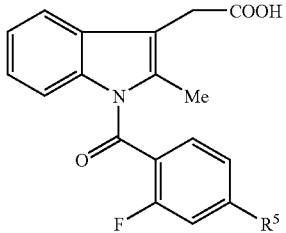
| No. | R⁵ |
|---|---|
| 20 | 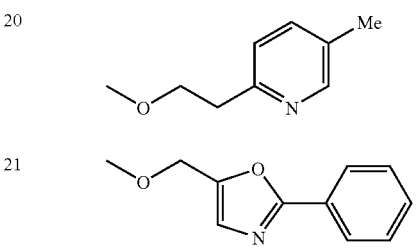 |
| 21 | 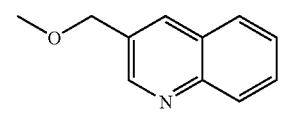 |
| 22 | 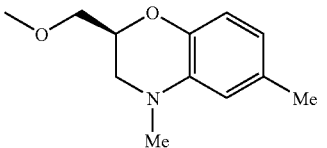 |
TABLE 29
(I-A-1-15)
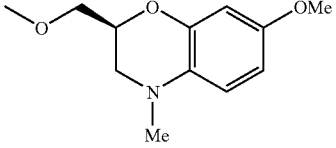
| No. | R⁵ |
|---|---|
| 1 | 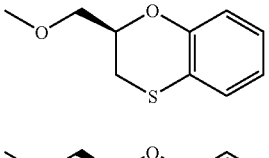 |
| 2 | 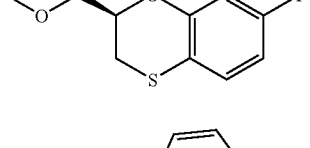 |
| 3 | 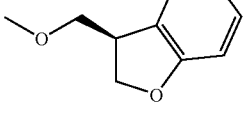 |
TABLE 29-continued
(I-A-1-15)
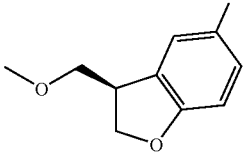
| No. | R⁵ |
|---|---|
| 4 | 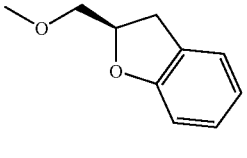 |
| 5 | 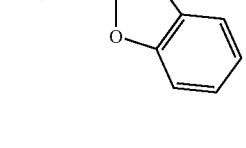 |
| 6 | 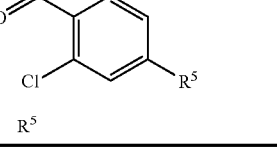 |
| 7 | 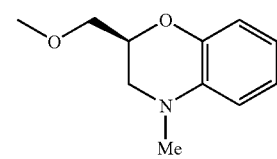 |
| 8 | 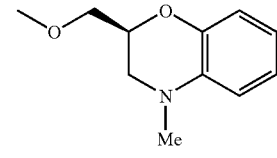 |
| 9 | |
| 10 | |
| 11 | |

TABLE 29-continued
(I-A-1-15)
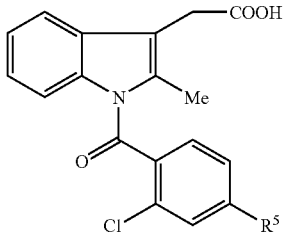
| No. | R⁵ |
|---|---|
| 12 | 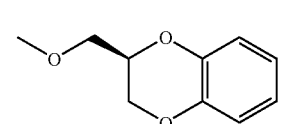 |
| 13 | 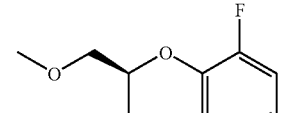 |
| 14 | 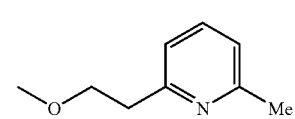 |
| 15 | 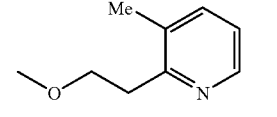 |
| 16 | 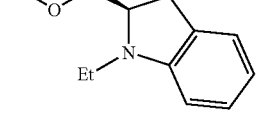 |
| 17 | 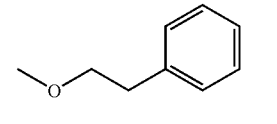 |
| 18 | 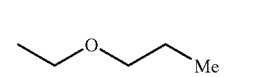 |
| 19 | 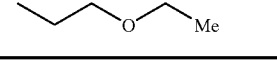 |
| 20 |  |
| 21 | 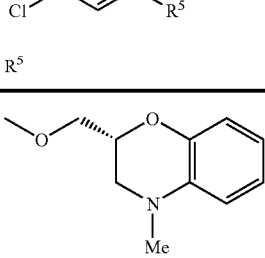 |
TABLE 30
(I-A-1-16)
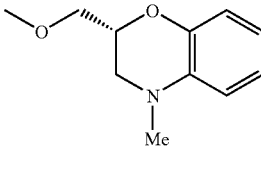
| No. | R⁵ |
|---|---|
| 1 | 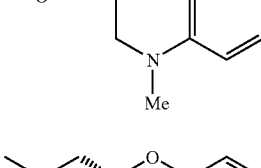 |
| 2 | 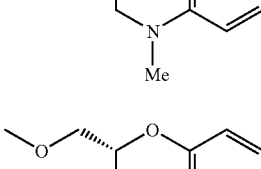 |
| 3 | 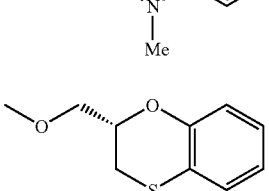 |
| 4 | 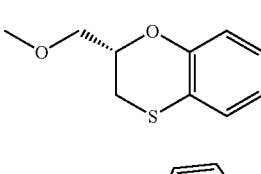 |
| 5 | 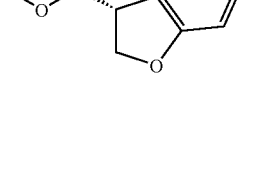 |
| 6 | |
| 7 | |
| 8 |  |

TABLE 30-continued (I-A-1-16)

| No. | R⁵ |
|---|---|
| 9 | 5-fluoro-2,3-dihydrobenzofuran-3-yl methoxymethyl |
| 10 | 2,3-dihydrobenzofuran-2-yl methoxymethyl |
| 11 | 2,3-dihydro-1,4-benzodioxin-2-yl methoxymethyl |
| 12 | 5-fluoro-2,3-dihydro-1,4-benzodioxin-2-yl methoxymethyl |
| 13 | 1-ethyl-2,3-dihydroindol-2-yl methoxymethyl |
| 14 | 4-methyl-6-fluoro-3,4-dihydro-2H-1,4-benzoxazin-2-yl methoxymethyl |
| 15 | 6-methyl-2,3-dihydrobenzofuran-2-yl methoxymethyl |
| 16 | 7-methyl-2,3-dihydrobenzofuran-2-yl methoxymethyl |
| 17 | 4-methyl-1,3-benzodioxol-2-yl methoxymethyl |
| 18 | 5-methyl-1,3-benzodioxol-2-yl methoxymethyl |
| 19 | 1-methylindol-2-yl methoxymethyl |
| 20 | 5-methylpyridin-2-yl methoxyethyl |
| 21 | 2-phenyloxazol-5-yl methoxymethyl |
| 22 | quinolin-3-yl methoxymethyl |

TABLE 31

(I-A-1-17)

| No. | R⁵ |
|---|---|
| 1 | 4-methyl-2-(methoxymethyl)-2,3-dihydro-1,4-benzoxazine |
| 2 | 7-fluoro-4-methyl-2-(methoxymethyl)-2,3-dihydro-1,4-benzoxazine |
| 3 | 7-methyl-4-methyl-2-(methoxymethyl)-2,3-dihydro-1,4-benzoxazine |
| 4 | 6-methyl-4-methyl-2-(methoxymethyl)-2,3-dihydro-1,4-benzoxazine |
| 5 | 7-methoxy-4-methyl-2-(methoxymethyl)-2,3-dihydro-1,4-benzoxazine |
| 6 | 2-(methoxymethyl)-2,3-dihydro-1,4-benzoxathiine |
| 7 | 7-fluoro-2-(methoxymethyl)-2,3-dihydro-1,4-benzoxathiine |
| 8 | 3-(methoxymethyl)-2,3-dihydrobenzofuran |
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-1,3-benzodioxole |
| 12 | 5-fluoro-2-(methoxymethyl)-1,3-benzodioxole |
| 13 | 2-(methoxymethyl)-2,3-dihydro-1,4-benzodioxine |
| 14 | 5-fluoro-2-(methoxymethyl)-2,3-dihydro-1,4-benzodioxine |
| 15 | 2-(2-methoxyethyl)-6-methylpyridine |
| 16 | 2-(2-methoxyethyl)-3-methylpyridine |
| 17 | 1-ethyl-2-(methoxymethyl)indoline |

TABLE 31-continued (I-A-1-17)

| No. | R[5] |
|---|---|
| 18 | [2-phenylethoxymethyl] |
| 19 | [methoxyethoxyethyl] |
| 20 | [ethoxypropyl] |
| 21 | [ethoxypropyl isomer] |

TABLE 32

(I-A-1-18)

| No. | R[5] |
|---|---|
| 1 | [(methoxymethyl)-4-methyl-3,4-dihydro-2H-benzo[1,4]oxazin-2-yl] |
| 2 | [(methoxymethyl)-7-fluoro-4-methyl-3,4-dihydro-2H-benzo[1,4]oxazin-2-yl] |
| 3 | [(methoxymethyl)-7-methyl-4-methyl-3,4-dihydro-2H-benzo[1,4]oxazin-2-yl] |

TABLE 32-continued (I-A-1-18)

| No. | R[5] |
|---|---|
| 4 | [(methoxymethyl)-6-methyl-4-methyl-3,4-dihydro-2H-benzo[1,4]oxazin-2-yl] |
| 5 | [(methoxymethyl)-7-methoxy-4-methyl-3,4-dihydro-2H-benzo[1,4]oxazin-2-yl] |
| 6 | [(methoxymethyl)-2,3-dihydro-benzo[1,4]oxathiin-2-yl] |
| 7 | [(methoxymethyl)-7-fluoro-2,3-dihydro-benzo[1,4]oxathiin-2-yl] |
| 8 | [(methoxymethyl)-2,3-dihydro-benzofuran-3-yl] |
| 9 | [(methoxymethyl)-5-fluoro-2,3-dihydro-benzofuran-3-yl] |
| 10 | [(methoxymethyl)-2,3-dihydro-benzofuran-2-yl] |
| 11 | [(methoxymethyl)-2,3-dihydro-benzo[1,4]dioxin-2-yl] |

TABLE 32-continued (I-A-1-18)

| No. | R⁵ |
|---|---|
| 12 | 8-fluoro-2,3-dihydro-1,4-benzodioxin-2-ylmethoxymethyl |
| 13 | 1-ethyl-2,3-dihydro-1H-indol-2-ylmethoxymethyl |
| 14 | 6-fluoro-4-methyl-3,4-dihydro-2H-1,4-benzoxazin-2-ylmethoxymethyl |
| 15 | 5-methyl-2,3-dihydro-1-benzofuran-2-ylmethoxymethyl |
| 16 | 7-methyl-2,3-dihydro-1-benzofuran-2-ylmethoxymethyl |
| 17 | 4-methyl-1,3-benzodioxol-2-ylmethoxymethyl |
| 18 | 5-methyl-1,3-benzodioxol-2-ylmethoxymethyl |
| 19 | 1-methyl-1H-indol-2-ylmethoxymethyl |

TABLE 32-continued (I-A-1-18)

| No. | R⁵ |
|---|---|
| 20 | (5-methylpyridin-2-yl)methoxymethyl (ethylene linker) |
| 21 | (2-phenyl-1,3-oxazol-5-yl)methoxymethyl |
| 22 | quinolin-3-ylmethoxymethyl |

TABLE 33

(I-A-1-19)

| No. | R⁵ |
|---|---|
| 1 | 4-methyl-3,4-dihydro-2H-1,4-benzoxazin-2-ylmethoxymethyl |
| 2 | 7-fluoro-4-methyl-3,4-dihydro-2H-1,4-benzoxazin-2-ylmethoxymethyl |
| 3 | 4,7-dimethyl-3,4-dihydro-2H-1,4-benzoxazin-2-ylmethoxymethyl |

TABLE 33-continued (I-A-1-19)

| No. | R⁵ |
|---|---|
| 4 | 6-methyl-4-methyl-2-(methoxymethyl)-3,4-dihydro-2H-benzo[1,4]oxazine |
| 5 | 7-methoxy-4-methyl-2-(methoxymethyl)-3,4-dihydro-2H-benzo[1,4]oxazine |
| 6 | 2-(methoxymethyl)-2,3-dihydro-1,4-benzoxathiine |
| 7 | 7-fluoro-2-(methoxymethyl)-2,3-dihydro-1,4-benzoxathiine |
| 8 | 3-(methoxymethyl)-2,3-dihydrobenzofuran |
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-1,3-benzodioxole |

TABLE 33-continued (I-A-1-19)

| No. | R⁵ |
|---|---|
| 12 | 5-fluoro-2-(methoxymethyl)-1,3-benzodioxole |
| 13 | 2-(methoxymethyl)-2,3-dihydro-1,4-benzodioxine |
| 14 | 5-fluoro-2-(methoxymethyl)-2,3-dihydro-1,4-benzodioxine |
| 15 | 2-(2-methoxyethyl)-6-methylpyridine |
| 16 | 2-(2-methoxyethyl)-3-methylpyridine |
| 17 | 1-ethyl-2-(methoxymethyl)-2,3-dihydro-1H-indole |
| 18 | (2-methoxyethyl)benzene |
| 19 | 1-ethoxy-2-methoxyethane |
| 20 | 1-ethoxypropane (ethyl propyl ether) |
| 21 | 1-ethoxybutane or similar |

TABLE 34

(I-A-1-20)

| No. | R⁵ |
|---|---|
| 1 | 4-methyl-2-(methoxymethyl)-3,4-dihydro-2H-1,4-benzoxazin-7-yl |
| 2 | 7-fluoro-4-methyl-2-(methoxymethyl)-3,4-dihydro-2H-1,4-benzoxazin-6-yl |
| 3 | 7-methyl-4-methyl-2-(methoxymethyl)-3,4-dihydro-2H-1,4-benzoxazin-6-yl |
| 4 | 6-methyl-4-methyl-2-(methoxymethyl)-3,4-dihydro-2H-1,4-benzoxazin-7-yl |
| 5 | 7-methoxy-4-methyl-2-(methoxymethyl)-3,4-dihydro-2H-1,4-benzoxazin-6-yl |
| 6 | 2-(methoxymethyl)-3,4-dihydro-2H-1,4-benzoxathiin-6-yl |
| 7 | 7-fluoro-2-(methoxymethyl)-3,4-dihydro-2H-1,4-benzoxathiin-6-yl |
| 8 | 3-(methoxymethyl)-2,3-dihydrobenzofuran-2-yl |

TABLE 34-continued (I-A-1-20)

| No. | R⁵ |
|---|---|
| 9 | 5-fluoro-3-(methoxymethyl)-2,3-dihydrobenzofuran-3-yl |
| 10 | 2-(methoxymethyl)-2,3-dihydrobenzofuran-2-yl |
| 11 | 2-(methoxymethyl)-2,3-dihydro-1,4-benzodioxin-2-yl |
| 12 | 5-fluoro-2-(methoxymethyl)-2,3-dihydro-1,4-benzodioxin-2-yl |
| 13 | 1-ethyl-2-(methoxymethyl)-2,3-dihydro-1H-indol-2-yl |
| 14 | 6-fluoro-4-methyl-2-(methoxymethyl)-3,4-dihydro-2H-1,4-benzoxazin-2-yl |
| 15 | 5-methyl-2-(methoxymethyl)-2,3-dihydrobenzofuran-2-yl |
| 16 | 7-methyl-2-(methoxymethyl)-2,3-dihydrobenzofuran-2-yl |

TABLE 34-continued (I-A-1-20)

| No. | R⁵ |
|---|---|
| 17 | 2-(methoxymethyl)-4-methyl-1,3-benzodioxole |
| 18 | 2-(methoxymethyl)-5-methyl-1,3-benzodioxole |
| 19 | 2-(methoxymethyl)-1-methyl-1H-indole |
| 20 | 2-(2-methoxyethyl)-5-methylpyridine |
| 21 | 5-(methoxymethyl)-2-phenyl-1,3-oxazole |
| 22 | 3-(methoxymethyl)quinoline |

TABLE 35

(I-A-1-21)

| No. | R⁵ |
|---|---|
| 1 | 2-(methoxymethyl)-4-methyl-3,4-dihydro-2H-1,4-benzoxazine |
| 2 | 7-fluoro-2-(methoxymethyl)-4-methyl-3,4-dihydro-2H-1,4-benzoxazine |
| 3 | 2-(methoxymethyl)-4,7-dimethyl-3,4-dihydro-2H-1,4-benzoxazine |
| 4 | 2-(methoxymethyl)-4,6-dimethyl-3,4-dihydro-2H-1,4-benzoxazine |
| 5 | 7-methoxy-2-(methoxymethyl)-4-methyl-3,4-dihydro-2H-1,4-benzoxazine |
| 6 | 2-(methoxymethyl)-2,3-dihydro-1,4-benzoxathiine |
| 7 | 7-fluoro-2-(methoxymethyl)-2,3-dihydro-1,4-benzoxathiine |
| 8 | 3-(methoxymethyl)-2,3-dihydro-1-benzofuran |

TABLE 35-continued (I-A-1-21)

[Structure: 5-methyl-indole-3-acetic acid with N-acyl group bearing 2-chloro-4-R⁵-benzoyl, and 2-methyl on indole]

| No. | R⁵ |
|---|---|
| 9 | 5-fluoro-2,3-dihydrobenzofuran-3-yl methoxymethyl |
| 10 | 2,3-dihydrobenzofuran-2-yl methoxymethyl |
| 11 | 1,3-benzodioxol-2-yl methoxymethyl |
| 12 | 5-fluoro-1,3-benzodioxol-2-yl methoxymethyl |
| 13 | 2,3-dihydro-1,4-benzodioxin-2-yl methoxymethyl |
| 14 | 5-fluoro-2,3-dihydro-1,4-benzodioxin-2-yl methoxymethyl |
| 15 | (6-methylpyridin-2-yl)ethoxymethyl |
| 16 | (3-methylpyridin-2-yl)ethoxymethyl |
| 17 | (1-ethylindolin-2-yl)methoxymethyl |

TABLE 35-continued (I-A-1-21)

[Same core structure]

| No. | R⁵ |
|---|---|
| 18 | 2-phenylethyl methoxymethyl |
| 19 | CH₃OCH₂CH₂OCH₂CH₃ (methoxyethoxyethyl) |
| 20 | CH₃CH₂OCH₂CH₂- type (ethoxyethyl) |
| 21 | propoxyethyl |

TABLE 36

(I-A-1-22)

[Structure: 5-methyl-indole-3-acetic acid with N-(2-chloro-4-R⁵-benzoyl), 2-methyl]

| No. | R⁵ |
|---|---|
| 1 | (4-methyl-3,4-dihydro-2H-1,4-benzoxazin-2-yl)methoxymethyl |
| 2 | (7-fluoro-4-methyl-3,4-dihydro-2H-1,4-benzoxazin-2-yl)methoxymethyl |
| 3 | (4,7-dimethyl-3,4-dihydro-2H-1,4-benzoxazin-2-yl)methoxymethyl |

TABLE 36-continued (I-A-1-22)

| No. | R⁵ |
|---|---|
| 4 | (methoxymethyl-methyl-methylbenzoxazine, Me substituent) |
| 5 | (methoxymethyl-methyl-methylbenzoxazine, OMe substituent) |
| 6 | (methoxymethyl-benzoxathiine) |
| 7 | (methoxymethyl-benzoxathiine, F substituent) |
| 8 | (methoxymethyl-dihydrobenzofuran) |
| 9 | (methoxymethyl-dihydrobenzofuran, F substituent) |
| 10 | (methoxymethyl-dihydrobenzofuran) |
| 11 | (methoxymethyl-benzodioxane) |
| 12 | (methoxymethyl-benzodioxane, F substituent) |
| 13 | (methoxymethyl-N-ethylindoline) |
| 14 | (methoxymethyl-methyl-benzoxazine, F substituent) |
| 15 | (methoxymethyl-dihydrobenzofuran, Me substituent) |
| 16 | (methoxymethyl-dihydrobenzofuran, Me substituent) |
| 17 | (methoxymethyl-benzodioxole, Me substituent) |
| 18 | (methoxymethyl-benzodioxole, Me substituent) |
| 19 | (methoxymethyl-N-methylindole) |

TABLE 36-continued (I-A-1-22)

| No. | R⁵ |
|---|---|
| 20 | 5-methyl-2-(methoxymethyl)pyridine |
| 21 | 5-(methoxymethyl)-2-phenyloxazole |
| 22 | 3-(methoxymethyl)quinoline |

TABLE 37

(I-A-1-23)

| No. | R⁵ |
|---|---|
| 1 | 2-(methoxymethyl)-4-methyl-3,4-dihydro-2H-benzo[1,4]oxazine |
| 2 | 2-(methoxymethyl)-7-fluoro-4-methyl-3,4-dihydro-2H-benzo[1,4]oxazine |
| 3 | 2-(methoxymethyl)-7-methyl-4-methyl-3,4-dihydro-2H-benzo[1,4]oxazine |

TABLE 37-continued (I-A-1-23)

| No. | R⁵ |
|---|---|
| 4 | 2-(methoxymethyl)-6-methyl-4-methyl-3,4-dihydro-2H-benzo[1,4]oxazine |
| 5 | 2-(methoxymethyl)-7-methoxy-4-methyl-3,4-dihydro-2H-benzo[1,4]oxazine |
| 6 | 2-(methoxymethyl)-2,3-dihydro-benzo[1,4]oxathiine |
| 7 | 2-(methoxymethyl)-7-fluoro-2,3-dihydro-benzo[1,4]oxathiine |
| 8 | 3-(methoxymethyl)-2,3-dihydrobenzofuran |
| 9 | 3-(methoxymethyl)-5-fluoro-2,3-dihydrobenzofuran |
| 10 | 2-(methoxymethyl)-2,3-dihydrobenzofuran |
| 11 | 2-(methoxymethyl)-1,3-benzodioxole |

TABLE 37-continued
(I-A-1-23)
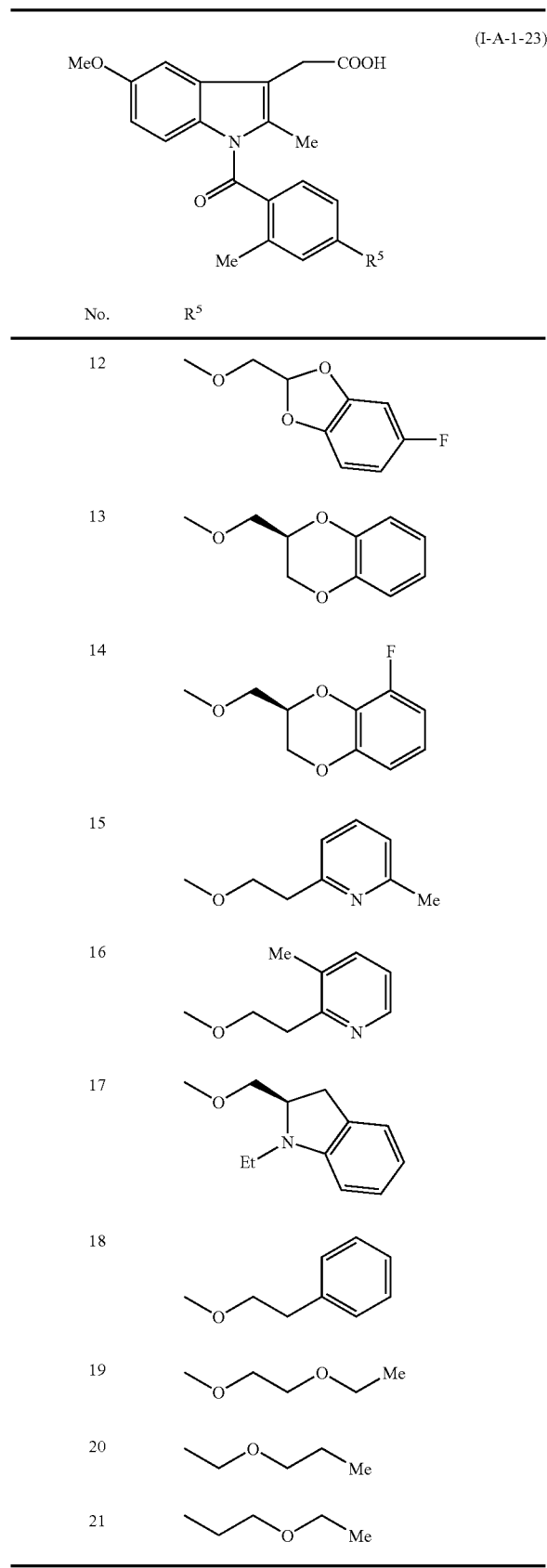
| No. | R⁵ |
| --- | --- |
| 12 | |
| 13 | |
| 14 | |
| 15 | |
| 16 | |
| 17 | |
| 18 | |
| 19 | |
| 20 | |
| 21 | |
TABLE 38
(I-A-1-24)
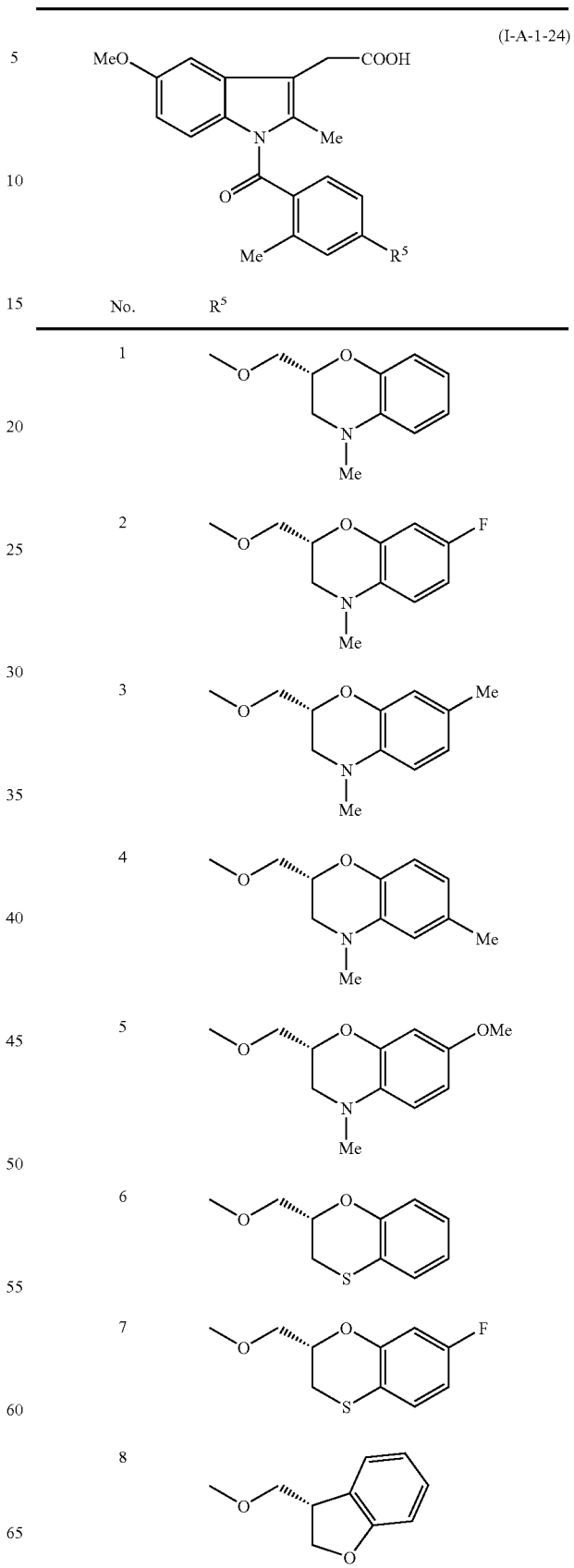
| No. | R⁵ |
| --- | --- |
| 1 | |
| 2 | |
| 3 | |
| 4 | |
| 5 | |
| 6 | |
| 7 | |
| 8 | |

TABLE 38-continued (I-A-1-24)

[Structure: 5-methoxy-2-methyl-1-(2-methyl-4-R⁵-benzoyl)-indol-3-yl acetic acid]

| No. | R⁵ |
|---|---|
| 9 | 5-fluoro-2,3-dihydrobenzofuran-3-yl with CH₂OMe substituent |
| 10 | 2,3-dihydrobenzofuran-2-yl with CH₂OMe substituent |
| 11 | 2,3-dihydro-1,4-benzodioxin-2-yl with CH₂OMe substituent |
| 12 | 5-fluoro-2,3-dihydro-1,4-benzodioxin-2-yl with CH₂OMe substituent |
| 13 | 1-ethyl-2,3-dihydroindol-2-yl with CH₂OMe substituent |
| 14 | 6-fluoro-4-methyl-3,4-dihydro-2H-1,4-benzoxazin-2-yl with CH₂OMe substituent |
| 15 | 6-methyl-2,3-dihydrobenzofuran-2-yl with CH₂OMe substituent |
| 16 | 7-methyl-2,3-dihydrobenzofuran-2-yl with CH₂OMe substituent |
| 17 | 4-methyl-1,3-benzodioxol-2-yl with CH₂OMe substituent |
| 18 | 5-methyl-1,3-benzodioxol-2-yl with CH₂OMe substituent |
| 19 | 1-methylindol-2-yl with CH₂OMe substituent |
| 20 | 5-methyl-2-(2-methoxyethyl)pyridine |
| 21 | 2-phenyl-5-(methoxymethyl)oxazole |
| 22 | 3-(methoxymethyl)quinoline |

TABLE 39

(I-A-1-25)

| No. | R⁵ |
|---|---|
| 1 | 4-methyl-2-(methoxymethyl)-3,4-dihydro-2H-benzo[b][1,4]oxazine |
| 2 | 7-fluoro-4-methyl-2-(methoxymethyl)-3,4-dihydro-2H-benzo[b][1,4]oxazine |
| 3 | 7-methyl-4-methyl-2-(methoxymethyl)-3,4-dihydro-2H-benzo[b][1,4]oxazine |
| 4 | 6-methyl-4-methyl-2-(methoxymethyl)-3,4-dihydro-2H-benzo[b][1,4]oxazine |
| 5 | 7-methoxy-4-methyl-2-(methoxymethyl)-3,4-dihydro-2H-benzo[b][1,4]oxazine |
| 6 | 2-(methoxymethyl)-3,4-dihydro-2H-benzo[b][1,4]thiazine-fused |
| 7 | 7-fluoro-2-(methoxymethyl)-3,4-dihydro-2H-benzo[b][1,4]oxathiine |
| 8 | 3-(methoxymethyl)-2,3-dihydrobenzofuran |
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-benzo[d][1,3]dioxole |
| 12 | 5-fluoro-2-(methoxymethyl)-benzo[d][1,3]dioxole |
| 13 | 2-(methoxymethyl)-2,3-dihydrobenzo[b][1,4]dioxine |
| 14 | 5-fluoro-2-(methoxymethyl)-2,3-dihydrobenzo[b][1,4]dioxine |
| 15 | 2-(2-methoxyethyl)-6-methylpyridine |
| 16 | 2-(2-methoxyethyl)-3-methylpyridine |
| 17 | 1-ethyl-2-(methoxymethyl)-2,3-dihydro-1H-indole |

TABLE 39-continued (I-A-1-25)

| No. | R⁵ |
|---|---|
| 18 | (methoxyethyl-phenyl group) |
| 19 | MeO-CH₂CH₂-O-CH₂CH₂-OMe-like (MeOCH₂CH₂OEt) |
| 20 | EtOCH₂CH₂-Me (propyl ethyl ether) |
| 21 | PrOEt (propyl-O-ethyl) |

TABLE 40

(I-A-1-26)

| No. | R⁵ |
|---|---|
| 1 | (2S)-2-(methoxymethyl)-4-methyl-3,4-dihydro-2H-1,4-benzoxazine |
| 2 | (2S)-7-fluoro-2-(methoxymethyl)-4-methyl-3,4-dihydro-2H-1,4-benzoxazine |
| 3 | (2S)-2-(methoxymethyl)-4,7-dimethyl-3,4-dihydro-2H-1,4-benzoxazine |

TABLE 40-continued (I-A-1-26)

| No. | R⁵ |
|---|---|
| 4 | (2S)-2-(methoxymethyl)-4,6-dimethyl-3,4-dihydro-2H-1,4-benzoxazine |
| 5 | (2S)-7-methoxy-2-(methoxymethyl)-4-methyl-3,4-dihydro-2H-1,4-benzoxazine |
| 6 | (2S)-2-(methoxymethyl)-2,3-dihydro-1,4-benzoxathiine |
| 7 | (2S)-7-fluoro-2-(methoxymethyl)-2,3-dihydro-1,4-benzoxathiine |
| 8 | (3S)-3-(methoxymethyl)-2,3-dihydro-1-benzofuran |
| 9 | (3S)-5-fluoro-3-(methoxymethyl)-2,3-dihydro-1-benzofuran |
| 10 | (2S)-2-(methoxymethyl)-2,3-dihydro-1-benzofuran |
| 11 | (2S)-2-(methoxymethyl)-2,3-dihydro-1,4-benzodioxine |

TABLE 40-continued (I-A-1-26)

| No. | R[5] |
|---|---|
| 12 | [5-fluoro-2,3-dihydro-1,4-benzodioxin-2-yl with CH2OMe] |
| 13 | [1-ethyl-2,3-dihydro-1H-indol-2-yl with CH2OMe] |
| 14 | [6-fluoro-4-methyl-3,4-dihydro-2H-1,4-benzoxazin-2-yl with CH2OMe] |
| 15 | [5-methyl-2,3-dihydro-1-benzofuran-2-yl with CH2OMe] |
| 16 | [7-methyl-2,3-dihydro-1-benzofuran-2-yl with CH2OMe] |
| 17 | [4-methyl-1,3-benzodioxol-2-yl with CH2OMe] |
| 18 | [5-methyl-1,3-benzodioxol-2-yl with CH2OMe] |
| 19 | [1-methyl-1H-indol-2-yl with CH2OMe] |

TABLE 40-continued (I-A-1-26)

| No. | R[5] |
|---|---|
| 20 | [5-methylpyridin-2-yl with CH2CH2OMe] |
| 21 | [2-phenyl-1,3-oxazol-5-yl with CH2OMe] |
| 22 | [quinolin-3-yl with CH2OMe] |

TABLE 41

(I-A-1-27)

| No. | R[5] |
|---|---|
| 1 | [4-methyl-3,4-dihydro-2H-1,4-benzoxazin-2-yl with CH2OMe] |
| 2 | [7-fluoro-4-methyl-3,4-dihydro-2H-1,4-benzoxazin-2-yl with CH2OMe] |
| 3 | [4,7-dimethyl-3,4-dihydro-2H-1,4-benzoxazin-2-yl with CH2OMe] |

TABLE 41-continued (I-A-1-27)

| No. | R⁵ |
|---|---|
| 4 | 6-methyl-4-methyl-2-(methoxymethyl)-3,4-dihydro-2H-1,4-benzoxazine |
| 5 | 7-methoxy-4-methyl-2-(methoxymethyl)-3,4-dihydro-2H-1,4-benzoxazine |
| 6 | 2-(methoxymethyl)-2,3-dihydro-1,4-benzoxathiine |
| 7 | 7-fluoro-2-(methoxymethyl)-2,3-dihydro-1,4-benzoxathiine |
| 8 | 3-(methoxymethyl)-2,3-dihydrobenzofuran |
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-1,3-benzodioxole |
| 12 | 5-fluoro-2-(methoxymethyl)-1,3-benzodioxole |
| 13 | 2-(methoxymethyl)-2,3-dihydro-1,4-benzodioxine |
| 14 | 5-fluoro-2-(methoxymethyl)-2,3-dihydro-1,4-benzodioxine |
| 15 | 2-(2-methoxyethyl)-6-methylpyridine |
| 16 | 2-(2-methoxyethyl)-3-methylpyridine |
| 17 | 1-ethyl-2-(methoxymethyl)-2,3-dihydro-1H-indole |
| 18 | (2-methoxyethyl)benzene |
| 19 | 1-ethoxy-2-methoxyethane |
| 20 | 1-ethoxy-2-methoxyethane (propyl variant) |
| 21 | 1-ethoxy-3-methoxypropane |

TABLE 42

(I-A-1-28)

| No. | R⁵ |
|---|---|
| 1 | 4-methyl-3,4-dihydro-2H-benzo[1,4]oxazin-2-yl methoxymethyl |
| 2 | 7-fluoro-4-methyl-3,4-dihydro-2H-benzo[1,4]oxazin-2-yl methoxymethyl |
| 3 | 7-methyl-4-methyl-3,4-dihydro-2H-benzo[1,4]oxazin-2-yl methoxymethyl |
| 4 | 6-methyl-4-methyl-3,4-dihydro-2H-benzo[1,4]oxazin-2-yl methoxymethyl |
| 5 | 7-methoxy-4-methyl-3,4-dihydro-2H-benzo[1,4]oxazin-2-yl methoxymethyl |
| 6 | 3,4-dihydro-2H-benzo[1,4]thiazin-2-yl methoxymethyl |
| 7 | 7-fluoro-3,4-dihydro-2H-benzo[1,4]thiazin-2-yl methoxymethyl |
| 8 | 2,3-dihydrobenzofuran-3-yl methoxymethyl |

TABLE 42-continued (I-A-1-28)

| No. | R⁵ |
|---|---|
| 9 | 5-fluoro-2,3-dihydrobenzofuran-3-yl methoxymethyl |
| 10 | 2,3-dihydrobenzofuran-2-yl methoxymethyl |
| 11 | 2,3-dihydrobenzo[1,4]dioxin-2-yl methoxymethyl |
| 12 | 5-fluoro-2,3-dihydrobenzo[1,4]dioxin-2-yl methoxymethyl |
| 13 | 1-ethyl-2,3-dihydro-1H-indol-2-yl methoxymethyl |
| 14 | 6-fluoro-4-methyl-3,4-dihydro-2H-benzo[1,4]oxazin-2-yl methoxymethyl |
| 15 | 5-methyl-2,3-dihydrobenzofuran-2-yl methoxymethyl |
| 16 | 7-methyl-2,3-dihydrobenzofuran-2-yl methoxymethyl |

TABLE 42-continued (I-A-1-28)

| No. | R⁵ |
|---|---|
| 17 | 4-methyl-1,3-benzodioxol-2-yl-methoxymethyl |
| 18 | 5-methyl-1,3-benzodioxol-2-yl-methoxymethyl |
| 19 | 1-methyl-1H-indol-2-yl-methoxymethyl |
| 20 | 5-methylpyridin-2-yl-methoxyethyl |
| 21 | 2-phenyl-1,3-oxazol-5-yl-methoxymethyl |
| 22 | quinolin-3-yl-methoxymethyl |

TABLE 43

(I-A-1-29)

| No. | R⁵ |
|---|---|
| 1 | 4-methyl-3,4-dihydro-2H-1,4-benzoxazin-2-yl-methoxymethyl |
| 2 | 7-fluoro-4-methyl-3,4-dihydro-2H-1,4-benzoxazin-2-yl-methoxymethyl |
| 3 | 4,7-dimethyl-3,4-dihydro-2H-1,4-benzoxazin-2-yl-methoxymethyl |
| 4 | 4,6-dimethyl-3,4-dihydro-2H-1,4-benzoxazin-2-yl-methoxymethyl |
| 5 | 7-methoxy-4-methyl-3,4-dihydro-2H-1,4-benzoxazin-2-yl-methoxymethyl |
| 6 | 2,3-dihydro-1,4-benzoxathiin-2-yl-methoxymethyl |
| 7 | 7-fluoro-2,3-dihydro-1,4-benzoxathiin-2-yl-methoxymethyl |
| 8 | 2,3-dihydro-1-benzofuran-3-yl-methoxymethyl |

TABLE 43-continued (I-A-1-29)

| No. | R⁵ |
|---|---|
| 9 | 5-fluoro-2,3-dihydrobenzofuran-3-yl-CH₂-O-CH₃ |
| 10 | 2,3-dihydrobenzofuran-2-yl-CH₂-O-CH₃ |
| 11 | 1,3-benzodioxol-2-yl-CH₂-O-CH₃ |
| 12 | 5-fluoro-1,3-benzodioxol-2-yl-CH₂-O-CH₃ |
| 13 | 2,3-dihydro-1,4-benzodioxin-2-yl-CH₂-O-CH₃ |
| 14 | 5-fluoro-2,3-dihydro-1,4-benzodioxin-2-yl-CH₂-O-CH₃ |
| 15 | (6-methylpyridin-2-yl)-CH₂CH₂-O-CH₃ |
| 16 | (3-methylpyridin-2-yl)-CH₂CH₂-O-CH₃ |
| 17 | (1-ethylindolin-2-yl)-CH₂-O-CH₃ |

TABLE 43-continued (I-A-1-29)

| No. | R⁵ |
|---|---|
| 18 | phenyl-CH₂CH₂-O-CH₃ |
| 19 | CH₃-O-CH₂CH₂-O-CH₂CH₃ |
| 20 | CH₃CH₂-O-CH₂CH₂-O-CH₃ |
| 21 | CH₃CH₂CH₂-O-CH₂CH₃ |

TABLE 44

(I-A-1-30)

| No. | R⁵ |
|---|---|
| 1 | (4-methyl-3,4-dihydro-2H-1,4-benzoxazin-2-yl)-CH₂-O-CH₃ |
| 2 | (7-fluoro-4-methyl-3,4-dihydro-2H-1,4-benzoxazin-2-yl)-CH₂-O-CH₃ |
| 3 | (4,7-dimethyl-3,4-dihydro-2H-1,4-benzoxazin-2-yl)-CH₂-O-CH₃ |

TABLE 44-continued (I-A-1-30)

| No. | R⁵ |
|---|---|
| 4 | 6-methyl-4-methyl-3,4-dihydro-2H-benzo[1,4]oxazin-2-ylmethoxymethyl |
| 5 | 7-methoxy-4-methyl-3,4-dihydro-2H-benzo[1,4]oxazin-2-ylmethoxymethyl |
| 6 | 2,3-dihydro-benzo[1,4]oxathiin-2-ylmethoxymethyl |
| 7 | 7-fluoro-2,3-dihydro-benzo[1,4]oxathiin-2-ylmethoxymethyl |
| 8 | 2,3-dihydro-benzofuran-3-ylmethoxymethyl |
| 9 | 5-fluoro-2,3-dihydro-benzofuran-3-ylmethoxymethyl |
| 10 | 2,3-dihydro-benzofuran-2-ylmethoxymethyl |
| 11 | 2,3-dihydro-benzo[1,4]dioxin-2-ylmethoxymethyl |
| 12 | 8-fluoro-2,3-dihydro-benzo[1,4]dioxin-2-ylmethoxymethyl |
| 13 | 1-ethyl-2,3-dihydro-1H-indol-2-ylmethoxymethyl |
| 14 | 6-fluoro-4-methyl-3,4-dihydro-2H-benzo[1,4]oxazin-2-ylmethoxymethyl |
| 15 | 5-methyl-2,3-dihydro-benzofuran-2-ylmethoxymethyl |
| 16 | 7-methyl-2,3-dihydro-benzofuran-2-ylmethoxymethyl |
| 17 | 4-methyl-benzo[1,3]dioxol-2-ylmethoxymethyl |
| 18 | 5-methyl-benzo[1,3]dioxol-2-ylmethoxymethyl |
| 19 | 1-methyl-1H-indol-2-ylmethoxymethyl |

TABLE 44-continued
(I-A-1-30)
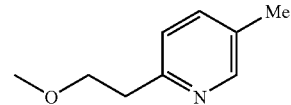
| No. | R⁵ |
|---|---|
| 20 | 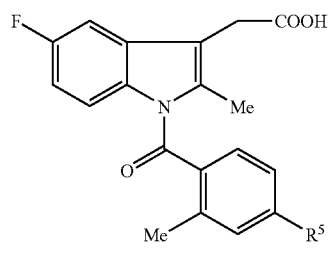 |
| 21 | 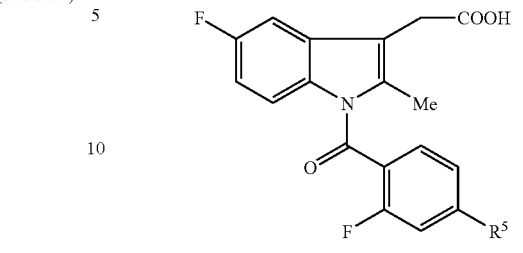 |
| 22 | 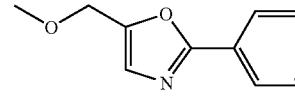 |
TABLE 45
(I-A-1-31)
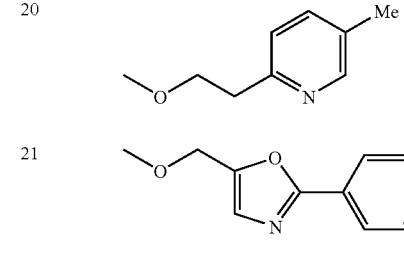
| No. | R⁵ |
|---|---|
| 1 | 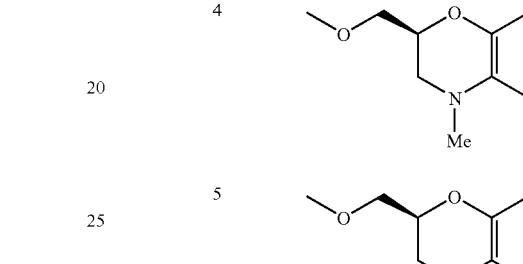 |
| 2 | 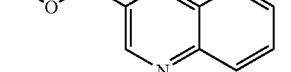 |
| 3 |  |
TABLE 45-continued
(I-A-1-31)
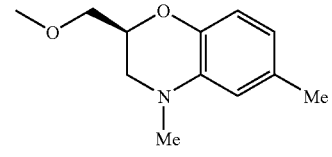
| No. | R⁵ |
|---|---|
| 4 | 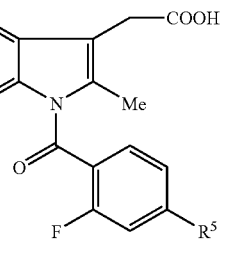 |
| 5 | 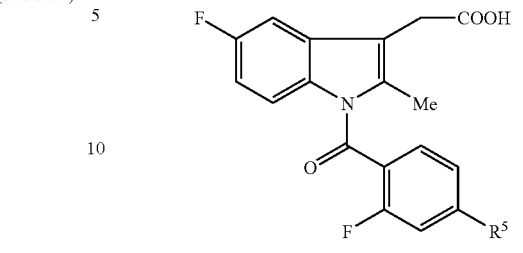 |
| 6 | 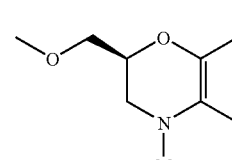 |
| 7 | 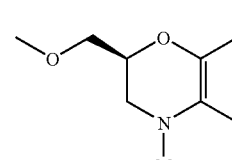 |
| 8 | 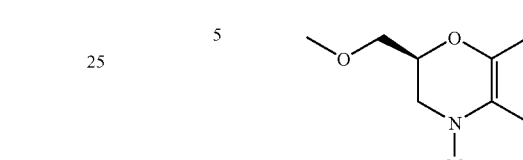 |
| 9 | 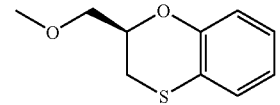 |
| 10 | 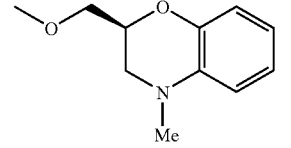 |
| 11 | 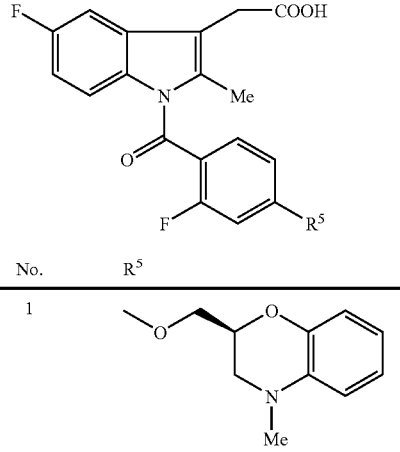 |

TABLE 45-continued (I-A-1-31)

| No. | R⁵ |
|---|---|
| 12 | 5-fluoro-1,3-benzodioxol-2-yl methoxymethyl |
| 13 | 2,3-dihydro-1,4-benzodioxin-2-yl methoxymethyl |
| 14 | 5-fluoro-2,3-dihydro-1,4-benzodioxin-2-yl methoxymethyl |
| 15 | (6-methylpyridin-2-yl)methoxyethyl |
| 16 | (3-methylpyridin-2-yl)methoxyethyl |
| 17 | 1-ethyl-2,3-dihydro-1H-indol-2-yl methoxymethyl |
| 18 | 2-phenylethoxymethyl |
| 19 | MeOCH₂CH₂OCH₂CH₂OMe (methoxyethoxyethyl methyl) |
| 20 | EtOCH₂CH₂CH₂Me |
| 21 | MeOCH₂CH₂CH₂OEt |

TABLE 46

(I-A-1-32)

| No. | R⁵ |
|---|---|
| 1 | 4-methyl-3,4-dihydro-2H-1,4-benzoxazin-2-yl methoxymethyl |
| 2 | 7-fluoro-4-methyl-3,4-dihydro-2H-1,4-benzoxazin-2-yl methoxymethyl |
| 3 | 4,7-dimethyl-3,4-dihydro-2H-1,4-benzoxazin-2-yl methoxymethyl |
| 4 | 4,6-dimethyl-3,4-dihydro-2H-1,4-benzoxazin-2-yl methoxymethyl |
| 5 | 7-methoxy-4-methyl-3,4-dihydro-2H-1,4-benzoxazin-2-yl methoxymethyl |
| 6 | 2,3-dihydro-1,4-benzoxathiin-2-yl methoxymethyl |
| 7 | 7-fluoro-2,3-dihydro-1,4-benzoxathiin-2-yl methoxymethyl |
| 8 | 2,3-dihydro-1-benzofuran-3-yl methoxymethyl |

TABLE 46-continued (I-A-1-32)

| No. | R⁵ |
|---|---|
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-2,3-dihydro-1,4-benzodioxine |
| 12 | 8-fluoro-2-(methoxymethyl)-2,3-dihydro-1,4-benzodioxine |
| 13 | 1-ethyl-2-(methoxymethyl)-2,3-dihydro-1H-indole |
| 14 | 6-fluoro-2-(methoxymethyl)-4-methyl-3,4-dihydro-2H-1,4-benzoxazine |
| 15 | 2-(methoxymethyl)-5-methyl-2,3-dihydrobenzofuran |
| 16 | 2-(methoxymethyl)-7-methyl-2,3-dihydrobenzofuran |
| 17 | 2-(methoxymethyl)-4-methyl-1,3-benzodioxole |
| 18 | 2-(methoxymethyl)-5-methyl-1,3-benzodioxole |
| 19 | 2-(methoxymethyl)-1-methyl-1H-indole |
| 20 | 2-(2-methoxyethyl)-5-methylpyridine |
| 21 | 5-(methoxymethyl)-2-phenyl-1,3-oxazole |
| 22 | 3-(methoxymethyl)quinoline |

TABLE 47

(I-A-1-33)

| No. | R⁵ |
|---|---|
| 1 | 4-methyl-2-(methoxymethyl)-3,4-dihydro-2H-1,4-benzoxazine |
| 2 | 7-fluoro-4-methyl-2-(methoxymethyl)-3,4-dihydro-2H-1,4-benzoxazine |
| 3 | 4,7-dimethyl-2-(methoxymethyl)-3,4-dihydro-2H-1,4-benzoxazine |
| 4 | 4,6-dimethyl-2-(methoxymethyl)-3,4-dihydro-2H-1,4-benzoxazine |
| 5 | 7-methoxy-4-methyl-2-(methoxymethyl)-3,4-dihydro-2H-1,4-benzoxazine |
| 6 | 2-(methoxymethyl)-3,4-dihydro-2H-1,4-benzoxathiine |
| 7 | 7-fluoro-2-(methoxymethyl)-3,4-dihydro-2H-1,4-benzoxathiine |
| 8 | 3-(methoxymethyl)-2,3-dihydrobenzofuran |

TABLE 47-continued (I-A-1-33)

| No. | R⁵ |
|---|---|
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-1,3-benzodioxole |
| 12 | 5-fluoro-2-(methoxymethyl)-1,3-benzodioxole |
| 13 | 2-(methoxymethyl)-2,3-dihydro-1,4-benzodioxine |
| 14 | 5-fluoro-2-(methoxymethyl)-2,3-dihydro-1,4-benzodioxine |
| 15 | 2-(2-methoxyethyl)-6-methylpyridine |
| 16 | 3-methyl-2-(2-methoxyethyl)pyridine |
| 17 | 1-ethyl-2-(methoxymethyl)-2,3-dihydroindole |

TABLE 47-continued (I-A-1-33)

| No. | R⁵ |
|---|---|
| 18 | methoxyethyl-phenyl |
| 19 | MeO-CH₂CH₂-O-Et |
| 20 | Et-O-CH₂CH₂-Me |
| 21 | propyl-O-Et |

TABLE 48

(I-A-1-34)

| No. | R⁵ |
|---|---|
| 1 | (2S)-2-(methoxymethyl)-4-methyl-3,4-dihydro-2H-1,4-benzoxazine |
| 2 | (2S)-2-(methoxymethyl)-7-fluoro-4-methyl-3,4-dihydro-2H-1,4-benzoxazine |
| 3 | (2S)-2-(methoxymethyl)-7-methyl-4-methyl-3,4-dihydro-2H-1,4-benzoxazine |

TABLE 48-continued (I-A-1-34)

| No. | R⁵ |
|---|---|
| 4 | (2S)-2-(methoxymethyl)-6-methyl-4-methyl-3,4-dihydro-2H-1,4-benzoxazine |
| 5 | (2S)-2-(methoxymethyl)-7-methoxy-4-methyl-3,4-dihydro-2H-1,4-benzoxazine |
| 6 | (2S)-2-(methoxymethyl)-2,3-dihydro-1,4-benzoxathiine |
| 7 | (2S)-2-(methoxymethyl)-7-fluoro-2,3-dihydro-1,4-benzoxathiine |
| 8 | (3S)-3-(methoxymethyl)-2,3-dihydrobenzofuran |
| 9 | (3S)-3-(methoxymethyl)-5-fluoro-2,3-dihydrobenzofuran |
| 10 | (2S)-2-(methoxymethyl)-2,3-dihydrobenzofuran |
| 11 | (2S)-2-(methoxymethyl)-2,3-dihydro-1,4-benzodioxine |

TABLE 48-continued (I-A-1-34)

| No. | R⁵ |
|---|---|
| 12 | 5-fluoro-2,3-dihydro-1,4-benzodioxin-2-yl methoxymethyl |
| 13 | 1-ethyl-2,3-dihydro-1H-indol-2-yl methoxymethyl |
| 14 | 6-fluoro-4-methyl-3,4-dihydro-2H-1,4-benzoxazin-2-yl methoxymethyl |
| 15 | 5-methyl-2,3-dihydrobenzofuran-2-yl methoxymethyl |
| 16 | 7-methyl-2,3-dihydrobenzofuran-2-yl methoxymethyl |
| 17 | 4-methyl-1,3-benzodioxol-2-yl methoxymethyl |
| 18 | 5-methyl-1,3-benzodioxol-2-yl methoxymethyl |
| 19 | 1-methyl-1H-indol-2-yl methoxymethyl |

TABLE 48-continued (I-A-1-34)

| No. | R⁵ |
|---|---|
| 20 | 5-methylpyridin-2-yl methoxyethyl |
| 21 | 2-phenyloxazol-5-yl methoxymethyl |
| 22 | quinolin-3-yl methoxymethyl |

TABLE 49

(I-A-1-35)

| No. | R⁵ |
|---|---|
| 1 | 4-methyl-3,4-dihydro-2H-1,4-benzoxazin-2-yl methoxymethyl |
| 2 | 7-fluoro-4-methyl-3,4-dihydro-2H-1,4-benzoxazin-2-yl methoxymethyl |
| 3 | 7-methyl-4-methyl-3,4-dihydro-2H-1,4-benzoxazin-2-yl methoxymethyl |

TABLE 49-continued (I-A-1-35)

| No. | R⁵ |
|---|---|
| 4 | 6-methyl-4-methyl-2-(methoxymethyl)-3,4-dihydro-2H-1,4-benzoxazin-2-yl |
| 5 | 7-methoxy-4-methyl-2-(methoxymethyl)-3,4-dihydro-2H-1,4-benzoxazin-2-yl |
| 6 | 2-(methoxymethyl)-2,3-dihydro-1,4-benzoxathiin-2-yl |
| 7 | 7-fluoro-2-(methoxymethyl)-2,3-dihydro-1,4-benzoxathiin-2-yl |
| 8 | 3-(methoxymethyl)-2,3-dihydrobenzofuran-3-yl |
| 9 | 5-fluoro-3-(methoxymethyl)-2,3-dihydrobenzofuran-3-yl |
| 10 | 2-(methoxymethyl)-2,3-dihydrobenzofuran-2-yl |
| 11 | 2-(methoxymethyl)-1,3-benzodioxol-2-yl |
| 12 | 5-fluoro-2-(methoxymethyl)-1,3-benzodioxol-2-yl |
| 13 | 2-(methoxymethyl)-2,3-dihydro-1,4-benzodioxin-2-yl |
| 14 | 5-fluoro-2-(methoxymethyl)-2,3-dihydro-1,4-benzodioxin-2-yl |
| 15 | 6-methyl-2-(2-methoxyethyl)pyridin-2-yl |
| 16 | 3-methyl-2-(2-methoxyethyl)pyridin-2-yl |
| 17 | 1-ethyl-2-(methoxymethyl)-2,3-dihydro-1H-indol-2-yl |
| 18 | 2-methoxyethylphenyl |
| 19 | 1-methoxy-2-ethoxyethane |
| 20 | 1-ethoxy-2-propane |
| 21 | 1-ethoxy-propane |

TABLE 50

(I-A-1-36)

| No. | R⁵ |
|---|---|
| 1 | (2-methoxymethyl-4-methyl-3,4-dihydro-2H-benzo[1,4]oxazin-7-yl) |
| 2 | (7-fluoro-2-methoxymethyl-4-methyl-3,4-dihydro-2H-benzo[1,4]oxazin-6-yl) |
| 3 | (2-methoxymethyl-4,7-dimethyl-3,4-dihydro-2H-benzo[1,4]oxazin-6-yl) |
| 4 | (2-methoxymethyl-4,6-dimethyl-3,4-dihydro-2H-benzo[1,4]oxazin-7-yl) |
| 5 | (2-methoxymethyl-7-methoxy-4-methyl-3,4-dihydro-2H-benzo[1,4]oxazin-6-yl) |
| 6 | (2-methoxymethyl-2,3-dihydro-benzo[1,4]thiazin-6-yl) |
| 7 | (7-fluoro-2-methoxymethyl-2,3-dihydro-benzo[1,4]thiazin-6-yl) |
| 8 | (3-methoxymethyl-2,3-dihydro-benzofuran-5-yl) |
| 9 | (5-fluoro-3-methoxymethyl-2,3-dihydro-benzofuran-6-yl) |
| 10 | (2-methoxymethyl-2,3-dihydro-benzofuran-5-yl) |
| 11 | (2-methoxymethyl-2,3-dihydro-benzo[1,4]dioxin-6-yl) |
| 12 | (5-fluoro-2-methoxymethyl-2,3-dihydro-benzo[1,4]dioxin-6-yl) |
| 13 | (1-ethyl-2-methoxymethyl-2,3-dihydro-1H-indol-5-yl) |
| 14 | (6-fluoro-2-methoxymethyl-4-methyl-3,4-dihydro-2H-benzo[1,4]oxazin-7-yl) |
| 15 | (2-methoxymethyl-5-methyl-2,3-dihydro-benzofuran-6-yl) |
| 16 | (2-methoxymethyl-7-methyl-2,3-dihydro-benzofuran-5-yl) |

TABLE 50-continued
(I-A-1-36)
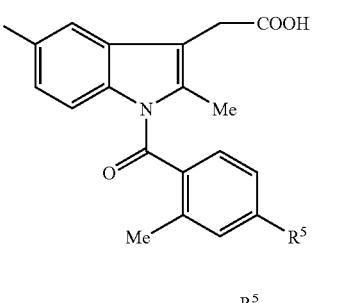
| No. | R⁵ |
|---|---|
| 17 | 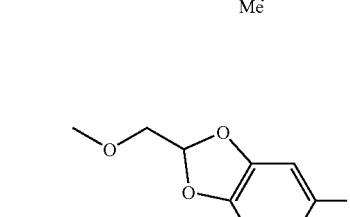 |
| 18 | 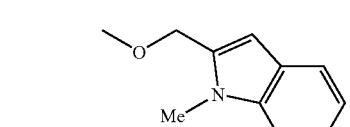 |
| 19 | 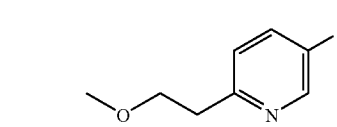 |
| 20 | 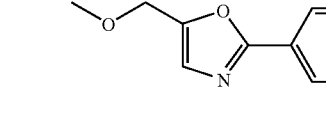 |
| 21 | 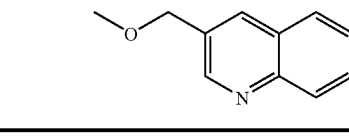 |
| 22 | 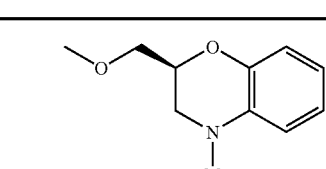 |
TABLE 51
(I-A-1-37)
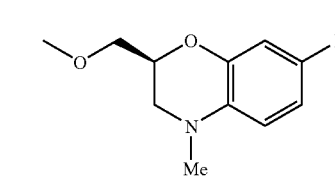
| No. | R⁵ |
|---|---|
| 1 | 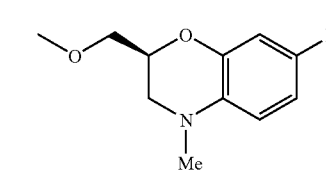 |
| 2 | 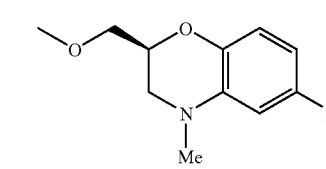 |
| 3 | 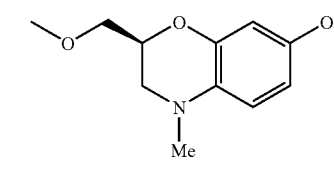 |
| 4 | 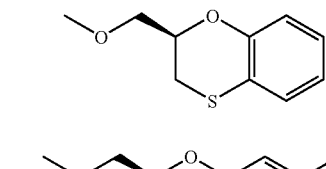 |
| 5 | 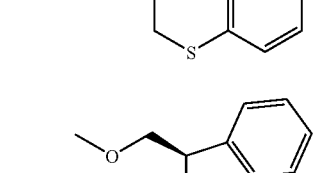 |
| 6 | 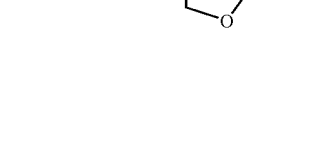 |
| 7 |  |
| 8 |  |

TABLE 51-continued (I-A-1-37)

[Structure: 5-chloro-1-(2-fluoro-4-R⁵-benzoyl)-2-methyl-1H-indol-3-yl acetic acid]

| No. | R⁵ |
|---|---|
| 9 | 5-fluoro-3-(methoxymethyl)-2,3-dihydrobenzofuran-3-yl |
| 10 | 2-(methoxymethyl)-2,3-dihydrobenzofuran-2-yl |
| 11 | 2-(methoxymethyl)-1,3-benzodioxol-2-yl |
| 12 | 5-fluoro-2-(methoxymethyl)-1,3-benzodioxol-2-yl |
| 13 | 2-(methoxymethyl)-2,3-dihydro-1,4-benzodioxin-2-yl |
| 14 | 5-fluoro-2-(methoxymethyl)-2,3-dihydro-1,4-benzodioxin-2-yl |
| 15 | 2-(2-methoxyethyl)-6-methylpyridin-... |
| 16 | 3-methyl-2-(2-methoxyethyl)pyridin-... |
| 17 | 1-ethyl-2-(methoxymethyl)-2,3-dihydro-1H-indol-2-yl |

TABLE 51-continued (I-A-1-37)

[Structure: 5-chloro-1-(2-fluoro-4-R⁵-benzoyl)-2-methyl-1H-indol-3-yl acetic acid]

| No. | R⁵ |
|---|---|
| 18 | 2-methoxyethylphenyl |
| 19 | CH₃OCH₂CH₂OCH₂CH₃ |
| 20 | CH₃CH₂OCH₂CH₂CH₃ |
| 21 | CH₃CH₂CH₂OCH₂CH₃ |

TABLE 52

(I-A-1-38)

[Structure: 5-chloro-1-(2-fluoro-4-R⁵-benzoyl)-2-methyl-1H-indol-3-yl acetic acid]

| No. | R⁵ |
|---|---|
| 1 | 2-(methoxymethyl)-4-methyl-3,4-dihydro-2H-1,4-benzoxazin-2-yl |
| 2 | 7-fluoro-2-(methoxymethyl)-4-methyl-3,4-dihydro-2H-1,4-benzoxazin-2-yl |
| 3 | 2-(methoxymethyl)-4,7-dimethyl-3,4-dihydro-2H-1,4-benzoxazin-2-yl |

TABLE 52-continued (I-A-1-38)

| No. | R⁵ |
|---|---|
| 4 | 6-methyl-4-methyl-2-(methoxymethyl)-3,4-dihydro-2H-1,4-benzoxazine |
| 5 | 7-methoxy-4-methyl-2-(methoxymethyl)-3,4-dihydro-2H-1,4-benzoxazine |
| 6 | 2-(methoxymethyl)-2,3-dihydro-1,4-benzoxathiine |
| 7 | 7-fluoro-2-(methoxymethyl)-2,3-dihydro-1,4-benzoxathiine |
| 8 | 3-(methoxymethyl)-2,3-dihydrobenzofuran |
| 9 | 5-fluoro-3-(methoxymethyl)-2,3-dihydrobenzofuran |
| 10 | 2-(methoxymethyl)-2,3-dihydrobenzofuran |
| 11 | 2-(methoxymethyl)-2,3-dihydro-1,4-benzodioxine |

TABLE 52-continued (I-A-1-38)

| No. | R⁵ |
|---|---|
| 12 | 5-fluoro-2-(methoxymethyl)-2,3-dihydro-1,4-benzodioxine |
| 13 | 1-ethyl-2-(methoxymethyl)-2,3-dihydro-1H-indole |
| 14 | 6-fluoro-4-methyl-2-(methoxymethyl)-3,4-dihydro-2H-1,4-benzoxazine |
| 15 | 5-methyl-2-(methoxymethyl)-2,3-dihydrobenzofuran |
| 16 | 7-methyl-2-(methoxymethyl)-2,3-dihydrobenzofuran |
| 17 | 4-methyl-2-(methoxymethyl)-1,3-benzodioxole |
| 18 | 5-methyl-2-(methoxymethyl)-1,3-benzodioxole |
| 19 | 1-methyl-2-(methoxymethyl)-1H-indole |

TABLE 52-continued
(I-A-1-38)
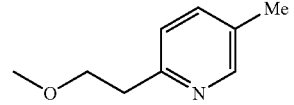
| No. | R⁵ |
|---|---|
| 20 | 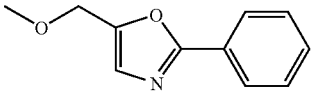 |
| 21 | 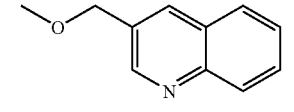 |
| 22 | 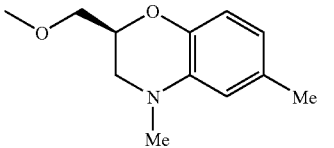 |
TABLE 53
(I-A-1-39)
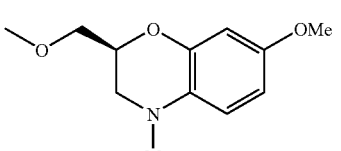
| No. | R⁵ |
|---|---|
| 1 | 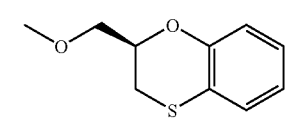 |
| 2 | 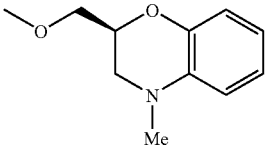 |
| 3 | 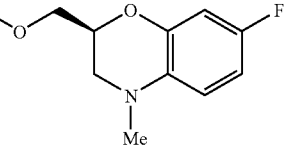 |
TABLE 53-continued
(I-A-1-39)
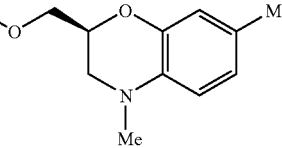
| No. | R⁵ |
|---|---|
| 4 | 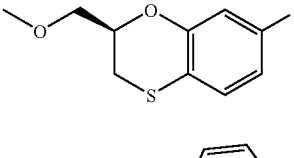 |
| 5 | 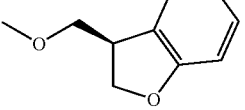 |
| 6 | 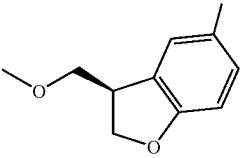 |
| 7 | 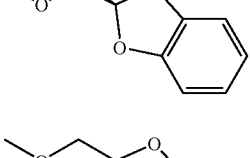 |
| 8 | 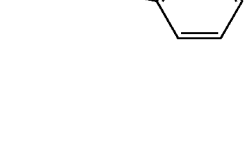 |
| 9 | |
| 10 | |
| 11 | |

TABLE 53-continued (I-A-1-39)

| No. | R⁵ |
|---|---|
| 12 | 5-fluoro-2-(methoxymethyl)-1,3-benzodioxole |
| 13 | (S)-2-(methoxymethyl)-2,3-dihydro-1,4-benzodioxine |
| 14 | (S)-5-fluoro-2-(methoxymethyl)-2,3-dihydro-1,4-benzodioxine |
| 15 | 2-(2-methoxyethyl)-6-methylpyridine |
| 16 | 3-methyl-2-(2-methoxyethyl)pyridine |
| 17 | 1-ethyl-2-(methoxymethyl)indoline |
| 18 | (2-methoxyethyl)benzene |
| 19 | MeOCH₂CH₂OEt |
| 20 | EtOCH₂CH₂Me |
| 21 | PrOEt |

TABLE 54

(I-A-1-40)

| No. | R⁵ |
|---|---|
| 1 | (S)-2-(methoxymethyl)-4-methyl-3,4-dihydro-2H-1,4-benzoxazine |
| 2 | (S)-7-fluoro-2-(methoxymethyl)-4-methyl-3,4-dihydro-2H-1,4-benzoxazine |
| 3 | (S)-2-(methoxymethyl)-4,7-dimethyl-3,4-dihydro-2H-1,4-benzoxazine |
| 4 | (S)-2-(methoxymethyl)-4,6-dimethyl-3,4-dihydro-2H-1,4-benzoxazine |
| 5 | (S)-7-methoxy-2-(methoxymethyl)-4-methyl-3,4-dihydro-2H-1,4-benzoxazine |
| 6 | (S)-2-(methoxymethyl)-2,3-dihydro-1,4-benzoxathiine |
| 7 | (S)-7-fluoro-2-(methoxymethyl)-2,3-dihydro-1,4-benzoxathiine |
| 8 | (S)-3-(methoxymethyl)-2,3-dihydrobenzofuran |

TABLE 54-continued (I-A-1-40)

| No. | R⁵ |
|---|---|
| 9 | 5-fluoro-2,3-dihydrobenzofuran-3-yl-CH₂-O-Me |
| 10 | 2,3-dihydrobenzofuran-2-yl-CH₂-O-Me |
| 11 | 2,3-dihydro-1,4-benzodioxin-2-yl-CH₂-O-Me |
| 12 | 5-fluoro-2,3-dihydro-1,4-benzodioxin-2-yl-CH₂-O-Me |
| 13 | 1-ethyl-2,3-dihydroindol-2-yl-CH₂-O-Me |
| 14 | 6-fluoro-4-methyl-3,4-dihydro-2H-benzo[1,4]oxazin-2-yl-CH₂-O-Me |
| 15 | 5-methyl-2,3-dihydrobenzofuran-2-yl-CH₂-O-Me |

TABLE 54-continued (I-A-1-40)

| No. | R⁵ |
|---|---|
| 16 | 7-methyl-2,3-dihydrobenzofuran-2-yl-CH₂-O-Me |
| 17 | 4-methyl-1,3-benzodioxol-2-yl-CH₂-O-Me |
| 18 | 5-methyl-1,3-benzodioxol-2-yl-CH₂-O-Me |
| 19 | 1-methylindol-2-yl-CH₂-O-Me |
| 20 | 5-methylpyridin-2-yl-CH₂CH₂-O-Me |
| 21 | 2-phenyloxazol-5-yl-CH₂-O-Me |
| 22 | quinolin-3-yl-CH₂-O-Me |

Processes for the Preparation of the Compound in the Present Invention:

The compound of the present invention represented by formula (I) may be prepared by the following processes and the processes shown in examples.

a) Among the compounds represented by formula (I), the compound that $R^6$ represents —$COR^6$ group and $R^1$ represents hydroxyl, that is, a compound represented by formula (IA)

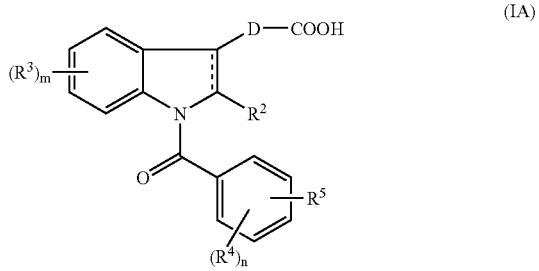

(IA)

wherein all symbols have the same meanings as described above may be prepared by the following method.

The compound represented by formula (IA) may be prepared by subjecting the compound represented by formula (II)

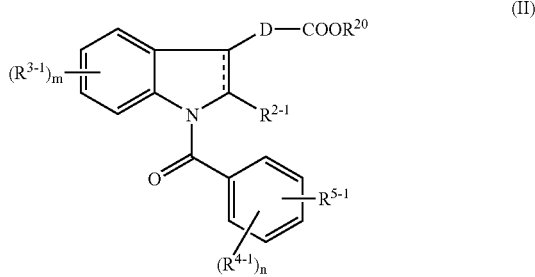

(II)

wherein $R^{20}$ in the formula represents allyl or benzyl group and $R^{2-1}$, $R^{3-1}$, $R^{4-1}$, and $R^{5-1}$ represent the same meaning as $R^2$, $R^3$, $R^4$ and $R^5$, and when protection of hydroxyl or amino group included in the group represented by $R^{2-1}$, $R^{3-1}$, $R^{4-1}$, and $R^{5-1}$ is necessary, it is considered to be protected. Other symbols represent the same meanings as described above to deprotection reaction of allyl group or benzyl group, and if necessary, deprotection reaction of protecting group.

A deprotection reaction of allylic ester, which is well known, may be reacted at temperature of 0–50° C., for example, in an organic solvent (dichloromethane, dimethyl formamide, tetrahydrofuran, dioxane, ethyl acetate, and ethanol, etc.), under the absence or presence of a trap reagent (tributyltin hydroxide, dimedon, morpholine, pyrrolidine, and 2-ethylhexanoic acid, etc.) and an organic acid(acetate, etc.), using a metal complex (tetrakis (triphenylphosphine) palladium(0), bis(triphenylphosphine) palladium(II) dichloride, palladium acetate(II), and tris(triphenylphosphine)rhodium(I) chloride, etc.).

A deprotection reaction of benzyl ester, which is well known, may be carried out at temperature of 0–200° C., for example, in a solvent(ether (tetrahydrofuran, dioxane, dimethoxyethane, and diethyl ether, etc.), alcohol (methanol and ethanol, etc.), benzene (benzene and toluene, etc.), ketones (acetone and methylethylketone, etc.), nitrile (acetonitrile etc.), amide (dimethylformamide etc.), water, ethyl acetate, acetate, or two or more mixed solvent(s) thereof, etc.), under the presence of a catalyst (palladium-carbon, palladium black, hydroxide palladium, platinum oxide, and raney nickel, etc.), atmospheric or pressurized hydrogen atmosphere, or formate ammonium.

Deprotection reactions of protecting groups may be carried out by the following methods.

The deprotection reactions of the protecting groups of hydroxyl or amino group are known well, for example, (1) alkaline hydrolysis, (2) a deprotection reaction under acid condition, (3) a deprotection reaction by hydrolysis, and (4) a deprotection reaction of silyl group, etc. are included.

These methods are concretely explained as follows, (1) The deprotection reaction by alkaline hydrolysis may be carried out at temperature of 0–40° C., for example, in an organic solvent (methanol, tetrahydrofuran, dioxane or these mixed solvents, etc.), using an alkali metal (sodium hydroxide, potassium hydroxide, and lithium hydroxide, etc.), an alkaline earth metal (barium hydroxide and calcium hydroxide, etc.), a carbonate (sodium carbonate and potassium carbonate, etc.), the solution, or these compounds.

(2) The deprotection reaction under acid condition may be carried out at temperature of 0–100° C., for example, under the presence or absence of an organic solvent (methylene chloride, chloroform, dioxane, ethyl acetate, anisole, methanol, ethanol, and isopropyl alcohol, etc.), or in the solution, an organic acid (acetate, trifluoroacetic acid, and methanesulfonic acid, etc.), an inorganic acid (hydrochloric acid and sulfate, etc.), or these compounds (hydrogen bromide/acetate etc.).

(3) The deprotection reaction by hydrolysis may be carried out at the temperature of 0–200° C., for example, in a solvent (ethers(tetrahydrofuran, dioxane, dimethoxyethane, and diethyl ether, etc.), alcohol (methanol and ethanol, etc.), benzenes (benzene and toluene, etc.), ketone (acetone and methyl ethyl ketone, etc.), nitriles (acetonitrile etc.), amide (dimethyl formamide etc.), water, ethyl acetate, acetate, or two or more mixed solvent(s) thereof, etc. ), under the presence of a catalyst (palladium-carbon, palladium black, hydroxide palladium, platinum oxide, and raney nickel, etc.), atmospheric or pressurized hydrogen atmosphere, or formate ammonium.

(4) The deprotection reaction of silyl group may be carried out at temperature of 0–40° C., for example, in water and an organic solvent (tetrahydrofuran and acetonitrile, etc.) that can be mixed, using tetrabutylammoniumfluoride.

As protecting groups of hydroxyl group, for example, methoxymethyl, 2-tetrahydropyranyl, tert-butyl dimethylsilyl, tert-butyl diphenyl silyl, acetyl, benzyl, and 4-methoxybenzyl group, etc. are included.

As protecting groups of amino group. for example, benzyloxycarbonyl, t-butoxycarbonyl, trifluoroacetyl, and 9-fluorenylmethoxycarbonyl group, etc. are included.

They only have to be a group that can be left easily and selectively except the above as protecting groups of hydroxyl or amino group, and are not especially limited. For example, the group described in T. W. Greene, Protective Groups in Organic Synthesis 3rd edition, Wiley, N.Y., (1999) may be used.

Though the persons skilled in the art can understand easily, the aimed compound of the present invention can be easily prepared by using these deprotection reactions properly.

b) Among the compounds represented by formula (I), a compound wherein $R^1$ represents —$COR^6$ and $R^6$ represents C1–6 alkoxy group, that is, the compound represented by formula (IB)

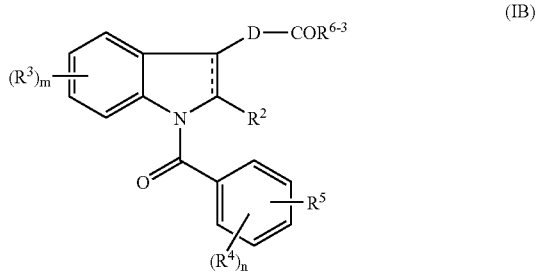

wherein $R^{6-3}$ represent C1–6 alkoxy group, and other symbols represent the same meaning as the described above may be prepared by the following method.

The compound represented by formula (IB) may be prepared by esterification of the compound represented by formula (III)

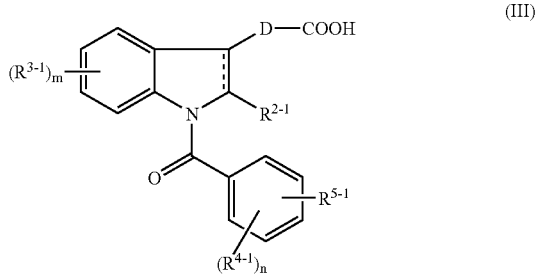

wherein all symbols have the same meanings as the above and the compound represented by formula (IV)

wherein $R^{21}$ represents C1–6 alkyl group, and then, if necessary by the deprotection of the protecting group.

As esterification reactions that are well-known, for example, (1) a method using acyl halide,
(2) a method using mixed acid anhydride, and
(3) a method using a condensing agent are included.

These methods are concretely explained as follows, (1) The method using acyl halide may be carried out, for example, by reacting carboxylic acid with acyl halide(oxalyl chloride or thionyl chloride, etc.) in an organic solvent (chloroform, methylene chloride, diethyl ether or tetrahydrofuran, etc.) or without a solvent at −20° C. to reflux temperature and then reacting the obtained acyl halide with alcohol in an inactive organic solvent (chloroform, methylene chloride, diethyl ether or tetrahydrofuran, etc.), under the presence of a tertiary amine (pyridine, triethyl amine, dimethyl aniline, dimethylaminopyridine or diisopropylethylamine, etc.) at 0–40° C. The method may be carried out by reacting with acyl halide in an organic solvent (dioxane, tetrahydrofuran) using an alkaline solution (sodium bicarbonate, sodium hydroxide, etc.) at 0–40° C.

(2) The method using mixed acid anhydride may be carried out, for example, by reacting carboxylic acid with acyl halide (epivaloyl chloride, tosyl chloride, mesyl chloride, etc.), or an acid derivative (ethyl chloroformate or isobutyl chloroformate, etc.) in an organic solvent (chloroform, methylene chloride, diethyl ether, tetrahydrofuran, etc.) or without a solvent, under the presence of a tertiary amine (pyridine, triethylamine, dimethylaniline, dimethylaminopyridine or diisopropylethylamine, etc.) at 0–40° C. and then reacting the obtained mixed acid anhydride with alchol in an organic solvent (chloroform, methylene chloride, diethyl ether or tetrahydrofuran, etc.) at 0–40° C.

(3) The method using a condensing agent may be carried out, for example, by reacting carboxylic acid with alchol in an organic solvent(chloroform, methylene chloride, dimethylformamide, diethyl ether or tetrahydrofuran, etc.), these mixed solvents, or without a solvent, under the presence or absence of a tertiary amine (pyridine, triethylamine, dimethylaniline or dimethylaminopyridine, etc.), using a condensing agent(1,3-dicyclohexyl carbodiimide (DCC), 1-ethyl-3-[3-(dimethylamino)propyl] carbodiimide (EDC), 1, 1'-carbodiimidazole (CDI), 2-chloro-1-methylpyridinium iodide, methanesulphonyloxybenzotriazole, 3-methyl-2-fluoropyridinium tosilate methyl or 1-propanephosphonic acid cyclic anhydride;PPA, etc.), with or without 1-hydroxybenzotiazole(HOBt), at 0–40° C.

It is suitable that the reaction described in (1), (2) and (3) may be carried out under an inert gas (argon and nitrogen, etc.) and water free condition.

The deprotection reaction of the protecting group may be carried out by the method similar to the above.

c) Among the compounds represented by formula (I), a compound wherein $R^1$ represents —$COR^6$ and $R^6$ represents —$NR^8R^9$, that is, the compound represented by formula (IC)

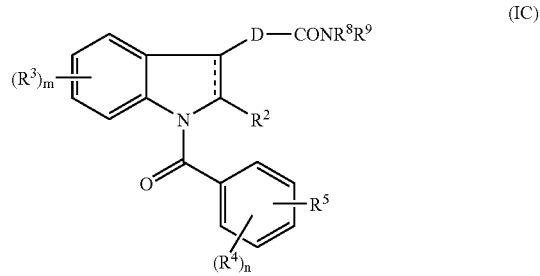

wherein all symbols represent the same meaning as the above may be prepared by the following method.

The compound represented by formula (IC) may be prepared by amidation reaction of the compound represented by formula (III) and a compound represented by formula (V)

wherein it is considered that hydroxyl or amino groups included in the group represented by $R^{8-1}$ and $R^{9-1}$ are optionally protected, and further, if necessary, by the deprotection of the protecting group.

As the amidation reactions that are well-known, for example, (1) a method using acyl halide,
(2) a method using mixed acid anhydride, and
(3) a method using a condensing agent are included.

These methods are concretely explained as follows.

(1) The method using acyl halide may be carried out, for example, by reacting carboxylic acid with acyl halide (oxalyl chloride or thionyl chloride, etc.) in an organic solvent (chloroform, methylene chloride, diethyl ether or tetrahydrofuran, etc.) or without a solvent at −20° C. to reflux temperature and then reacting the obtained acyl halide with amine in an inactive organic solvent (chloroform, methylene chloride, diethyl ether or tetrahydrofuran, etc.), under the presence of tertiary amine(pyridine, triethyl amine, dimethyl aniline, dimethylaminopyridine or diisopropylethylamine, etc.) at 0–40° C. The method may be carried out by reacting with the acyl halide in an organic solvent (dioxane, tetrahydrofuran) using an alkaline solution (sodium bicarbonate, sodium hydroxide, etc.) at 0–40° C.

(2) The method using a mixed acid anhydride may be carried out, for example, by reacting carboxylic acid with acyl halide (epivaloyl chloride, tosyl chloride, mesyl chloride, etc.), or an acid derivative (ethyl chloroformate or isobutyl chloroformate, etc.) in an organic solvent (chloroform, methylene chloride, diethyl ether, tetrahydrofuran, etc.) or without a solvent, under the presence of a tertiary amine(pyridine, triethylamine, dimethylaniline, dimethylaminopyridine or diisopropylethylamine, etc.), at 0–40° C. and then reacting the obtained mixed acid anhydride with amine in an organic solvent (chloroform, methylene chloride, diethyl ether or tetrahydrofuran, etc.) at 0–40° C.

(3) The method using a condensing agent may be carried out, for example, by reacting carboxylic acid with amine in an organic solvent(chloroform, methylene chloride, dimethylformamide, diethyl ether or tetrahydrofuran, etc.) or without a solvent, under the presence or absence of a tertiary amine(pyridine, triethylamine, dimethylaniline or dimethylaminopyridine, etc.), using a condensing agent(1,3-dicyclohexyl carbodiimide (DCC), 1-ethyl-3-[3-(dimethylamino)propyl] carbodiimide (EDC), 1, 1'-carbodiimidazole (CDI), 2-chloro-1-methylpyridinium iodide, methanesulphonyloxybenzotriazole, 3-methyl-2-fluoropyridinium tosilate methyl or 1-propanephosphonic acid cyclic anhydride; PPA, etc.), with or without 1-hydroxybenzotiazole(HOBt), at 0–40° C.

It is suitable that the reaction described in (1), (2) and (3) may be carried out under an inert gas (argon and nitrogen, etc.) and water free condition.

The deprotection reaction of the protecting group may be carried out by the method similar to the above.

d) Among the compounds represented by formula (I), a compound wherein $R^1$ represents —$CH_2OR^7$ and $R^7$ represents a hydrogen atom, that is, a compound represented by formula (ID)

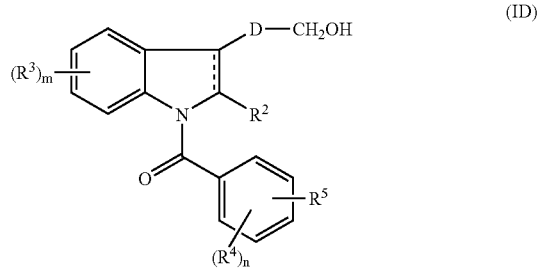

(ID)

wherein all symbols represent the same meaning as the described above may be prepared by the following method.

The compound represented by formula (ID) may be prepared by reductive reaction of the compound represented by formula (III), and then, if necessary, by the deprotection of the protecting group.

The reductive reaction, which is well-known, may be carried out at 0–80° C., for example, in an organic solvent (tetrahydrofuran etc.) using an borane complex(borane-tetrahydrofuran complex, and borane-dimethylsulfide complex, etc.) or by reacting carboxylic acid with the acid derivative chloro ethyl formate and chloro formate isobutyl, etc.) at 0–40° C. in an inert organic solvent (chloroform, methylene chloride, diethyl ether, and tetrahydrofuran, etc.) or without a solvent under the presence of tertiary amine (pyridine, triethylamine, dimethyl aniline, and dimethylaminopyridine, etc.), and further, reacting the obtained mixed acid anhydride at 0–40° C. in an inert organic solvent (chloroform, methylene chloride, diethyl ether, and tetrahydrofuran, etc.) using a reducing agent (sodium borohydride etc.).

The deprotection reaction of the protecting group may be carried out by the method similar to the above.

e) Among the compounds represented by formula (I), a compound wherein $R^1$ represents —$CH_2OR^7$ and $R^7$ represents C2–6 acyl group, that is, a compound represented by formula (IE)

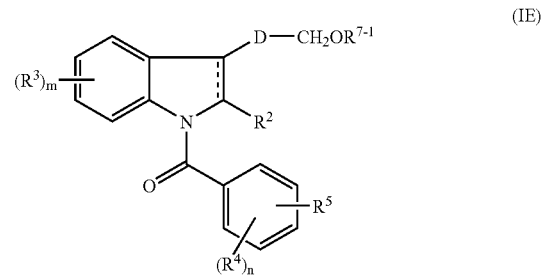

(IE)

wherein $R^{7-1}$ represents C2–6 acyl group, other symbols represent the same meaning as the described above may be prepared by the following method.

The compound represented by formula (IE) may be prepared by esterification reaction of the compound represented by formula (VI)

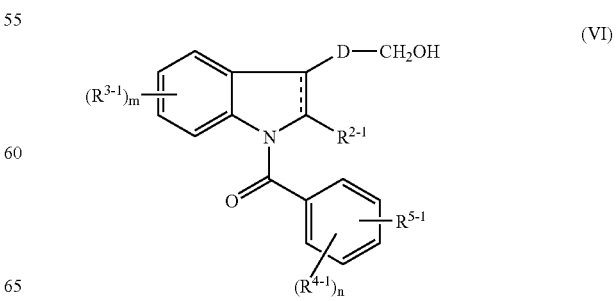

(VI)

wherein all symbols represent the same meaning as the described above and a compound represented by formula (VII)

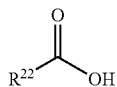
(VII)

wherein $R^{22}$ represents C1–5 alkyl group and then, if necessary, by the deprotection of the protecting group.

The esterification reaction and the deprotection reaction of the protecting group may be carried out by the method similar to the above.

f) among the compounds represented by formula (I), a compound wherein $R^1$ represents —$COR^6$ and $R^6$ represents C1–6 alkoxy or C2–6 alkenyloxy group, that is, a compound represented by formula (IF)

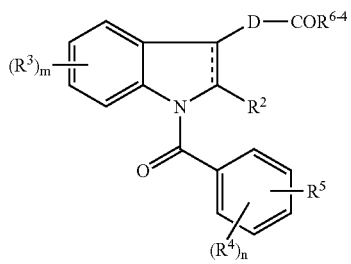
(IF)

wherein $R^{6-4}$ represents C1–6 alkoxy group substituted by phenyl or C2–6 alkenyloxy group, other symbols represent the same meaning as the described above may be prepared by the following method.

The compound represented by formula (IF) may be prepared by amidation reaction of a compound represented by formula (VIII)

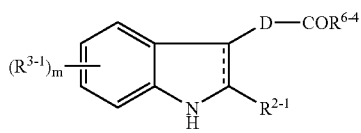
(VIII)

wherein all symbols represent the same meaning as the described above and a compound represented by formula (VII)

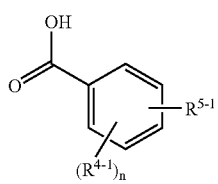
(IX)

wherein $R^{22}$ represents C1–5 alkyl group and then, if necessary, by the deprotection of the protecting group.

The amidation reaction and the deprotection reaction of the protecting group may be carried out by the method similar to the above.

Among the compounds represented by formula (IF), a compound wherein $R^5$ represents

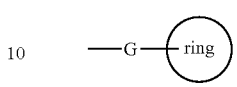

and G represents —O—(C1–5 alkylene)-, that is, a compound represented by formula (IF-1)

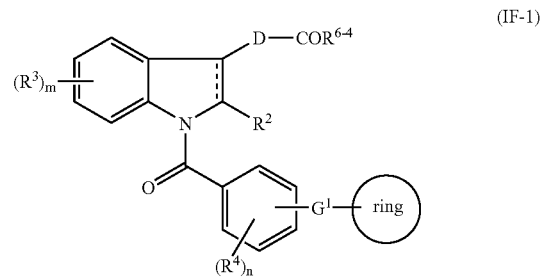
(IF-1)

wherein $G^1$ represents —O—(C1–5 alkylene)-, other symbols represent the same meaning as the described above may be prepared by the etherification reaction of a compound represented by formula (X)

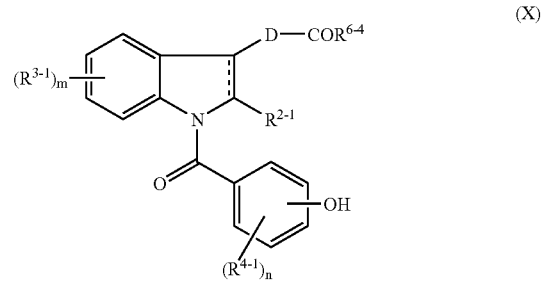
(X)

wherein all symbols represent the same meaning as the described above and a compound represented by formula (XI)

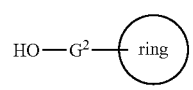
(XI)

wherein G2 represents C1–5 alkylene group, other symbols represent the same meaning as the above and then, if necessary, by the deprotection of the protecting group.

This etherification reaction, which is well-known, may be carried out at 0–60° C. by reacting with the corresponding alcohol compound, for example, in an organic solvent- (dichloromethane, diethyl ether, tetrahydrofuran, acetonitrile, benzene, and toluene, etc.) under the presence of an azo compound(diethyl azodicarboxylate (DEAD), azodicarboxylate diisopropyl, 1,1'-(azodicarbonyl)dipiperidine, 1,1'-azobis(N,N-dimethylformamide), etc.), and phosphine compounds (triphenylphosphine, tributylphosphine, trimethylphosphine, and polymer support triphenylphosphine, etc.).

The deprotection reaction of the protecting group may be carried out by the method similar to the above.

The compounds represented by formula (II), (IV), (V), (VII), (VIII), (IX), (X), and (XI) are well-known or may be easily prepared by a well-known method.

For example, the compound represented by formula (II) may be prepared by the method shown by the following reaction process 1 and 2.

For example, the compounds represented by formula (VIII) and (X) may be prepared by the method shown by the following reaction process 3 and 4.

$D^1$ represents a single bond or C1–6 alkylene group, $D^2$ represents C2–6 alkenylene group, $D^3$ represents C1–6 alkylene group, $R^{23}$ represents halogen atom or the hydroxyl, $R^{24}$ represents the protecting group of hydroxyl, and other symbols represent the same meaning as the described above in the reaction process.

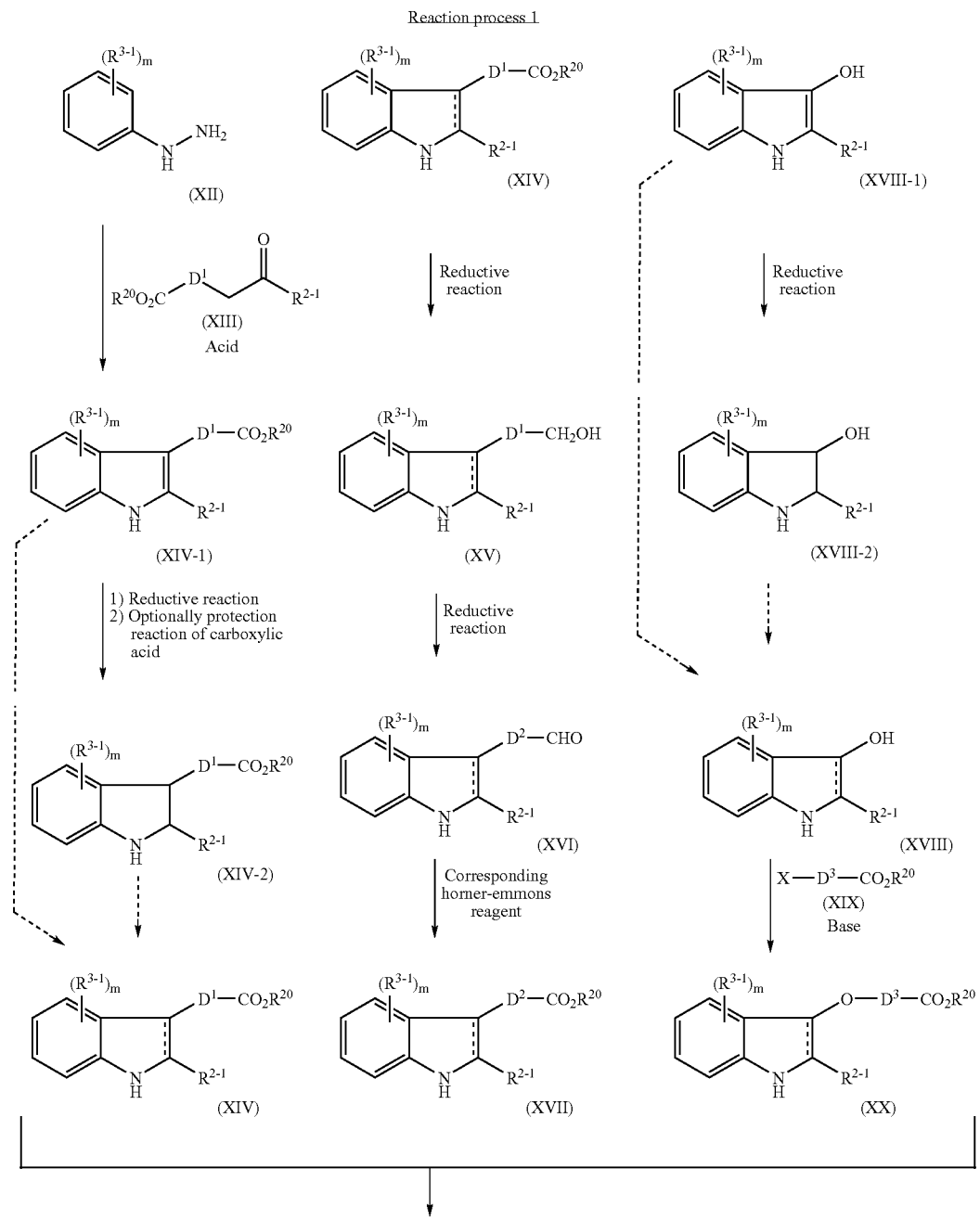

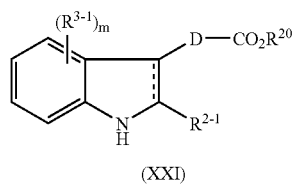
(XXI)
Reaction process 2
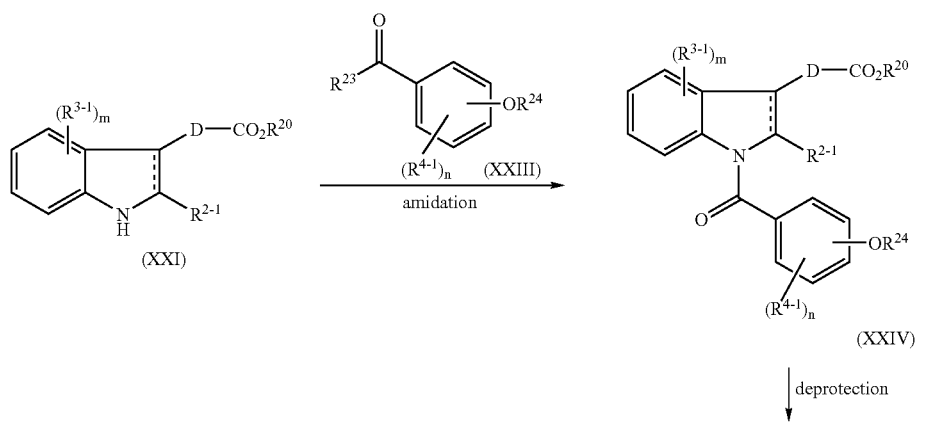
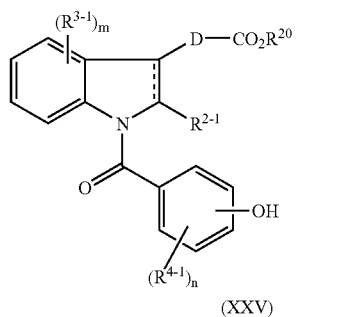
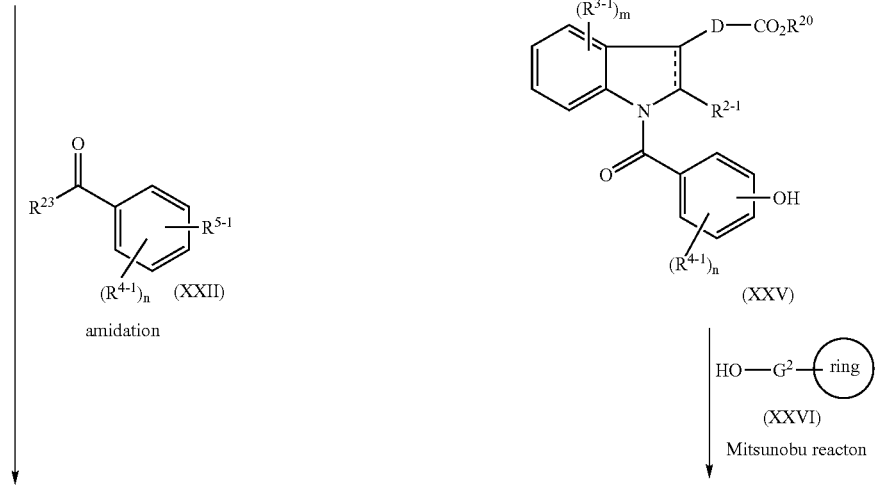
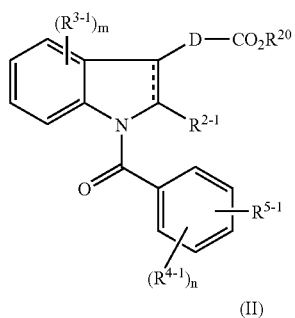
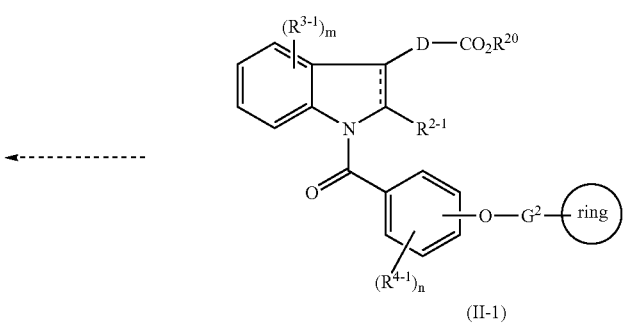

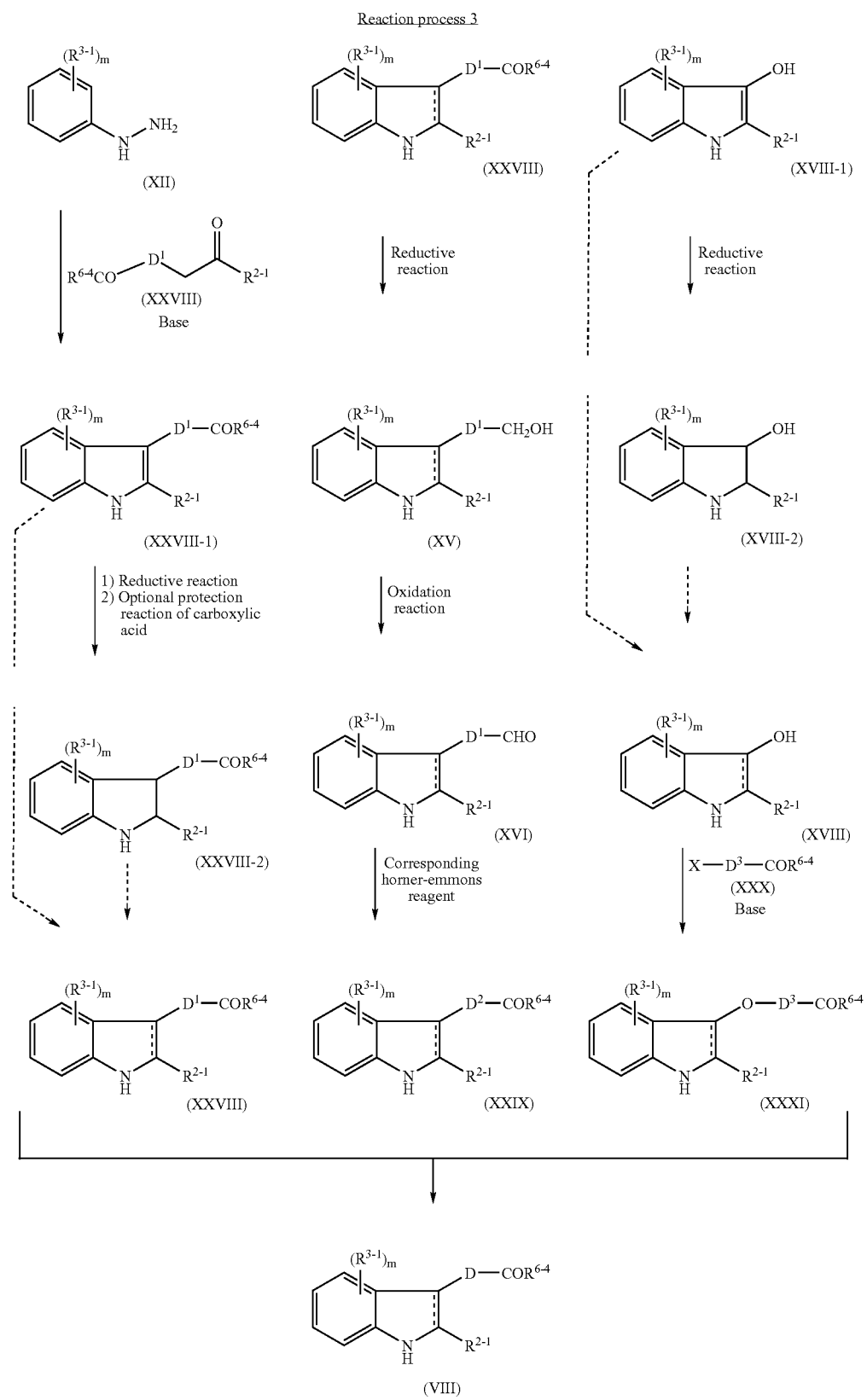

Reaction process 4

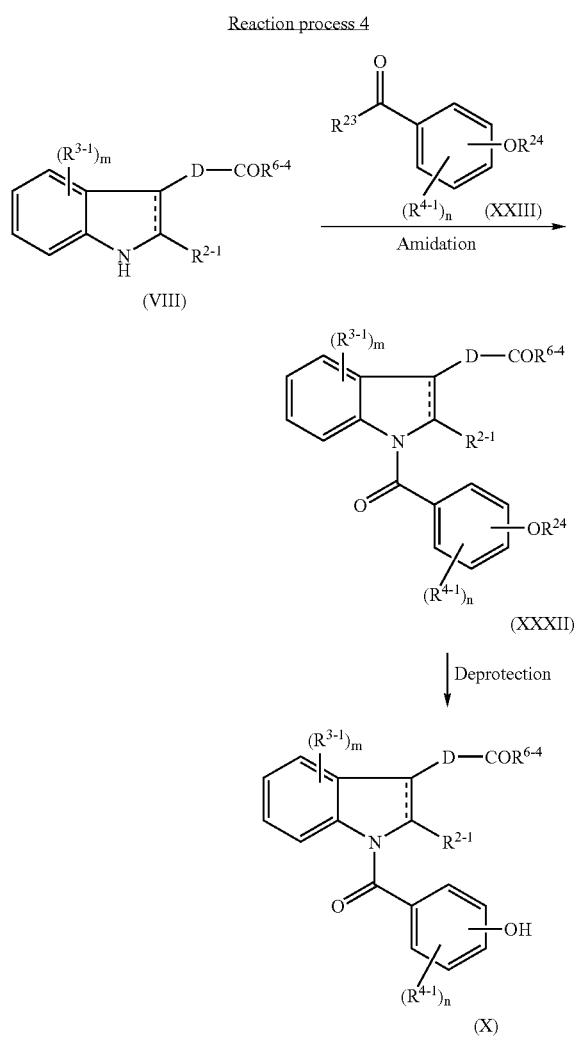

In the reaction process 1 to 4, the compounds represented by formula (XII), (XIII), (XVIII-1), (XIX), (XXII), (XXIII), (XVI), (XVII) and (XXX), which are used as starting materials, are well-known or may be easily prepared by a well-known method.

For example, the compound represented by formula (XIV-1) may be prepared according to a method described in Tetrahedron., 30, 1445–1455 (1974).

The reaction product may be purified by usual purification methods, for example, distillation and silicagel under normal or reduced pressure, high performance liquid chromatography, thin layer chromatography or column chromatography that used magnesium trisilicate, or wash and recrystallization, etc. The purification may be carried out at each reaction or after some reactions.

Pharmacological Activities:

The compound of the present invention represented by formula (I) potently binds to a DP receptor and shows an antagonistic activity. This effect was confirmed by the following receptor binding test using prostanoid receptor-expressing cells.

(i) Receptor Binding Test Using Prostanoid DP Receptor-expressing Cells

CHO cells expressing mouse DP receptors were prepared according to the method of Hirata et al. (*Proc. Natl. Acad. Sci.*, 91, 11192–11196 (1994)) and used as a membrane standard.

A reaction solution (200 μL) containing the prepared membrane standard (30–166 μg) and $^3$H-PGD$_2$ was incubated at room temperature for 20 minutes. The reaction was stopped with an ice-cold buffer (1 mL) and the binding $^3$H-PGD$_2$ was trapped in on a glass filter by immediate aspiration-filtration under a reduced pressure, and its binding radioactivity was measured using a liquid scintillation counter.

Kd value and Bmax value were obtained from Scatchard plots (*Ann. N. Y. Acad. Sci.*, 51, 660 (1949)]. Non-specific binding was obtained as the binding radioactivity in the presence of unlabeled PGD$_2$ at an excess amount (10 μmol/L). $^3$H-PGD$_2$ binding inhibition by the compound of the present invention was measured by adding $^3$H-PGD$_2$ (2.5 nmol/L) and the compound of the present invention as various concentrations. Also, the following buffers were used for the reactions.

Incubation Buffer:
  HEPES-NaOH (25 mmol/L, pH 7.4)
  EDTA (1 mmol/L)
  MgCl$_2$ (5 mmol/L)
  MnCl$_2$ (10 mmol/L)

Buffer for Washing:
  Tris-HCl (10 mmol/L, pH 7.5)
  NaCl (0.1 mol/L)
  Bovine serum albumin (0.01%)

The dissociation constant (Ki) (μmol/L) of each compound was obtained by the following equation.

$$Ki = IC_{50}/(1+([L^*]/Kd))$$

[L*]: Concentration of radioligand
The result is shown in table 55.

TABLE 55

| Example No | DP Ki (μM) |
|---|---|
| 4 (4) | 0.0074 |

As shown in the above results, it is apparent that the compound of the present invention potently binds to DP receptor.

(ii) DP antagonistic activity assay using prostanoid DP receptor-expressing cells may be examined by the following method.

CHO cells expressing mouse DP receptor were prepared, inoculated onto a 24-well microplate at 10$^5$ cells/well, followed by culturing for 2 days, and used for the assay. Each well was washed with 500 μL of MEM (minimum essential medium), and 450 μL of assay medium (MEM containing 1 mmol/L IBMX, 2 μmol/L diclofenac and 0.1 or 1% BSA), followed by incubation at 37° C. for 10 minutes. Then, an assay medium (50 μL) containing PGD$_2$ alone or PGD$_2$ with a compound of the present invention was added thereto to start the reaction, and after the reaction at 37° C. for 10 minutes, 500 μL of ice-cold trichloroacetatic acid (TCA) (10% w/v) was added thereto to stop the reaction. The reaction solution was frozen once (−80° C.) and thawed, and cells were peeled using a scraper, followed by centrifugation at 13,000 rpm for 3 minutes. The cAMP concentration was measured with a cAMP assay kit using the resulting supernatant. That is, [$^{125}$I]-cAMP assay kit buffer was added to 125 μL of the supernatant to give a total amount of 500 μL, and the resulting mixture was mixed with 1 mL of a chloroform solution of 0.5 mol/L tri-n-octylamine. Trichloroacetic acid (TCA) was extracted to the chloroform layer and removed, the cAMP amount in a sample was determined using the aqueous layer as the sample according to the method described in the [$^{125}$I]cAMP assay kit.

Also, with regard to the antagonistic activity (IC$_{50}$) of the test compound, the IC$_{50}$ value was calculated as an inhibition rate based on the reaction at 100 nM which was a concentration showing submaximal cAMP production by PGD$_2$ alone.

Toxicity:

The toxicity of the compound represented by formula (I) of the present invention is very low so that it is confirmed that the compound is sufficiently safe for using as a pharmaceutical.

INDUSTRIAL APPLICABILITY

Application to Pharmaceuticals:

Since the compound represented by formula (I) in the present invention binds and is antagonistic to PGD$_2$ receptor, especially DP receptor, it is considered to be useful for the prevention and/or treatment of diseases, for example, allergic diseases (allergic rhinitis, allergic conjunctivitis, atopic dermatitis, bronchial asthma, food allergy, etc.), systemic mastocytosis, disorders due to systemic mastocyte activation, anaphylactic shock, bronchoconstriction, urticaria, eczema, allergic bronchopulmonary aspergillosis, paranasal sinusitis, migraine, nasal polyp, hypersensitive angitis, eosinophilia, contact dermatitis, diseases accompanied with itching (such as atopic dermatitis, urticaria, allergic conjunctivitis, allergic rhinitis, contact dermatitis, etc.), secondary diseases (such as cataracta, retinodialysis, inflammation, infection, dysgryphia, etc.) generated by behaviors caused by itching(scratching behaviors, beating, etc.), inflammation, chronic obstructive pulmonary disease, ischemic reperfusion disorder, cerebrovascular disorder, pleuritis complicated by rheumatoid arthritis, ulcerative colitis and the like. Moreover, it is considered to relate to sleeping and platelet aggregation and to be useful for these diseases.

Since a compound that weakly binds with receptors other than DP receptor doesn't appear other actions, it is a possibility to become a medicine having a little side reaction.

Since the compound represented by formura (I) in the present invention binds to CRTH2 receptor and it expected to be antagonistic to the biological activity, it is considered to be useful for the prevention and/or treatment of diseases, allergic diseases, for example, allergic rhinitis, allergic conjunctivitis, atopic dermatitis, bronchial asthma, and food allergy, etc., systemic mastocytosis, disorders due to systemic mastocyte activation, bronchoconstriction, urticaria, eczema, psoriasis, allergic bronchopulmonary aspergillosis, paranasal sinusitis, nasal polyp, hypersensitive angitis, eosinophilia, contact dermatitis, diseases accompanied with itching such as atopic dermatitis, urticaria, allergic conjunctivitis, allergic rhinitis, contact dermatitis, etc., secondary diseases such as cataracta, retinodialysis, inflammation, infection, dysgryphia, etc. generated by behaviors caused by itching(scratching behaviors, beating, etc.), inflammation, chronic obstructive pulmonary disease, ischemic reperfusion disorder, cerebrovascular disorder, pleuritis complicated by rheumatoid arthritis, osteoarthrosis, crohn disease, ulcerative colitis and the like.

The compound represented by formula (I) may be administered as other concomitant drug combining with other medicines, in order to 1) supplement and/or reinforce the prophylactic and/or therapeutic effect of the compounds,
2) improve the movement and absorption of the compounds, and to decrease the dosage, and/or
3) reduce the side effects of the compounds.

A combind drug with the compound represented by formula (I) and other medicine may be administered in the compounding agent that mixes both elements in a formulation or in the form administered as separate formulation. In the form administered as separate formulation, the different and simultaneous administration are included. In the different administration, the compound represented by formula (I) may be previously administered, followed by other medicines, or other medicines may be previously administered, followed by the compound represented by formula (I). Each medication method may be different or same.

Illnesses that the prophylactic and/or therapeutic effects of the above combind drugs can be expected, which only has to be one that the prophylactic and/or therapeutic effects of the compound represented by formula (I) is/are supplemented and/or reinforced, are not limited especially.

As other medicines to supplement and/or reinforce the prophylactic and/or therapeutic effects of the compounds represented by the formula (I) on allergic rhinitis, for example, antihistamine agents, mediator release inhibitors, thromboxane synthesis enzyme inhibitors, thromboxane A2 receptor antagonists, leukotriene receptor antagonists, steroid drugs, alpha-adrenergic receptor agonists, xanthine derivatives, cholinergic-blocking agents, and nitric oxide synthase inhibitors, etc. are included.

As other medicines to supplement and/or reinforce the prophylactic and/or therapeutic effects of the compounds represented by the formula (I) on allergic conjunctivitis, for example, leukotriene receptor antagonists, antihistamine agents, mediator release inhibitors, nonsteroidal anti-inflammatory drugs, prostaglandins, steroid drugs, and nitric oxide synthase inhibitors, etc. are included.

As antihistamine agents, for example, ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, lolatadine, desloratadine, olopatadine hydrochloride, TAK-427, ZCR-2060, NIP-530, mometasone furoate, mizolastine, BP-294, andolast, auranofine, and acribastin, etc. are included.

As mediator release inhibitiors, for example, tranilast, sodium cromoglycate, amlexanox, repirinast, ibudilast, tazanolast, and pemirolast potassium, etc. are included.

As thromboxane synthesis enzyme inhibitors, for example, ozagrel hydrochloride and imitrodast sodium, etc. are included.

As thromboxane A2 receptor antagonists, for example, seratrodast, ramatroban, domitroban calcium hydrate, and KT-2-962, etc. are included.

As leukotriene receptor antagonist, for example, pranlukast hydrate, montelukast, zafirlukast, MCC-847, KCA-757, CS-615, YM-158, L-740515, CP-195494, LM-1484, RS-635, A-93178, S-36496, BIIL-284, and ONO-4057, etc. are included.

In steroid drugs, for example, as drugs for external use, clobetasol propionate, diflorazone diacetate, fluocinonide, mometasone furancarboxylate, betamethasone dipropionate, betamethasone butyrate propionate, betamethasone valerate, difluprednate, budesonid, diflucortolone valerate, amcinonide, halcinonide, dexamethasone, dexamethasone propionate, dexamethason valerate, dexamethasone acetate, hydrocortisone acetate, hydrocortisone butyrate, hydrocortisone butyrate propionate, deprodone propionate, prednisolone valerate-acetate, fluocinolone acetonide, beclometasone dipropionate, triamcinolone acetonide, flumetasone pivalate, alclometasone propionate, clobetasone butyrate, prednisolone, beclomethasone propionate, and fludroxycortide, etc. are included.

As internal medicines and injections, cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, sodium methylprednisolone succinate, triamcinolone, triamcinolone diacetate, triamcinolone acetonide, dexamethasone, dexamethasone acetate, dexamethasone sodium phosphate, dexamethasone palmitate, paramethasone acetate, and betamethasone, etc. are included.

As inhalants, beclometasone dipropionate, fluticasone propionate, budesonide, flunisolide, triamcinolone, ST-126P, ciclesonide, dexamethasone palmitate, mometasone furancarboxylate, prasterone sulfonate, deflazacort, methylprednisolone suleptanate, and methylprednisolone sodium succinate, etc. are included.

As xanthine derivatives, for example, aminophylline, theophylline, doxophylline, cipamfylline, and diprophylline, etc. are enumerated.

As cholilytic drugs, for example, ipratropium bromide, oxitropium bromide, flutropium bromde, cimetropium bromide, temiverine, tiotropium bromide, and revatropate (UK-112166), etc. are enumerated.

As non-steroidal anti-inflammatory drugs, for example, sasapyrine, sodiumsalicylate, aspirin, aspirin dialuminates combination, diflunisal, indomethacin, suprofen, ufenamate, dimethylisopropylazulene, bufexamac, felbinac, diclofenac, tolmetin sodium, clinoril, fenbufen, nabumetone, puroglumetacine, indomethacin farnesyl, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, aluminoprophen, zaltoprofen, mefenamic acid, mefenamic acid aluminum, tolfenamic acid, floctafenine, ketophenylbutazone, oxyphenbutazone, piroxicam, tenoxicam, ampiroxicam, napageln ointment, epirizole, tiaramide hydrochloride, tinoridine hydrochloride, emorfazone sulpyrine, migrenin, saridon, sedes G, amipylo-N, sorbon, pyrine drug for common cold, acetaminophen, phenacetin, dimetotiazine mesilate, simetride combination drug, and non-pyrine drug for common cold, etc. are included.

As prostaglandins (hereafter, abbreviated with PG), PG receptor agonists and PG receptor antagonist, etc. are included.

As PG receptor, PGE receptor (EP1, EP2, EP3, EP4), PGD receptor (DP, CRTH2), PGF receptor (FP), PGI receptor (IP), and TX receptor (TP), etc. are included.

Mass ratio of the compound represented by the formula (I) to other medicine is not especially limited.

Other medicines may be administered combining with two arbitrary kinds or more.

In other medicines that supplement and/or reinforce prophylactic and/or therapeutic effects of the compounds represented by the formula (I), not only one that has been found by present according on the above mechanism but also one that will be found in the future are included.

To use the compound represented by formula (I) or non-toxic salt thereof, or a combind drug containing the compound represented by formula (I) and other medicines by the above purpose, it is usually administered systemically or locally, and orally or parenterally.

The dosage is determined depending on age, body weight, symptom, therapeutic effect, administration route, duration of the treatment and the like. Generally, 1 mg to 1000 mg per adult is orally administered once to several times per day, or 1 mg to 100 mg per adult is parenterally administered (preferably, nose drop, ophthalmic solution, ointment) once to several times per day, or intravenously administered for 1 to 24 hours per day, continuously.

Since the dose changes depending on various conditions as described above, there are cases in which doses lower than or greater than the above ranges may be used.

When the compound represented by the formula (I) or the combind drug containing it and other medicines are administered, they are used as solid medicines, liquid medicines, and other compositions for internal use, and injections, external preparations, and suppositoriums, etc. for parenteral administration.

The solid compositions for oral administration include compressed tablets, pills, capsules, dispersing powders, granules, etc.

The capsules include hard capsules and soft capsules.

In such solid compositions, one or more active compound(s) is/are mixed with at least one inert diluent such as lactose, mannitol, glucose, hydroxypropyl cellulose, microcrystalline cellulose, starch, polyvinyl pyrrolidone or magnesium metasilicate aluminate. The compositions may also contain additional substances other than inert diluents, for example, lubricating agents such as magnesium stearate, disintegrating agents such as cellulose calcium glycolate, stabilizers such as lactose and solubilizers such as glutamic acid or asparatic acid according to usual methods. The tablets or pills may, if desired, be coated with film of gastric or enteric coating agents such as sugar, gelatin, hydroxypropyl cellulose or hydroxypropyl cellulose phthalate, or be coated with two or more films. Furthermore, capsules of absorbable materials such as gelatin are included.

The liquid compositions for oral administration include pharmaceutically acceptable emulsions, solutions, syrups and elixirs. In such liquid compositions, one or more active compound(s) is/are contained in inert diluents commonly used (purified water and ethanol, etc.). Furthermore, these compositions may also contain wetting agents, adjuvants such as suspending agents, sweetening agents, flavoring agents, perfuming agents, and preserving agents besides inert diluents.

Other compositions for oral administration include sprays that are prepared by known methods, and one or more active compound(s). These compositions may contain stabilizing agents such as sodium hydrogen sulfate, buffers to give isotonicity, and isotonic solutions such as sodium chloride, sodium citrate or citric acid besides inert diluents. Processes for preparing the sprays have been described in U.S. Pat. Nos. 2,868,691 and 3,095,355.

The injections for parenteral administration include sterile aqueous and/or non-aqueous solutions, suspensions and emulsions. The aqueous solutions or suspensions include, for example, distilled water for injection and a physiological salt solution. The non-aqueous solutions or suspensions include propylene glycol, polyethylene glycol, plant oil such as olive oil, alcohol such as ethanol, POLYSORBATE 80(registered trade mark), and the like. They may be used mixing sterile aqueous or non-aqueous solutions, suspensions and emulsions. These compositions may contain preserving agents, wetting agents, emulsifying agents, dispersing agents, stabilizing agents(for example, lactose), and adjuvants such as solubilizer(glutamic acid and aspartic acid, etc.). These may be sterilized by filtrating through a bacteria-retaining filter, mixing with antimicrobial agents, or irradiation. These may also be manufactured, for example, by making to be aseptic or dissolving to aseptic distilled water for injection or other solvents before use of sterile solid compositions.

As dosage forms of the ophthalmic solution for parenteral administration, ophthalmic solutions, ophthalmic suspensions, ophthalmic emulsions, ophthalmic solutions dissolved time of use, and ophthalmic ointment are included.

These ophthalmic solutions are manufactured based on a well-known method. For example, the ophthalmic solutions are made with tonicity agents (sodium chloride and concentrated glycerin, etc.), buffers (sodium phosphate and sodium acetate, etc.), surfactants (polysorbate 80 (trade name), polyoxyl 40 stearate, and polyoxyethylene hydrogenated castor oil, etc.), stabilizers (sodium citrate and disodium edetate, etc.), and preservatives (benzalkonium chloride and paraben, etc.), etc., which are properly selected, if necessary. These are sterilized in the final process or manufactured by the aseptic manipulation.

Inhalants for parenteral administration may include aerosol agents, inhalant powders or inhalant liquids, which may be used by being dissolved or suspended in water or other suitable media before using.

The inhalants are manufactured acccording on a well-known method.

For example, inhalant liquids are prepared properly selecting, if necessary, preservatives(benzalkonium chloride and paraben, etc.), coloring agents, buffers(sodium phosphate and sodium acetate, etc.), tonicity agents(sodium chloride and concentrated glycerin, etc.), thickeners(carboxyvinyl polymer, etc.), and absorption enhancers, etc.

Inhalant powders are prepared properly selecting, if necessary, lubricants (stearic acid and the salt, etc.), binders (starch and dextrin, etc.), fillers (lactose and cellulose, etc.), coloring agents, preservatives (benzalkonium chloride and paraben, etc.), and absorption enhancers, etc.

When the inhalant liquid is administered, a sprayer (atomizer and nebulizer) is usually used, and when the inhalant powder is administered, an inhalation administering machine for powder is usually used.

As other compositions for parenteral administration, liquids for external use, ointments, liniments, suppositories for intrarectal administration, and pessaries for administering in vagina, which contain one or more activators and are prescribed with common procedure, are included.

BEST MODE FOR CARRYING OUT THE INVENTION

The following reference examples and examples illustrate the present invention, but do not limit the present invention.

The solvents in the parentheses in chromatographic separations or TLC show the developing or eluting solvents and the ratio shows volume ratio. The solvents in the parentheses in NMR show the solvents for measurement.

MS represents a trimethylsilyl group, and Bn represents a benzyl group.

Reference Example 1

N-formyl-2-fluoroaniline

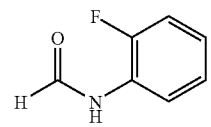

Under argon gas, formate (6.1 mL) was added to acetic anhydride (15.5 mL) at 0° C. and the mixture was stirred at 50° C. for 2 hours. The reaction mixture was cooled to room temperature and diluted with tetrahydrofuran (10 mL). Tetrahydrofuran (20 mL) solution containing 2-fluoroaniline (5.56 g) was added into the diluent at room temperature and stirred at room temperature for 1 hour. A title compound having the following physical properties was obtained by concentrating the reaction mixture. The obtained title compound was used for the following reaction without further purification.

TLC: Rf 0.70(hexane:ethyl acetate=2:1).

Reference Example 2

N-methyl-2-fluoroaniline

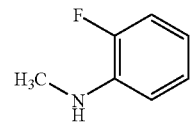

Borane tetrahydrofuran complex (1M tetrahydrofuran solution; 125 mL) were added into anhydrous tetrahydrofuran (25 mL) solution containing the compound prepared according to reference example 1 at 0° C., which was stirred at 50° C. for 2 hours. The reaction mixture was cooled to room temperature, in ice bath, methanol (30 mL) and 4N hydrogen chloride dioxane solution (10 mL) are added into the mixture and stirred at 60° C. for 1 hour. The reaction mixture was concentrated and added into 2N sodium hydroxide solution, and then extracted with ethyl acetate. The extract was washed with saturated brine and dried by sulfuric anhydride sodium. The solution was filtered by celite (registered trademark) and the filtrate was concentrated. The mixed solvent (hexane:ethyl acetate=10:1) was added to the residue, followed by be filtered on silicagel. A title compound (6.45 g) having the following physical properties was obtained by concentrating the effluent.

TLC: Rf 0.85(hexane:ethyl acetate=5:1);

NMR(CDCl$_3$):δ 7.00–6.91 (m, 2H), 6.80–6.55 (m, 2H), 3.90 (br.s, 1H), 2.82 (s, 3H).

Reference Example 3

(2S)-3-(N-(2-fluorophenyl)-N-methylamino)-1,2-propanediol

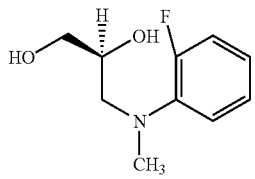

Under argon gas, a mixture of the compound (1.24 g) prepared according to reference example 2, (R) -(+)-glycidol (1.11 g, made by aldrich and 98% ee), and ethanol (1 mL) was stirred at 50° C. for 12 hours. By concentrating the reaction mixture, a title compound having the following physical properties was obtained and used for the following reaction without further purification.

TLC: Rf 0.40(hexane:ethyl acetate=1:1).

Reference Example 4

(2S)-2-hydroxymethyl-4-methyl-3,4-dihydro-2H-1,4-benzoxazine

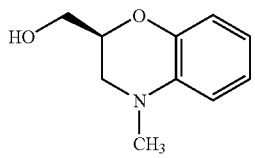

Potassium tert-butoxide (1.68 g) was added into anhydrous dimethyl formamide (10 mL) solution containing the compound prepared according to reference example 3 in water bath and the mixture was stirred at 80° C. at 3 hours. The reaction mixture was added into water and extracted with ethyl acetate. The extract was washed with saturated brine and dried by sulfuric anhydride sodium. The solution was filtered by celite (registered trademark) and the filtrate was concentrated. The residue is purified by silica gel column chromatography (hexane:ethyl acetate=3:1) to give a title compound (1.55 g, 97.6 % ee) having the following physical properties.

TLC: Rf 0.35(hexane:ethyl acetate=2:1);

NMR(CDCl$_3$):δ 7.90–6.79 (m, 2H), 6.70–6.60 (m, 2H), 4.33 (m, 1H), 3.82 (dd, J=13.0, 4.2 Hz, 1H), 3.79 (dd, J=13.0, 4.2 Hz, 1H), 3.19 (dd, J=10.2, 2.1 Hz, 1H), 3.17 (dd, J=11.4, 5.4 Hz, 1H), 2.86 (s, 3H).

The optical purity of this title compound was decided by using high performance liquid chromatography (HPLC).

A column: CHIRALCEL OD (Daicel Chemical Industries Ltd.)

0.46 cmϕ×25 cm,

Flow rate: 1 ml/minute,

Solvent: Hexane: 2-propanol=93:7,

Detection wave-length: 254 nm,

Retention time: 30.70 minutes,

Temperature: 24° C.

Reference Example 5

(2S)-2-mesyloxymethyl-4-methyl-3,4-dihydro-2H-1,4-benzoxazine

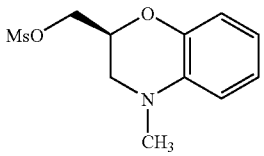

Triethylamine (23 mL) was added to the compound (20 g) prepared according to reference example 4 in toluene (80 mL) solution and the mixture was cooled at 5° C., methanesulfonyl chloride (9.5 mL) was dropped into the solution, which was stirred for 30 minutes at 5° C. The reaction mixture was added into water and extracted with ethyl acetate. The extract was sequentially washed with water and saturated brine and dried by sulfuric anhydride sodium. The solution was filtered by celite. The filtrate was concentrated to give a title compound having the following physical properties. The obtained title compound was used for the following reaction without further purification.

TLC: Rf 0.55(hexane:ethyl acetate=1:1);

NMR(CDCl$_3$):δ 6.88 (m, 1H), 6.81 (dd, J=8.4, 1.5 Hz, 1H), 6.75–6.65 (m, 2H), 4.54 (m, 1H), 4.40 (d, J=5.4 Hz, 2H), 3.27 (dd, J=11.7, 2.7 Hz, 1H), 3.17 (dd, J=11.7, 6.3 Hz, 1H), 3.07 (s, 3H), 2.88 (s, 3H).

Reference Example 6

4-((2S)-4-methyl-3,4-dihydro-2H-1,4-benzoxazin-2-ylmethoxy)benzoic acid methyl ester

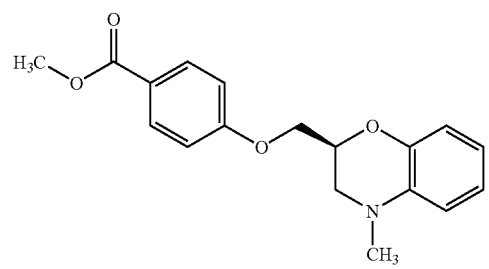

Potassium carbonate (38.3 g) was added to dimethyl formamide (200 mL) solution containing the compound prepared according to reference example 5 and 4-hydroxybenzoic acid methyl ester (23.2 g) at the room temperature and the mixture was stirred for 15 hours at 80° C. The reaction mixture was added into water and extracted with mixed solvent (ethyl acetate:hexane=1:2). The extract was sequentially washed with 1 N sodium hydroxide solution, water, and saturated brine, and dried by sulfuric anhydride sodium. The solution was filtered by celite. The filtrate was concentrated to give a title compound having the following physical properties. The obtained title compound was used for the following reaction without further purification.

TLC: Rf 0.62(hexane:ethyl acetate=2:1);

NMR(CDCl$_3$):δ 7.99(d, J=9.0 Hz, 2H), 6.96 (d, J=9.0 Hz, 2H), 6.94–6.79 (m, 2H), 6.70 (d, J=7.5 Hz, 1H), 6.68 (t, J=7.5 Hz, 1H), 4.65 (m, 1H), 4.27 (dd, J=9.9, 4.8 Hz, 1H), 4.17 (dd, J=9.9, 6.6 Hz, 1H), 3.89 (s, 3H), 3.39 (dd, J=11.7, 2.7 Hz, 1H), 3.25 (dd, J=11.7, 6.6 Hz, 1H), 2.90 (s, 3H).

Reference Example 7

4-((2S)-4-methyl-3,4-dihydro-2H-1,4-benzoxazin-2-yl-methoxy)benzoic acid

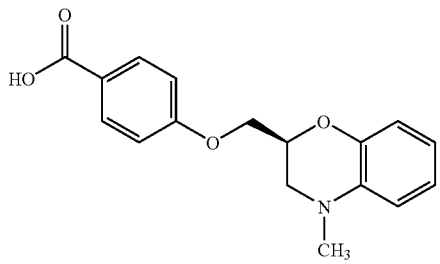

The compound prepared according to reference example 6 was dissolved into methanol (150 mL) and tetrahydrofuran (150 mL), 5N sodium hydroxide solution (100 mL) in room temperature was added to the mixture, which was stirred for 15 hours at room temperature. The reaction mixture was added into water and washed with mixed solvent (ethyl acetate:hexane=1:2). The crystal generated in the water layer acidified by 2N hydrochloric acid (260 mL) was acquired by filtration. The cake was washed by water. A title compound (39 g) having the following physical properties was obtained by being dried for 2 days under decompress.

TLC: Rf 0.13(hexane:ethyl acetate=2:1).

Reference Example 8

4-((2S)-4-methyl-3,4-dihydro-2H-1,4-benzoxazin-2-yl-methoxy)benzoyl chloride

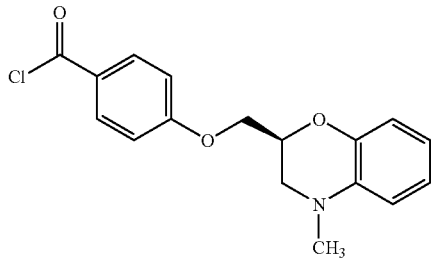

Oxalylchloride (2.75 mL) was added to dimethoxyethane (21 mL) solution containing the compound prepared according to reference example 7, which was stirred at 40° C. for 1 hour. The reaction mixture was concentrated to give a title compound (4.7 g) having the following physical properties.

NMR(CDCl$_3$): δ 8.12 (d, J=8.7 Hz, 2H), 7.50 (dd, J=8.1, 1.5 Hz, 1H), 7.35 (dt, J=1.5, 8.1 Hz, 1H), 7.16–6.95 (m, 4H), 5.07–4.96 (m, 1H), 4.52–4.40 (m, 2H), 3.87 (dd, J=12.9, 2.1 Hz, 1H), 3.68 (dd, J=12.9, 10.5 Hz, 1H), 3.29 (s, 3H).

Reference Example 9

2-(2-methylindol-3-yl)acetic acid benzyl ester

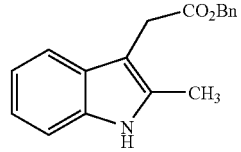

Under argon gas, potassium carbonate (2.52 g) and benzyl bromide (1.2 mL) were added to dimethyl formamide (20 mL) solution containing 2-(2-methylindol-3-yl)acetic acid (1.73 g), which was stirred at room temperature for 2 hours. The reaction mixture was radiationally cooled and water was added, and then the mixture was extracted by ethyl acetate. The extract was sequentially washed with water and saturated brine and dried by sulfuric anhydride sodium, and concentrated. The residue was purified by silica gel column chromatography (hexane:ethyl acetate=4:1) to give a title compound (2.63 g) having the following physical properties was obtained.

TLC: Rf 0.52(hexane:ethyl acetate=7:3);

NMR(CDCl$_3$):δ 7.83 (brs, 1H), 7.55–7.48 (m, 1H), 7.37–7.25(m, 6H), 7.16–7.04 (m, 2H), 5.11 (s, 2H), 3.74 (s, 2H), 2.40 (s, 3H).

EXAMPLE 1

2-(1-(4-((2S)-4-methyl-3,4-dihydro-2H-1,4-benzoxazin-2-ylmethoxy)benzoyl)-2-methylindol-3-yl)acetic acid benzyl ester

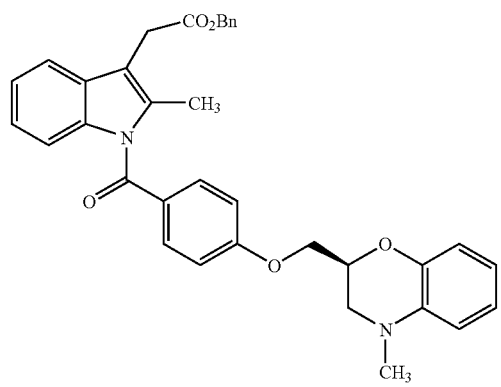

Under argon gas, dichloromethane (5 mL) solution containing benzyltriethylammonium chloride (82 mg) and the compound (1.52 g) preparedd according to reference example 8 were added to dichloromethane (5 mL) solution containing the compound (1 g) prepared according to reference example 9 and sodium hydroxide (716 mg) was added, and then the mixture was stirred at room temperature for 1 hour. Further, water was added to the reactive mixture, which was extracted by ethyl acetate. The extract was sequentially washed with water and saturated brine, and dried by sulfuric anhydride sodium, and then concentrated.

The residue was purified by silica gel column chromatography (toluene:ethyl acetate=20:1) to give this invention compound (2 g) having the following physical properties.

TLC: Rf 0.63(toluene:ethyl acetate=9:1);

NMR(CDCl$_3$):δ 7.76–6.67 (m, 17H), 5.13 (s, 2H), 4.74–4.62 (m, 1H), 4.32 (dd, J=9.9, 5.4 Hz, 1H), 4.21 (dd, J=9.9, 6.3 Hz, 1H), 3.76 (s, 2H), 3.41 (dd, J=11.7, 2.7 Hz, 1H), 3.28 (dd, J=11.4, 6.6 Hz, 1H), 2.92 (s, 3H), 2.40 (s, 3H).

EXAMPLE 2

2-(1-(4-((2S)-4-methyl-3,4-dihydro-2H-1,4-benzoxazin-2-ylmethoxy)benzoyl)-2-methylindol-3-yl)acetic acid

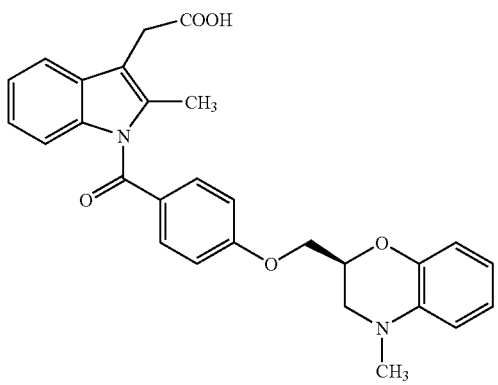

Under argon gas, 20% hydroxide palladium (100 mg) was added to ethyl acetate (20 mL) solution containing the compound (2 g) prepared according to example 1 and after hydrogen replacement, the mixture was stirred for 80 minutes at room temperature. The reaction mixture was filtered by celite, and the filtrate was concentrated. The residue was purified by silica gel column chromatography (chloroform:methanol=20:1) to give the compound (380 mg) of the present invention having the following physical properties.

TLC: Rf 0.42(chloroform:methanol=9:1);

NMR(CDCl$_3$):δ 7.73 (d, J=8.7 Hz, 2H), 7.51 (d, J=8.1 Hz, 1H), 7.17 (dt, J=1.5, 8.1 Hz, 1H), 7.09–6.94 (m, 4H), 6.93–6.81 (m, 2H), 6.75–6.66 (m, 2H), 4.74–4.64 (m, 1H), 4.32 (dd, J=9.9, 5.1 Hz, 1H), 4.21 (dd, J=9.9, 6.3 Hz, 1H), 3.75 (s, 2H), 3.41 (dd, J=11.7, 2.4 Hz, 1H), 3.28 (dd, J=11.7, 6.6 Hz, 1H), 2.93 (s, 3H), 2.43 (s, 3H).

EXAMPLE 3(1) TO EXAMPLE 3 (12)

Using 2-(2-methylindol-3-yl)acetic acid or the corresponding carboxylic acid derivative, and the compound prepared according to reference example 8 or a corresponding acid halide derivative, the following compounds of the present invention were obtained by carrying out an operation similar to a method sequentially represented by reference example 9, example 1, and example 2.

EXAMPLE 3(1)

2-(1-(4-((2S)-4-methyl-3,4-dihydro-2H-1,4-benzoxazin-2-ylmethoxy)benzoyl)-2-methyl-5-methoxyindol-3-yl)acetic acid

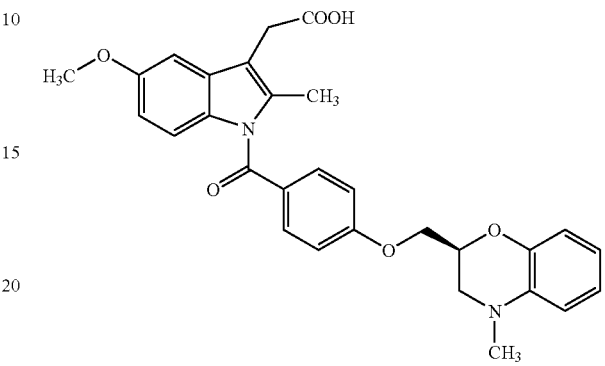

TLC: Rf 0.42(chloroform:methanol=9:1);

NMR(CDCl$_3$):δ 7.71 (d, J=8.7 Hz, 2H), 7.04–6.94 (m, 3H), 6.94–6.80 (m, 3H), 6.76–6.62 (m, 3H), 4.74–4.64 (m, 1H), 4.31 (dd, J=9.6, 5.1 Hz, 1H), 4.21 (dd, J=9.6, 6.0 Hz, 1H), 3.83 (s, 3H), 3.71 (s, 2H), 3.41 (dd, J=11.7, 2.4 Hz, 1H), 3.28 (dd, J=11.7, 6.3 Hz, 1H), 2.91 (s, 3H), 2.42 (s, 3H).

EXAMPLE 3(2)

3-(1-(4-((2S)-4-methyl-3,4-dihydro-2H-1,4-benzoxazin-2-ylmethoxy)benzoyl)-2-methylindol-3-yl)propanoic acid

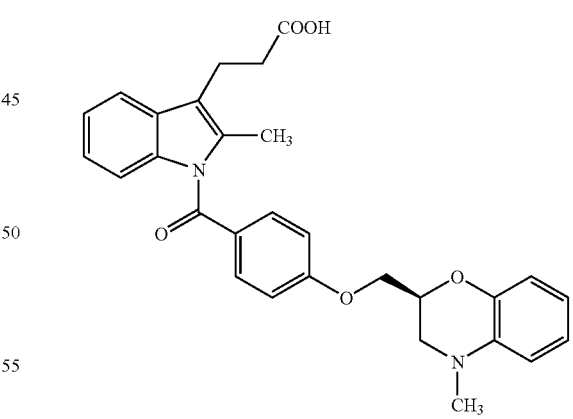

TLC: Rf 0.49(chloroform:methanol=9:1);

NMR(CDCl$_3$):δ 7.71 (d, J=8.7 Hz, 2H), 7.48 (d, J=7.5 Hz, 1H), 7.20–7.12 (m, 1H), 7.08–6.94 (m, 4H), 6.92–6.81 (m, 2H), 6.76–6.66 (m, 2H), 4.74–4.60 (m, 1H), 4.31 (dd, J=9.9, 5.1 Hz, 1H), 4.21 (dd, J=9.9, 6.3 Hz, 1H), 3.41 (dd, J=11.4, 2.7 Hz, 1H), 3.28 (dd, J=11.4, 6.6 Hz, 1H), 3.07 (t, J=8.1 Hz, 2H), 2.92 (s, 3H), 2.70 (t, J=8.1 Hz, 2H), 2.40 (s, 3H).

EXAMPLE 3(3)

2-(1-(4-propoxy methylbenzoyl)-2-methyl-5-methoxyindol-3-yl)acetic acid

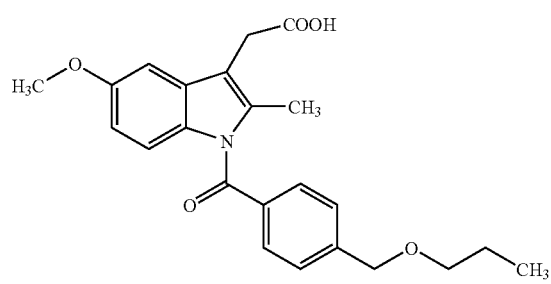

TLC: Rf 0.53(chloroform:methanol=8:2);

NMR(CDCl$_3$):δ 7.71–7.68 (m, 2H), 7.47–7.44 (m, 2H), 6.95 (d, J=2.0 Hz, 1H), 6.88 (d, J=9.0 Hz, 1H), 6.65 (dd, J=9.0, 2.0 Hz, 1H), 4.61 (s, 2H), 3.82 (s, 3H), 3.70 (s, 2H), 3.50 (t, J=6.5 Hz, 2H), 2.38 (s, 3H), 1.68 (tq, J=6.5, 7.0 Hz, 2H), 0.97 (J=7.0 Hz, 3H).

EXAMPLE 3(4)

2-(1-(4-(2-ethoxyethyl)benzoyl)-2-methyl-5-methoxyindol-3-yl)acetic acid

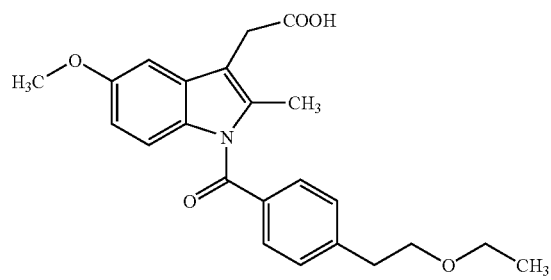

TLC: Rf 0.35(chloroform:methanol=9:1);

NMR(CDCl$_3$):δ 7.66–7.63 (m, 2H), 7.36–7.33 (m, 2H), 6.95 (d, J=1.5 Hz, 1H), 6.98 (d, J=6.0 Hz, 1H), 6.65 (dd, J=6.0, 1.5 Hz, 1H), 3.83 (s, 3H), 3.70 (s, 2H), 3.69 (t, J=4.5 Hz, 2H), 3.51 (q, J=4.5 Hz, 2H), 2.98 (t, J=4.5 Hz, 2H), 2.38 (s, 2H), 1.20 (t, J=4.5 Hz, 3H).

EXAMPLE 3(5)

2-(1-(4-phenoxybenzoyl)-2-methyl-5-methoxyindol-3-yl)acetic acid

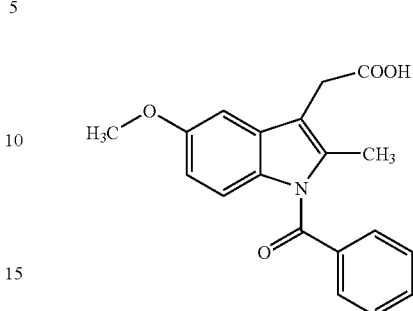

TLC: Rf 0.51(chloroform:methanol=9:1);

NMR(CDCl$_3$):δ 7.70 (d, J=9.0 Hz, 2H), 7.46–7.37 (m, 2H), 7.25–7.18 (m, 1H), 7.14–7.08 (m, 2H), 7.02 (d, J=9.0 Hz, 2H), 6.97–6.91 (m, 2H), 6.69 (dd, J=9.0, 2.4 Hz, 1H), 3.83 (s, 3H), 3.71 (s, 2H), 2.41 (s, 3H).

EXAMPLE 3(6)

2-(1-(4-benzyloxybenzoyl)-2-methyl-5-methoxyindol-3-yl)acetic acid

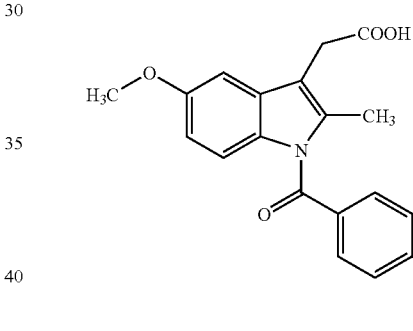

TLC: Rf 0.60(chloroform:methanol=9:1);

NMR(CDCl$_3$):δ 7.71 (d, J=8.7 Hz, 2H), 7.48–7.32 (m, 5H), 7.03 (d, J=8.7 Hz, 2H), 6.95 (d, J=2.4 Hz, 1H), 6.88 (d, J=9.0 Hz, 1H), 6.66 (dd, J=9.0, 2.4 Hz, 1H), 5.15 (s, 2H), 3.83 (s, 3H), 3.71 (s, 2H), 2.41 (s, 3H).

EXAMPLE 3(7)

2-(1-(4-(2-phenylethoxy)benzoyl)-2-methyl-5-methoxyindol-3-yl)acetic acid

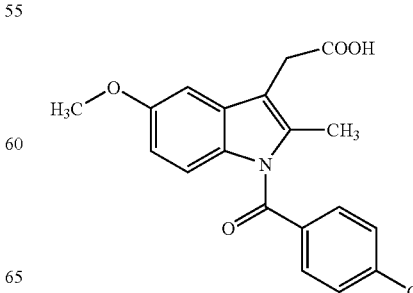

TLC: Rf 0.54(chloroform:methanol=9:1);

NMR(CDCl₃):δ 7.68 (d, J=8.7 Hz, 2H), 7.38–7.22 (m, 5H), 6.98–6.90 (m, 3H), 6.87 (d, J=9.0 Hz, 1H), 6.65 (dd, J=9.0, 2.7 Hz, 1H), 4.26 (t, J=6.9 Hz, 2H), 3.82 (s, 3H), 3.70 (s, 2H), 3.14 (t, J=6.9 Hz, 2H), 2.40 (s, 3H).

EXAMPLE 3(8)

2-(1-(4-(2-methoxyethoxy)benzoyl)-2-methyl-5-methoxy-indol-3-yl)acetic acid

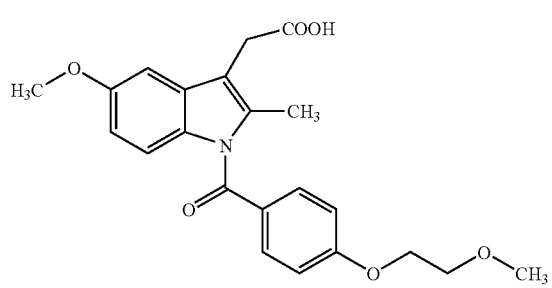

TLC: Rf 0.23(methanol:chloroform=1:10);

NMR(CDCl₃):δ 7.69 (d, J=8.8 Hz, 2H), 6.98 (d, J=8.8 Hz, 2H), 6.95 (d, J=2.6 Hz, 1H), 6.85 (d, J=9.0 Hz, 1H), 6.65 (dd, J=9.0, 2.6 Hz, 1H), 4.20 (m, 2H), 3.83 (s, 3H), 3.80 (m, 2H), 3.71 (s, 2H), 3.46 (s, 3H), 2.41 (s, 3H).

EXAMPLE 3(9)

2-(1-(4-(2-ethoxyethoxy)benzoyl)-2-methyl-5-methoxyindol-3-yl)acetic acid

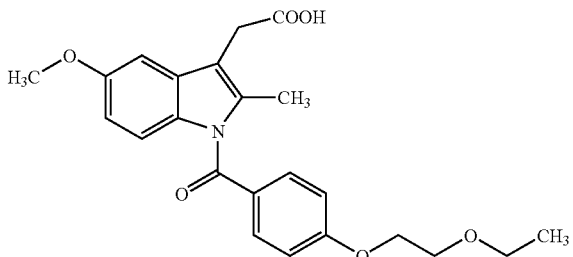

TLC: Rf 0.25(chloroform:methanol=1:10);

NMR(CDCl₃):δ 7.69 (d, J=8.8 Hz, 2H), 6.98 (d, J=8.8 Hz, 2H), 6.95 (d, J=2.8 Hz, 1H), 6.85 (d, J=9.0 Hz, 1H), 6.65 (dd, J=9.0, 2.8 Hz, 1H), 4.21 (m, 2H), 3.86–3.78 (m, 2H), 3.83 (s, 3H), 3.70 (s, 2H), 3.62 (q, J=7.0 Hz, 2H), 2.41 (s, 3H), 1.26 (t, J=7.0 Hz, 3H).

EXAMPLE 3(10)

2-(1-(3-(2-phenylethoxy)benzoyl)-2-methyl-5-methoxyindol-3-yl)acetic acid

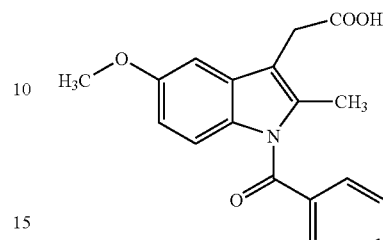

TLC: Rf 0.51(chloroform:methanol=10:1);

NMR(DMSO-d₆):δ 8.72 (s, 1H), 7.89–7.82 (m, 3H), 7.80 (s, 1H), 7.71–7.61 (m, 2H), 7.52–7.42 (m, 3H), 7.30–7.23 (m, 2H), 7.07 (s, 1H), 7.06 (d, J=7.5 Hz, 1H), 6.78 (d, J=7.8 Hz, 1H), 5.46 (s, 2H), 4.22 (t, J=6.6 Hz, 2H), 3.18 (t, J=6.6 Hz, 2H), 2.69 (t, J=8.1 Hz, 2H), 2.34 (t, J=8.1 Hz, 2H).

EXAMPLE 3(11)

2-(1-(3-(2-ethoxyethoxy)benzoyl)-2-methyl-5-methoxyindol-3-yl)acetic acid

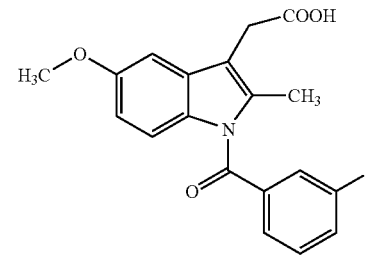

TLC: Rf 0.53(chloroform:methanol=10:1);

NMR(CDCl₃):δ 7.84–7.76 (m, 3H), 7.75 (s, 1H), 7.49–7.38 (m, 3H), 7.06 (d, J=6.9 Hz, 1H), 6.78–6.70 (m, 2H), 4.29 (s, 2H), 4,26 (t, J=6.3 Hz, 2H), 3.36–3.22 (m, 2H), 3.26 (t, J=6.3 Hz, 2H), 3.19–3.09 (m, 2H), 2.88 (t, J=7.8 Hz, 2H), 2.82 (s, 3H), 2.52 (t, J=7.8 Hz, 2H).

EXAMPLE 3(12)

2-(1-(4-(3-phenylpropoxy)benzoyl)-2-methyl-5-methoxyindol-3-yl)acetic acid

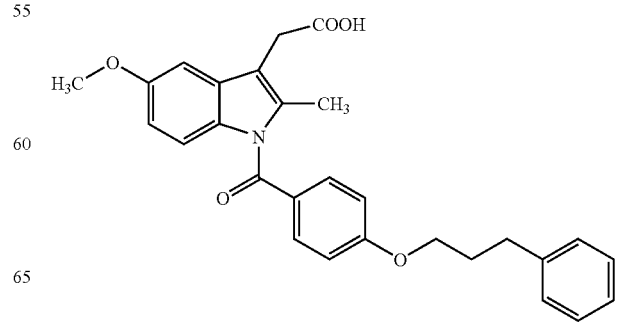

TLC: Rf 0.35(ethyl acetate);

NMR(DMSO-$d_6$):δ 12.02 (s, 1H), 9.47 (s, 1H), 8.29 (d, J=8.1 Hz, 1H), 7.94 (d, J=7.8 Hz, 1H), 7.83 (d, J=7.8 Hz, 1H), 7.73 (dd, J=6.6, 2.1 Hz, 1H), 7.60–7.46 (m, 4H), 7.42–7.34 (m, 1H), 7.23 (d, J=1.8 Hz, 1H), 7.12 (d, J=8.1 Hz, 1H), 7.02 (dd, J=8.1, 1.8 Hz, 1H), 6.38 (d, J=9.0 Hz, 1H), 6.20 (dt, J=1.5, 6.6 Hz, 1H), 5.01 (s, 2H), 4.69–4.64 (m, 1H), 2.40–2.35 (m, 2H), 1.99 (t, J=7.5 Hz, 2H), 1.59–1.50 (m, 5H).

Reference Example 10

2-(1-(4-acetyloxybenzoyl)-2-methylindol-3-yl)acetic acid benzyl ester

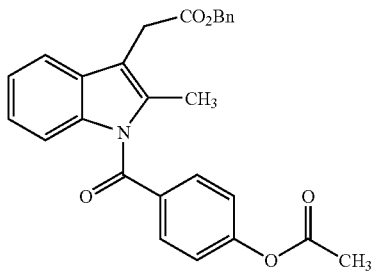

Uner argon gas, dichloromethane (24 mL) solution containing benzyltriethylammonium chloride (281 mg) and 4-acetyloxybenzoyl chloride (3.68 g) was added to dichloromethane (100 mL) solution containing the compound(3.45 g) prepared according to reference example 9 and sodium hydroxide (2.47 g) was added, and then the mixture was stirred for 40 minutes at room temperature. The reactive mixture was filtered with celite, and the filtrate was used for the following reaction as it was.

TLC: Rf 0.49(hexane:ethyl acetate=7:3).

Reference Example 11

2-(1-(4-hydroxybenzoyl)-2-methylindol-3-yl)acetic acid benzyl ester

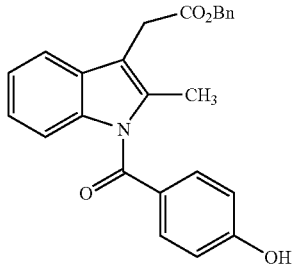

Piperidine (3.46 mL) was added to the filtrate prepared according to reference example 10 at room temperature, which was stirred for 1.5 hours at room temperature. Water is added to the reactive mixture, which was separated. The organic layer was sequentially washed with water and saturated brine, and dried by sulfuric anhydride sodium, and concentrated. The residue was purified by silica gel column chromatography (hexane:ethyl acetate=7:3) to give a title compound (3 g) having the following physical properties.

TLC: Rf 0.24(hexane:ethyl acetate=7:3);

NMR(CDCl$_3$):δ 7.66 (d, J=9.0 Hz, 2H), 7.49 (d, J=7.5 Hz, 1H), 7.38–7.26 (m, 5H), 7.15 (dt, J=1.8, 7.5 Hz, 1H), 7.10–6.97 (m, 2H), 6.88 (d, J=9.0 Hz, 2H), 5.15 (s, 2H), 3.76 (s, 2H), 2.40 (s, 3H).

EXAMPLE 4

2-(1-(4-((2S)-4,7-dimethyl-3,4-dihydro-2H-1,4-benzoxazin-2-ylmethoxy)benzoyl)-2-methylindol-3-yl)acetic acid benzyl ester

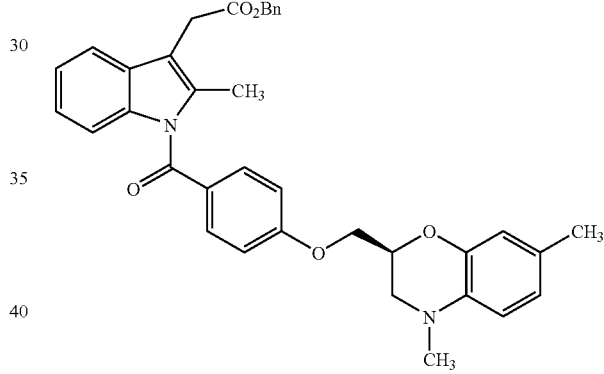

Under argon gas, triphenylphosphine (216 mg) was added to tetrahydrofuran (3 mL) solution containing the compound (100 mg) prepared according to reference example 11 and (2S)-2-hydroxymethyl-4,7-dimethyl-3,4-dihydro-2H-1,4-benzoxazines (64.2 mg) and diethylazodicarboxylate (0.38 mL; 40% toluene solution) was dropped to the mixture, which was stirred for 40 minutes at room temperature. The reactive mixture was concentrated. The residue was purified by silica gel column chromatography (hexane:ethyl acetate=4:1) to give a title compound (50 mg) having the following physical properties.

TLC: Rf 0.50(hexane:ethyl acetate=7:3);

NMR(CDCl$_3$):δ 7.71 (d, J=8.7 Hz, 2H), 7.50 (d, J=8.1 Hz, 1H), 7.40–7.24 (m, 5H), 7.15 (t, J=6.9 Hz, 1H), 7.09–6.96 (m, 4H), 6.73–6.60 (m, 3H), 5.14 (s, 2H), 4.72–4.63 (m, 1H), 4.30 (dd, J=9.9, 4.8 Hz, 1H), 4.21 (dd, J=9.9, 6.0 Hz, 1H), 3.76 (s, 2H), 3.36 (dd, J=11.4, 2.7 Hz, 1H), 3.22 (dd, J=11.4, 6.6 Hz, 1H), 2.88(s, 3H), 2.40 (s, 3H), 2.23 (s, 3H).

EXAMPLE 5

2-(1-(4-((2S)-4,7-dimethyl-3,4-dihydro-2H-1,4-benzoxazin-2-ylmethoxy)benzoyl)-2-methylindol-3-yl)acetic acid

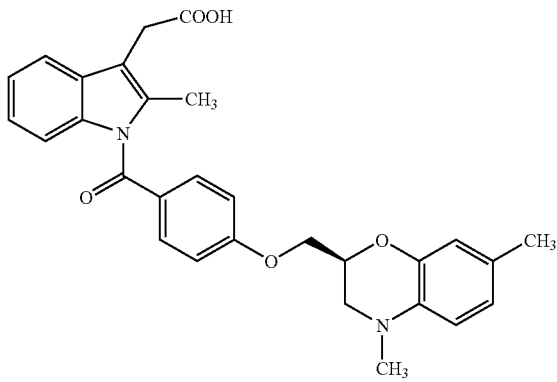

Using the compound prepared according to example 4 instead of the compound prepared according to example 1, the compound of the present compound having the following physical properties was obtained by the operation similar to example 2.

TLC: Rf 0.26(hexane:ethyl acetate=1:1);

NMR(CDCl$_3$):δ 7.73 (d, J=8.7 Hz, 2H), 7.51 (d, J=8.1 Hz, 1H), 7.17 (t, J=6.9 Hz, 1H), 7.09–6.92 (m, 4H), 6.74–6.60 (m, 3H), 4.72–4.63 (m, 1H), 4.30 (dd, J=9.9, 4.8 Hz, 1H), 4.21 (dd, J=9.9, 6.0 Hz, 1H), 3.75 (s, 2H), 3.36 (dd, J=11.4, 2.7 Hz, 1H), 3.22 (dd, J=11.4, 6.6 Hz, 1H), 2.88(s, 3H), 2.43 (s, 3H), 2.23 (s, 3H).

EXAMPLE 6 (1) TO EXAMPLE 6 (10)

This following invention compounds were obtained by the operation from example 4 to example 2 using the corresponding alcoholic derivative instead of (2S)-2-hydroxymethyl-4,7-dimethyl-3,4-dihydro-2H-1,4-benzoxazine.

EXAMPLE 6(1)

2-(1-(4-((2S)-4,6-dimethyl-3,4-dihydro-2H-1,4-benzoxazin-2-ylmethoxy)benzoyl)-2-methylindol-3-yl)acetic acid

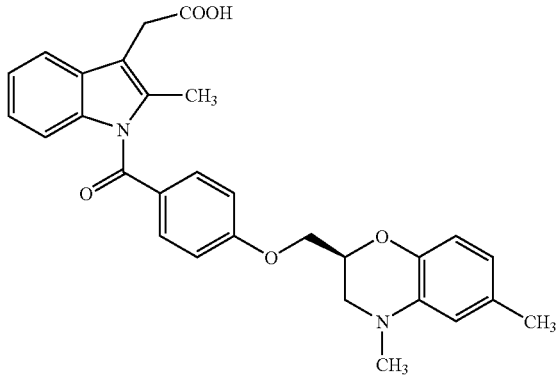

TLC: Rf 0.27(hexane:ethyl acetate=1:1);

NMR(CDCl$_3$):δ 7.73 (d, J=8.7 Hz, 2H), 7.51 (d, J=7.8 Hz, 1H), 7.17 (t, J=7.8 Hz, 1H), 7.10–6.92 (m, 4H), 6.73 (d, J=7.8 Hz, 1H), 6.55–6.45 (m, 2H), 4.70–4.60 (m, 1H), 4.30 (dd, J=10.2, 4.8 Hz, 1H), 4.20 (dd, J=10.2, 6.3 Hz, 1H), 3.75 (s, 2H), 3.39 (dd, J=11.7, 2.7 Hz, 1H), 3.26 (dd, J=11.7, 6.6 Hz, 1H), 2.90 (s, 3H), 2.43 (s, 3H), 2.28 (s, 3H).

EXAMPLE 6(2)

2-(1-(4-((3R)-5-fluoro-2,3-dihydrobenzofuran-3-ylmethoxy)benzoyl)-2-methylindol-3-yl)acetic acid

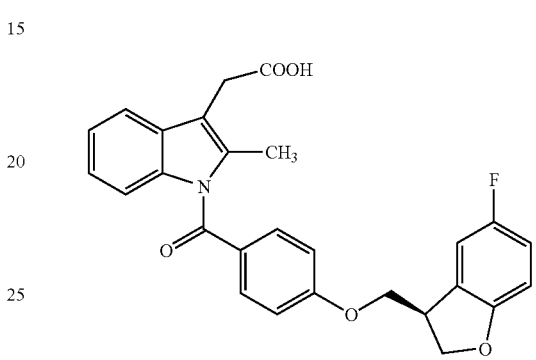

TLC: Rf 0.22(hexane:ethyl acetate=1:1);

NMR(CDCl$_3$):δ 7.72 (d, J=8.7 Hz, 2H), 7.51 (d, J=7.8 Hz, 1H), 7.21–7.11 (m, 2H), 7.05 (t, J=7.8 Hz, 1H), 7.01–6.93 (m, 3H), 6.68–6.56 (m, 2H), 4.76 (t, J=9.3 Hz, 1H), 4.68 (dd, J=9.3, 3.9 Hz, 1H), 4.46–4.40 (m, 1H), 4.20–4.06 (m, 2H), 3.74 (s, 2H), 2.42 (s, 3H).

EXAMPLE 6(3)

2-(1-(4-(2, 3-dihydrobenzofuran-3-ylmethoxy)benzoyl)-2-methylindol-3-yl)acetic acid

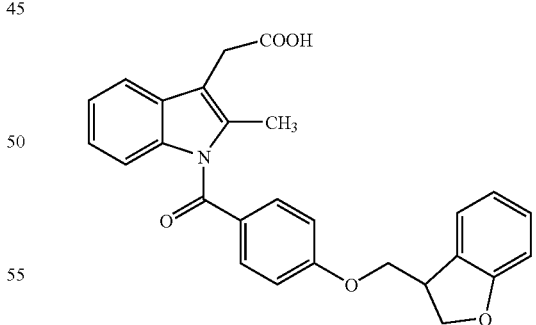

TLC: Rf 0.16(hexane:ethyl acetate=1:1);

NMR(CDCl$_3$):δ 7.73 (d, J=9.0 Hz, 2H), 7.51 (d, J=7.8 Hz, 1H), 7.31 (d, J=7.8 Hz, 1H), 7.24–7.13 (m, 2H), 7.04 (t, J=7.8 Hz, 1H), 7.01–6.83 (m, 5H), 4.73 (t, J=9.0 Hz,1H), 4.55 (dd, J=9.0, 5.1 Hz,1 H ), 4.24 (dd, J=9.0, 5.7 Hz, 1H), 4.11 (t, J=9.0 Hz, 1H), 4.04–3.92 (m, 1H), 3.75 (s, 2H), 2.43 (s, 3H).

EXAMPLE 6(4)

2-(1-(4-(2-(6-methylpyridin-2-yl)ethoxy)benzoyl)-2-methylindol-3-yl)acetic acid

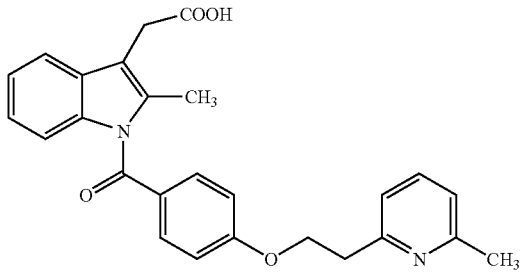

TLC: Rf 0.54(ethyl acetate:methanol=10:1);

NMR(CDCl$_3$):δ 7.63 (d, J=8.1 Hz, 2H), 7.55 (dd, J=7.8, 7.5 Hz, 1H), 7.53 (d, J=7.8 Hz, 1H), 7.17–6.93 (m, 5H), 6.84 (d, J=8.1 Hz, 2H), 4.31 (t, J=6.6 Hz, 2H), 3.71 (s, 2H), 3.24 (t, J=6.6 Hz, 2H), 2.56 (s, 3H), 2.40 (s, 3H).

EXAMPLE 6(5)

2-(1-(4-(2-(3-methylpyridin-2-yl)ethoxy)benzoyl)-2-methylindol-3-yl)acetic acid

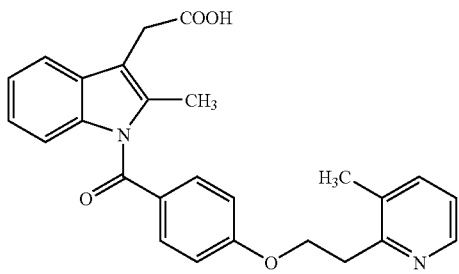

TLC: Rf 0.53(ethyl acetate:methanol=10:1);

NMR(CDCl$_3$):δ 8.43 (d, J=4.5 Hz, 1H), 7.70–7.49 (m, 4H), 7.16–7.10 (m, 2H), 7.01 (m, 1H), 6.93 (d, J=7.8 Hz, 1H), 6.82 (d, J=8.4 Hz, 2H), 4.37 (t, J=6.6 Hz, 2H), 3.71 (s, 2H), 3.30 (t, J=6.6 Hz, 2H), 2.41 (s, 3H), 2.41 (s, 3H).

EXAMPLE 6(6)

2-(1-(4-((2R)-1,4-benzodioxan-2-ylmethoxy)benzoyl)-2-methylindol-3-yl)acetic acid

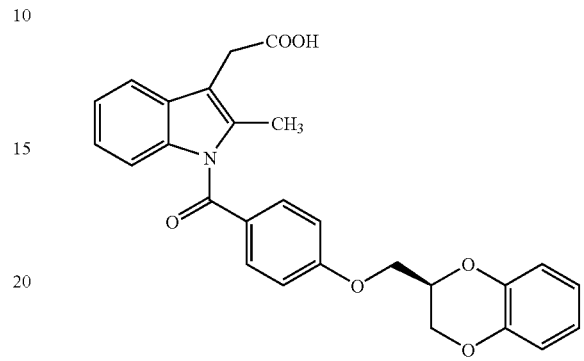

TLC: Rf 0.57(ethyl acetate);

NMR(CDCl$_3$):δ 7.77–7.70 (m, 2H), 7.50 (d, J=7.5 Hz, 1H), 7.17 (m, 1H), 7.08–6.85 (m, 8H), 4.61 (m, 1H), 4.42 (dd, J=11.4, 2.1 Hz, 1H), 4.33 (dd, J=10.2, 5.1 Hz, 1H), 4.26 (dd, J=11.4, 6.3 Hz, 1H), 4.25 (dd, J=10.2, 6.3 Hz, 1H), 3.74 (s, 2H), 2.42 (s, 3H).

EXAMPLE 6(7)

2-(1-(4-(1,3-dioxanindan-2-ylmethoxy)benzoyl)-2-methylindol-3-yl)acetic acid

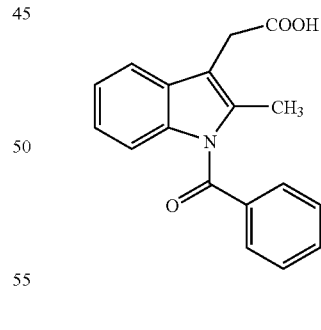

TLC: Rf 0.60(ethyl acetate);

NMR(CDCl$_3$):δ 7.73 (d, J=8.4 Hz, 2H), 7.50 (d, J=7.8 Hz, 1H), 7.17 (dd, J=7.8, 7.2 Hz, 1H), 7.06–6.93 (m, 4H), 6.86 (s, 4H), 6.49 (t, J=3.9 Hz, 1H), 4.35 (d, J=3.9 Hz, 2H), 3.73 (s, 2H), 2.42 (s, 3H).

EXAMPLE 6(8)

2-(1-(4-((2S)-7-fluoro-4-methyl-3,4-dihydro-2H-1,4-benzoxazin-2-ylmethoxy)benzoyl)-2-methylindol-3-yl)acetic acid

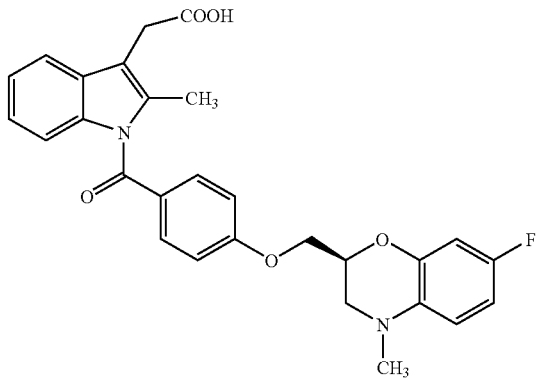

TLC: Rf 0.49(chloroform:methanol=9:1);
NMR(CDCl₃):δ 7.74 (d, J=9.0 Hz, 2H), 7.51 (d, J=7.5 Hz, 1H), 7.18 (dt, J=1.2, 7.5 Hz, 1H), 7.08–6.94 (m, 3H), 6.64–6.56 (m, 3H), 4.85–4.75 (m, 1H), 4.30 (dd, J=9.9, 5.1 Hz, 1H), 4.21 (dd, J=9.9, 6.0 Hz, 1H), 3.75 (s, 2H), 3.36 (dd, J=11.7, 2.7 Hz, 1H), 3.22 (dd, J=11.7, 6.6 Hz, 1H), 2.88(s, 3H), 2.43 (s, 3H).

EXAMPLE 6(9)

2-(1-(4-((2S)-2,3-dihydrobenzofuran-2-ylmethoxy)benzoyl)-2-methylindol-3-yl)acetic acid

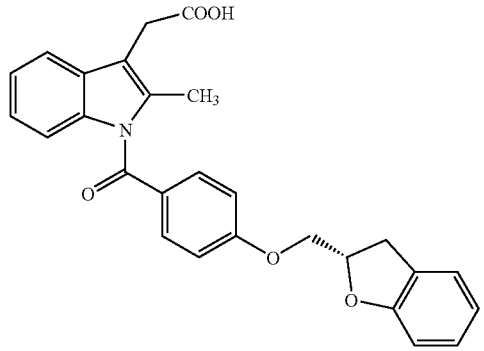

TLC: Rf 0.37(chloroform:methanol=10:1);
NMR(CDCl₃):δ 7.74–7.69 (m, 2H), 7.49 (d, J=7.8 Hz, 1H), 7.24–7.11 (m, 3H), 7.06–6.81 (m, 6H), 5.19 (m, 1H), 4.29 (dd, J=9.9, 6.3 Hz, 1H), 4.20 (dd, J=9.9, 4.2 Hz, 1H), 3.73 (s, 2H), 3.42 (dd, J=16.2, 9.6 Hz, 1H), 3.17 (dd, J=16.2, 7.2 Hz, 1H), 2.41 (s, 3H).

EXAMPLE 6(10)

2-(1-(4-((2S)-7-methoxy-4-methyl-3,4-dihydro-2H-1,4-benzoxazin-2-ylmethoxy)benzoyl)-2-methylindol-3-yl)acetic acid

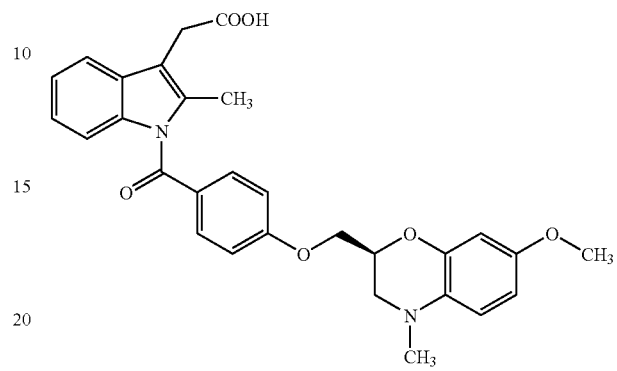

TLC: Rf 0.50(chloroform:methanol=9:1);
NMR(CDCl₃):δ 7.73 (d, J=8.7 Hz, 2H), 7.51 (d, J=8.1 Hz, 1H), 7.17 (dt, J=1.5, 8.1 Hz, 1H), 7.08–6.94 (m, 4H), 6.70–6.62 (m, 1H), 6.52–6.44 (m, 2H), 4.74–4.65 (m, 1H), 4.31 (dd, J=9.9, 5.1 Hz, 1H), 4.22 (dd, J=9.9, 6.0 Hz, 1H), 3.74 (s, 5H), 3.33 (dd, J=11.7, 2.7 Hz, 1H), 3.18 (dd, J=11.7, 6.6 Hz, 1H), 2.86 (s, 3H), 2.42 (s, 3H).

EXAMPLE 7(1) TO EXAMPLE 7(40)

Using the compound prepared according to reference example 9 or the substitute derivative and the compound prepared according to reference example 8 or the substitute derivative, this following invention compounds were obtained by the operation similar to example 1.

EXAMPLE 7(1)

(2E)-4-(1-(4-((2S)-4-methyl-3,4-dihydro-2H-1,4-benzoxazin-2-ylmethoxy)benzoyl)-2-methylindol-3-yl)-2-butenoic acid benzyl ester

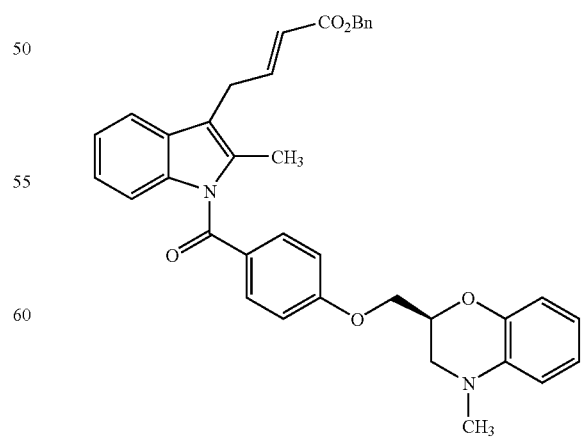

TLC: Rf 0.41 (hexane:ethyl acetate=7:3)

EXAMPLE 7(2)

2-(1-(4-((2S)-4-methyl-3,4-dihydro-2H-1,4-benzoxazin-2-ylmethoxy)benzoyl)-2,5-dimethylindol-3-yl)acetic acid benzyl ester

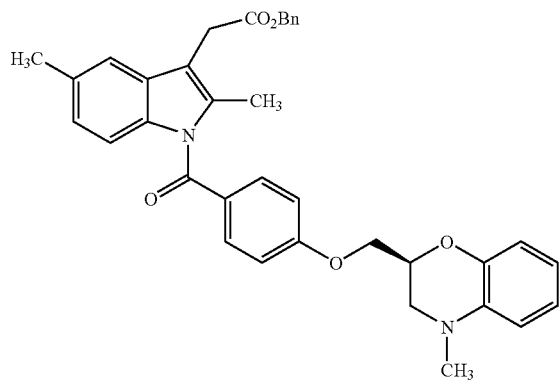

TLC: Rf 0.46(hexane:ethyl acetate=1:1).

EXAMPLE 7(3)

2-(1-(4-((2S)-4-methyl-3,4-dihydro-2H-1,4-benzoxazin-2-ylmethoxy)benzoyl)-5-fluoro-2-methylindol-3-yl)acetic acid benzyl ester

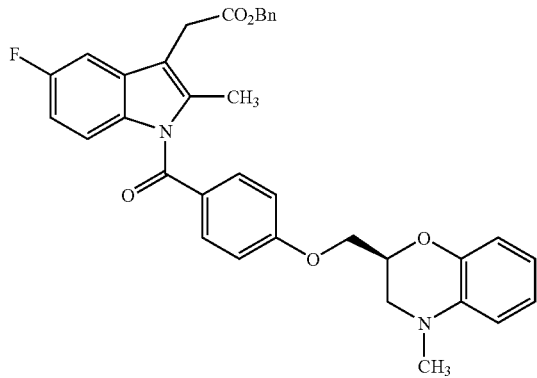

TLC: Rf 0.46(hexane:ethyl acetate=1:1).

EXAMPLE 7(4)

2-(1-(4-((2S)-4-methyl-3,4-dihydro-2H-1,4-benzoxazin-2-ylmethoxy)benzoyl)-5-chloro-2-methylindol-3-yl)acetic acid benzyl ester TLC: Rf 0.81(hexane:ethyl acetate=2:1).

EXAMPLE 7(5)

2-(1-(4-((2S)-4-methyl-3,4-dihydro-2H-1,4-benzoxazin-2-ylmethoxy)benzoyl)-5-trifluoromethyl-2-methylindol-3-yl)acetic acid benzyl ester

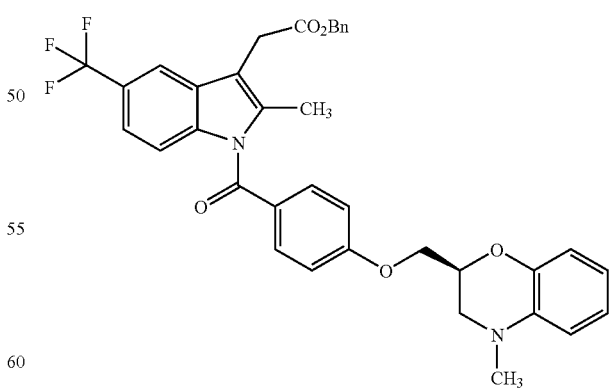

TLC: Rf 0.81 (hexane:ethyl acetate=2:1).

EXAMPLE 7(6)

2-(1-(4-((2S)-4-methyl-3,4-dihydro-2H-1,4-benzoxazin-2-ylmethoxy)-2-methylbenzoyl)-2-methylindol-3-yl)acetic acid benzyl ester

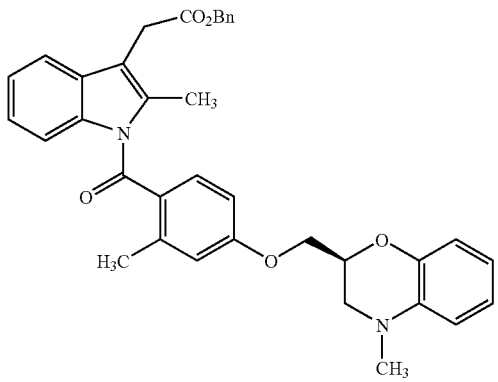

TLC: Rf 0.48(hexane:ethyl acetate=7:3);

NMR(CDCl$_3$):δ 7.47 (d, J=7.5 Hz, 1H), 7.40–7.25 (m, 7H), 7.20–7.00 (m, 3H), 6.93–6.76 (m, 3H), 6.75–6.67 (m, 2H), 5.13 (s, 2H), 4.73–4.63 (m, 1H), 4.29 (dd, J=9.6, 4.8 Hz, 1H), 4.18 (dd, J=9.6, 6.3 Hz, 1H ), 3.74 (s, 2H), 3.41 (dd, J=11.4, 2.7 Hz, 1H), 3.28 (dd, J=11.4, 6.6 Hz, 1H), 2.92 (s, 3H), 2.31 (s, 3H), 2.29 (s, 3H).

EXAMPLE 7(7)

2-(1-(4-((2S)-4-methyl-3,4-dihydro-2H-1,4-benzoxazin-2-ylmethoxy)-2-methylbenzoyl)-5-methoxy-2-methylindol-3-yl)acetic acid benzyl ester

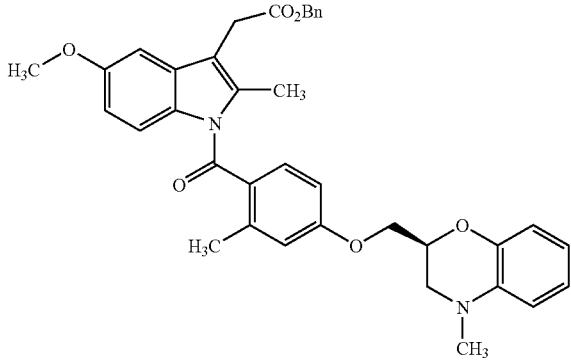

TLC: Rf 0.31 (hexane:ethyl acetate=7:3);

NMR(CDCl$_3$):δ 7.40–7.24 (m, 6H), 7.00–6.76 (m, 6H), 6.76–6.64 (m, 3H), 5.13 (s, 2H), 4.74–4.62 (m, 1H), 4.28 (dd, J=9.6, 5.1 Hz, 1H), 4.18 (dd, J=9.6, 6.3 Hz, 1H), 3.76 (s, 3H), 3.70 (s, 2H), 3.41 (dd, J=11.7, 2.7 Hz, 1H), 3.28 (dd, J=11.7, 6.6 Hz, 1H), 2.92 (s, 3H), 2.29 (s, 3H), 2.27 (s, 3H).

EXAMPLE 7(8)

2-(1-(4-((2S)-4-methyl-3,4-dihydro-2H-1,4-benzoxazin-2-ylmethoxy)-2-chlorobenzoyl)-5-methoxy-2-methylindol-3-yl)acetic acid benzyl ester

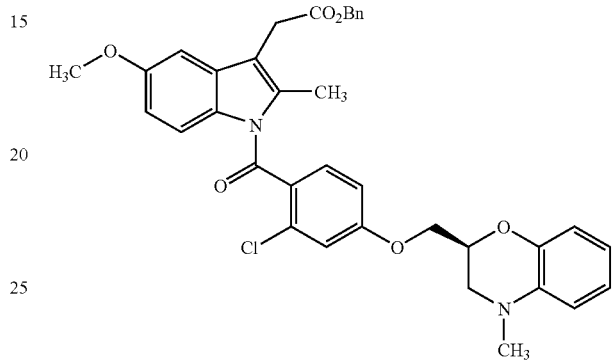

TLC: Rf 0.30(hexane:ethyl acetate=7:3).

EXAMPLE 7(9)

2-(1-(4-((2S)-4-methyl-3,4-dihydro-2H-1,4-benzoxazin-2-ylmethoxy)-2-methylbenzoyl)-5-chloro-2-methylindol-3-yl)acetic acid benzyl ester

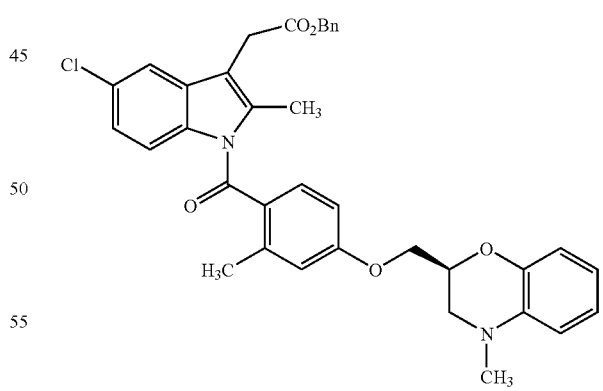

TLC: Rf 0.52(hexane:ethyl acetate=7:3);

NMR(CDCl$_3$):δ 7.45 (d, J=2.1 Hz,$_1$H), 7.39–7.23 (m, 6H), 7.02–6.76 (m, 6H), 6.75–6.66 (m, 2H), 5.14 (s, 2H), 4.72–4.62 (m, 1H), 4.28 (dd, J=9.9, 5.4 Hz, 1H), 4.18 (dd, J=9.9, 6.6 Hz, 1H), 3.69 (s, 2H), 3.41 (dd, J=11.1, 2.4 Hz, 1H), 3.28 (dd, J=11.1, 6.6 Hz, 1H), 2.92 (s, 3H), 2.29 (s, 6H).

EXAMPLE 7(10)

2-(1-(4-((2S)-4-methyl-3,4-dihydro-2H-1,4-benzoxazin-2-ylmethoxy)-2-methylbenzoyl)-5-fluoro-2-methylindol-3-yl)acetic acid benzyl ester

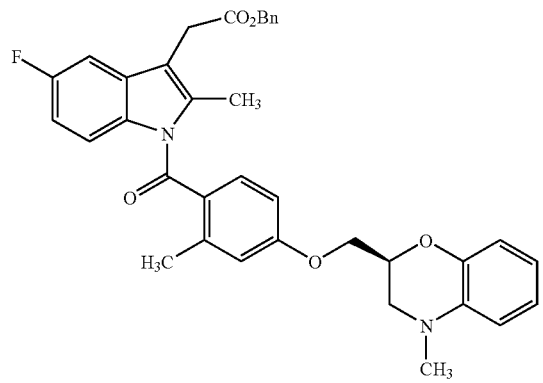

TLC: Rf 0.48(hexane:ethyl acetate=7:3);

NMR(CDCl$_3$):δ 7.40–7.24 (m, 6H), 7.13 (dd, J=8.7, 2.4 Hz,1H), 7.03 (dd, J=9.0, 4.8 Hz, 1H), 6.92–6.75 (m, 5H), 6.75–6.67 (m, 2H), 5.13 (s, 2H), 4.73–4.63 (m, 1H), 4.28 (dd, J=9.9, 4.8 Hz, 1H), 4.18 (dd, J=9.9, 6.3 Hz, 1H), 3.68 (s, 2H), 3.41 (dd, J=11.4, 2.1 Hz, 1H), 3.28 (dd, J=11.4, 6.6 Hz, 1H), 2.92 (s, 3H), 2.28 (s, 3H), 2.27 (s, 3H).

EXAMPLE 7(11)

2-(1-(4-((2S)-4-methyl-3,4-dihydro-2H-1,4-benzoxazin-2-ylmethoxy)-2-chlorobenzoyl)-2-methylindol-3-yl)acetic acid benzyl ester

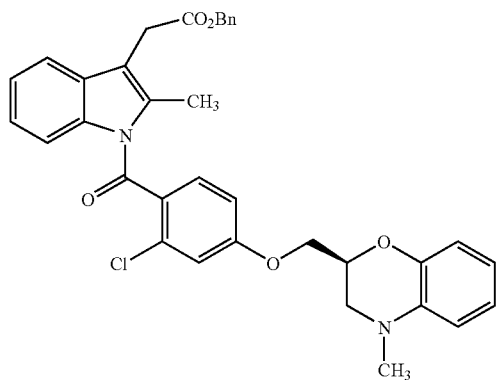

TLC: Rf 0.42(hexane:ethyl acetate=7:3);

NMR(CDCl$_3$):δ 7.54–7.40 (m, 2H), 7.40–7.03 (m, 9H), 6.97–6.82 (m, 3H), 6.75–6.67 (m, 2H), 5.12 (s, 2H), 4.72–4.64 (m, 1H), 4.29 (dd, J=9.9, 4.8 Hz, 1H), 4.20 (dd, J=9.9, 6.0 Hz, 1H), 3.73 (s, 2H), 3.40 (dd, J=12.0, 2.7 Hz, 1H), 3.27 (dd, J=12.0, 6.0 Hz, 1H), 2.92 (s, 3H), 2.30 (s, 3H).

EXAMPLE 7(12)

2-(1-(4-((2S)-4-methyl-3,4-dihydro-2H-1,4-benzoxazin-2-ylmethoxy)-2,3-dimethylbenzoyl)-2-methylindol-3-yl)acetic acid benzyl ester

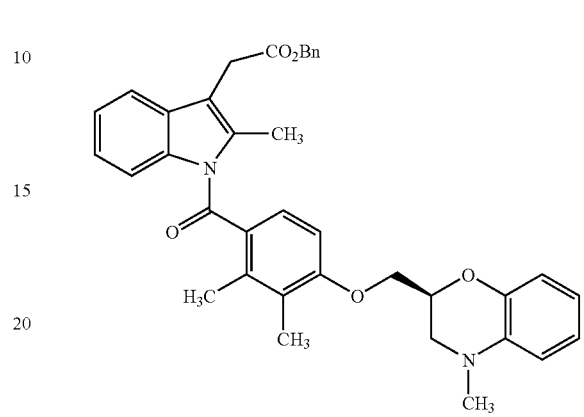

TLC: Rf 0.57(hexane:ethyl acetate=2:1);

NMR(CDCl$_3$):δ 7.47 (d, J=7.5 Hz, 1H), 7.35–7.27 (m, 5H), 7.19–7.14 (m, 2H), 7.10–7.03 (m, 2H), 6.92–6.83 (m, 2H), 6.77–4.67 (m, 3H), 5.13 (s, 2H), 4.72–4.67 (m, 1H), 4.30–4.08 (m, 2H), 3.74 (s, 2H), 3.45–3.29 (m, 2H), 2.93 (s, 3H), 2.29 (s, 3H), 2.23 (s, 3H), 2.22 (s, 3H).

EXAMPLE 7(13)

2-(1-(4-((2S)-4-methyl-3,4-dihydro-2H-1,4-benzoxazin-2-ylmethoxy)-3-methylbenzoyl)-2-methylindol-3-yl)acetic acid benzyl ester

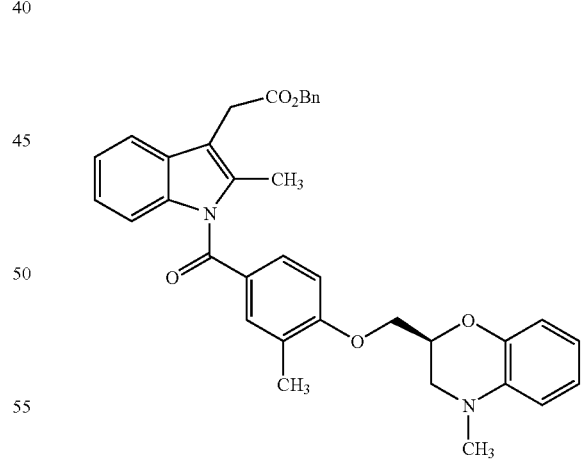

TLC: Rf 0.50(hexane:ethyl acetate=2:1);

NMR(CDCl$_3$):δ 7.61 (d, J=2.1 Hz, 1H), 7.54 (dd, J=8.1, 2.1 Hz, 1H), 7.50 (d, J=7.8 Hz, 1H), 7.34–7.29 (m, 5H), 7.19–7.14 (m, 2H), 7.15 (dt, J=7.8, 2.1 Hz, 1H), 7.10–6.98 (m, 2H), 5.14 (s, 2H), 4.75–4.65 (m, 1H), 4.34–4.17 (m, 2H), 3.76 (s, 2H), 3.45–3.28 (m, 2H), 2.92 (s, 3H), 2.40 (s, 3H), 2.27 (s, 3H).

EXAMPLE 7(14)

2-(1-(4-((2S)-4-methyl-3,4-dihydro-2H-1,4-benzoxazin-2-ylmethoxy)-2-methylbenzoyl)-2,5-dimethylindol-3-yl)acetic acid benzyl ester

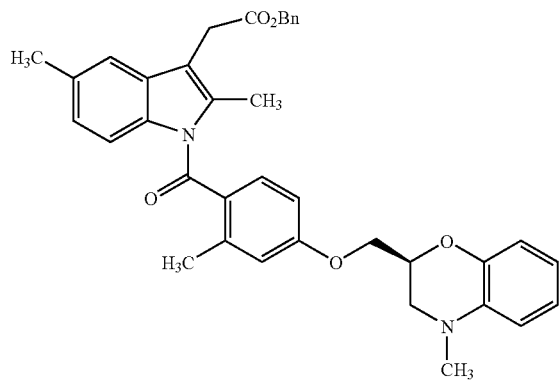

TLC: Rf 0.58(toluene:ethyl acetate=9:1);
NMR(CDCl$_3$):δ 7.36–7.23 (m, 6H), 6.96–6.76 (m, 7H), 6.76–6.66 (m, 2H), 5.13 (s, 2H), 4.72–4.62 (m, 1H), 4.28 (dd, J=9.9, 5.4 Hz, 1H), 4.17 (dd, J=9.9, 6.0 Hz, 1H), 3.71 (s, 2H), 3.41 (dd, J=12.0, 3.0 Hz, 1H), 3.28 (dd, J=12.0, 6.6 Hz, 1H), 2.92 (s, 3H), 2.38 (s, 3H), 2.30 (s, 3H), 2.27 (s, 3H).

EXAMPLE 7(15)

2-(1-(4-((2S)-4-methyl-3,4-dihydro-2H-1,4-benzoxazin-2-ylmethoxy)-3-methoxybenzoyl)-2-methylindol-3-yl)acetic acid benzyl ester

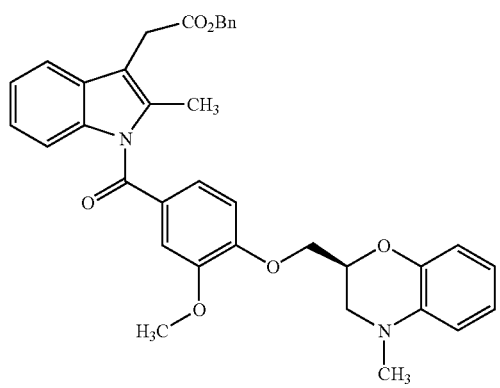

TLC: Rf 0.38(hexane:ethyl acetate=2:1);
NMR(CDCl$_3$):δ 7.50 (d, J=8.1 Hz, 1H), 7.36 (d, J=2.4 Hz, 1H), 7.33–7.26 (m, 6H), 7.18–7.03 (m, 3H), 6.94–6.82 (m, 3H), 6.72–6.67 (m, 2H), 5.14 (s, 2H), 4.78–4.70 (m, 1H), 4.38–4.22 (m, 2H), 3.87 (s, 3H), 3.76 (s, 2H), 3.43 (dd, J=11.4, 2.7 Hz, 1H), 3.30 (dd, J=11.4, 6.6 Hz 1H), 2.91 (s, 3H), 2.41 (s, 3H).

EXAMPLE 7(16)

2-(1-(4-((2S)-4-methyl-3,4-dihydro-2H-1,4-benzoxazin-2-ylmethoxy)-3-fluorobenzoyl)-2-methylindol-3-yl)acetic acid benzyl ester

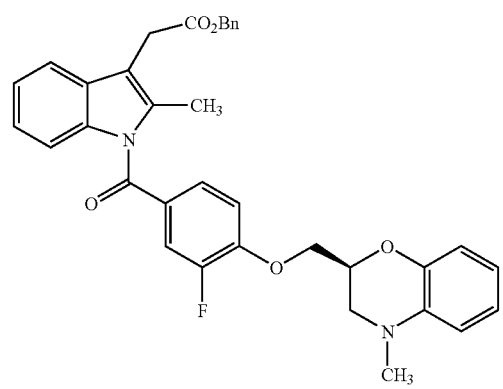

TLC: Rf 0.30(hexane:ethyl acetate=3:1);
NMR(CDCl$_3$):δ 7.56–6.68 (m, 16H), 5.14 (s, 2H), 4.76–4.65 (m, 1H), 4.40–4.25 (m, 2H), 3.75 (s, 2H), 3.45–3.28 (m, 2H), 2.92 (s, 3H), 2.40 (s, 3H).

EXAMPLE 7(17)

2-(1-(4-((2S)-4-methyl-3,4-dihydro-2H-1,4-benzoxazin-2-ylmethoxy)-2-methoxybenzoyl)-2-methylindol-3-yl)acetic acid benzyl ester TLC: Rf 0.37(hexane:ethyl acetate=7:3);
NMR(CDCl$_3$):δ 7.55–7.00 (m, 10H), 6.95–6.80 (m, 2H), 6.76–6.65 (m, 2H), 6.62–6.47 (m, 2H), 5.12 (s, 2H), 4.72–4.62 (m, 1H), 4.30 (dd, J=9.9, 5.1 Hz, 1H), 4.20 (dd, J=9.9, 6.0 Hz, 1H), 3.73 (s, 2H), 3.58 (s, 3H), 3.41 (dd, J=12.0, 2.7 Hz, 1H), 3.29 (dd, J=12.0, 6.3 Hz, 1H), 2.93 (s, 3H), 2.32 (s, 3H).

EXAMPLE 7(18)

2-(1-(4-((2S)-4-methyl-3,4-dihydro-2H-1,4-benzoxazin-2-ylmethoxy)-3-chlorobenzoyl)-2-methylindol-3-yl)acetic acid benzyl ester

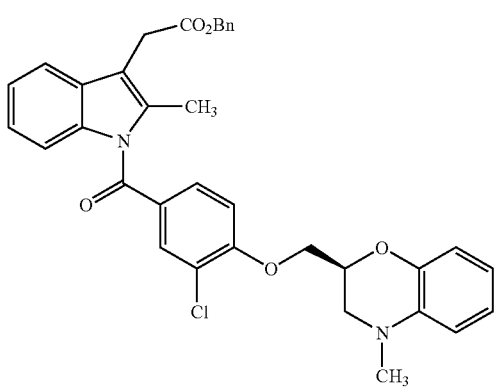

TLC: Rf 0.49(hexane:ethyl acetate=2:1).

EXAMPLE 7(19)

2-(1-(4-((2S)-4-methyl-3,4-dihydro-2 H-1,4-benzoxazin-2-ylmethoxy)-2-fluorobenzoyl)-2-methylindol-3-yl)acetic acid benzyl ester

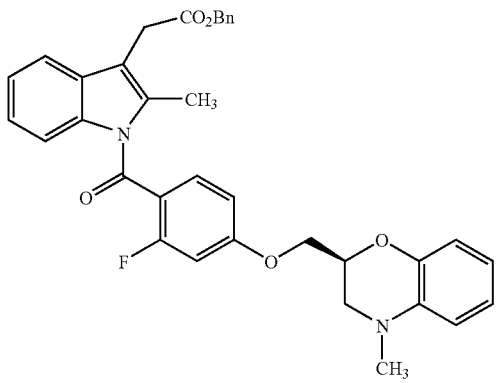

TLC: Rf 0.53(hexane:ethyl acetate=2:1);
NMR(CDCl$_3$):δ 7.56–7.47 (m, 3H), 7.34–7.26 (m, 4H), 7.21–7.05 (m, 3H), 6.92–6.82 (m, 3H), 6.74–6.68 (m, 3H), 5.13 (s, 2H), 4.72–4.64 (m, 1H), 4.32–4.09 (m, 2H), 3.74 (s, 2H), 3.42–3.25 (m, 2H), 2.92 (s, 3H), 2.38 (s, 3H).

EXAMPLE 7(20)

2-(1-(4-((2S)-4-methyl-3,4-dihydro-2H-1,4-benzoxazin-2-ylmethoxy)-3-methylbenzoyl)-2,5-dimethylindol-3-yl)acetic acid benzyl ester

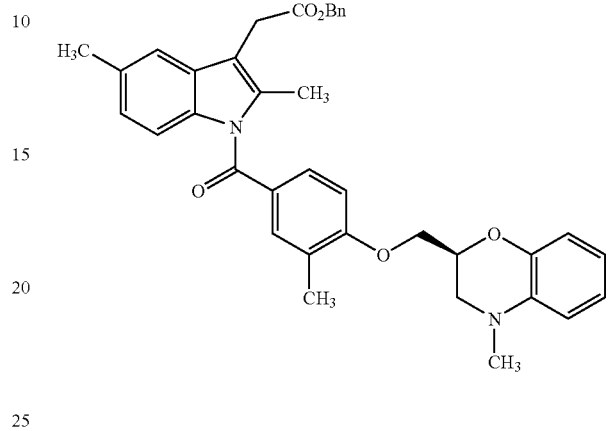

TLC: Rf 0.54(toluene:ethyl acetate=9:1);
NMR(CDCl$_3$):δ 7.59 (brs, 1H), 7.53 (dd, J=8.7, 2.4 Hz, 1H), 7.37–7.24 (m, 6H), 6.96–6.81 (m, 5H), 6.76–4.66 (m, 2H), 5.14 (s, 2H), 4.75–4.65 (m, 1H), 4.31 (dd, J=9.9, 4.8 Hz,1H), 4.22 (dd, J=9.9, 6.0 Hz,1H), 3.73 (s, 2H), 3.42 (dd, J=11.1, 2.4 Hz, 1H), 3.32 (dd, J=11.1, 6.0 Hz, 1H), 2.93 (s, 3H), 2.39 (s, 3H), 2.38 (s, 3H), 2.26 (s, 3H).

EXAMPLE 7(21)

2-(1-(4-((2S)-4-methyl-3,4-dihydro-2H-1,4-benzoxazin-2-ylmethoxy)-3-methylbenzoyl)- 5-fluoro-2-methylindol-3-yl)acetic acid benzyl ester

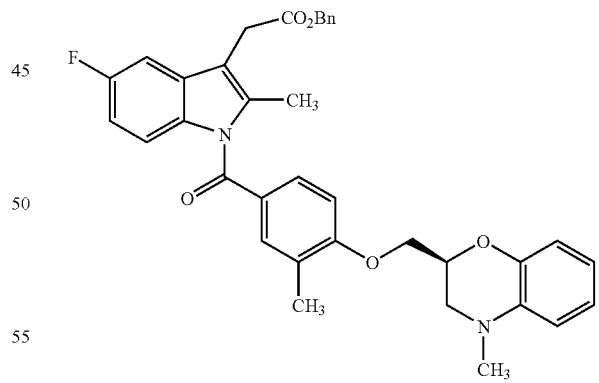

TLC: Rf 0.55(toluene:ethyl acetate=9:1);
NMR(CDCl$_3$):δ 7.60–7.56 (m, 1H), 7.51 (dd, J=8.7, 2.7 Hz, 1H), 7.38–7.27 (m, 5H), 7.14 (dd, J=9.0, 2.7 Hz, 1H), 6.95 (dd, J=9.0, 4.5 Hz, 1H), 6.93–4.67 (m, 6H), 5.15 (s, 2H), 4.74–4.65 (m, 1H), 4.31 (dd, J=9.9, 5.1 Hz, 1H), 4.22 (dd, J=9.9, 6.3 Hz, 1H), 3.71 (s, 2H), 3.42 (dd, J=11.4, 2.7 Hz, 1H), 3.31 (dd, J=11.4, 6.6 Hz, 1H), 2.92 (s, 3H), 2.37 (s, 3H), 2.27 (s, 3H).

EXAMPLE 7(22)

2-(1-(4-((2S)-4-methyl-3,4-dihydro-2H-1,4-benzoxazin-2-ylmethoxy)-3-methylbenzoyl)-5-chloro-2-methylindol-3-yl)acetic acid benzyl ester

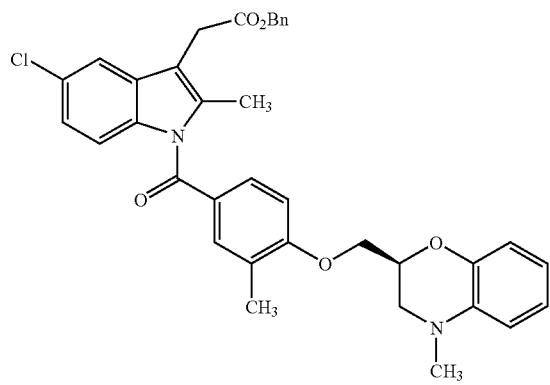

TLC: Rf 0.57(toluene:ethyl acetate=9:1);
NMR(CDCl$_3$):δ 7.60–7.45 (m, 3H), 7.41–7.24 (m, 5H), 7.04–6.81 (m, 5H), 6.76–6.66 (m, 2H), 5.12 (s, 2H), 4.75–4.66 (m, 1H), 4.32 (dd, J=9.6, 4.8 Hz, 1H), 4.23 (dd, J=9.6, 6.3 Hz, 1H), 3.69 (s, 2H), 3.42 (dd, J=11.4, 2.7 Hz, 1H), 3.31 (dd, J=11.4, 6.3 Hz, 1H), 2.93 (s, 3H), 2.39 (s, 3H), 2.27 (s, 3H).

EXAMPLE 7(23)

2-(1-(4-((2S)-4-methyl-3,4-dihydro-2H-1,4-benzoxazin-2-ylmethoxy)-3-methylbenzoyl)-5-methoxy-2-methylindol-3-yl)acetic acid benzyl ester

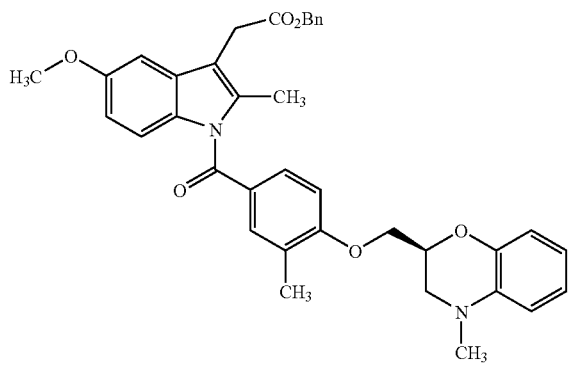

TLC: Rf 0.50(toluene:ethyl acetate=9:1);

NMR(CDCl$_3$):δ 7.60–7.50 (m, 2H), 7.37–7.27 (m, 5H), 6.95–6.81 (m, 5H), 6.76–6.62 (m, 3H), 5.14 (s, 2H), 4.75–4.65 (m, 1H), 4.32 (dd, J=9.9, 5.1 Hz, 1H), 4.22 (dd, J=9.9, 6.3 Hz, 1H), 3.76 (s, 3H), 3.73 (s, 2H), 3.42 (dd, J=11.7, 3.0 Hz, 1H), 3.32 (dd, J=11.7, 6.3 Hz, 1H), 2.93 (s, 3H), 2.39 (s, 3H), 2.26 (s, 3H).

EXAMPLE 7(24)

2-(1-(4-((2S)-4-methyl-3,4-dihydro-2H-1,4-benzoxazin-2-ylmethoxy)-2,3-dimethylbenzoyl)-5-fluoro-2-methylindol-3-yl)acetic acid benzyl ester

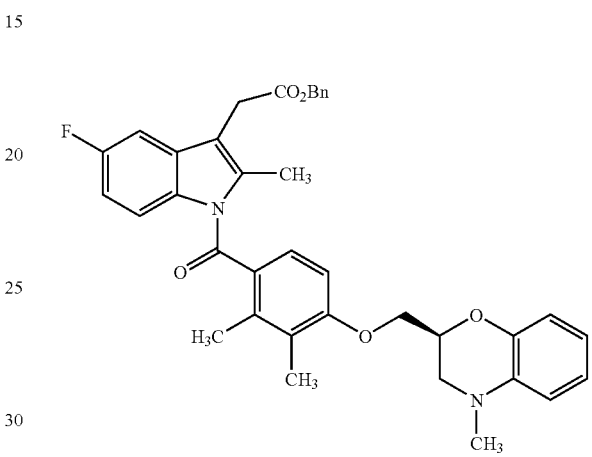

TLC: Rf 0.54(hexane:ethyl acetate=2:1).

EXAMPLE 7(25)

2-(1-(4-((2S)-4-methyl-3,4-dihydro-2H-1,4-benzoxazin-2-ylmethoxy)-3-methoxybenzoyl)- 5-fluoro-2-methylindol-3-yl)acetic acid benzyl ester

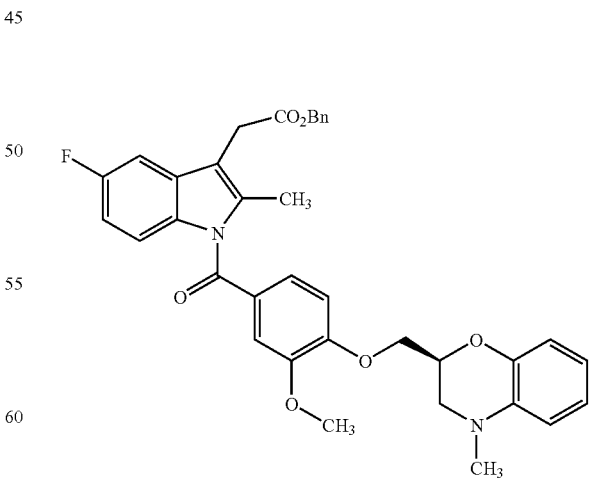

TLC: Rf 0.55(hexane:ethyl acetate=2:1).

EXAMPLE 7(26)

2-(2-(4-(((2S)-4-methyl-3,4-dihydro-2H-1,4-benzoxazin-2-ylmethoxy)-3-fluorobenzoyl)-5-fluoro-2-methylindol-3-yl)acetic acid benzyl ester

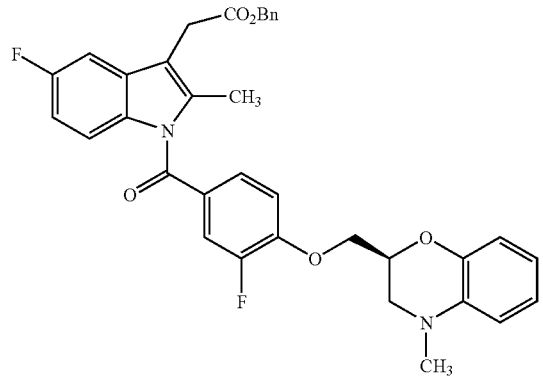

TLC: Rf 0.55(hexane:ethyl acetate=2:1).

EXAMPLE 7(27)

2-(1-(3-((2S)-4-methyl-3,4-dihydro-2H-1,4-benzoxazin-2-ylmethoxy)benzoyl)-2-methylindol-3-yl)acetic acid benzyl ester

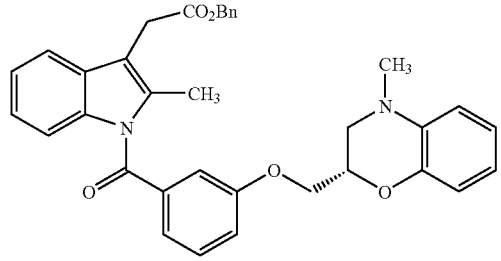

TLC: Rf 0.61(toluene:ethyl acetate=9:1);

NMR(CDCl$_3$):δ 7.54–7.46 (m, 1H), 7.40–7.00 (m, 12H), 6.90–6.79 (m, 2H), 6.74–6.63 (m, 2H), 5.14 (s, 2H), 4.68–4.58 (m, 1H), 4.25 (dd, J=9.6, 5.1 Hz, 1H), 4.15 (dd, J=9.6, 6.3 Hz, 1H), 3.75 (s, 2H), 3.37 (dd, J=11.7, 2.7 Hz, 1H), 3.24 (dd, J=11.7, 6.9 Hz, 1H), 2.89 (s, 3H), 2.41 (s, 3H).

EXAMPLE 7(28)

2-(1-(4-(((2S)-4-methyl-3,4-dihydro-2H-1,4-benzoxazin-2-ylmethoxy)-2-chlorobenzoyl)-5-fluoro-2-methylindol-3-yl)acetic acid benzyl ester

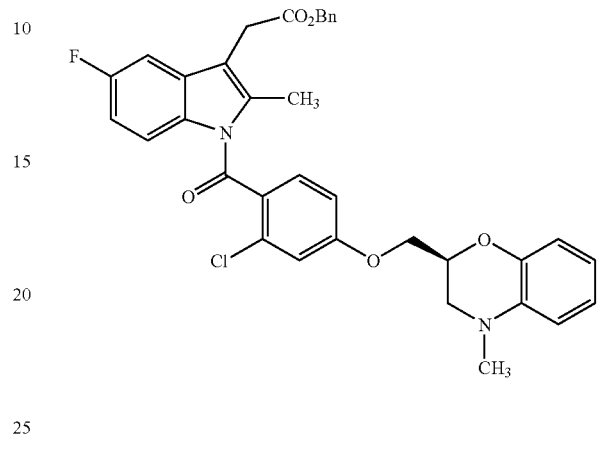

TLC: Rf 0.48(hexane:ethyl acetate=7:3);

NMR(CDCl$_3$):δ 7.42 (d, J=8.4 Hz, 1H), 7.40–7.10 (m, 7H), 7.04 (d, J=2.7 Hz, 1H), 6.98–6.80 (m, 4H), 6.76–6.68 (m, 2H), 5.13 (s, 2H), 4.73–4.63 (m, 1H), 4.29 (dd, J=9.6, 5.4 Hz, 1H), 4.20 (dd, J=9.6, 5.7 Hz, 1H), 3.67 (s, 2H), 3.40 (dd, J=11.1, 2.4 Hz, 1H), 3.27 (dd, J=11.1, 6.3 Hz, 1H), 2.92 (s, 3H), 2.24 (s, 3H).

EXAMPLE 7(29)

2-(1-(4-(((2S)-4-methyl-3,4-dihydro-2H-1,4-benzoxazin-2-ylmethoxy)-2-chlorobenzoyl)-5-chloro-2-methylindol-3-yl)acetic acid benzyl ester

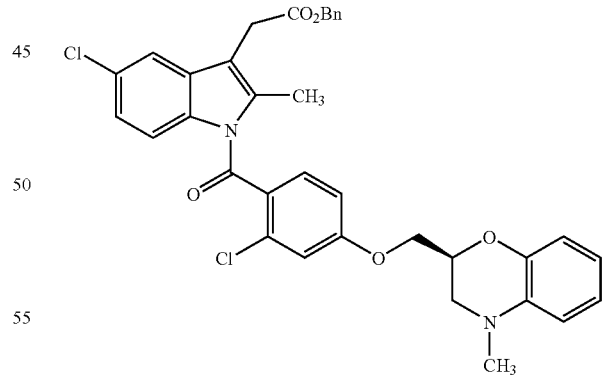

TLC: Rf 0.45(hexane:ethyl acetate=7:3);

NMR(CDCl$_3$):δ 7.47–7.40 (m, 2H), 7.40–7.24 (m, 5H), 7.20–7.00 (m, 3H), 6.98–6.82 (m, 3H), 6.76–6.67 (m, 2H), 5.13 (s, 2H), 4.73–4.63 (m, 1H), 4.29 (dd, J=9.9, 4.8 Hz, 1H), 4.20 (dd, J=9.9, 5.7 Hz, 1H), 3.68 (s, 2H), 3.40 (dd, J=11.7, 2.7 Hz, 1H), 3.27 (dd, J=11.7, 6.3 Hz, 1H), 2.92 (s, 3H), 2.26 (s, 3H).

EXAMPLE 7(30)

2-(1-(4-((2S)-4-methyl-3,4-dihydro-2H-1,4-benzoxazin-2-ylmethoxy)-2-fluorobenzoyl)-5-fluoro-2-methylindol-3-yl)acetic acid benzyl ester

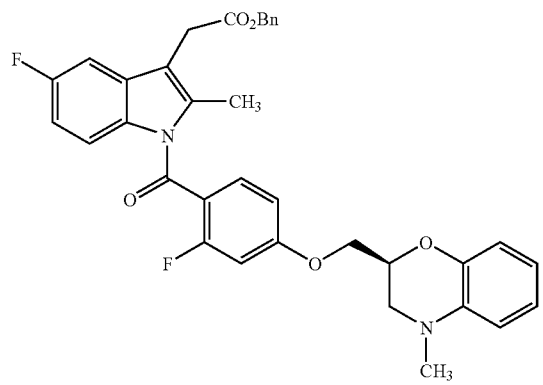

TLC: Rf 0.52(toluene:ethyl acetate=9:1).

EXAMPLE 7(31)

2-(1-(4-((2S)-4-methyl-3,4-dihydro-2H-1,4-benzoxazin-2-ylmethoxy)-2-fluorobenzoyl)-5-chloro-2-methylindol-3-yl)acetic acid benzyl ester

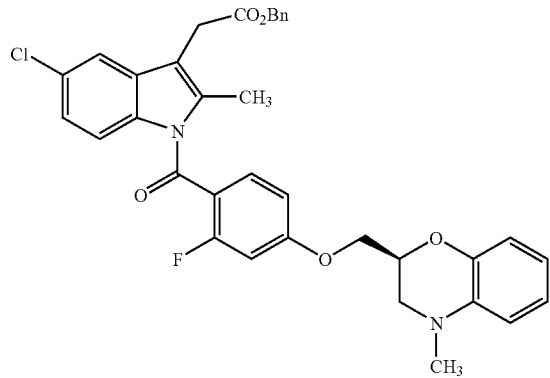

TLC: Rf 0.49(hexane:ethyl acetate=2:1).

EXAMPLE 7(32)

2-(1-(4-((2S)-4-methyl-3,4-dihydro-2H-1,4-benzoxazin-2-ylmethoxy)-2-fluorobenzoyl)-2,5-dimethylindol-3-yl)acetic acid benzyl ester

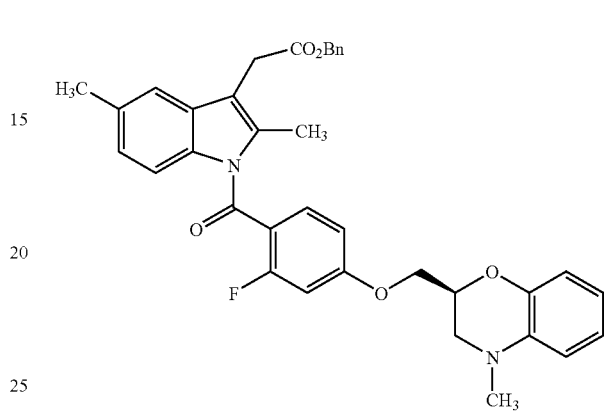

TLC: Rf 0.55(hexane:ethyl acetate=2:1).

EXAMPLE 7(33)

2-(1-(4-((2S)-4-methyl-3,4-dihydro-2H-1,4-benzoxazin-2-ylmethoxy)-2-fluorobenzoyl)-5-methoxy-2-methylindol-3-yl)acetic acid benzyl ester TLC: Rf 0.49(hexane:ethyl acetate=2:1).

EXAMPLE 7(34)

2-(1-(4-((2S)-4-methyl-3,4-dihydro-2H-1,4-benzoxazin-2-ylmethoxy)-2,5-dimethylbenzoyl)-2-methylindol-3-yl)acetic acid benzyl ester

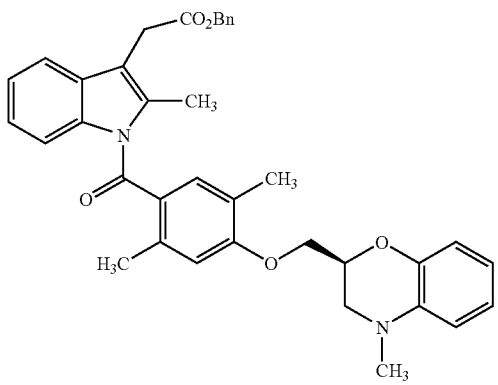

TLC: Rf 0.74(hexane:ethyl acetate=2:1).

EXAMPLE 7(35)

2-(1-(4-((2S)-4-methyl-3,4-dihydro-2H-1,4-benzoxazin-2-ylmethoxy)-2-chlorobenzoyl)-2,5-dimethylindol-3-yl)acetic acid benzyl ester

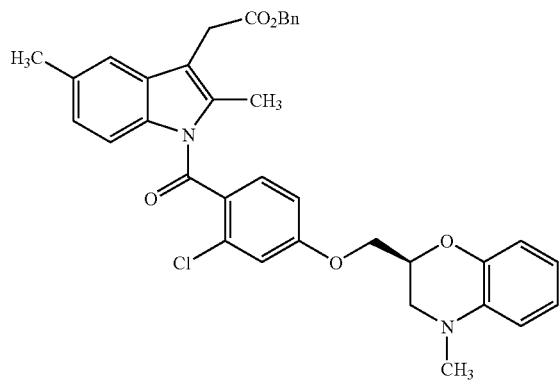

TLC: Rf 0.44(hexane:ethyl acetate=7:3);
NMR(CDCl$_3$):δ 7.44–7.20 (m, 6H), 7.07–6.80 (m, 7H), 6.76–6.65 (m, 2H), 5.12 (s, 2H), 4.72–4.62 (m, 1H), 4.28 (dd, J=9.9, 5.4 Hz, 1H), 4.19 (dd, J=9.9, 6.0 Hz, 1H), 3.70 (s, 2H), 3.40 (dd, J=11.7, 2.7 Hz, 1H), 3.27 (dd, J=11.7, 6.6 Hz, 1H), 2.92 (s, 3H), 2.38 (s, 3H), 2.28 (s, 3H).

EXAMPLE 7(36)

2-(1-(4-((2S)-4-methyl-3,4-dihydro-2H-1,4-benzoxazin-2-ylmethoxy)-3,5-dimethylbenzoyl)-2-methylindol-3-yl)acetic acid benzyl ester

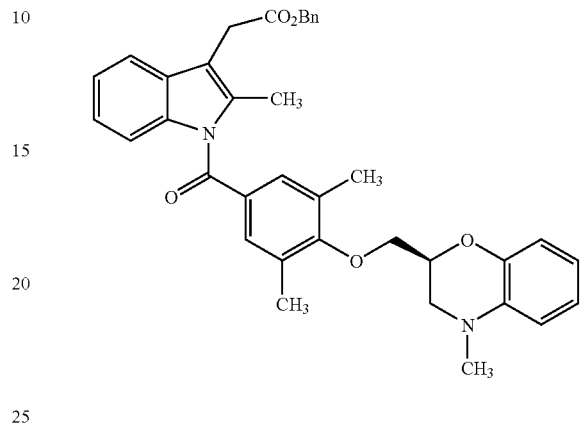

TLC: Rf 0.49(hexane:ethyl acetate=7:3);
NMR(CDCl$_3$):δ 7.56–7.24 (m, 8H), 7.18–6.96 (m, 3H), 6.91–6.80 (m, 2H), 6.76–6.66 (m, 2H), 5.15 (s, 2H), 4.74–4.64 (m, 1H), 4.10–4.00 (m, 2H), 3.76 (s, 2H), 3.44 (dd, J=11.4, 2.7 Hz, 1H), 3.34 (dd, J=11.4, 6.3 Hz, 1H), 2.93 (s, 3H), 2.38 (s, 3H), 2.32 (s, 6H).

EXAMPLE 7(37)

2-(1-(4-((2S)-4-methyl-3,4-dihydro-2H-1,4-benzoxazin-2-ylmethoxy)-2-methylbenzoyl)-5-trifluoromethoxy-2-methylindol-3-yl)acetic acid benzyl ester

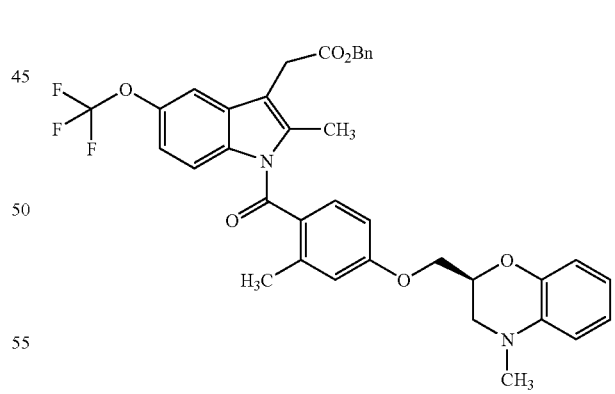

TLC: Rf 0.48(hexane:ethyl acetate=7:3);
NMR(CDCl$_3$):δ 7.38–7.25 (m, 7H), 7.06 (d, J=9.0 Hz, 1H), 6.96–4.76 (m, 5H), 6.75–6.66 (m, 2H), 5.13 (s, 2H), 4.72–4.62 (m, 1H), 4.29 (dd, J=9.9, 5.1 Hz, 1H), 4.18 (dd, J=9.9, 6.3 Hz, 1H), 3.71 (s, 2H), 3.40 (dd, J=11.7, 3.0 Hz, 1H), 3.27 (dd, J=11.7, 6.3 Hz, 1H), 2.92 (s, 3H), 2.30 (s, 3H), 2.29 (s, 3H).

EXAMPLE 7(38)

2-(1-(4-((2S)-4-methyl-3,4-dihydro-2H-1,4-benzoxazin-2-ylmethoxy)-2,5-dimethylbenzoyl)-5-chloro-2-methylindol-3-yl)acetic acid benzyl ester

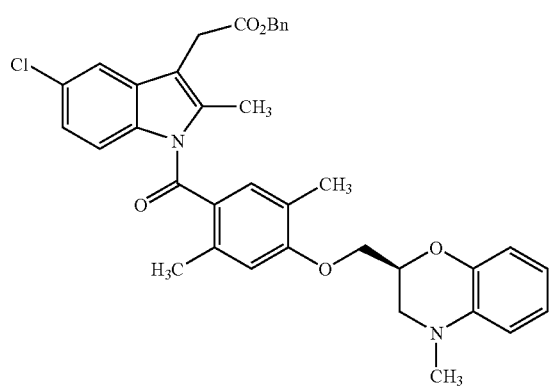

TLC: Rf 0.59(hexane:ethyl acetate=7:3);

NMR(CDCl$_3$):δ 7.46–7.43 (m, 1H), 7.39–7.27 (m, 5H), 7.16 (s, 1H), 7.04–6.82 (m, 4H), 6.75–6.67 (m, 3H), 5.14 (s, 2H), 4.74–4.64 (m, 1H), 4.31 (dd, J=9.6, 4.5 Hz, 1H), 4.20 (dd, J=9.6, 6.0 Hz, 1H), 3.69 (s, 2H), 3.42 (dd, J=11.7, 3.0 Hz, 1H), 3.31 (dd, J=11.7, 6.6 Hz, 1H), 2.93 (s, 3H), 2.30 (s, 3H), 2.22 (s, 3H), 2.18 (s, 3H).

EXAMPLE 7(39)

2-(1-(4-((2S)-4-methyl-3,4-dihydro-2H-1,4-benzoxazin-2-ylmethoxy)-2,5-dimethylbenzoyl)-5-fluoro-2-methylindol-3-yl)acetic acid benzyl ester

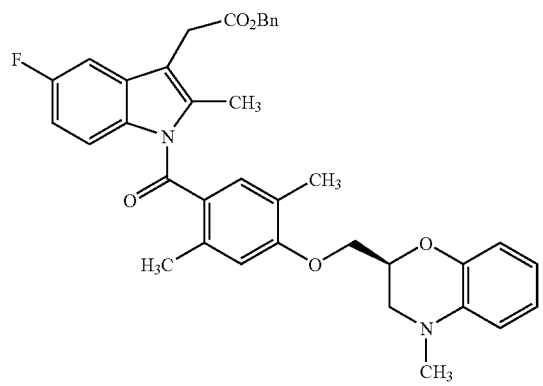

TLC: Rf 0.52(hexane:ethyl acetate=7:3);

NMR(CDCl$_3$):δ 7.40–7.23 (m, 5H), 7.20–7.08 (m, 2H), 7.07–6.97 (m, 1H), 6.93–6.66 (m, 6H), 5.13 (s, 2H), 4.74–4.64 (m, 1H), 4.30 (dd, J=9.6, 4.5 Hz, 1H), 4.20 (dd, J=9.6, 6.6 Hz, 1H), 3.68 (s, 2H), 3.42 (dd, J=11.4, 3.0 Hz, 1H), 3.31 (dd, J=11.4, 6.0 Hz, 1H), 2.93 (s, 3H), 2.27 (s, 3H), 2.21 (s, 3H), 2.18 (s, 3H).

EXAMPLE 7(40)

2-(1-(4-((2S)-4-methyl-3,4-dihydro-2H-1,4-benzoxazin-2-ylmethoxy)-2,5-dimethylbenzoyl)-2,5-dimethylindol-3-yl)acetic acid benzyl ester

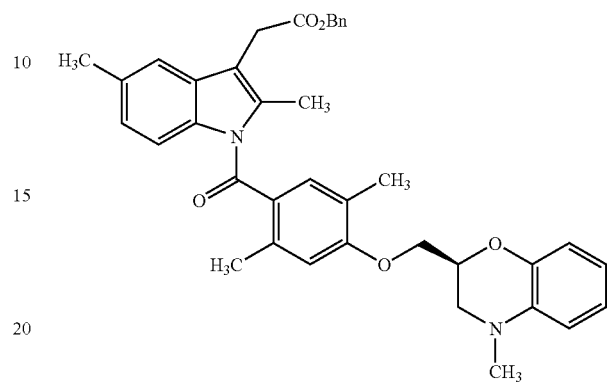

TLC: Rf 0.56(hexane:ethyl acetate=7:3);

NMR(CDCl$_3$):δ 7.39–7.26 (m, 5H), 7.18 (s, 1H), 6.96–6.82 (m, 5H), 6.75–6.67 (m, 3H), 5.13 (s, 2H), 4.73–4.63 (m, 1H), 4.30 (dd, J=9.6, 4.5 Hz, 1H), 4.20 (dd, J=9.6, 6.3 Hz, 1H), 3.71 (s, 2H), 3.42 (dd, J=11.4, 3.0 Hz, 1H), 3.31 (dd, J=11.4, 6.6 Hz, 1H), 2.93 (s, 3H), 2.37 (s, 3H), 2.30 (s, 3H), 2.21 (s, 3H), 2.18 (s, 3H).

EXAMPLE 8(1) TO EXAMPLE 8(40)

Using the compound prepared according to example 7(1) to example 7(40) instead of the compound prepared according to example 1, this following invention compounds were obtained by the operation similar to example 2.

EXAMPLE 8(1)

4-(1-(4-((2S)-4-methyl-3,4-dihydro-2H-1,4-benzoxazin-2-ylmethoxy)benzoyl)-2-methylindol-3-yl)butane

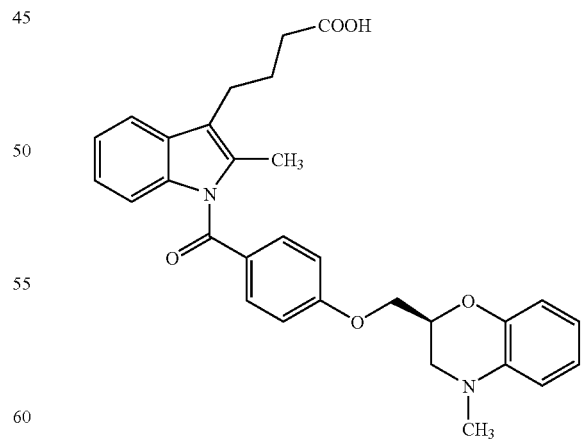

TLC: Rf 0.45(chloroform:methanol=9:1);

NMR(CDCl$_3$):δ 7.72 (d, J=8.7 Hz, 2H), 7.49 (d, J=7.8 Hz, 1H), 7.19–7.12 (m, 1H), 7.08–6.95 (m, 4H), 6.92–6.80 (m, 2H), 6.76–6.66 (m, 2H), 4.73–4.63 (m, 1H), 4.32 (dd, J=9.6, 5.1 Hz, 1H), 4.21 (dd, J=9.6, 6.3 Hz, 1H), 3.41 (dd, J=11.7, 2.7 Hz, 1H), 3.28 (dd, J=11.7, 6.6 Hz, 1H), 2.92 (s, 3H), 2.78 (t, J=7.5 Hz, 2H), 2.44 (t, J=7.5 Hz, 2H), 2.37 (s, 3H), 2.08–1.93 (m, 2H).

EXAMPLE 8(2)

2-(1-(4-((2S)-4-methyl-3,4-dihydro-2H-1,4-benzoxazin-2-ylmethoxy)benzoyl)-2,5-dimethylindol-3-yl)acetic acid

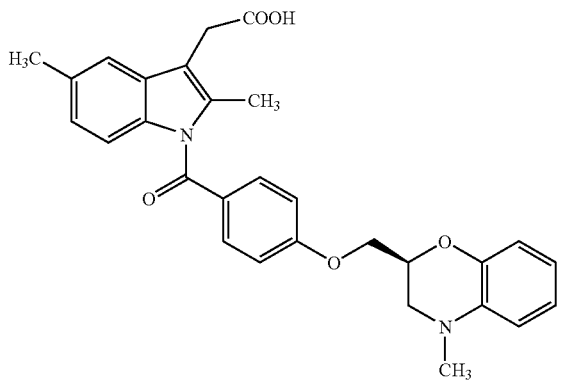

TLC: Rf 0.39(methanol:chloroform=1:10);
NMR(CDCl$_3$):δ 7.71 (d, J=9.6 Hz, 2H), 7.28 (s, 1H), 6.99 (d, J=9.6 Hz, 2H), 6.90–6.80 (m, 4H), 6.73–6.70 (m, 2H), 4.67 (m, 1H), 4.30 (dd, J=9.9, 4.8 Hz, 1H), 4.21 (dd, J=9.9, 6.3 Hz, 1H), 3.71 (s, 2H), 3.40 (dd, J=11.7, 3.0 Hz, 1H), 3.28 (dd, J=11.7, 6.6 Hz, 1H), 2.92 (s, 3H), 2.41 (s, 3H), 2.40 (s, 3H).

EXAMPLE 8(3)

2-(1-(4-((2S)-4-methyl-3,4-dihydro-2H-1,4-benzoxazin-2-ylmethoxy)benzoyl)-5-fluoro-2-methylindol-3-yl)acetic acid

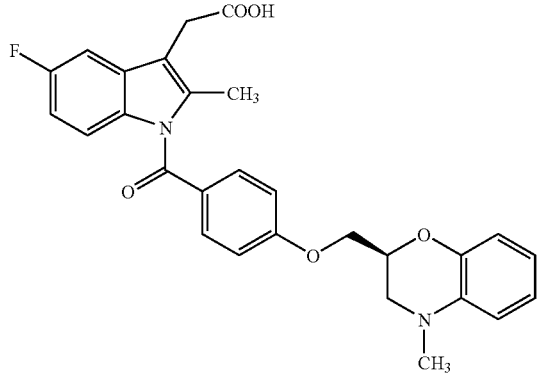

TLC: Rf 0.42(methanol:chloroform=1:10);
NMR(CDCl$_3$):δ 7.70 (d, J=9.0 Hz, 2H), 7.15 (m, 1H), 7.00 (d, J=9.0 Hz, 2H), 6.95–6.65 (m, 6H), 4.68 (m, 1H), 4.30 (dd, J=9.6, 4.8 Hz, 1H), 4.21 (dd, J=9.6, 6.0 Hz, 1H), 3.68 (s, 2H), 3.39 (dd, J=11.7, 2.7 Hz, 1H), 3.28 (dd, J=11.7, 6.6 Hz, 1H), 2.91 (s, 3H), 2.39 (s, 3H).

EXAMPLE 8(4)

2-(1-(4-((2S)-4-methyl-3,4-dihydro-2H-1,4-benzoxazin-2-ylmethoxy)benzoyl)-5-chloro-2-methylindol-3-yl)acetic acid

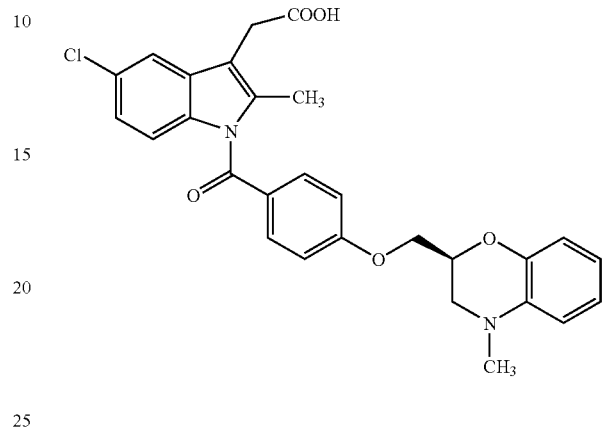

TLC: Rf 0.40(chloroform:methanol=10:1);
NMR(CDCl$_3$):δ 7.71 (d, J=9.0 Hz, 2H), 7.47 (d, J=1.8 Hz, 1H), 7.05–6.95 (m, 3H), 6.92–6.80 (m, 3H), 6.73–6.70 (m, 2H), 4.69 (m, 1H), 4.31 (dd, J=9.9, 5.1 Hz, 1H), 4.22 (dd, J=9.9, 6.0 Hz, 1H), 3.71 (s, 2H), 3.40 (dd, J=11.7, 2.7 Hz, 1H), 3.28 (dd, J=11.7, 6.3 Hz, 1H), 2.92 (s, 3H), 2.41 (s, 3H).

EXAMPLE 8(5)

2-(1-(4-((2S)-4-methyl-3,4-dihydro-2H-1,4-benzoxazin-2-ylmethoxy)benzoyl)-5-trifluoromethyl-2-methylindol-3-yl)acetic acid

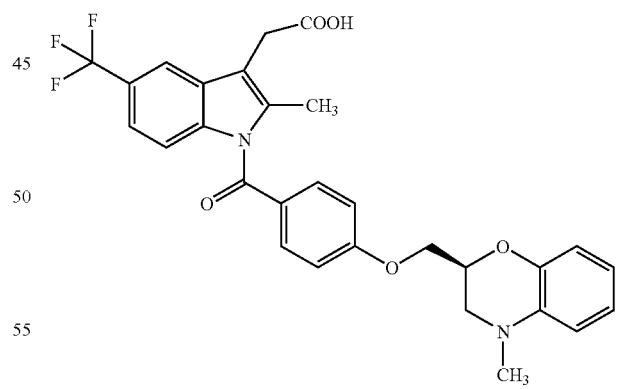

TLC: Rf 0.40(chloroform:methanol=10:1);
NMR(CDCl$_3$):δ 7.78 (s, 1H), 7.71 (d, J=9.0 Hz, 2H), 7.25 (dd, J=8.8, 0.7 Hz, 1H), 7.06 (d, J=8.8 Hz, 1H), 7.00 (d, J=9.0 Hz, 2H), 6.90–6.80 (m, 2H), 6.73–6.65 (m, 2H), 4.67 (m, 1H), 4.31 (dd, J=9.9, 5.1 Hz, 1H), 4.21 (dd, J=9.9, 6.0 Hz, 1H), 3.75 (s, 2H), 3.39 (dd, J=11.7, 2.7 Hz, 1H), 3.27 (dd, J=11.7, 6.6 Hz, 1H), 2.91 (s, 3H), 2.42 (s, 3H).

EXAMPLE 8(6)

2-(1-(4-((2S)-4-methyl-3,4-dihydro-2H-1,4-benzoxazin-2-ylmethoxy)-2-methylbenzoyl)-2-methylindol-3-yl)acetic acid

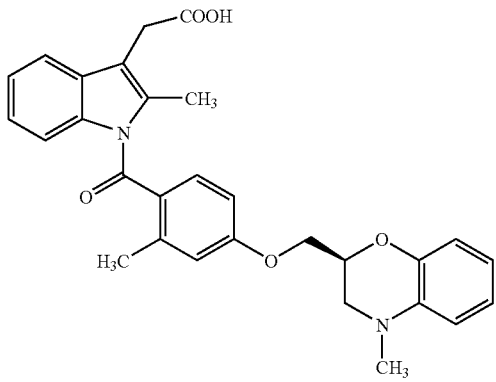

TLC: Rf 0.52(chloroform:methanol=9:1);
NMR(CDCl$_3$):δ 7.48 (d, J=7.8 Hz,1H), 7.40–7.28 (m, 2H), 7.23–7.13 (m, 1H) 7.11–6.95 (m, 2H), 6.94–6.76 (m, 3H), 6.76–6.65 (m, 2H), 4.72–4.62 (m, 1H), 4.29 (dd, J=9.9, 5.1 Hz, 1H), 4.19 (dd, J=9.9, 6.3 Hz, 1H), 3.72 (s, 2H), 3.40 (dd, J=11.4, 1.8 Hz, 1H), 3.27 (dd, J=11.4, 6.6 Hz, 1H), 2.92 (s, 3H), 2.34 (s, 3H), 2.32 (s, 3H).

EXAMPLE 8(7)

2-(1-(4-((2S)-4-methyl-3,4-dihydro-2H-1,4-benzoxazin-2-ylmethoxy)-2-methylbenzoyl)-5-methoxy-2-methylindol-3-yl)acetic acid

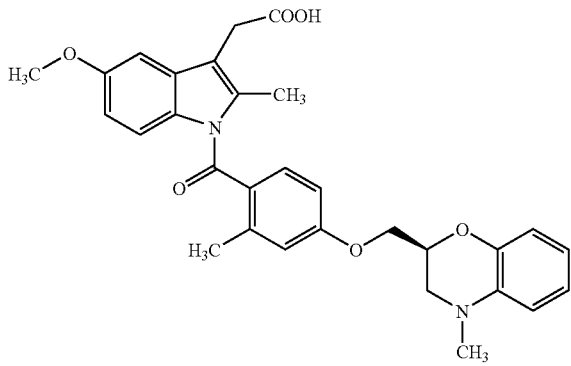

TLC: Rf 0.52(chloroform:methanol=9:1);
NMR(CDCl$_3$):δ 7.32 (d, J=8.7 Hz, 1H), 6.96–6.76 (m, 6H), 6.75–6.64 (m, 3H), 4.72–4.62 (m, 1H), 4.28 (dd, J=9.6, 5.1 Hz, 1H), 4.18 (dd, J=9.6, 6.3 Hz, 1H), 3.82 (s, 3H), 3.69 (s, 2H), 3.40 (dd, J=11.4, 2.7 Hz, 1H), 3.27 (dd, J=11.4, 6.6 Hz, 1H), 2.92 (s, 3H), 2.32 (s, 3H), 2.30 (s, 3H).

EXAMPLE 8(8)

2-(1-(4-((2S)-4-methyl-3,4-dihydro-2H-1,4-benzoxazin-2-ylmethoxy)-2-chlorobenzoyl)-5-methoxy-2-methylindol-3-yl)acetic acid

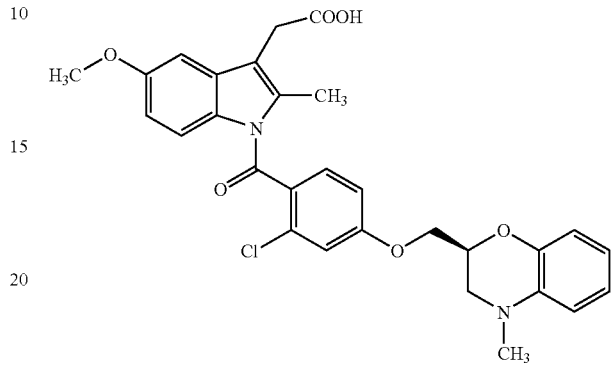

TLC: Rf 0.53(chloroform:methanol=9:1);
NMR(CDCl$_3$):δ 7.42 (d, J=8.7 Hz, 1H), 7.11 (d, J=8.7 Hz, 1H), 7.04 (d, J=2.4 Hz, 1H), 7.00–6.80 (m, 4H), 6.75–6.65 (m, 3H), 4.72–4.62 (m, 1H), 4.28 (dd, J=9.9, 5.4 Hz, 1H), 4.19 (dd, J=9.9, 6.0 Hz, 1H ), 3.83 (s, 3H), 3.67 (s, 2H), 3.40 (dd, J=11.7, 3.0 Hz, 1H), 3.27 (dd, J=11.7, 6.6 Hz, 1H), 2.92 (s, 3H), 2.82 (s, 3H).

EXAMPLE 8(9)

2-(1-(4-((2S)-4-methyl-3,4-dihydro-2H-1,4-benzoxazin-2-ylmethoxy)-2-methylbenzoyl)-5-chloro-2-methylindol-3-yl)acetic acid

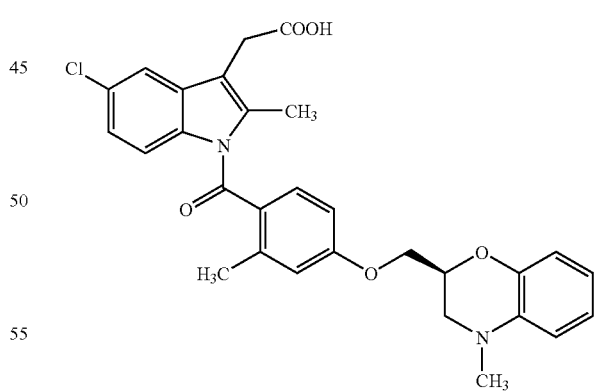

TLC: Rf 0.43(chloroform:methanol=9:1);
NMR(CDCl$_3$):δ 7.45 (d, J=2.1 Hz, 1H), 7.30 (d, J=8.4 Hz, 1H), 7.02 (dd, J=9.0, 2.1 Hz, 1H), 6.98–6.76 (m, 5H), 6.75–6.67 (m, 2H), 4.72–4.62 (m, 1H), 4.28 (dd, J=9.9, 5.4 Hz, 1H), 4.18 (dd, J=9.9, 6.6 Hz, 1H), 3.69 (s, 2H), 3.40 (dd, J=11.1, 2.4 Hz, 1H), 3.27 (dd, J=11.1, 6.6 Hz, 1H), 2.92 (s, 3H), 2.32 (s, 3H), 2.31 (s, 3H).

EXAMPLE 8(10)

2-(1-(4-((2S)-4-methyl-3,4-dihydro-2H-1,4-benzoxazin-2-ylmethoxy)-2-methylbenzoyl)-5-fluoro-2-methylindol-3-yl)acetic acid

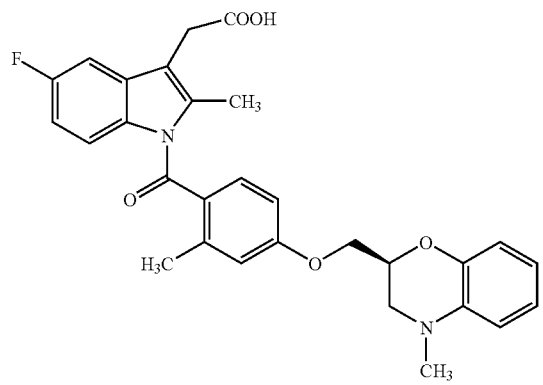

TLC: Rf 0.43(chloroform:methanol=9:1);
NMR(CDCl₃):δ 7.31 (d, J=8.7 Hz, 1H), 7.14 (d, J=8.7, 2.4 Hz, 1H), 7.01 (dd, J=9.3, 4.5 Hz, 1H), 6.92–6.74 (m, 5H), 6.74–6.66 (m, 2H), 4.72–4.62 (m, 1H), 4.29 (dd, J=9.9, 4.8 Hz, 1H), 4.18 (dd, J=9.9, 6.3 Hz, 1H), 3.68 (s, 2H), 3.41 (dd, J=11.4, 2.1 Hz, 1H), 3.27 (dd, J=11.4, 6.6 Hz, 1H), 2.92 (s, 3H), 2.31 (s, 3H), 2.30 (s, 3H).

EXAMPLE 8(11)

2-(1-(4-((2S)-4-methyl-3,4-dihydro-2H-1,4-benzoxazin-2-ylmethoxy)-2-chlorobenzoyl)-2-methylindol-3-yl)acetic acid

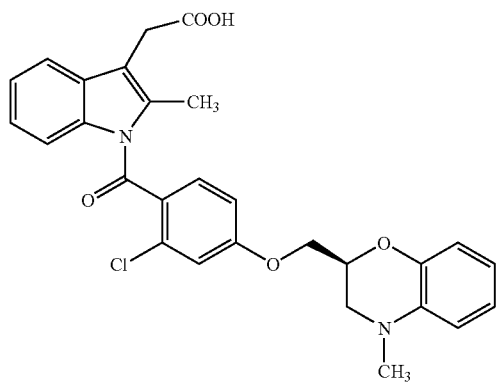

TLC: Rf 0.53(chloroform:methanol=9:1);
NMR(CDCl₃):δ 7.52–7.42 (m, 2H), 7.33–7.04 (m, 4H), 6.98–6.82 (m, 3H), 6.76–6.68 (m, 2H), 4.72–4.64 (m, 1H), 4.29 (dd, J=9.9, 4.8 Hz, 1H), 4.20 (dd, J=9.9, 6.0 Hz, 1H), 3.72 (s, 2H), 3.40 (dd, J=12.0, 2.7 Hz, 1H), 3.27 (dd, J=12.0, 6.0 Hz, 1H), 2.92 (s, 3H), 2.32 (s, 3H).

EXAMPLE 8(12)

2-(1-(4-((2S)-4-methyl-3,4-dihydro-2H-1,4-benzoxazin-2-ylmethoxy)-2,3-dimethylbenzoyl)-2-methylindol-3-yl)acetic acid

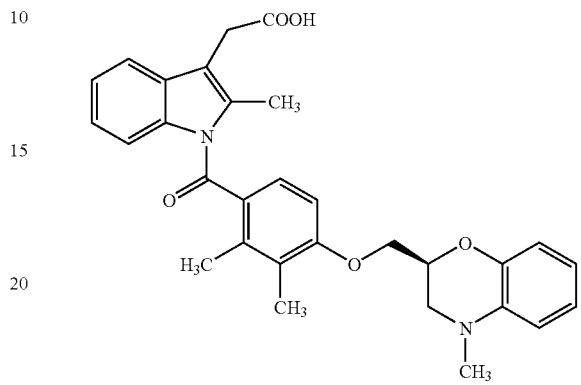

TLC: Rf 0.63(chloroform:methanol: acetic acid=9:1:0.1);
NMR(CDCl₃):δ 7.47 (d, J=7.8 Hz, 1H), 7.21–7.16 (m, 2H), 7.06–7.04 (m, 2H), 6.91–6.83 (m, 2H), 6.77–6.67 (m, 3H), 4.73–4.66 (m, 1H), 4.30–4.15 (m, 2H), 3.71 (s, 2H), 3.45–3.28 (m, 2H), 2.93 (s, 3H), 2.31 (s, 3H), 2.24 (s, 6H).

EXAMPLE 8(13)

2-(1-(4-((2S)-4-methyl-3,4-dihydro-2H-1,4-benzoxazin-2-ylmethoxy)-3-methylbenzoyl)-2-methylindol-3-yl)acetic acid

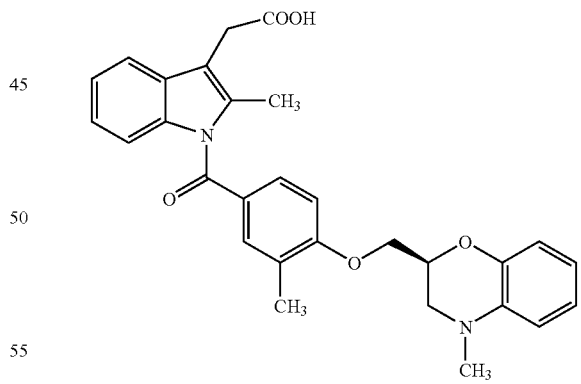

TLC: Rf 0.52(chloroform:methanol:acetic acid=9:1:0.1);
NMR(CDCl₃):δ 7.61 (d, J=1.2 Hz, 1H), 7.56 (dd, J=8.7, 2.4 Hz, 1H), 7.50 (d, J=7.8 Hz, 1H), 7.16 (dt, J=6.9, 1.2 Hz, 1H), 7.04 (dt, J=8.4, 1.2 Hz, 1H), 6.99 (d, J=7.8 Hz, 1H), 6.92–6.82 (m, 3H), 6.73–6.68 (m, 2H), 4.74–4.66 (m, 1H), 4.34–4.19 (m, 2H), 3.74 (s, 2H), 3.42 (dd, J=11.4, 2.7 Hz, 1H), 3.31 (dd, J=11.4, 6.6 Hz, 1H), 2.92 (s, 3H), 2.41 (s, 3H), 2.26 (s, 3H).

EXAMPLE 8(14)

2-(1-(4-((2S)-4-methyl-3,4-dihydro-2H-1,4-benzoxazin-2-ylmethoxy)-2-methylbenzoyl)-2,5-dimethylindol-3-yl)acetic acid

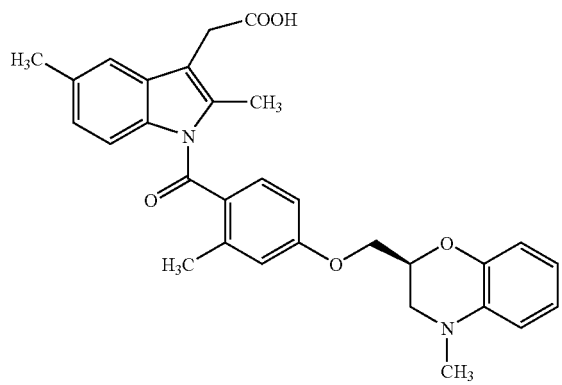

TLC: Rf 0.42(chloroform:methanol=9:1);

NMR(CDCl$_3$):δ 7.32 (d, J=8.4 Hz, 1H), 6.93–6.76 (m, 7H), 6.75–6.66 (m, 2H), 4.72–4.62 (m, 1H), 4.28 (dd, J=9.6, 5.1 Hz, 1H), 4.18 (dd, J=9.6, 6.6 Hz, 1H), 3.70 (s, 2H), 3.41 (dd, J=11.4, 2.4 Hz, 1H), 3.28 (dd, J=11.4, 6.6 Hz, 1H), 2.92 (s, 3H), 2.40 (s, 3H), 2.34 (s, 3H), 2.30 (s, 3H).

EXAMPLE 8(15)

2-(1-(4-((2S)-4-methyl-3,4-dihydro-2H-1,4-benzoxazin-2-ylmethoxy)-3-methoxybenzoyl)-2-methylindol-3-yl)acetic acid

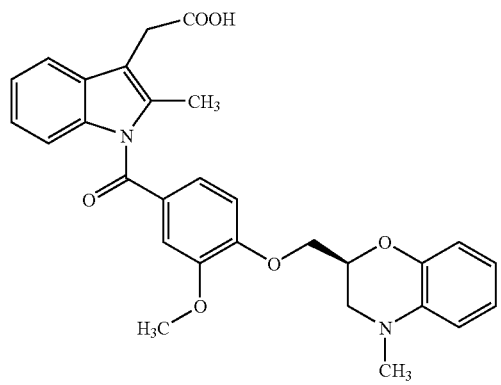

TLC: Rf 0.65(chloroform:methanol:acetic acid=9:1:0.1);

NMR(CDCl$_3$):δ 7.50 (d, J=7.5 Hz, 1H), 7.35 (d, J=1.8 Hz, 1H), 7.30(dd, J=8.4, 2.1 Hz, 1H), 7.20–7.15(m, 1H), 7.08–6.81 (m, 5H), 6.72–6.66 (m, 2H), 4.77–4.69 (m, 1H), 4.38–4.22 (m, 2H), 3.87 (s, 3H), 3.74(s, 2H), 3.45–3.26 (m, 2H), 2.91 (s, 3H), 2.42 (s, 3H).

EXAMPLE 8(16)

2-(1-(4-((2S)-4-methyl-3,4-dihydro-2H-1,4-benzoxazin-2-ylmethoxy)-3-fluorobenzoyl)-2-methylindol-3-yl)acetic acid

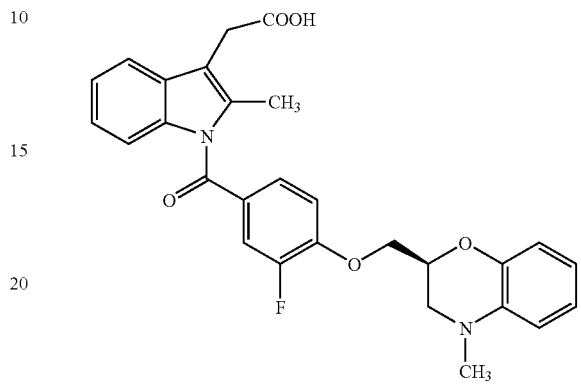

TLC: Rf 0.55(chloroform:methanol=9:1);

NMR(CDCl$_3$):δ 7.57–7.48 (m, 3H), 7.19 (dt, J=7.4, 1.2 Hz, 1H), 7.09–7.03 (m, 2H), 6.97 (d, J=8.1 Hz, 1H), 6.92–6.81 (m, 2H), 6.73–6.67 (m, 2H), 4.75–4.68 (m, 1H), 4.40–4.25 (m, 2H), 3.74 (s, 2H), 3.45–3.28 (m, 2H), 2.92 (s, 3H), 2.42 (s, 3H), 1.90 (brs, 1H).

EXAMPLE 8(17)

2-(1-(4-((2S)-4-methyl-3,4-dihydro-2H-1,4-benzoxazin-2-ylmethoxy)-2-methoxybenzoyl)-2-methylindol-3-yl)acetic acid

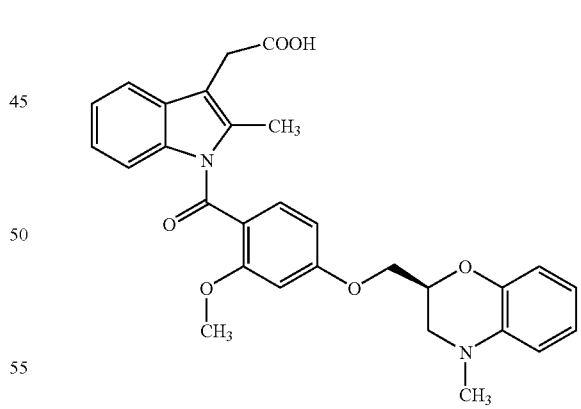

TLC: Rf 0.50(chloroform:methanol=9:1);

NMR(CDCl$_3$):δ 7.50–7.40 (m, 2H), 7.24–7.14 (m, 2H), 7.12–7.04 (m, 1H), 6.93–6.83 (m, 2H), 6.76–6.67 (m, 2H), 6.59 (dd, J=8.4, 2.1 Hz, 1H), 6.54 (d, J=2.1 Hz, 1H), 4.72–4.64 (m, 1H), 4.30 (dd, J=9.6, 5.1 Hz, 1H), 4.20 (dd, J=9.6, 6.0 Hz, 1H), 3.72 (s, 2H), 3.61 (s, 3H), 3.41 (dd, J=11.7, 2.7 Hz, 1H), 3.29 (dd, J=11.7, 6.6 Hz, 1H), 2.93 (s, 3H), 2.34 (s, 3H).

EXAMPLE 8(18)

2-(1-(4-((2S)-4-methyl-3,4-dihydro-2H-1,4-benzoxazin-2-ylmethoxy)-3-chlorobenzoyl)-2-methylindol-3-yl)acetic acid

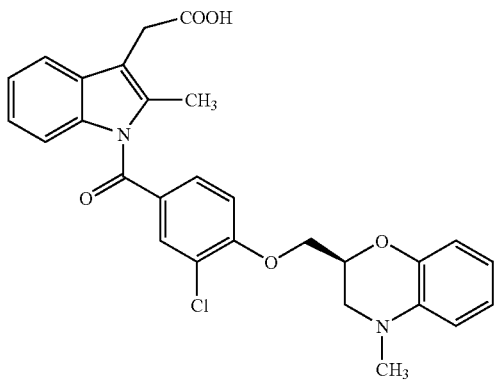

TLC: Rf 0.52(chloroform:methanol=9:1);
NMR(CDCl$_3$):δ 7.84 (d, J=2.1 Hz, 1H), 7.62 (dd, J=8.4, 2.1 Hz, 1H), 7.51 (d, J=7.8 Hz, 1H), 7.19 (dt, J=6.9, 1.2 Hz, 1H), 7.09–6.96 (m, 3H), 6.92–6.82 (m, 2H), 6.73–6.67 (m, 2H), 4.78–4.71 (m, 1H), 4.41–4.24 (m, 2H), 3.74 (s, 2H), 3.45 (dd, J=11.4, 2.7 Hz, 1H), 3.36 (dd, J=11.4, 6.0 Hz, 1H), 2.93 (s, 3H), 2.42 (s, 3H).

EXAMPLE 8(19)

2-(1-(4-((2S)-4-methyl-3,4-dihydro-2H-1,4-benzoxazin-2-ylmethoxy)-2-fluorobenzoyl)-2-methylindol-3-yl)acetic acid

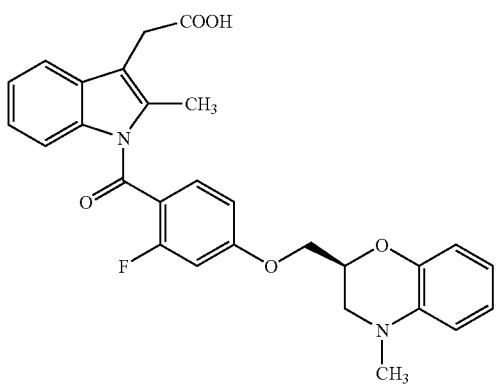

TLC: Rf 0.63(chloroform:methanol=9:1);
NMR(CDCl$_3$):δ 7.55 (t, J=8.4 Hz, 1H), 7.49 (d, J=7.5 Hz, 1H), 7.20 (dt, J=6.6, 1.5 Hz, 1H), 7.15–7.06 (m, 2H), 6.92–6.83 (m, 3H), 6.75–6.68 (m, 3H), 4.72–4.65 (m, 1H), 4.32–4.17 (m, 2H), 3.72 (s, 2H), 3.4 0 (dd, J=11.4, 2.7 Hz, 1H), 3.27 (dd, J=11.4, 6.3 Hz, 1H), 2.92 (s, 3H), 2.42 (s, 3H).

EXAMPLE 8(20)

2-(1-(4-((2S)-4-methyl-3,4-dihydro-2H-1,4-benzoxazin-2-ylmethoxy)-3-methylbenzoyl)-2,5-dimethylindol-3-yl)acetic acid

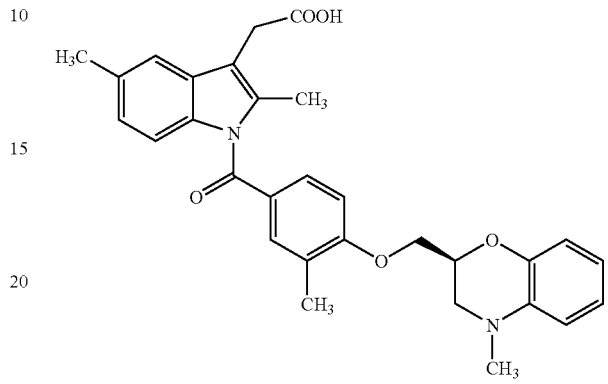

TLC: Rf 0.45(chloroform:methanol=9:1);
NMR(CDCl$_3$):δ 7.62–7.52 (m, 2H), 7.28 (s, 1H), 6.93–6.81 (m, 5H), 6.75–6.66 (m, 2H), 4.74–4.65 (m, 1H), 4.31 (dd, J=9.9, 4.8 Hz, 1H), 4.22 (dd, J=9.9, 6.3 Hz, 1H), 3.71 (s, 2H), 3.42 (dd, J=11.7, 3.0 Hz, 1H), 3.31 (dd, J=11.7, 6.6 Hz, 1H), 2.92 (s, 3H), 2.41 (s, 3H), 2.40 (s, 3H), 2.26 (s, 3H).

EXAMPLE 8(21)

2-(1-(4-((2S)-4-methyl-3,4-dihydro-2H-1,4-benzoxazin-2-ylmethoxy)-3-methylbenzoyl)-5-fluoro-2-methylindol-3-yl)acetic acid

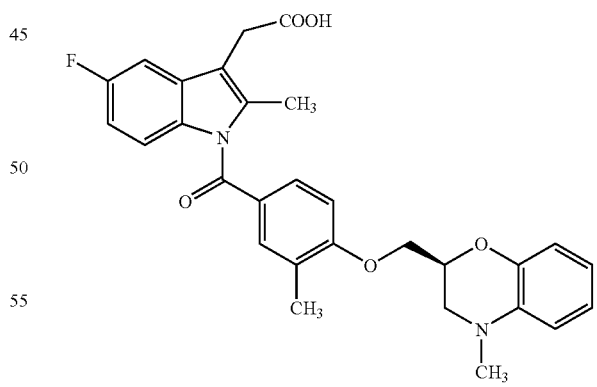

TLC: Rf 0.48(chloroform:methanol=9:1);
NMR(CDCl$_3$):δ 7.61–7.51 (m, 2H), 7.15 (dd, J=8.7, 2.1 Hz, 1H), 6.98–6.67 (m, 7H), 4.74–4.66 (m, 1H), 4.32 (dd, J=9.6, 5.1 Hz, 1H), 4.22 (dd, J=9.6, 6.3 Hz, 1H), 3.69 (s, 2H), 3.42 (dd, J=11.4, 2.4 Hz, 1H ), 3.31 (dd, J=11.4, 6.6 Hz, 1H), 2.92 (s, 3H), 2.39 (s, 3H), 2.27 (s, 3H).

EXAMPLE 8(22)

2-(1-(4-((2S)-4-methyl-3,4-dihydro-2H-1,4-benzoxazin-2-ylmethoxy)-3-methylbenzoyl)-5-chloro-2-methylindol-3-yl)acetic acid

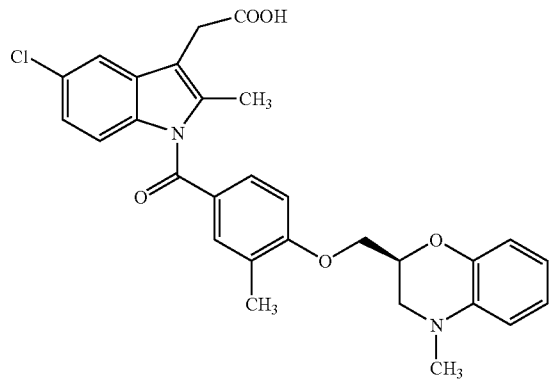

TLC: Rf 0.37(chloroform:methanol=9:1);
NMR(CDCl$_3$):δ 7.60–7.50 (m, 2H), 7.47 (d, J=1.8 Hz, 1H), 6.99 (dd, J=8.7, 1.8 Hz, 1H), 6.94–6.81 (m, 4H), 6.75–6.67 (m, 2H), 4.75–4.66 (m, 1H), 4.32 (dd, J=9.9, 5.1 Hz, 1H), 4.23 (dd, J=9.9, 6.3 Hz, 1H), 3.70 (s, 2H), 3.42 (dd, J=11.7, 3.0 Hz, 1H), 3.31 (dd, J=11.7, 6.6 Hz, 1H), 2.93 (s, 3H), 2.40 (s, 3H), 2.27 (s, 3H).

EXAMPLE 8(23)

2-(1-(4-((2S)-4-methyl-3,4-dihydro-2H-1,4-benzoxazin-2-ylmethoxy)-3-methylbenzoyl)-5-methoxy-2-methylindol-3-yl)acetic acid

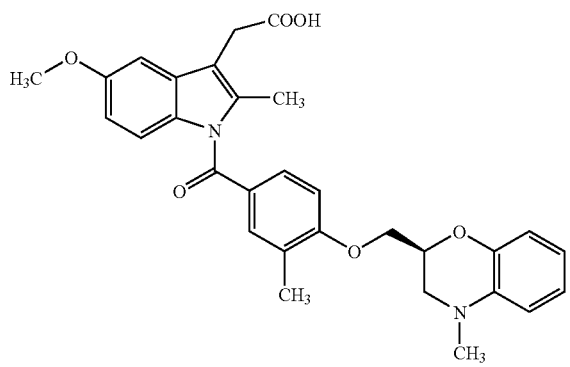

TLC: Rf 0.40(chloroform:methanol=9:1);
NMR(CDCl$_3$):δ 7.62–7.52 (m, 2H), 6.95 (d, J=2.4 Hz, 1H), 6.93–6.81 (m, 4H), 6.76–6.63 (m, 3H), 4.74–4.65 (m, 1H), 4.32 (dd, J=9.6, 5.1 Hz, 1H), 4.22 (dd, J=9.6, 6.3 Hz, 1H), 3.83 (s, 3H), 3.71 (s, 2H), 3.42 (dd, J=11.4, 2.7 Hz, 1H), 3.31 (dd, J=11.4, 6.6 Hz, 1H), 2.93 (s, 3H), 2.41 (s, 3H), 2.27 (s, 3H).

EXAMPLE 8(24)

2-(1-(4-((2S)-4-methyl-3,4-dihydro-2H-1,4-benzoxazin-2-ylmethoxy)-2,3-dimethylbenzoyl)-5-fluoro-2-methylindol-3-yl)acetic acid

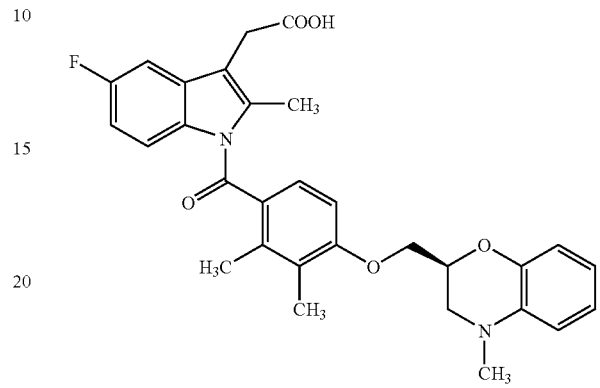

TLC: Rf 0.54(chloroform:methanol=9:1);
NMR(CDCl$_3$):δ 7.18–7.02 (m, 3H), 6.92–6.67 (m, 6H), 4.73–4.66 (m, 1H), 4.30–4.16 (m, 2H), 3.66 (s, 2H), 3.43 (dd, J=11.4, 2.7 Hz, 1H), 3.32 (dd, J=11.4, 6.9 Hz, 1H), 2.93 (s, 3H), 2.27 (s, 3H), 2.24 (s, 3H), 2.23 (s, 3H).

EXAMPLE 8(25)

2-(1-(4-((2S)-4-methyl-3,4-dihydro-2H-1,4-benzoxazin-2-ylmethoxy)-3-methoxybenzoyl)-5-fluoro-2-methylindol-3-yl)acetic acid

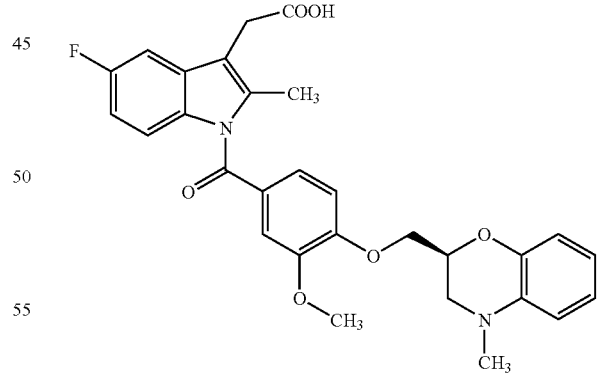

TLC: Rf 0.58(chloroform:methanol=9:1);
NMR(CDCl$_3$):δ 7.33 (d, J=1.8 Hz, 1H), 7.27 (dd, J=8.7, 1.8 Hz, 1H), 7.19–7.14 (m, 1H), 7.00–6.66 (m, 7H), 4.77–4.69 (m, 1H), 4.38–4.22 (m, 2H), 3.88 (s, 3H), 3.70 (s, 2H), 3.43 (dd, J=11.4, 2.7 Hz, 1H), 3.30 (dd, J=11.4, 6.3 Hz, 1H), 2.91 (s, 3H), 2.40 (s, 3H).

EXAMPLE 8(26)

2-(1-(4-((2S)-4-methyl-3,4-dihydro-2H-1,4-benzoxazin-2-ylmethoxy)-3-fluorobenzoyl)-5-fluoro-2-methylindol-3-yl)acetic acid

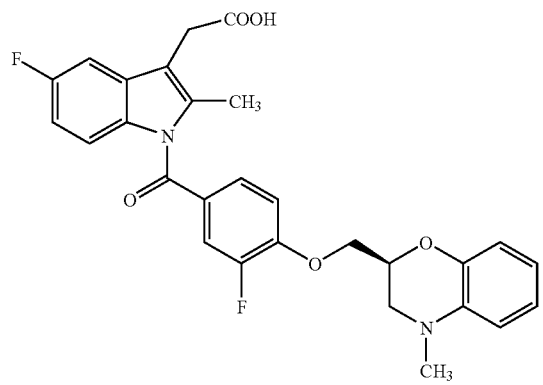

TLC: Rf 0.43(chloroform:methanol=9:1);

NMR(CDCl₃):δ 7.55–7.46 (m, 3H), 7.19–6.70 (m, 7H), 4.75–4.68 (m, 1H), 4.40–4.26 (m, 2H), 3.69 (s, 2H), 3.44–3.27 (m, 2H), 2.92 (s, 3H), 2.40 (s, 3H).

EXAMPLE 8(27)

2-(1-(3-((2S)-4-methyl-3,4-dihydro-2H-1, 4-benzoxazin-2-ylmethoxy)benzoyl)-2-methylindol-3-yl)acetic acid

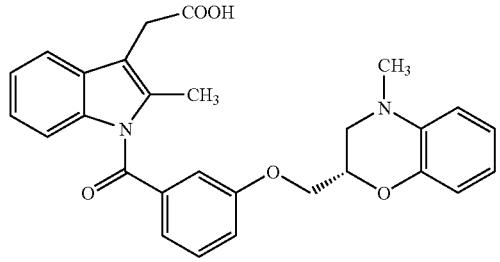

TLC: Rf 0.50(chloroform:methanol=9:1);

NMR(CDCl₃):δ 7.50 (dd, J=7.8, 0.9 Hz, 1H), 7.39 (t, J=7.8 Hz, 1H), 7.34–7.24 (m, 2H), 7.24–7.15 (m, 2H), 7.10–7.02 (m, 2H), 6.91–6.78 (m, 2H), 6.74–6.64 (m, 2H), 4.68–4.58 (m, 1H), 4.24 (dd, J=9.9, 5.4 Hz, 1H), 4.13 (dd, J=9.9, 6.9 Hz, 1H), 3.73 (s, 2H), 3.36 (dd, J=11.4, 2.7 Hz, 1H), 3.23 (dd, J=11.4, 6.3 Hz, 1H), 2.89 (s, 3H), 2.38 (s, 3H).

EXAMPLE 8(28)

2-(1-(4-((2S)-4-methyl-3,4-dihydro-2H-1,4-benzoxazin-2-ylmethoxy)-2-chlorobenzoyl)-5-fluoro-2-methylindol-3-yl)acetic acid

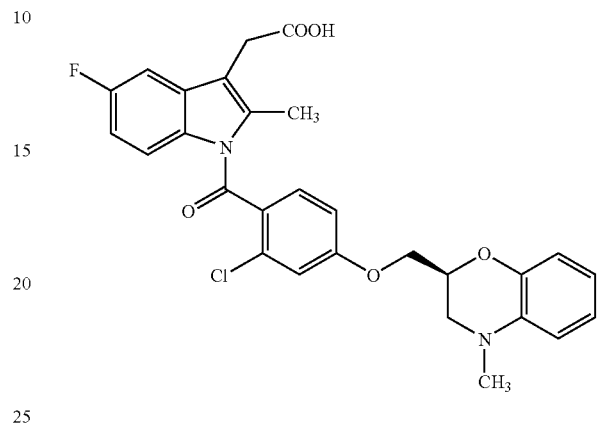

TLC: Rf 0.48(chloroform:methanol=9:1);

NMR(CDCl₃):δ 7.44 (d, J=8.7 Hz, 1H), 7.22 (dd, J=8.7, 4.5 Hz, 1H), 7.15 (dd, J=8.7, 2.1 Hz, 1H), 7.05 (d, J=2.1 Hz, 1H), 7.00–6.80 (m, 4H), 6.75–6.68 (m, 2H), 4.73–4.63 (m, 1H), 4.29 (dd, J=9.9, 5.4 Hz, 1H), 4.20 (dd, J=9.9, 6.0 Hz, 1H), 3.67 (s, 2H), 3.40 (dd, J=11.4, 2.7 Hz, 1H), 3.27 (dd, J=11.4, 6.3 Hz, 1H), 2.92 (s, 3H), 2.27 (s, 3H).

EXAMPLE 8(29)

2-(1-(4-((2S)-4-methyl-3,4-dihydro-2H-1,4-benzoxazin-2-ylmethoxy)-2-chlorobenzoyl)-5-chloro-2-methylindol-3-yl)acetic acid

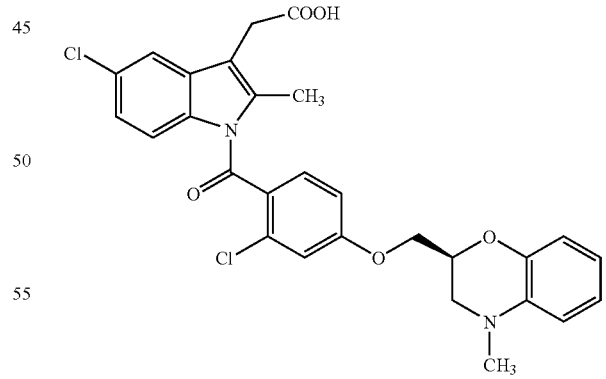

TLC: Rf 0.48(chloroform:methanol=9:1);

NMR(CDCl₃):δ 7.47–7.42 (m, 2H), 7.14 (d, J=8.7 Hz, 1H), 7.10–7.03 (m, 2H), 6.99–6.82 (m, 3H), 6.75–6.68 (m, 2H), 4.72–4.62 (m, 1H), 4.29 (dd, J=9.9, 5.1 Hz, 1H), 4.20 (dd, J=9.9, 6.0 Hz, 1H), 3.67 (s, 2H), 3.40 (dd, J=11.4, 2.7 Hz, 1H), 3.27 (dd, J=11.4, 6.3 Hz, 1H), 2.92 (s, 3H), 2.29 (s, 3H).

EXAMPLE 8(30)

2-(1-(4-((2S)-4-methyl-3,4-dihydro-2H-1,4-benzoxazin-2-ylmethoxy)-2-fluorobenzoyl)-5-fluoro-2-methylindol-3-yl)acetic acid

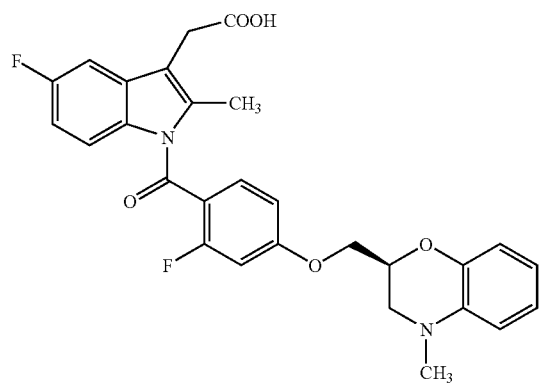

TLC: Rf 0.40(chloroform:methanol=9:1);

NMR(CDCl$_3$):δ 7.53 (t, J=8.1 Hz, 1H), 7.17–7.12 (m, 2H), 6.92–6.68 (m, 7H), 4.75–4.64 (m, 1H), 4.31–4.17 (m, 2H), 3.64 (s, 2H), 3.39 (dd, J=11.4, 3.0 Hz, 1H), 3.26 (dd, J=11.4, 6.3 Hz, 1H), 2.92 (s, 3H), 2.34 (s, 3H).

EXAMPLE 8(31)

2-(1-(4-((2S)-4-methyl-3,4-dihydro-2H-1,4-benzoxazin-2-ylmethoxy)-2-fluorobenzoyl)-5-chloro-2-methylindol-3-yl)acetic acid

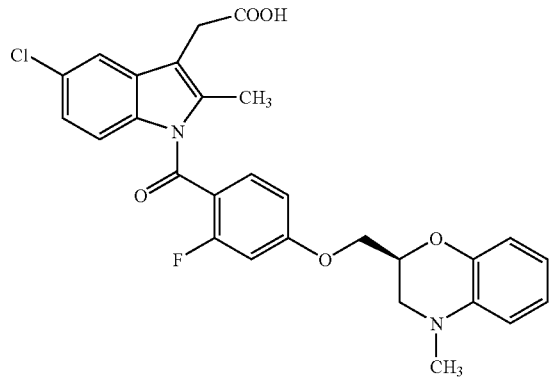

TLC: Rf 0.43(chloroform:methanol=9:1);

NMR(CDCl$_3$):δ 7.54 (t, J=8.4 Hz, 1H), 7.45 (d, J=2.1 Hz, 1H), 7.11–7.02 (m, 2H), 6.92–6.82 (m, 3H), 6.73–6.68 (m, 3H), 4.71–4.65 (m, 1H), 4.31–4.17 (m, 2H), 3.67 (s, 2H), 3.39 (dd, J=11.4, 2.7 Hz, 1H), 3.27 (dd, J=11.4, 6.3 Hz, 1H), 2.92 (s, 3H), 2.36 (s, 3H).

EXAMPLE 8(32)

2-(1-(4-((2S)-4-methyl-3,4-dihydro-2H-1,4-benzoxazin-2-ylmethoxy)-2-fluorobenzoyl)-2,5-dimethylindol-3-yl)acetic acid

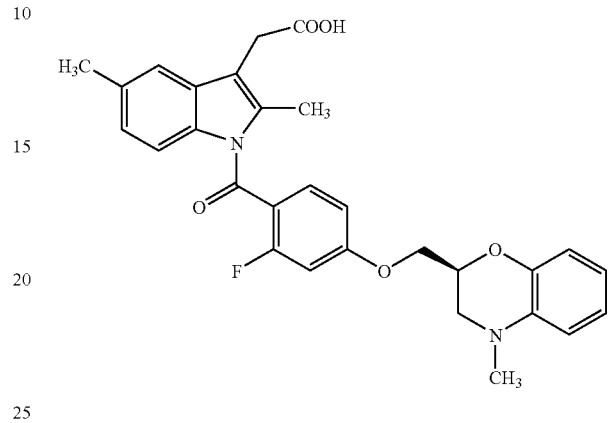

TLC: Rf 0.49(chloroform:methanol=9:1);

NMR(CDCl$_3$):δ 7.54 (t, J=8.1 Hz, 1H), 6.99 (d, J=8.1, 1H), 6.92–4.83 (m, 4H), 6.74–6.70 (m, 4H), 4.71–4.64 (m, 1H), 4.31–4.17 (m, 2H), 3.71 (s, 2H), 3.40 (dd, J=11.7, 2.7 Hz, 1H), 3.27 (dd, J=11.7, 6.3 Hz, 1H), 2.92 (s, 3H), 2.42 (s, 6H).

EXAMPLE 8(33)

2-(1-(4-((2S)-4-methyl-3,4-dihydro-2H-1,4-benzoxazin-2-ylmethoxy)-2-fluorobenzoyl)-5-methoxy-2-methylindol-3-yl)acetic acid

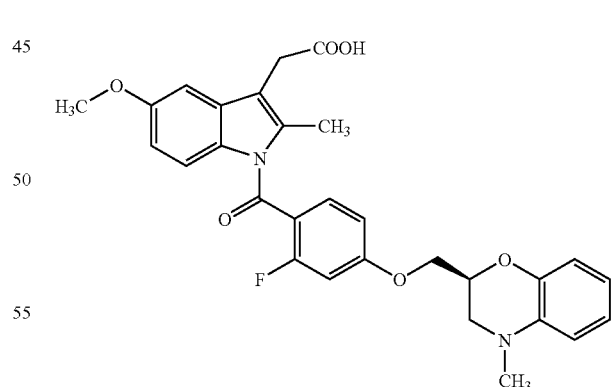

TLC: Rf 0.42(chloroform:methanol=9:1);

NMR(CDCl$_3$):δ 7.53 (t, J=8.4 Hz, 1H), 7.06 (d, J=8.7 Hz, 1H), 6.95–6.83 (m, 4H), 6.74–6.68 (m, 4H), 4.71–4.64 (m, 1H), 4.31–4.17 (m, 2H), 3.83 (s, 3H), 3.68 (s, 2H), 3.40 (dd, J=11.7, 2.7 Hz, 1H), 3.27 (d d, J=11.7, 6.6 Hz, 1H), 2.92 (s, 3H), 2.42 (s, 3H).

EXAMPLE 8(34)

2-(1-(4-((2S)-4-methyl-3,4-dihydro-2H-1,4-benzoxazin-2-ylmethoxy)-2,5-dimethylbenzoyl)-2-methylindol-3-yl)acetic acid

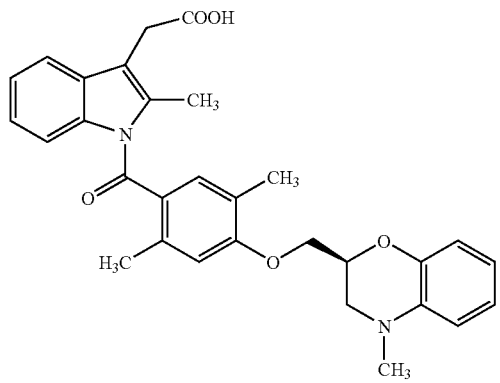

TLC: Rf 0.35(chloroform:methanol=9:1);

NMR(CDCl$_3$):δ 7.48 (t, J=7.5 Hz, 1H), 7.21–7.15 (m, 2H), 7.09–6.99 (m, 2H), 6.92–6.82 (m, 2H), 6.75–6.68 (m, 3H), 4.73–4.66 (m, 1H), 4.33–4.18 (m, 2H), 3.72 (s, 2H), 3.42 (dd, J=11.4, 2.7 Hz, 1H), 3.31 (dd, J=11.4, 6.6 Hz, 1H), 2.93 (s, 3H), 2.34 (s, 3H), 2.26 (s, 3H), 2.17 (s, 3H).

EXAMPLE 8(35)

2-(1-(4-((2S)-4-methyl-3,4-dihydro-2H-1,4-benzoxazin-2-ylmethoxy)-2-chlorobenzoyl)-2, 5-dimethylindol-3-yl)acetic acid

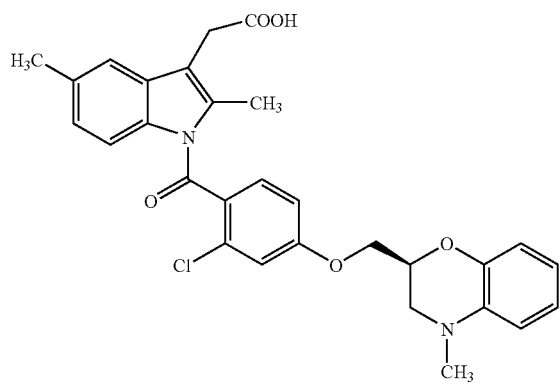

TLC: Rf 0.51(chloroform:methanol=9:1);

NMR(CDCl$_3$):δ 7.43 (d, J=8.7 Hz, 1H), 7.06–6.82 (m, 7H), 6.75–6.67 (m, 2H), 4.72–4.62 (m, 1H), 4.29 (dd, J=9.6, 4.8 Hz, 1H), 4.20 (dd, J=9.6, 6.3 Hz, 1H), 3.70 (s, 2H), 3.40 (dd, J=11.7, 3.0 Hz, 1H), 3.27 (dd, J=11.7, 6.6 Hz, 1H), 2.92 (s, 3H), 2.41 (s, 3H), 2.32 (s, 3H).

EXAMPLE 8(36)

2-(1-(4-((2S)-4-methyl-3,4-dihydro-2H-1,4-benzoxazin-2-ylmethoxy)-3,5-dimethylbenzoyl)-2-methylindol-3-yl)acetic acid

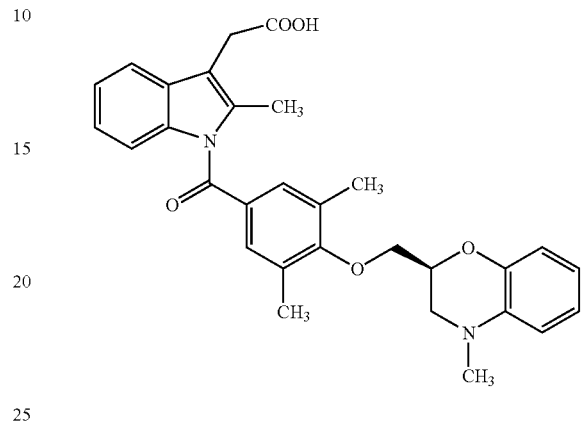

TLC: Rf 0.50(chloroform:methanol=9:1);

NMR(CDCl$_3$):δ 7.50 (d, J=7.8 Hz, 1H), 7.42 (s, 2H), 7.22–7.13 (m, 1H), 7.09–6.95 (m, 2H), 6.91–6.79 (m, 2H), 6.74–6.65 (m, 2H), 4.73–4.64 (m, 1H), 4.12–4.01 (m, 2H), 3.75 (s, 2H), 3.43 (dd, J=11.1, 2.7 Hz, 1H), 3.34 (dd, J=11.1, 6.3 Hz, 1H), 2.93 (s, 3H), 2.40 (s, 3H), 2.32 (s, 6H).

EXAMPLE 8(37)

2-(1-(4-((2S)-4-methyl-3,4-dihydro-2H-1,4-benzoxazin-2-ylmethoxy)-2-methylbenzoyl)-5-trifluoromethoxy-2-methylindol-3-yl)acetic acid

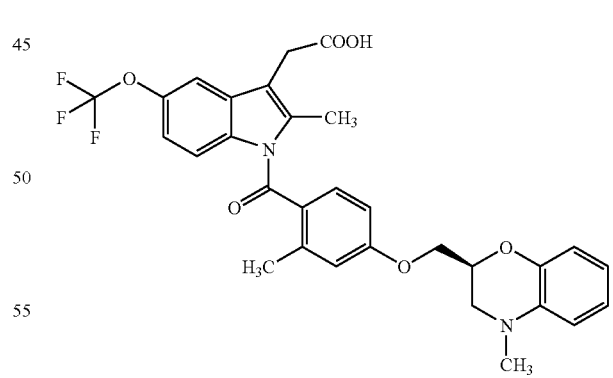

TLC: Rf 0.53(chloroform:methanol=9:1);

NMR(CDCl$_3$):δ 7.37–7.28 (m, 2H), 7.03 (d, J=9.0 Hz, 1H), 6.96–4.75 (m, 5H), 6.75–6.66 (m, 2H), 4.72–4.62 (m, 1H), 4.29 (dd, J=9.6, 4.8 Hz, 1H), 4.19 (dd, J=9.6, 6.3 Hz, 1H), 3.70 (s, 2H), 3.40 (dd, J=11.4, 2.7 Hz, 1H), 3.27 (dd, J=11.4, 6.6 Hz, 1H), 2.92 (s, 3H), 2.33 (s, 3H), 2.32 (s, 3H).

EXAMPLE 8(38)

2-(1-(4-((2S)-4-methyl-3,4-dihydro-2H-1,4-benzoxazin-2-ylmethoxy)-2,5-dimethylbenzoyl)-5-chloro-2-methylindol-3-yl)acetic acid

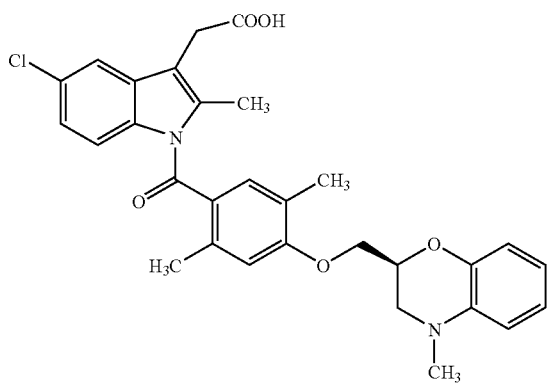

TLC: Rf 0.44(chloroform:methanol=9:1);

NMR(CDCl₃):δ 7.45 (d, J=2.1 Hz, 1H), 7.16 (s, 1H), 7.01 (dd, J=9.0, 2.1 Hz, 1H), 6.98–6.82 (m, 3H), 6.76–6.67 (m, 3H), 4.75–4.65 (m, 1H), 4.31 (dd, J=9.9, 4.8 Hz, 1H), 4.20 (dd, J=9.9, 6.6 Hz, 1H), 3.69 (s, 2H), 3.42 (dd, J=11.7, 2.7 Hz, 1H), 3.31 (dd, J=11.7, 6.6 Hz, 1H), 2.93 (s, 3H), 2.32 (s, 3H), 2.25 (s, 3H), 2.18 (s, 3H).

EXAMPLE 8(39)

2-(1-(4-((2S)-4-methyl-3,4-dihydro-2H-1,4-benzoxazin-2-ylmethoxy)-2,5-dimethylbenzoyl)-5-fluoro-2-methylindol-3-yl)acetic acid

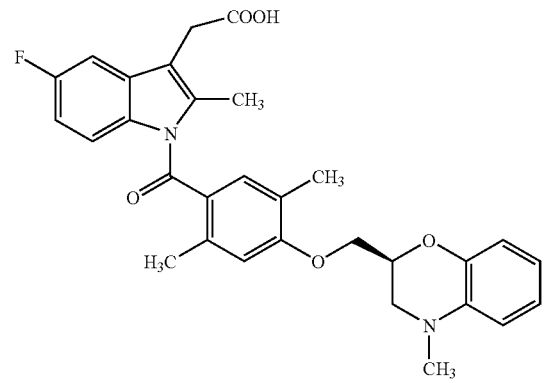

TLC: Rf 0.44(chloroform:methanol=9:1);

NMR(CDCl₃):δ 7.19–7.11 (m, 2H), 7.06–6.96 (m, 1H), 6.93–6.67 (m, 6H), 4.74–4.64 (m, 1H), 4.31 (dd, J=9.6, 3.9 Hz, 1H), 4.20 (dd, J=9.6, 6.6 Hz, 1H), 3.68 (s, 2H), 3.42 (dd, J=11.7, 3.0 Hz, 1H), 3.31 (dd, J=11.7, 6.3 Hz, 1H), 2.93 (s, 3H), 2.31 (s, 3H), 2.25 (s, 3H), 2.18 (s, 3H).

EXAMPLE 8(40)

2-(1-(4-((2S)-4-methyl-3,4-dihydro-2H-1,4-benzoxazin-2-ylmethoxy)-2,5-dimethylbenzoyl)-2, 5-dimethylindol-3-yl) acetic acid

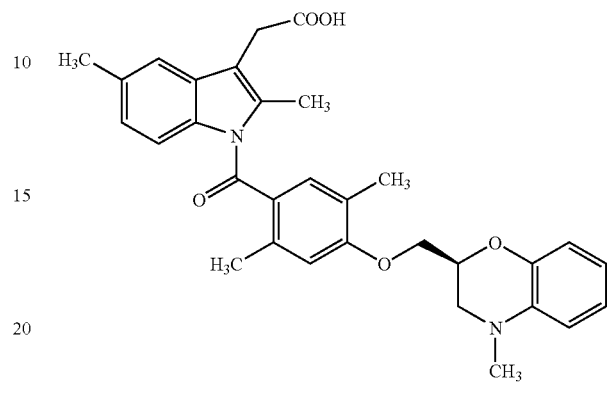

TLC: Rf 0.44(chloroform:methanol=9:1);

NMR(CDCl₃):δ 7.18 (s, 1H), 6.94–6.82 (m, 5H), 6.76–6.67 (m, 3H), 4.74–4.64 (m, 1H), 4.30 (dd, J=9.9, 5.1 Hz, 1H), 4.20 (dd, J=9.9, 6.6 Hz, 1H), 3.71 (s, 2H), 3.43 (dd, J=11.7, 3.0 Hz, 1H), 3.31 (dd, J=11.7, 6.6 Hz, 1H), 2.93 (s, 3H), 2.40 (s, 3H), 2.33 (s, 3H), 2.25 (s, 3H), 2.18 (s, 3H).

EXAMPLE 9(1) TO EXAMPLE 9(15)

Using the compound prepared according to reference example 11, the substitute derivatives, (2S)-2-hydroxymethyl-4,7-dimethyl-3,4-dihydro-2H-1,4-benzoxazine, or the substitute derivatives, this following invention compounds were obtained by the operation similar to example 4.

EXAMPLE 9(1)

2-(1-(4-(quinolin-3-ylmethoxy)benzoyl)-2-methylindol-3-yl)acetic acid allylic ester

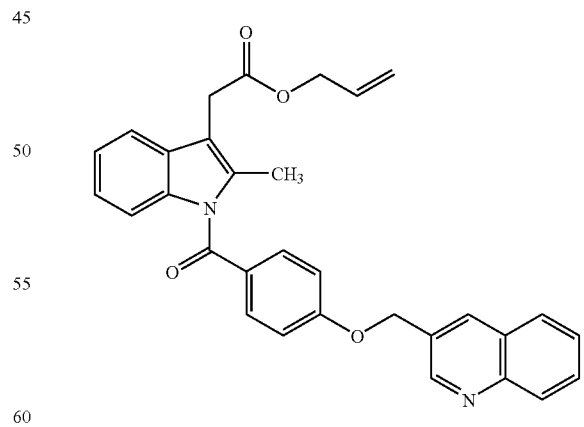

TLC: Rf 0.66(hexane:ethyl acetate=2:1);

NMR(CDCl₃):δ 9.01 (d, J=2.4 Hz, 1H), 8.23 (s, 1H), 8.15 (d, J=8.1 Hz, 1H), 7.87 (d, J=7.8 Hz, 1H), 7.79–7.74 (m, 3H), 7.63–7.50 (m, 2H), 7.19–6.98 (m, 5H), 5.91 (m, 5H), 5.84 (s, 2H), 5.84–5.19 (m, 2H), 4.61–4.59 (m, 2H), 3.74 (s, 2H), 2.43 (s, 3H).

EXAMPLE 9(2)

2-(1-(4-(2-phenyloxazol-5-ylmethoxy)benzoyl)-2-methylindol-3-yl)acetic acid allylic ester

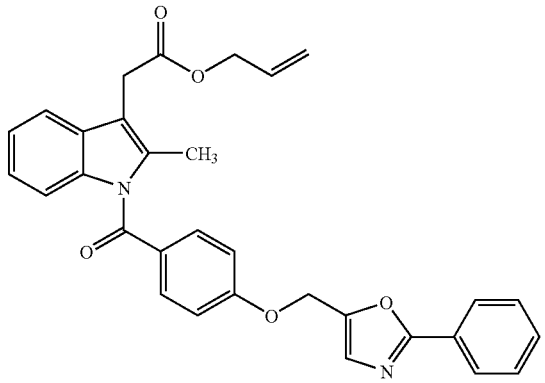

TLC: Rf 0.66(hexane:ethyl acetate=4:1).

EXAMPLE 9(3)

2-(1-(4-(1-methylindol-2-ylmethoxy)benzoyl)-2-methylindol-3-yl)acetic acid allylic ester

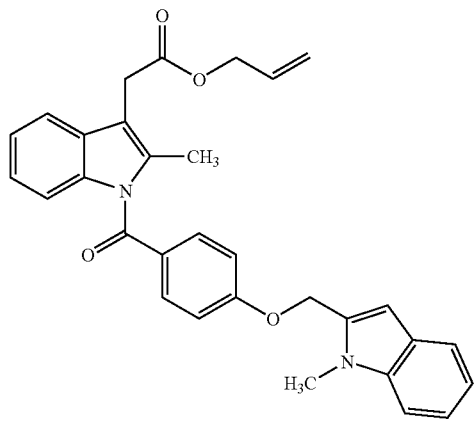

TLC: Rf 0.42(hexane:ethyl acetate=3:1).

EXAMPLE 9(4)

2-(1-(4-((2S)-7-fluoro4-methyl-3,4-dihydro-2H-1,4-benzoxazin-2-ylmethoxy)-2-methylbenzoyl)-2-methylindol-3-yl)acetic acid benzyl ester

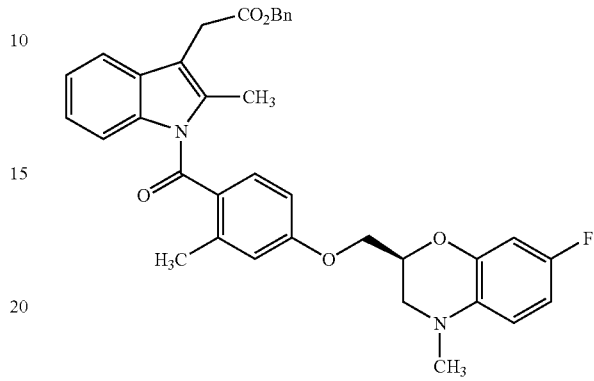

TLC: Rf 0.40(hexane:ethyl acetate=7:3);

NMR(CDCl$_3$):δ 7.47 (d, J=7.8 Hz, 1H), 7.36–7.24 (m, 5H), 7.20–7.00 (m, 4H), 6.86 (d, J=2.1 Hz, 1H), 6.78 (dd, J=8.4, 2.1 Hz, 1H), 6.64–6.58 (m, 3H), 5.13 (s, 2H), 4.74–4.64 (m, 1H), 4.27 (dd, J=9.9, 5.1 Hz, 1H), 4.17 (dd, J=9.9, 6.3 Hz, 1H), 3.74 (s, 2H), 3.36 (dd, J=11.4, 2.7 Hz, 1H), 3.22 (dd, J=11.4, 6.6 Hz, 1H), 2.88 (s, 3H), 2.31 (s, 3H), 2.29 (s, 3H).

EXAMPLE 9(5)

2-(1-(4-((2S)-4,7-dimethyl-3,4-dihydro-2H-1,4-benzoxazin-2-ylmethoxy)-2-methylbenzoyl)-2-methylindol-3-yl)acetic acid benzyl ester

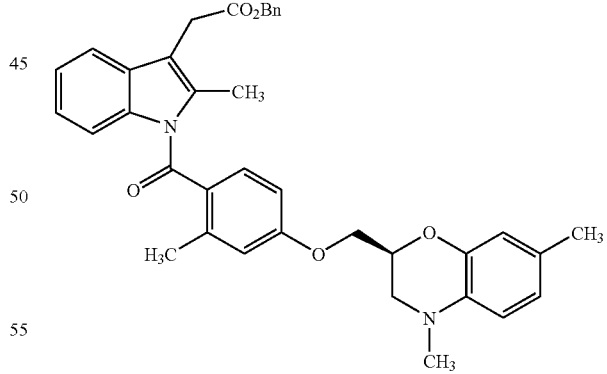

TLC: Rf 0.50(hexane:ethyl acetate=7:3);

NMR(CDCl$_3$):δ 7.47 (d, J=7.5 Hz, 1H), 7.38–7.35 (m, 5H), 7.21–6.99 (m, 4H), 6.86 (d, J=2.4 Hz, 1H), 6.78 (dd, J=8.7, 2.4 Hz, 1H), 6.73–4.60 (m, 3H), 5.13 (s, 2H), 4.72–4.62 (m, 1H), 4.27 (dd, J=9.3, 5.4Hz, 1H), 4.17 (dd, J=9.3, 6.3 Hz, 1H), 3.74 (s, 2H), 3.36 (dd, J=11.1, 2.4 Hz, 1H), 3.22 (dd, J=11.1, 6.6 Hz, 1H), 2.88 (s, 3H), 2.31 (s, 3H), 2.29 (s, 3H), 2.23 (s, 3H).

EXAMPLE 9(6)

2-(1-(4-((2S)-4,6-dimethyl-3,4-dihydro-2H-1,4-benzoxazin-2-ylmethoxy)-2-methylbenzoyl)-2-methylindol-3-yl)acetic acid benzyl ester

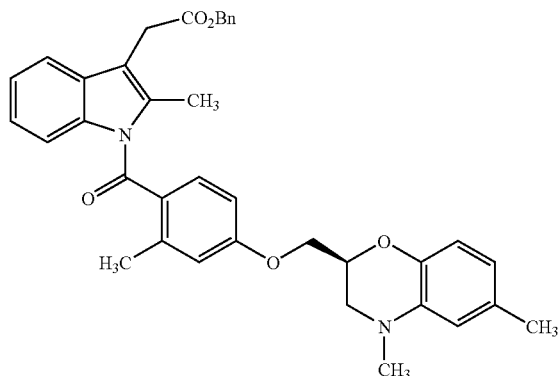

TLC: Rf 0.50(hexane:ethyl acetate=7:3);

NMR(CDCl$_3$):δ 7.47 (d, J=7.5 Hz, 1H), 7.40–7.24 (m, 5H), 7.22–7.00 (m, 4H), 6.86 (d, J=2.4 Hz, 1H), 6.83–6.69 (m, 2H), 6.56–6.44 (m, 2H), 5.13 (s, 2H), 4.68–4.58 (m, 1H), 4.27 (dd, J=9.9, 5.1 Hz, 1H), 4.16 (dd, J=9.9, 6.0 Hz, 1H), 3.74 (s, 2H), 3.39 (dd, J=11.7, 2.7 Hz, 1H), 3.25 (dd, J=11.7, 6.3 Hz, 1H), 2.91 (s, 3H), 2.31 (s, 3H), 2.29 (s, 3H), 2.28 (s, 3H).

EXAMPLE 9(7)

2-(1-(4-((3R)-5-methyl-2,3-dihydrobenzofuran-3-ylmethoxy)-2-methylbenzoyl)-2-methylindol-3-yl)acetic acid benzyl ester

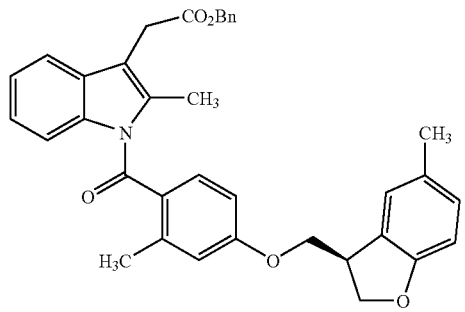

TLC: Rf 0.68(hexane:ethyl acetate=7:3);

NMR(CDCl$_3$):δ 7.50–7.44 (m, 1H), 7.38–7.24 (m, 6H), 7.21–6.97 (m, 4H), 6.86–6.80 (m, 2H), 6.79–6.70 (m, 2H), 5.13 (s, 2H), 4.71 (t, J=8.7 Hz, 1H), 4.53 (dd, J=9.3, 5.1 Hz, 1H), 4.21 (dd, J=9.3, 6.0 Hz, 1H), 4.05 (t, J=8.7 Hz, 1H), 3.98–3.86 (m, 1H), 3.74 (s, 2H), 2.31 (s, 6H), 2.29 (s, 3H).

EXAMPLE 9(8)

2-(1-(4-((3R)-2,3-dihydrobenzofuran-3-ylmethoxy)-2-methylbenzoyl)-2-methylindol-3-yl)acetic acid benzyl ester

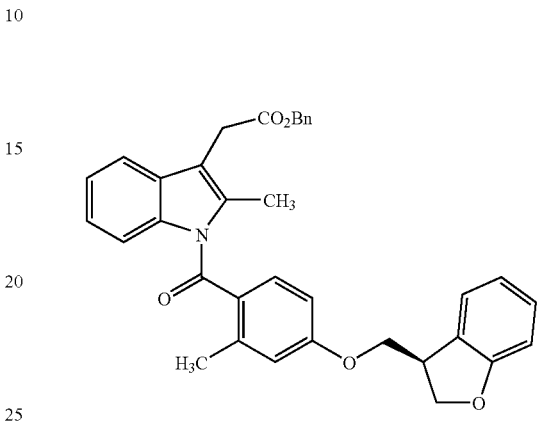

TLC: Rf 0.53(hexane:ethyl acetate=7:3);

NMR(CDCl$_3$):δ 7.47 (d, J=7.5 Hz,1H), 7.40–6.72 (m, 15H), 5.13 (s, 2H), 4.73 (t, J=9.0 Hz, 1H), 4.55 (dd, J=9.6, 5.1 Hz, 1H), 4.28–3.90 (m, 3H), 3.74 (s, 2H), 2.31 (s, 3H), 2.29 (s, 3H).

EXAMPLE 9(9)

2-(1-(4-(2-(3-methylpyridine-6-yl)ethoxy)-2-methylbenzoyl)-2-methylindol-3-yl)acetic acid benzyl ester

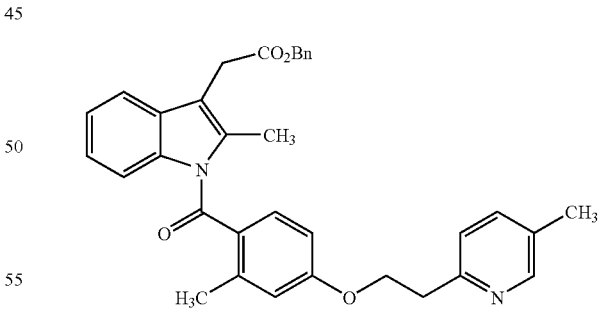

TLC: Rf 0.60(hexane:ethyl acetate=1:1);

NMR(CDCl$_3$):δ 8.41–8.38 (m, 1H), 7.50–7.40 (m, 2H), 7.35–7.12 (m, 8H), 7.09–6.98 (m, 2H), 6.81 (d, J=2.1 Hz, 1H), 6.77–6.71 (m, 1H), 5.12 (s, 2H), 4.41 (t, J=6.6 Hz, 2H), 3.73 (s, 2H), 3.25 (t, J=6.6 Hz, 2H), 2.32 (s, 3H), 2.30 (s, 3H), 2.27 (s, 3H).

EXAMPLE 9(10)

2-(1-(4-(5-methyl-1,3-dioxanindan-2-ylmethoxy)-2-methylbenzoyl)-2-methylindol-3-yl)acetic acid benzyl ester

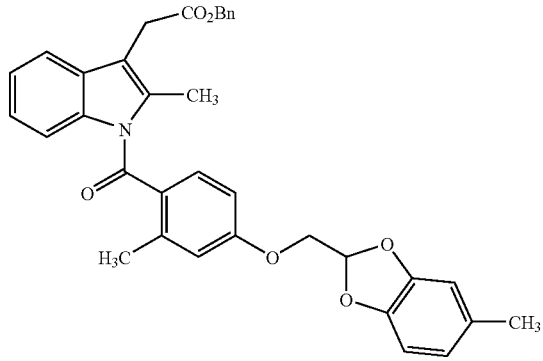

TLC: Rf 0.66(hexane:ethyl acetate=7:3);

NMR(CDCl$_3$):δ 7.47 (d, J=7.5 Hz, 1H), 7.38–7.24 (m, 6H), 7.22–6.97 (m, 3H), 6.90–6.58 (m, 5H), 6.45 (t, J=4.2 Hz, 1H), 5.13 (s, 2H), 4.31 (d, J=4.2 Hz, 2H), 3.73 (s, 2H), 2.31 (s, 3H), 2.29 (s, 3H), 2.28 (s, 3H).

EXAMPLE 9(11)

2-(1-(4-((3R)-5-fluoro-2,3-dihydrobenzofuran-3-ylmethoxy)-2-methylbenzoyl)-2-methylindol-3-yl)acetic acid benzyl ester

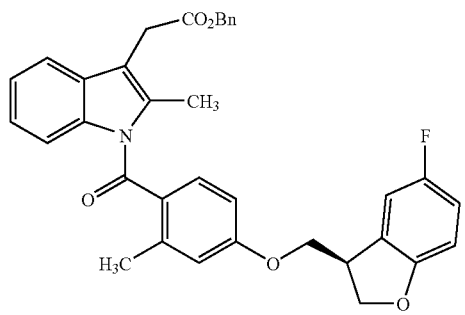

TLC: Rf 0.63(hexane:ethyl acetate=7:3);

NMR(CDCl$_3$):δ 7.47 (d, J=7.5 Hz, 1H), 7.36–7.24 (m, 6H), 7.20–7.00 (m, 4H), 6.82 (d, J=3.0 Hz, 1H), 6.75 (dd, J=8.7, 3.0 Hz, 1H), 6.68–6.56 (m, 2H), 5.13 (s, 2H), 4.80–4.64 (m, 2H), 4.44–4.37 (m, 1H), 4.17–4.02 (m, 2H), 3.73 (s, 2H), 2.31 (s, 3H), 2.28 (s, 3H).

EXAMPLE 9(12)

2-(1-(4-((2S)-6-fluoro-4-methyl-3,4-dihydro-2H-1,4-benzoxazin-2-ylmethoxy)-2-methylbenzoyl)-2-methylindol-3-yl)acetic acid benzyl ester

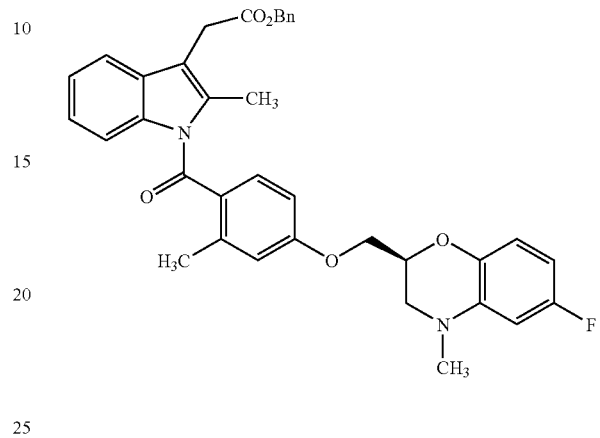

TLC: Rf 0.58(hexane:ethyl acetate=7:3);

NMR(CDCl$_3$):δ 7.47 (d, J=7.5 Hz, 1H), 7.36–7.24 (m, 6H), 7.21–7.12 (m, 1H), 7.10–6.99 (m, 2H), 6.86 (d, J=2.4 Hz, 1H), 6.82–6.70 (m, 2H), 6.45–6.31 (m, 2H), 5.13 (s, 2H), 4.74–4.64 (m, 1H), 4.27 (dd, J=9.9, 5.7 Hz, 1H), 4.16 (dd, J=9.9, 6.3 Hz, 1H), 3.74 (s, 2H), 3.41 (dd, J=11.4, 3.0 Hz, 1H), 3.30 (dd, J=11.4, 6.9 Hz, 1H), 2.92 (s, 3H), 2.32 (s, 3H), 2.29 (s, 3H).

EXAMPLE 9(13)

2-(1-(4-(1-ethylindolin-2-ylmethoxy)-2-methylbenzoyl)-2-methylindol-3-yl)acetic acid benzyl ester

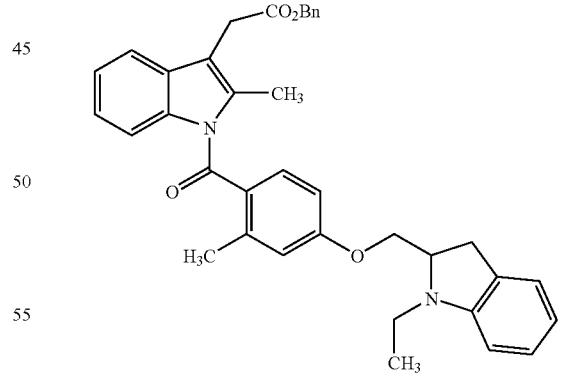

TLC: Rf 0.75(hexane:ethyl acetate=7:3);

NMR(CDCl$_3$):δ 7.47 (d, J=7.8 Hz, 1H), 7.36–7.24 (m, 6H), 7.21–7.00 (m, 5H), 6.85 (d, J=2.7 Hz, 1H), 6.76 (dd, J=8.4, 2.7 Hz, 1H), 6.66 (t, J=7.8 Hz, 1H), 6.47 (d, J=7.8 Hz, 1H), 5.13 (s, 2H), 4.24–4.05 (m, 3H), 3.74 (s, 2H), 3.47–3.24 (m, 3H), 2.95–2.85 (m, 1H), 2.32 (s, 3H), 2.30 (s, 3H), 1.17 (t, J=6.9 Hz, 3H).

EXAMPLE 9(14)

2-(1-(4-(4-methyl-1,3-dioxanindan-2-ylmethoxy)-2-methylbenzoyl)-2-methylindol-3-yl)acetic acid benzyl ester

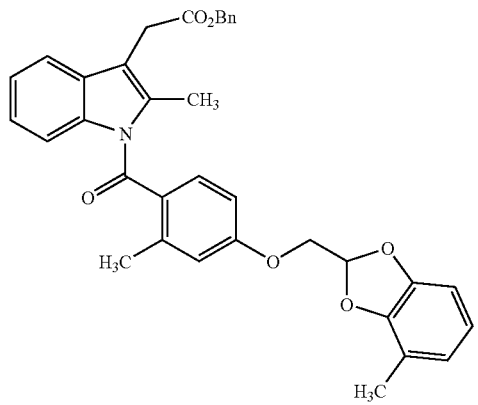

TLC: Rf 0.53(hexane:ethyl acetate=7:3);

NMR(CDCl$_3$):δ 7.47 (d, J=7.5 Hz, 1H), 7.36–7.25 (m, 6H), 7.20–6.98 (m, 3H), 6.90–6.57 (m, 4H), 6.46 (t, J=3.3 Hz, 1H), 5.13 (s, 2H), 4.34 (d, J=3.3 Hz, 2H), 3.74 (s, 2H), 2.31 (s, 3H), 2.29 (s, 3H), 2.24 (s, 3H).

EXAMPLE 9(15)

2-(1-(4-((3R)-7-methyl-2,3-dihydrobenzofuran-3-yl-methoxy)-2-methylbenzoyl)-2-methylindol-3-yl)acetic acid benzyl ester

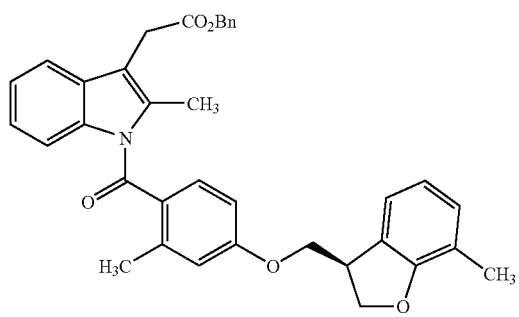

TLC: Rf 0.60(hexane:ethyl acetate=7:3);

NMR(CDCl$_3$):δ 7.47 (d, J=7.8 Hz, 1H), 7.36–7.20 (m, 6H), 7.20–6.90(m, 5H), 6.86–6.72 (m, 3H), 5.13 (s, 2H), 4.72 (t, J=9.0 Hz, 1H), 4.55 (dd, J=9.0, 5.1 Hz, 1H), 4.25–3.90 (m, 3H), 3.73 (s, 2H), 2.31 (s, 3H), 2.28 (s, 3H), 2.24 (s, 3H).

EXAMPLE 10(1) TO EXAMPLE 10(15)

Using the compound prepared according to example 9(1) to example 9(15) instead of the compound prepared according to example 1, this following invention compounds were obtained by the operation similar to example 2.

EXAMPLE 10(1)

2-(1-(4-(quinolin-3-ylmethoxy)benzoyl)-2-methylindol-3-yl)acetic acid

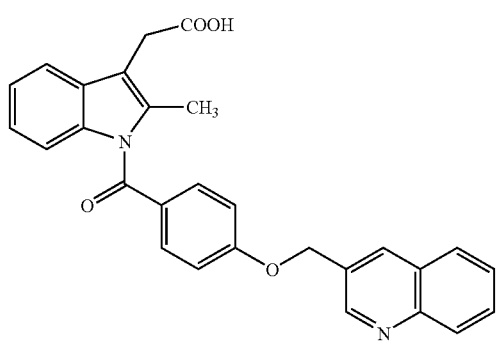

TLC: Rf 0.61(methanol:chloroform=1:10);

NMR(CDCl$_3$):δ 9.02 (d, J=0.9 Hz, 1H), 8.47 (s, 1H), 8.07–8.00 (m, 2H), 7.78 (m, 1H), 7.70–7.60 (m, 3H), 7.50 (d, J=7.5 Hz, 1H), 7.26 (d, J=8.4 Hz, 2H), 7.13 (t, J=7.8 Hz, 1H), 7.03 (t, J=7.2 Hz, 1H), 6.95 (d, J=8.1 Hz, 1H), 5.47 (s, 2H), 3.68 (s, 2H), 2.28 (s, 3H).

EXAMPLE 10(2)

2-(1-(4-(2-phenyloxazol-5-ylmethoxy)benzoyl)-2-methylindol-3-yl)acetic acid

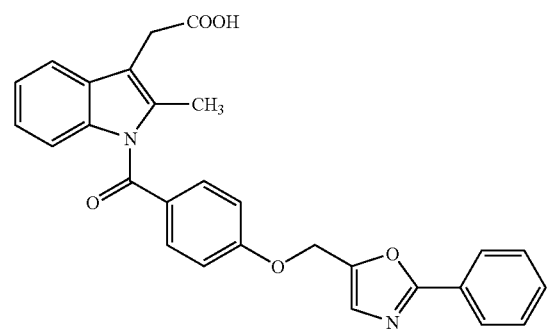

TLC: Rf 0.55(chloroform:methanol=10:1);

NMR(CDCl$_3$):δ 8.06 (m, 2H), 7.76 (d, J=9.0 Hz, 2H), 7.55–7.45 (m, 3H), 7.30 (s, 1H), 7.15 (m, 1H), 7.09–6.95 (m, 5H), 5.20 (s, 2H), 3.73 (s, 2H), 2.42 (s, 3H).

EXAMPLE 10(3)

2-(1-(4-(1-methylindol-2-ylmethoxy)benzoyl)-2-methylindol-3-yl)acetic acid

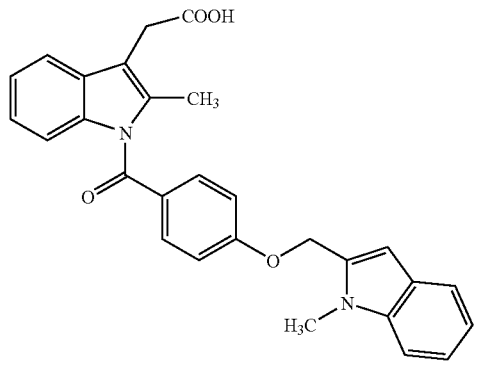

TLC: Rf 0.46(methanol:chloroform=1:10);

NMR(DMSO-$d_6$):δ 7.67 (d, J=9.0 Hz, 2H), 7.56–7.45 (m, 3H), 7.27 (d, J=9.0 Hz, 2H), 7.30–7.10 (m, 2H), 7.05–7.00 (m, 2H), 6.97 (m, 1H), 6.66 (s, 1H), 5.45 (s, 2H), 3.79 (s, 3H), 3.68 (s, 2H), 2.28 (s, 3H).

EXAMPLE 10(4)

2-(1-(4-((2S)-7-fluoro-4-methyl-3,4-dihydro-2H-1,4-benzoxazin-2-ylmethoxy)-2-methylbenzoyl)-2-methylindol-3-yl)acetic acid

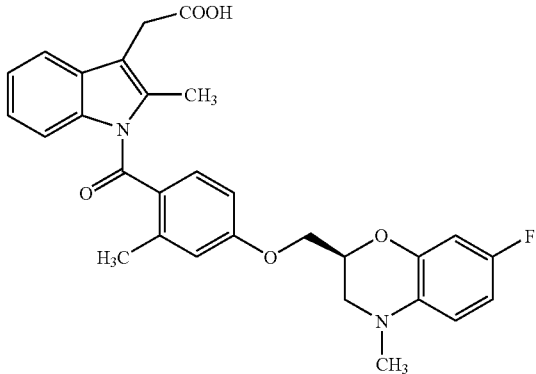

TLC: Rf 0.45(chloroform:methanol=9:1);

NMR(CDCl$_3$):δ 7.52–7.46 (m, 1H), 7.34 (d, J=8.4Hz, 1H), 7.23–7.15 (m, 1H), 7.10–6.97 (m, 2H), 6.90–6.86 (m, 1H), 6.82–6.77 (m, 1H), 6.64–6.57 (m, 3H), 4.74–4.64 (m, 1H), 4.27 (dd, J=9.6, 5.1 Hz, 1H), 4.18 (dd, J=9.6, 6.0 Hz, 1H), 3.74 (s, 2H), 3.35 (dd, J=11.1, 3.3 Hz, 1H), 3.22 (dd, J=11.1, 6.6 Hz, 1H), 2.88 (s, 3H), 2.35 (s, 3H), 2.33 (s, 3H).

EXAMPLE 10(5)

2-(1-(4-((2S)-4,7-dimethyl-3,4-dihydro-2H-1,4-benzoxazin-2-ylmethoxy)-2-methylbenzoyl)-2-methylindol-3-yl)acetic acid

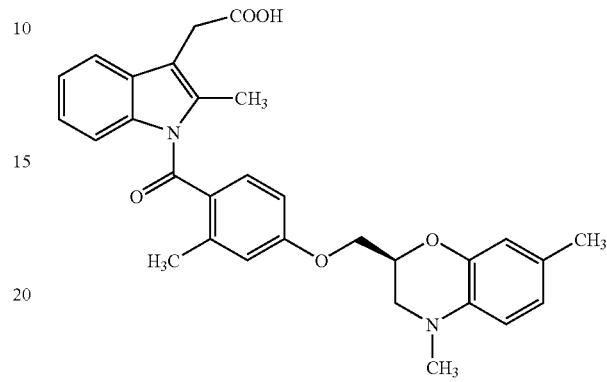

TLC: Rf 0.45(chloroform:methanol=9:1);

NMR(CDCl$_3$):δ 7.49 (d, J=7.2 Hz, 1H), 7.36–6.97 (m, 4H), 6.88 (d, J=2.4 Hz, 1H), 6.79 (dd, J=9.0, 2.4 Hz, 1H), 6.73–6.60 (m, 3H), 4.72–4.62 (m, 1H), 4.28 (dd, J=9.6, 5.1 Hz, 1H), 4.18 (dd, J=9.6, 6.3 Hz, 1H), 3.73 (s, 2H), 3.36 (dd, J=11.4, 2.7 Hz, 1H), 3.21 (dd, J=11.4, 6.3 Hz, 1H), 2.88 (s, 3H), 2.35 (s, 3H), 2.32 (s, 3H), 2.23 (s, 3H).

EXAMPLE 10(6)

2-(1-(4-((2S)-4,6-dimethyl-3,4-dihydro-2H-1,4-benzoxazin-2-ylmethoxy)-2-methylbenzoyl)-2-methylindol-3-yl)acetic acid

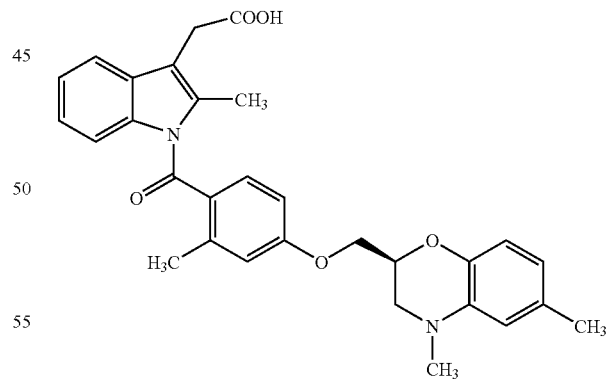

TLC: Rf 0.45(chloroform:methanol=9:1);

NMR(CDCl$_3$):δ 7.48 (d, J=7.8 Hz, 1H), 7.36–6.96 (m, 4H), 6.90–6.84 (m, 1H), 6.83–6.75 (m, 1H), 6.73 (d, J=7.8 Hz, 1H), 6.56–6.45 (m, 2H), 4.68–4.58 (m, 1H), 4.27 (dd, J=9.9, 5.4 Hz, 1H), 4.17 (dd, J=9.9, 6.6 Hz, 1H), 3.73 (s, 2H), 3.39 (dd, J=12.0, 2.7 Hz, 1H), 3.25 (dd, J=12.0, 6.6 Hz, 1H), 2.91 (s, 3H), 2.35 (s, 3H), 2.32 (s, 3H), 2.28 (s, 3H).

EXAMPLE 10(7)

2-(1-(4-((3R)-5-methyl-2,3-dihydrobenzofuran-3-yl-methoxy)-2-methylbenzoyl)-2-methylindol-3-yl)acetic acid

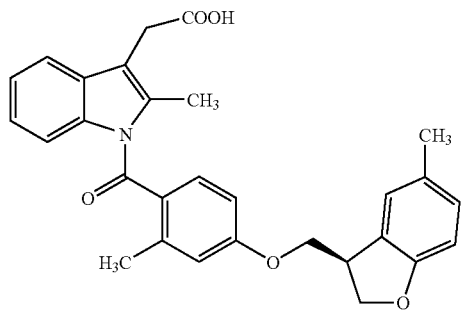

TLC: Rf 0.49(chloroform:methanol=9:1);
NMR(CDCl$_3$):δ 7.48 (d, J=8.1 Hz, 1H), 7.33 (d, J=8.1 Hz, 1H), 7.19 (td, J=8.1, 0.9 Hz, 1H), 7.12–6.96 (m, 4H), 6.87–6.80 (m, 1H), 6.79–6.71 (m, 2H), 4.70 (t, J=8.7 Hz, 1H), 4.53 (dd, J=9.6, 5.1 Hz, 1H ), 4.21 (dd, J=9.6, 5.7 Hz, 1H), 4.05 (t, J=8.7 Hz, 1H), 3.98–3.86 (m, 1H), 3.73 (s, 2H), 2.35 (s, 3H), 2.32 (s, 3H), 2.31 (s, 3H).

EXAMPLE 10(8)

2-(1-(4-((3R)-2,3-dihydrobenzofuran-3-ylmethoxy)-2-methylbenzoyl)-2-methylindol-3-yl)acetic acid

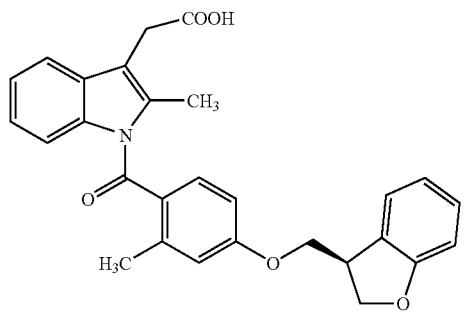

TLC: Rf 0.49(chloroform:methanol=9:1);
NMR(CDCl$_3$):δ 7.51–7.45 (m, 1H), 7.35–7.28 (m, 2H), 7.25–6.80 (m, 7H), 6.79–6.73 (m, 1H), 4.73 (t, J=8.4 Hz, 1H), 4.55 (dd, J=9.3, 5.1 Hz, 1H), 4.21 (dd, J=5.7 Hz, 1H), 4.08 (t, J=8.4 Hz, 1H), 4.02–3.90 (m, 1H), 3.72 (s, 2H), 2.34 (s, 3H), 2.32 (s, 3H).

EXAMPLE 10(9)

2-(1-(4-(2-(3-methylpyridin-6-yl)ethoxy)-2-methylbenzoyl)-2-methylindol-3-yl)acetic acid

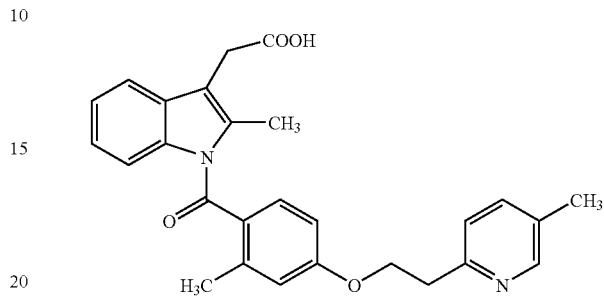

TLC: Rf 0.53(chloroform:methanol=9:1);
NMR(CDCl$_3$):δ 8.42 (d, J=1.5 Hz, 1H), 7.58–7.46 (m, 2H), 7.30–7.13 (m, 3H), 7.07–6.95 (m, 2H), 6.75 (d, J=2.1 Hz, 1H), 6.61 (dd, J=8.7, 2.1 Hz, 1H), 4.29 (t, J=6.3 Hz, 2H), 3.71 (s, 2H), 3.23 (t, J=6.3 Hz, 2H), 2.33 (s, 3H), 2.32 (s, 3H), 2.25 (s, 3H).

EXAMPLE 10(10)

2-(1-(4-(5-methyl-1,3-dioxanindan-2-ylmethoxy)-2-methylbenzoyl)-2-methylindol-3-yl)acetic acid

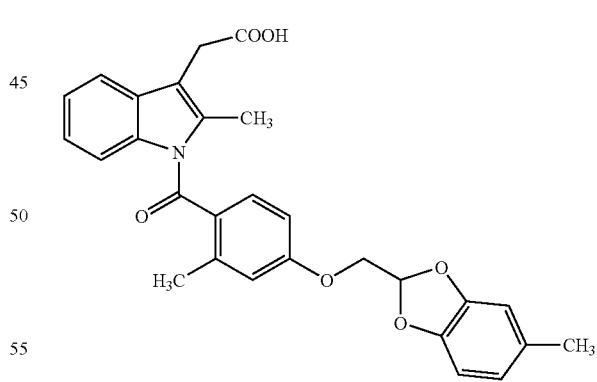

TLC: Rf 0.53(chloroform:methanol=9:1);
NMR(CDCl$_3$):δ 7.48 (d, J=7.5 Hz, 1H), 7.33 (d, J=8.7 Hz, 1H), 7.23–7.02 (m, 2H), 6.97 (d, J=7.5 Hz, 1H), 6.90–6.85 (m, 1H), 6.83–6.60 (m, 4H), 6.44 (t, J=4.2 Hz, 1H), 4.31 (d, J=4.2 Hz, 2H), 3.72 (s, 2H), 2.34 (s, 3H), 2.31 (s, 3H), 2.29 (s, 3H).

EXAMPLE 10(11)

2-(1-(4-((3R)-5-fluoro-2,3-dihydrobenzofuran-3-yl-methoxy)-2-methylbenzoyl)-2-methylindol-3-yl)acetic acid

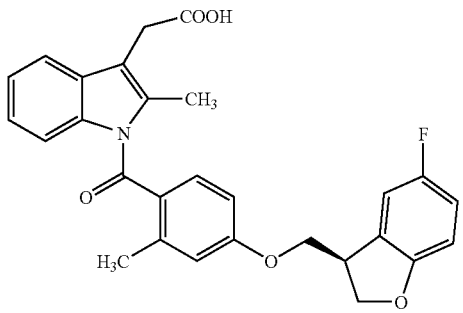

TLC: Rf 0.53(chloroform:methanol=9:1);
NMR(CDCl$_3$):δ 7.48 (d, J=7.8 Hz, 1H), 7.32 (d, J=8.4 Hz, 1H), 7.22–6.97 (m, 4H), 6.84 (d, J=2.4 Hz, 1H), 6.76 (dd, J=8.4, 2.4 Hz, 1H), 6.67–6.57 (m, 2H), 4.80–4.64 (m, 2H), 4.44–4.36 (m, 1H), 4.18–4.03 (m, 2H), 3.72 (s, 2H), 2.34 (s, 3H), 2.32 (s, 3H).

EXAMPLE 10(12)

2-(1-(4-((2S)-6-fluoro-4-methyl-3,4-dihydro-2H-1,4-benzoxazin-2-ylmethoxy)-2-methylbenzoyl)-2-methylindol-3-yl)acetic acid

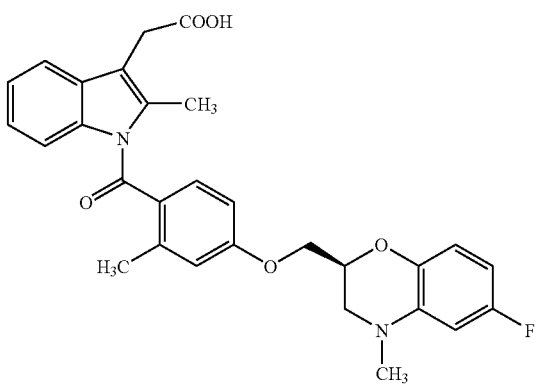

TLC: Rf 0.53(chloroform:methanol=9:1);
NMR(CDCl$_3$):δ 7.48 (d, J=7.5 Hz, 1H), 7.33 (d, J=8.4 Hz, 1H), 7.18 (td, J=7.5, 0.9 Hz, 1H), 7.10–6.96 (m, 2H), 6.87 (d, J=2.4 Hz, 1H), 6.83–6.70 (m, 2H), 6.45–6.30 (m, 2H), 4.65–4.55 (m, 1H), 4.27 (dd, J=9.9, 5.1 Hz, 1H), 4.16 (dd, J=9.9, 6.3 Hz, 1H), 3.72 (s, 2H), 3.41 (dd, J=11.4, 2.7 Hz, 1H), 3.30 (dd, J=11.4, 6.9 Hz, 1H), 2.91 (s, 3H), 2.34 (s, 3H), 2.32 (s, 3H).

EXAMPLE 10(13)

2-(1-(4-(1-ethylindolin-2-ylmethoxy)-2-methylbenzoyl)-2-methylindol-3-yl)acetic acid

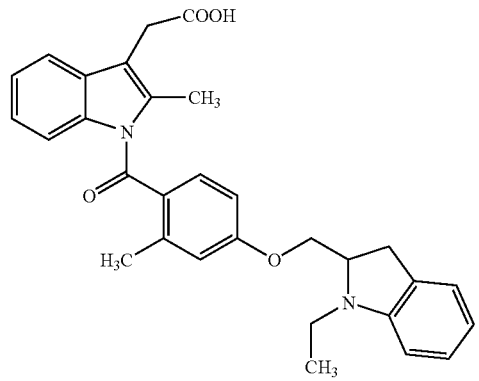

TLC: Rf 0.53(chloroform:methanol=9:1);
NMR(CDCl$_3$):δ 7.48 (d, J=7.8 Hz, 1H), 7.33 (d, J=8.4 Hz, 1H), 7.22–6.97 (m, 5H), 6.86 (d, J=2.1 Hz, 1H), 6.77 (dd, J=8.7, 2.1 Hz, 1H), 6.66 (t, J=7.8 Hz, 1H), 6.47 (d, J=7.8 Hz, 1H), 4.30–4.04 (m, 3H ), 3.72 (s, 2H), 3.47–3.22 (m, 3H), 2.89 (dd, J=16.2, 7.2 Hz, 1H), 2.34 (s, 3H), 2.33 (s, 3H), 1.17 (t, J=7.5 Hz, 3H).

EXAMPLE 10(14)

2-(1-(4-(4-methyl-1,3-dioxanindan-2-ylmethoxy)-2-methylbenzoyl)-2-methylindol-3-yl)acetic acid

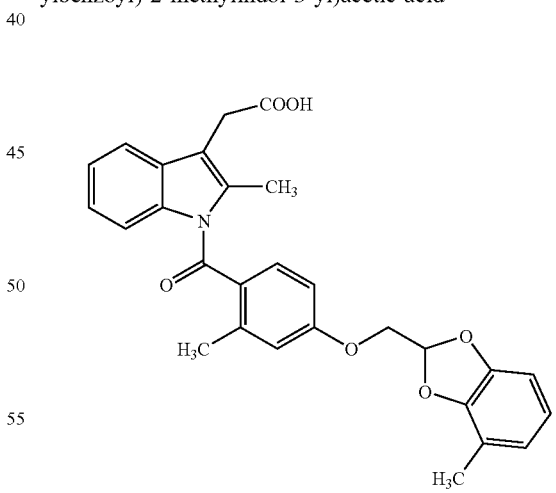

TLC: Rf 0.53(chloroform:methanol=9:1);
NMR(CDCl$_3$):δ 7.48 (d, J=7.5 Hz,1H), 7.34 (d, J=8.4 Hz, 1H), 7.19 (t, J=7.5 Hz, 1H), 7.10–6.95 (m, 2H), 6.92–6.87 (m, 1H), 6.84–6.66 (m, 4H), 6.45 (t, J=3.9 Hz, 1H), 4.34 (d, J=3.9 Hz, 2H), 3.73 (s, 2H), 2.35 (s, 3H), 2.32 (s, 3H), 2.24 (s, 3H).

EXAMPLE 10(15)

2-(1-(4-((3R)-7-methyl-2,3-dihydrobenzofuran-3-yl-methoxy)-2-methylbenzoyl)-2-methylindol-3-yl)acetic acid

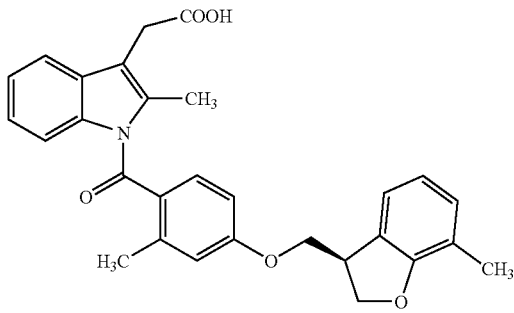

TLC: Rf 0.53(chloroform:methanol=9:1);

NMR(CDCl$_3$):δ 7.48 (d, J=8.1 Hz, 1H), 7.32 (d, J=8.1 Hz, 1H), 7.23–7.10 (m, 2H), 7.10–6.90 (m, 3H), 6.88–6.73 (m, 3H), 4.72 (t, J=8.7 Hz, 1H), 4.59–7.51 (m, 1H), 4.25–4.16 (m, 1H), 4.15–3.90 (m, 2H), 3.72 (s, 2H), 2.34 (s, 3H), 2.31 (s, 3H), 2.24 (s, 3H).

Formulation Example 1

The following components were admixed in conventional method and punched out to obtain 100 tablets each containing 5 mg of active ingredient.

| | |
|---|---|
| 2-(1-(4-((2S)-4-methyl-3,4-dihydro-2H-1,4-benzoxazine-2-ylmethoxy)benzoyl)-2-methylindol-3-yl)acetic acid | 5.0 g |
| Carboxymethyl cellulose calcium (disintegrator) | 0.2 g |
| Magnesium stearate (lubricant) | 0.1 g |
| Microcrystalline cellulose | 4.7 g |

Formulation Example 2

After the following components were admixed in conventional method, the solution was sterilized in conventional manner, placed 5 ml portions into ampoules and freeze-dried to obtain 100 ampoules each containing 20 mg of the active ingredient.

| | |
|---|---|
| 2-(1-(4-((2S)-4-methyl-3,4-dihydro-2H-1,4-benzoxazine-2-ylmethoxy)benzoyl)-2-methylindol-3-yl)acetic acid | 2.0 g |
| Mannitol | 20 g |
| Distilled water | 1000 mL |

What is claimed is:

1. An indole derivative compound represented by formula (I):

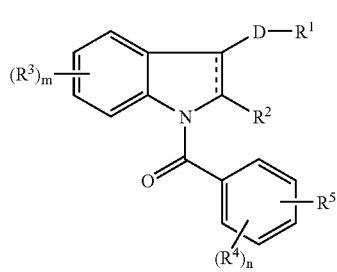

wherein $R^1$ represents —COR$^6$, $R^6$ represents a hydroxyl group, C1–6 alkoxy group, —NR$^8$R$^9$, C1–6 alkoxy group substituted by phenyl group, or C2–6 alkenyloxy group, $R^8$ and $R^9$ represent hydrogen atom, C1–6 alkyl group or —SO$_2$R$^{10}$, $R^{10}$ represents C1–6 alkyl group, carbocyclic ring or heterocycle, D represents a single bond, C1–6 alkylene group, C2–6 alkenylene group, or —O—(C1–6 alkylene)- group, $R^2$ represents C1–6 alkyl group, C1–6 alkoxy group, halogen atom, trihalomethyl group, cyano group, or hydroxyl group, $R^3$ and $R^4$ each independently represent a hydrogen atom, C1–6 alkyl group, and C1–6 alkoxy group, C1–6 alkyl group substituted by C1–6 alkoxy group, a halogen atom, nitro group, —NR$^{11}$R$^{12}$, trihalomethyl group, cyano group, hydroxyl group, or trihalomethoxy group, $R^{11}$ and $R^{12}$ represent a hydrogen atom or C1–6 alkyl group, m represents 1 to 4, n represents 1 to 4, $R^5$ represents

C1–6 alkyl group substituted by C1–6 alkoxy group, or C1–6 alkoxy group substituted by C1–6 alkoxy group, G represents a single bond, C1–6 alkylene group, which may be substituted by hydroxyl group or C1–4 alkoxy group, wherein each of 1 or 2 carbon atoms of the C1–6 alkylene group independently may be replaced by an oxygen atom or a sulfur atom, C2–6 alkenylene group, which may be substituted by hydroxyl group or C1–4 alkoxy group, wherein each of 1 or 2 carbon atoms of the C2–6 alkenylene group independently may be replaced by an oxygen atom or a sulfur atom, —CONR$^{13}$—, —NR$^{14}$CO—, —SO$_2$NR$^{15}$—, —NR$^{16}$SO$_2$—, or —N═N—, $R^{13}$, $R^{14}$, $R^{15}$, and $R^{16}$ each independently represent a hydrogen atom or C1–6 alkyl group,

represents carbocyclic ring or heterocycle,
  carbocyclic ring represents C3–15 monocycle, dicyclic or tricycle carbocyclic ring aryls that may be saturated all or partially,
  heterocycle represents C6 monocyclic, dicyclic, or tricyclic heterocyclic ring aryls that may be saturated all or partially, which contain 2 hetero atom(s) independently selected from oxygen atom and nitrogen atom,
  each carbocyclic ring and each heterocycle independently may be substituted by 1–5 group(s) selected from C1–6 alkyl group, C1–10 alkoxy group, C1–6 alkyl group substituted by C1–6 alkoxy group, halogen atom, hydroxyl group, trihalomethyl group, nitro group, —$NR^{17}R^{18}$, phenyl group, phenoxy group, oxo group, C2–6 acyl group, cyano group, and —$SO_2R^{19}$,
  $R^{17}$ and $R^{18}$ each independently represent hydrogen atom or C1–6 alkyl group,
  $R^{19}$ represents C1–6 alkyl group, and

===== represents a single bond or a double bond, except for 2-(1-(4-benzyloxybenzoyl)-2-methyl-5-methoxyindol-3-yl)acetic acid methyl or a non-toxic salt thereof.

2. The indole derivative compound of claim 1, wherein the compound is
  (1) 2-(1-(4-propoxymethylbenzoyl)-2-methyl-5-methoxyindol-3-yl)acetic acid,
  (2) 2-(1-(4-(2-ethoxyethyl)benzoyl)-2-methyl-5-methoxyindol-3-yl)acetic acid,
  (3) 2-(1-(4-phenoxybenzoyl)-2-methyl-5-methoxyindol-3-yl)acetic acid,
  (4) 2-(1-(4-benzyloxybenzoyl)-2-methyl-5-methoxyindol-3-yl)acetic acid,
  (5) 2-(1-(4-(2-phenylethoxy)benzoyl)-2-methyl-5-methoxyindol-3-yl)acetic acid,
  (6) 2-(1-(4-(2-methoxyethoxy)benzoyl)-2-methyl-5-methoxyindol-3-yl)acetic acid,
  (7) 2-(1-(4-(2-ethoxyethoxy)benzoyl)-2-methyl-5-methoxyindol-3-yl)acetic acid,
  (8) 2-(1-(3-(2-phenylethoxy)benzoyl)-2-methyl-5-methoxyindol-3-yl)acetic acid,
  (9) 2-(1-(3-(2-ethoxyethoxy)benzoyl)-2-methyl-5-methoxyindol-3-yl)acetic acid,
  (10) 2-(1-(4-(3-phenylpropoxy)benzoyl)-2-methyl-5-methoxyindol-3-yl)acetic acid,
  or a non-toxic salt thereof.

3. A medicinal composition comprising the indole derivative compound represented by formula (I) of claim 1 or a non-toxic salt thereof, and a pharmaceutically acceptable carrier or diluent.

4. A method for medical treatment of allergic diseases, wherein the allergic disease is delected from the group consisting of allergic rhinitis, allergic conjunctivitis, atopic dermatitis, bronchial asthma and food allergy, which comprises administering to a subject an indole derivative compound represented by formula (I) of claim 1 or a non-toxic salt thereof.

* * * * *